US012297433B2

(12) United States Patent
Borrajo

(10) Patent No.: US 12,297,433 B2
(45) Date of Patent: May 13, 2025

(54) TARGETED TRANS-SPLICING USING CRISPR/Cas13

(71) Applicant: Massachusetts Institute of Technology, Cambridge, MA (US)

(72) Inventor: Jacob Borrajo, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/449,850

(22) Filed: Aug. 15, 2023

(65) Prior Publication Data

US 2024/0035031 A1 Feb. 1, 2024

Related U.S. Application Data

(63) Continuation of application No. 16/994,230, filed on Aug. 14, 2020, now Pat. No. 11,767,528.

(60) Provisional application No. 62/985,633, filed on Mar. 5, 2020, provisional application No. 62/888,210, filed on Aug. 16, 2019.

(51) Int. Cl.
*C07H 21/04* (2006.01)
*C12N 9/22* (2006.01)
*C12N 15/113* (2010.01)

(52) U.S. Cl.
CPC .............. *C12N 15/113* (2013.01); *C12N 9/22* (2013.01); *C12N 2310/20* (2017.05)

(58) Field of Classification Search
None
See application file for complete search history.

(56) References Cited

U.S. PATENT DOCUMENTS

2014/0206546 A1 7/2014 Chenchik
2015/0025127 A1 1/2015 McGarrity

FOREIGN PATENT DOCUMENTS

WO WO 2000/009734 A2 2/2000
WO WO 2010/012472 A1 2/2010
WO WO 2013/025461 A1 2/2013
WO WO 2018/071663 A1 4/2018
WO WO 2019/040664 A1 2/2019

OTHER PUBLICATIONS

O'Connell, M ("Molecular mechanisms of RNA targeting by Cas 13-containing type VI CRISPR-Cas systems." Journal of molecular biology 431.1 (2019): 66-87).*
Berger, Adeline, et al. "m RNA trans-splicing in gene therapy for genetic diseases." Wiley Interdisciplinary Reviews: RNA 7.4 (2016): 487-498.*
Jackson et al. ("Conformational regulation of CRISPR-associated nucleases." Current opinion in microbiology 37 (2017): 110-119).*
Butt et al., "Efficient CRISPR/Cas9-Mediated Genome Editing Using a Chimeric Single-Guide RNA Molecule", *Frontiers in Plant Science* 8; https://doi.org/10.3389/fpls.2017.01441 (2017).
Coady et al., "Restoration of SMN Function: Delivery of Trans-splicing RNA Re-directs SMN2 Pre-mRNA Splicing", *Molecular Therapy* 15(8):1471-1478 (2007).
International Search Report and Written Opinion for International Application No. PCT/US2020/046523 dated Nov. 4, 2020, 17 pages.
Konermann et al., "Transcriptome Engineering with RNA-Targeting Type Vi-D Crispr Effectors", Cell 173(3):665-676 (2018).
Koonin et al., "Diversity, classification and evolution of CRISPR-Cas systems", Current Opinion in Microbiology 37:67-78 (2017).
U.S. Appl. No. 16/994,230, filed Aug. 14, 2020, 2021-0071178 A1, Mar. 11, 2021, U.S. Pat. No. 11,767,528, Sep. 26, 2023, Jacob Borrajo.
U.S. Appl. No. 18/449,850, filed Aug. 15, 2023, Jacob Borrajo.
U.S. Appl. No. 18/503,058, filed Nov. 6, 2023, Jacob Borrajo.
Fine et al., "Trans-spliced Cas9 allows cleavage of HBB and CCR5 genes in human cells using compact expression cassettes", Scientific Reports, Jul. 1, 2015, 5: 10777.
Zhang et al., "Construction of human HPRT1 gene site-directed mutation cell line using CRISPR/Cas9 system", heredity, 2019, 41(10): 939-949, Chinese language document—English abstract included.

* cited by examiner

*Primary Examiner* — Kimberly Chong
(74) *Attorney, Agent, or Firm* — Lathrop GPM LLP; Laura A. Labeots

(57) ABSTRACT

This disclosure provides compositions and methods of using these compositions to mediate a targeted trans-splicing event on a pre-mRNA in a cell.

19 Claims, 24 Drawing Sheets

Specification includes a Sequence Listing.

SEQUENCE LISTING

```
Sequence total quantity: 101
SEQ ID NO: 1             moltype = DNA  length = 3282
FEATURE                  Location/Qualifiers
misc_feature             1..3282
                         note = dPspCas13b nucleic acid sequence
source                   1..3282
                         mol_type = other DNA
                         organism = synthetic construct
SEQUENCE: 1
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaacgcat acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgagatcatg cccatgagct tcaccttcga gaaaggcggc  2820
aagaagtaca ccatcaccag cgagggcatg aagctgaaga actacggcga cttctttgtg  2880
ctggctagcg acaagaggat cggcaacctg ctggaactcg tgggcagcga catcgtgtcc  2940
aaagaggata tcatggaaga gttcaacaaa tacgaccagt gcaggcccga gatcagctcc  3000
atcgtgttca acctggaaaa gtgggccttc gacacatacc ccgagctgtc tgccagagtg  3060
gaccgggaag agaaggtgga cttcaagagc atcctgaaaa tcctgctgaa caacaagaac  3120
atcaacaaag agcagagcga catcctgcgg aagatccgga acgccttcga tgcaaacaat  3180
taccccgaca aaggcgtggt ggaaatcaag gccctgcctg agatcgccat gagcatcaag  3240
aaggcctttg ggagtacgc catcatgaag ggaagcctgc ag                    3282
```

-continued

```
SEQ ID NO: 2            moltype = AA  length = 1094
FEATURE                 Location/Qualifiers
REGION                  1..1094
                        note = dPspCas13b amino acid sequence
source                  1..1094
                        mol_type = protein
                        organism = synthetic construct
SEQUENCE: 2
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNAYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWKTPAMK TLGRIYSEDL PVELPRQMFD NEIKSHLKSL PQMEGIDFNN ANVTYLIAEY  780
MKRVLDDDFQ TFYQWNRNYR YMDMLKGEYD RKGSLQHCFT SVEEREGLWK ERASRTERYR  840
KQASNKIRSN RQMRNASSEE IETILDKRLS NSRNEYQKSE KVIRRYRVQD ALLFLLAKKT  900
LTELADFDGE RFKLKEIMPD AEKGILSEIM PMSFTFEKGG KKYTITSEGM KLKNYGDFFV  960
LASDKRIGNL LELVGSDIVS KEDIMEEFNK YDQCRPEISS IVFNLEKWAF DTYPELSARV  1020
DREEKVDFKS ILKILLNNKN INKEQSDILR KIRNAFDANN YPDKGVVEIK ALPEIAMSIK  1080
KAFGEYAIMK GSLQ                                                  1094

SEQ ID NO: 3            moltype = DNA  length = 3717
FEATURE                 Location/Qualifiers
misc_feature            1..3717
                        note = dPspCas13b-SV40NLS-linker-MS2 nucleic acid sequence
source                  1..3717
                        mol_type = other DNA
                        organism = synthetic construct
SEQUENCE: 3
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaacgcat acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc ccccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgtttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
```

-continued

```
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgagatcatg cccatgagct tcaccttcga gaaaggcggc  2820
aagaagtaca ccatcaccag cgagggcatg aagctgaaga actacggcga cttctttgtg  2880
ctggctagcg acaagaggat cggcaacctg ctggaactcg tgggcagcga catcgtgtcc  2940
aaagaggata tcatggaaga gttcaacaaa tacgaccagt gcaggcccga gatcagctcc  3000
atcgtgttca acctggaaaa gtgggccttc gacacatacc ccgagctgtc tgccagagtg  3060
gaccgggaag agaaggtgga cttcaagagc atcctgaaaa tcctgctgaa caacaagaac  3120
atcaacaaag agcagagcga catcctgcgg aagatccgga acgccttcga tgcaaacaat  3180
taccccgaca aaggcgtggt ggaaatcaag gccctgcctg agatcgccat gagcatcaag  3240
aaggcctttg gggagtacgc catcatgaag ggaagcctgc agccaaagaa gaagcggaag  3300
gtcggtggat ccggaggagg tggaagcatg gcttcaaact ttactcagtt cgtgctcgtg  3360
gacaatggtg ggacagggga tgtgacagtg gctccttcta atttcgctaa tggggtggca  3420
gagtggatca gctccaactc acggagccag gcctacaagg tgacatgcag cgtcaggcag  3480
tctagtgccc agaagagaaa gtataccatc aaggtggagg tccccaaagt ggctacccag  3540
acagtgggcg gagtcgaact gcctgtcgcc gcttggaggt cctacctgaa catggagctc  3600
actatcccaa ttttcgctac caattctgac tgtgaactca tcgtgaaggc aatgcagggg  3660
ctcctcaaag acggtaatcc tatcccttcc gccatcgccg ctaactcagg tatctac     3717
```

```
SEQ ID NO: 4            moltype = AA  length = 1239
FEATURE                 Location/Qualifiers
REGION                  1..1239
                        note = dPspCas13b-SV40NLS-linker-MS2 amino acid sequence
source                  1..1239
                        mol_type = protein
                        organism = synthetic construct
SEQUENCE: 4
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNAYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWKTPAMK TLGRIYSEDL PVELPRQMFD NEIKSHLKSL PQMEGIDFNN ANVTYLIAEY  780
MKRVLDDDFQ TFYQWNRNYR YMDMLKGEYD RKGSLQHCFT SVEEREGLWK ERASRTERYR  840
KQASNKIRSN RQMRNASSEE IETILDKRLS NSRNEYQKSE KVIRRYRVQD ALLFLLAKKT  900
LTELADFDGE RFKLKEIMPD AEKGILSEIM PMSFTFEKGG KKYTITSEGM KLKNYGDFFV  960
LASDKRIGNL LELVGSDIVS KEDIMEEFNK YDQCRPEISS IVFNLEKWAF DTYPELSARV  1020
DREEKVDFKS ILKILLNNKN INKEQSDILR KIRNAFDANN YPDKGVVEIK ALPEIAMSIK  1080
KAFGEYAIMK GSLQPKKKRK VGGSGGGGSM ASNFTQFVLV DNGGTGDVTV APSNFANGVA  1140
EWISSNSRSQ AYKVTCSVRQ SSAQKRKYTI KVEVPKVATQ TVGGVELPVA AWRSYLNMEL  1200
TIPIFATNSD CELIVKAMQG LLKDGNPIPS AIAANSGIY                        1239
```

```
SEQ ID NO: 5            moltype = DNA  length = 390
FEATURE                 Location/Qualifiers
misc_feature            1..390
                        note = MS2 coat protein nucleic acid sequence
source                  1..390
                        mol_type = other DNA
                        organism = synthetic construct
SEQUENCE: 5
atggcttcaa actttactca gttcgtgctc gtggacaatg gtgggacagg ggatgtgaca  60
gtggctcctt ctaatttcgc taatggggtg gcagagtgga tcagctccaa ctcacggagc  120
caggcctaca aggtgacatg cagcgtcagg cagtctagtg cccagaagag aaagtatacc  180
atcaaggtgg aggtccccaa agtggctacc cagacagtgg gcggagtcga actgcctgtc  240
gccgcttgga ggtcctacct gaacatggag ctcactatcc caattttcgc taccaattct  300
gactgtgaac tcatcgtgaa ggcaatgcag gggctcctca aagacggtaa tcctatccct  360
tccgccatcg ccgctaactc aggtatctac                                  390
```

```
SEQ ID NO: 6            moltype = AA  length = 130
FEATURE                 Location/Qualifiers
REGION                  1..130
                        note = MS2 coat protein amino acid sequence
source                  1..130
                        mol_type = protein
                        organism = synthetic construct
SEQUENCE: 6
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY                                                        130
```

-continued

```
SEQ ID NO: 7           moltype = AA  length = 22
FEATURE                Location/Qualifiers
REGION                 1..22
                       note = LambdaN amino acid sequence
source                 1..22
                       mol_type = protein
                       organism = synthetic construct
SEQUENCE: 7
MNARTRRRER RAEKQAQWKA AN                                           22

SEQ ID NO: 8           moltype = AA  length = 133
FEATURE                Location/Qualifiers
REGION                 1..133
                       note = QBeta coat protein amino acid seqeunce
source                 1..133
                       mol_type = protein
                       organism = synthetic construct
SEQUENCE: 8
MAKLETVTLG NIGKDGKQTL VLNPRGVNPT NGVASLSQAG AVRALEKRVT VSVSQPSRNR  60
KNYKVQVKIQ NPTAGTANGS GDPSVTRQAY ADVTFSFTQY STDEERAFVR TELAALLASP  120
LLIDAIDQLR PAY                                                     133

SEQ ID NO: 9           moltype = AA  length = 123
FEATURE                Location/Qualifiers
REGION                 1..123
                       note = PP7 coat protein amino acid sequence
source                 1..123
                       mol_type = protein
                       organism = synthetic construct
SEQUENCE: 9
MASKTIVLSV GEATRTLTEI QSTADRQIFE EKVGPLVGRL RLTASLRQNG AKTAYRVNLK  60
LDQADVVDSG LPKVRYTQVW SHDVTIVANS TEASRKSLYD LTKSLVATSQ VEDLVVNLVP  120
LGR                                                                123

SEQ ID NO: 10          moltype = DNA  length = 36
FEATURE                Location/Qualifiers
misc_feature           1..36
                       note = PspCas13b direct repeat
source                 1..36
                       mol_type = other DNA
                       organism = synthetic construct
SEQUENCE: 10
gttgtggaag gtccagtttt gaggggctat tacaac                            36

SEQ ID NO: 11          moltype = DNA  length = 56
FEATURE                Location/Qualifiers
misc_feature           1..56
                       note = PspCas13 gRNA
misc_difference        1..20
                       note = misc_feature - n is a, c, g, or t
source                 1..56
                       mol_type = other DNA
                       organism = synthetic construct
SEQUENCE: 11
nnnnnnnnnn nnnnnnnnnn gttgtggaag gtccagtttt gaggggctat tacaac      56

SEQ ID NO: 12          moltype = DNA  length = 56
FEATURE                Location/Qualifiers
misc_feature           1..56
                       note = PspCas13b gRNA
source                 1..56
                       mol_type = other DNA
                       organism = synthetic construct
SEQUENCE: 12
tagcggtaca ggtattcctg gttgtggaag gtccagtttt gaggggctat tacaac      56

SEQ ID NO: 13          moltype = DNA  length = 19
FEATURE                Location/Qualifiers
misc_feature           1..19
                       note = MS2 hairpin
source                 1..19
                       mol_type = other DNA
                       organism = synthetic construct
SEQUENCE: 13
acatgaggat cacccatgt                                               19

SEQ ID NO: 14          moltype = DNA  length = 17
FEATURE                Location/Qualifiers
misc_feature           1..17
```

-continued

```
                        note = boxB hairpin
source                  1..17
                        mol_type = other DNA
                        organism = synthetic construct
SEQUENCE: 14
ggccctgaaa aagggcc                                              17

SEQ ID NO: 15           moltype = DNA  length = 20
FEATURE                 Location/Qualifiers
misc_feature            1..20
                        note = QBeta hairpin
source                  1..20
                        mol_type = other DNA
                        organism = synthetic construct
SEQUENCE: 15
atgcatgtct aagacagcat                                           20

SEQ ID NO: 16           moltype = DNA  length = 25
FEATURE                 Location/Qualifiers
misc_feature            1..25
                        note = PP7 hairpin
source                  1..25
                        mol_type = other DNA
                        organism = synthetic construct
SEQUENCE: 16
taaggagttt atatggaaac cctta                                     25

SEQ ID NO: 17           moltype = DNA  length = 4170
FEATURE                 Location/Qualifiers
misc_feature            1..4170
                        note = LshCas13a nucleic acid sequence
source                  1..4170
                        mol_type = other DNA
                        organism = synthetic construct
SEQUENCE: 17
atggggaacc tgttcggaca caagcggtgg tacgaggtgc gagataagaa agacttcaag  60
atcaagcgaa aggtgaaagt caagcggaat tatgacggga acaagtacat tctgaacatc  120
aacgaaaaca acaacaaaga gaagatcgac aacaacaagt tcatcagaaa gtacatcaac  180
tacaagaaaa acgataatat tctgaaggag ttcactagga aatttcatgc aggaaatatc  240
ctgttcaaac tgaagggcaa agaagggatc attagaattg agaataacga cgacttcctg  300
gagacagagg aagtggtgct gtatatcgag gcctacggca agagcgagaa gctgaaagca  360
ctggggatca caaagaaaaa gatcattgac gaggccatca ggcagggcat tactaaggac  420
gataaaaaga tcgagatcaa gcgacaggag aacgaggaag agatcgaaat tgacatccgg  480
gatgagtaca ctaataagac cctgaacgac tgctccatca ttctgcgcat cattgaaaac  540
gatgaactgg agacaaagaa gagcatctac gagatcttca agaacatcaa tatgagcctg  600
tataagatca tcgagaagat catcgaaaac gagacagaaa aggtgtttga aaatagatac  660
tacgaagagc acctgaggga gaagctgctg aaagacgata agattgacgt gatcctgacc  720
aacttcatgg aaatccggga gaagatcaag tctaatctgg agatcctggg cttcgtgaag  780
ttttacctga acgtcggcgg ggacaaaaag aaaagtaaaa ataagaaaat gctggtggaa  840
aagattctga acatcaatgt ggatctgacc gtcgaggaca ttgccgattt cgtgatcaag  900
gagctggaat tttggaacat cacaaagcgc attgagaaag tgaagaaagt caataacgag  960
ttcctggaga agcggagaaa tcggacatac atcaagtcct atgtgctgct ggacaagcac  1020
gaaaagttta aaatcgagag agaaaacaag aaggataaga tcgtgaagtt ctttgtcgag  1080
aacattaaga acaactctat caaggaaaag attgagaaga tcctggctga gttcaagatc  1140
gacgagctga ttaagaaact ggagaaggaa ctgaagaaag ggaactgtga taccgagatc  1200
ttcggaatct ttaagaagca ttacaaggtg aacttcgaca gcaagaaatt ttccaagaaa  1260
tctgatgaag agaaggagct gtataagatc atctacagat acctgaaggg cagaattgaa  1320
aaaatcctgg tgaacgagca gaaggtcaga ctgaagaaaa tggagaagat cgagatcgaa  1380
aagattctga atgaaagtat cctgtcagag aaaattctga agagagtgaa acagtataca  1440
ctggagcaca ttatgtacct ggggaagctg aggcataacg acatcgatat gaccacagtg  1500
aatactgacg atttcagccg cctgcacgcc aaggaagagc tggacctgga actgatcacc  1560
ttctttgcca gcacaaatat ggagctgaac aagatctttt cccgagaaaa catcaacaac  1620
gacgagaaca tcgatttctt tggaggcgac cgggagaaga actatgtgct ggataagaaa  1680
atcctgaata gtaagatcaa gatcatccgc gacctggatt tcatcgataa caagaacaac  1740
atcacaaaca acttcattcg aaagtttaca aagatcggca ctaatgaaag gaaccgcatc  1800
ctgcatgcca tttccaaaga gagggacctg caggggactc aggacgatta caacaaagtg  1860
atcaacatca ttcagaatct gaagatctcc gatgaagagg tgagcaaagc tctgaacctg  1920
gacgtggtct ttaaggacaa gaaaaacatc atcacaaaga tcaatgacat caagatctct  1980
gaagagaaca acaacgatat caagtatctg cccagcttca gcaaagtgct gcccgaaatc  2040
ctgaacctgt accgcaacaa tcccaagaat gagccttttg acacaatcga gactgaaaaa  2100
attgtgctga acgctctgat ctacgtcaat aaggagctgt ataagaaact gatcctggag  2160
gacgatctgg aagagaacga gtccaagaat atcttcctgc aggaactgaa gaaaaccctg  2220
ggcaacattg acgaaatcga tgagaacatc atcgagaact actacaagaa cgcacagatt  2280
tctgccagta aggggaacaa caaggcaatc aagaaatatc agaagaaagt gatcgagtgc  2340
tacattggat atctgcgcaa aaactacgaa gagctgttcg acttttcaga cttcaagatg  2400
aacatccagg aaatcaagaa acagattaag gacatcaacg ataacaagac ttatgagtgg  2460
atcaccgtga aaaccagcga caaaaccatt gtcatcaacg acgatttcga gtacatcatt  2520
tctatctttg cactgctgaa cagtaatgcc gtgattaata agatccgaaa cagattcttc  2580
gccaccagcg tgtggctgaa cacctcagaa taccagaata tcattgacat cctggatgag  2640
```

-continued

```
attatgcagc tgaataccct gcggaacgaa tgcatcacag agaactggaa tctgaacctg  2700
gaagagttca ttcagaagat gaaagagatc gaaaaggatt tcgacgactt caagatccag  2760
actaagaaag aaatcttcaa caactactac gaggacatca agaacaacat tctgaccgag  2820
tttaaagacg atatcaacgg ctgtgatgtg ctggaaaaga aactggagaa gattgtcatc  2880
ttcgacgatg aaaccaagtt cgagatcgac aagaaatcca acatcctgca ggatgaacag  2940
agaaagctgt ctaacatcaa caagaaggac ctgaagaaaa aggtggatca gtatatcaag  3000
gacaaagatc aggagatcaa gtctaaaatc ctgtgcagga tcattttcaa cagtgacttt  3060
ctgaaaaagt acaagaagga aatcgacaat ctgattgagg atatggagtc tgaaaatgag  3120
aacaagttcc aggagatcta ctatcccaag gaacggaaga acgagctgta tatctacaaa  3180
aagaatctgt tcctgaacat cggaaatcct aactttgaca agatctacgg cctgattagc  3240
aacgacatca agatggccga tgctaaattc ctgtttaata tcgatggaaa gaacatcaga  3300
aagaacaaaa tcagtgagat cgacgctatt ctgaagaatc tgaacgataa actgaacggc  3360
tactcaaagg aatacaagga gaagtacatc aaaaagctga aggagaacga cgatttcttt  3420
gcaaagaaca tccagaataa gaactacaaa tccttcgaaa aggactataa ccgcgtgtct  3480
gagtacaaaa agattcgaga tctggtcgag ttcaactatc tgaacaaaat cgagtcctac  3540
ctgattgaca tcaactggaa gctggctatt cagatggcaa gattcgaaag ggatatgcac  3600
tatatcgtga atggactgag ggagctgggc atcattaagc tgtcaggcta taacaccggg  3660
atcagcaggg catacccaaa gcgcaatgga agcgacggct tttacactac cacagcctac  3720
tacaagttct tgatgaaga gtcctacaag aagttcgaga agatttgcta cgggtttgga  3780
atcgacctga gcgaaaattc cgagatcaac aagcctgaaa atgagagcat tcggaactat  3840
atctcccatt tctacatcgt gagaaatcca tttgccgact acagtattgc tgagcagatc  3900
gatcgggtga gcaacctgct gtcatatagc acacgctaca acaattcaac ttatgccagc  3960
gtgttcgaag tctttaaaaa ggacgtgaat ctggactacg atgagctgaa aaagaaattc  4020
aaactgatcg gcaacaatga tattctggag cgcctgatga agcccaagaa agtgagcgtc  4080
ctggaactgg agtcctacaa cagtgactac attaagaatc tgatcattga actgctgacc  4140
aaaatcgaga atactaacga taccctgtga                                  4170
```

```
SEQ ID NO: 18           moltype = AA  length = 1389
FEATURE                 Location/Qualifiers
REGION                  1..1389
                        note = LshCas13a amino acid sequence
source                  1..1389
                        mol_type = protein
                        organism = synthetic construct
SEQUENCE: 18
MGNLFGHKRW YEVRDKKDFK IKRKVKVKRN YDGNKYILNI NENNNKEKID NNKFIRKYIN  60
YKKNDNILKE FTRKFHAGNI LFKLKGKEGI IRIENNDDFL ETEEVVLYIE AYGKSEKLKA  120
LGITKKKIID EAIRQGITKD DKKIEIKRQE NEEEIEIDIR DEYTNKTLND CSIILRIIEN  180
DELETKKSIY EIFKNINMSL YKIIEKIIEN ETEKVFENRY YEEHLREKLL KDDKIDVILT  240
NFMEIREKIK SNLEILGFVK FYLNVGGDKK KSKNKKMLVE KILNINVDLT VEDIADFVIK  300
ELEFWNITKR IEKVKKVNNE FLEKRRNRTY IKSYVLLDKH EKFKIERENK KDKIVKFFVE  360
NIKNNSIKEK IEKILAEFKI DELIKKLEKE LKKGNCDTEI FGIFKKHYKV NFDSKKFSKK  420
SDEEKELYKI IYRYLKGRIE KILVNEQKVR LKKMEKIEIE KILNESILSE KILKRVKQYT  480
LEHIMYLGKL RHNDIDMTTV NTDDFSRLHA KEELDLELIT FFASTNMELN KIFSRENINN  540
DENIDFFGGD REKNYVLDKK ILNSKIKIIR DLDFIDNKNN ITNNFIRKFT KIGTNERNRI  600
LHAISKERDL QGTQDDYNKV INIIQNLKIS DEEVSKALNL DVVFKDKKNI ITKINDIKIS  660
EENNNDIKYL PSFSKVLPEI LNLYRNNPKN EPFDTIETEK IVLNALIYVN KELYKKLILE  720
DDLEENESKN IFLQELKKTL GNIDEIDENI IENYYKNAQI SASKGNNKAI KKYQKKVIEC  780
YIGYLRKNYE ELFDFSDFKM NIQEIKKQIK DINDNKTYEW ITVKTSDKTI VINDDFEYII  840
SIFALLNSNA VINKIRNRFF ATSVWLNTSE YQNIIDILDE IMQLNTLRNE CITENWNLNL  900
EEFIQKMKEI EKDFDDFKIQ TKKEIFNNYY EDIKNNILTE FKDDINGCDV LEKKLEKIVI  960
FDDETKFEID KKSNILQDEQ RKLSNINKKD LKKKVDQYIK DKDQEIKSKI LCRIIFNSDF  1020
LKKYKKEIDN LIEDMESENE NKFQEIYYPK ERKNELYIYK KNLFLNIGNP NFDKIYGLIS  1080
NDIKMADAKF LFNIDGKNIR KNKISEIDAI LKNLNDKLNG YSKEYKEKYI KKLKENDDFF  1140
AKNIQNKNYK SFEKDYNRVS EYKKIRDLVE FNYLNKIESY LIDINWKLAI QMARFERDMH  1200
YIVNGLRELG IIKLSGYNTG ISRAYPKRNG SDGFYTTTAY YKFFDEESYK KFEKICYGFG  1260
IDLSENSEIN KPENESIRNY ISHFYIVRNP FADYSIAEQI DRVSNLLSYS TRYNNSTYAS  1320
VFEVFKKDVN LDYDELKKKF KLIGNNDILE RLMKPKKVSV LELESYNSDY IKNLIIELLT  1380
KIENTNDTL                                                         1389
```

```
SEQ ID NO: 19           moltype = DNA  length = 28
FEATURE                 Location/Qualifiers
misc_feature            1..28
                        note = LshCas13a direct repeat
source                  1..28
                        mol_type = other DNA
                        organism = synthetic construct
SEQUENCE: 19
ccaccccaat atcgaagggg actaaaac                                     28
```

```
SEQ ID NO: 20           moltype = DNA  length = 3456
FEATURE                 Location/Qualifiers
misc_feature            1..3456
                        note = LwaCas13a nucleic acid sequence
source                  1..3456
                        mol_type = other DNA
                        organism = synthetic construct
SEQUENCE: 20
atgaaagtga ccaaggtcga cggcatcagc cacaagaagt acatcgaaga gggcaagctc  60
```

-continued

```
gtgaagtcca ccagcgagga aaaccggacc agcgagagac tgagcgagct gctgagcatc  120
cggctggaca tctacatcaa gaacccccgac aacgcctccg aggaagagaa ccggatcaga  180
agagagaacc tgaagaagtt ctttagcaac aaggtgctgc acctgaagga cagcgtgctg  240
tatctgaaga accggaaaga aaagaacgcc gtgcaggaca agaactatag cgaagaggac  300
atcagcgagt acgacctgaa aaacaagaac agcttctccg tgctgaagaa gatcctgctg  360
aacgaggacg tgaactctga ggaactggaa atctttcgga aggacgtgga agccaagctg  420
aacaagatca acagcctgaa gtacagcttc gaagagaaca aggccaacta ccagaagatc  480
aacgagaaca acgtggaaaa agtgggcggc aagagcaagc ggaacatcat ctacgactac  540
tacagagaga gcgccaagcg caacgactac atcaacaacg tgcaggaagc cttcgacaag  600
ctgtataaga aagaggatat cgagaaactg tttttcctga tcgagaacag caagaagcac  660
gagaagtaca agatccgcga gtactatcac aagatcatcg gccggaagaa cgacaaagag  720
aacttcgcca agattatcta cgaagagatc cagaacgtga acaacatcaa agagctgatt  780
gagaagatcc ccgacatgtc tgagctgaag aaaagccagg tgttctacaa gtactacctg  840
gacaaagagg aactgaacga caagaatatt aagtacgcct tctgccactt cgtggaaatc  900
gagatgtccc agctgctgaa aaactacgtg tacaagcggc tgagcaacat cagcaacgat  960
aagatcaagc ggatcttcga gtaccagaat ctgaaaaagc tgatcgaaaa caaactgctg  1020
aacaagctgg acacctacgt gcggaactgc ggcaagtaca actactatct gcaagtgggc  1080
gagatcgcca cctccgactt tatcgcccgg aaccggcaga acgaggcctt cctgagaaac  1140
atcatcggcg tgtccagcgt ggcctacttc agcctgagga acatcctgga aaccgagaac  1200
gagaacggta tcaccggccg gatgcggggc aagaccgtga agaacaacaa gggcgaagag  1260
aaatacgtgt ccggcgaggt ggacaagatc tacaatgaga acaagcagaa cgaagtgaaa  1320
gaaaatctga agatgttcta cagctacgac ttcaacatgg acaacaagaa cgagatcgag  1380
gacttcttcg ccaacatcga cgaggccatc agcagcatca gacacggcat cgtgcacttc  1440
aacctggaac tggaaggcaa ggacatcttc gccttcaaga atatcgcccc cagcgagatc  1500
tccaagaaga tgtttcagaa cgaaatcaac gaaaagaagc tgaagctgaa aatcttcaag  1560
cagctgaaca gcgccaacgt gttcaactac tacgagaagg atgtgatcat caagtacctg  1620
aagaatacca agttcaactt cgtgaacaaa aacatcccct tcgtgcccag cttcaccaag  1680
ctgtacaaca agattgagga cctgcggaat accctgaagt ttttttggag cgtgcccaag  1740
gacaaagaag agaaggacgc ccagatctac ctgctgaaga atatctacta cggcgagttc  1800
ctgaacaagt tcgtgaaaaa ctccaaggtg ttctttaaga tcaccaatga agtgatcaag  1860
attaacaagc agcggaacca gaaaaccggc cactacaagt atcagaagtt cgagaacatc  1920
gagaaaaccg tgcccgtgga atacctggcc atcatccaga gcagagagat gatcaacaac  1980
caggacaaag aggaaaagaa tacctacatc gactttattc agcagatttt cctgaagggc  2040
ttcatcgact acctgaacaa gaacaatctg aagtatatcg agagcaacaa caacaatgac  2100
aacaacgaca tcttctccaa gatcaagatc aaaaaggata acaaagagaa gtacgacaag  2160
atcctgaaga actatgagaa gcacaatcgg aacaaagaaa tccctcacga gatcaatgag  2220
ttcgtgcgcg agatcaagct ggggaagatt ctgaagtaca ccgagaatct gaacatgttt  2280
tacctgatcc tgaagctgct gaaccacaaa gagctgacca acctgaaggg cagcctggaa  2340
aagtaccagt ccgccaacaa agaagaaacc ttcagcgacg agttggaact gatcaacctg  2400
ctgaacctgg acaacaacag agtgaccgag gacttcgagc tggaagccaa cgagatcggc  2460
aagttcctgg acttcaacga aaacaaaatc aaggaccgga aagagctgaa aaagttcgac  2520
accaacaaga tctatttcga cggcgagaac atcatcaagc accgggcctt ctacaatatc  2580
aagaaatacg gcatgctgaa tctgctggaa aagatcgccg ataaggccaa gtataagatc  2640
agcctgaaag aactgaaaga gtacagcaac aagaagaatg agattgaaaa gaactacacc  2700
atgcagcaga acctgcaccg gaagtacgcc agacccaaga aggacgaaaa gttcaacgac  2760
gaggactaca aagagtatga gaaggccatc ggcaacatcc agaagtacac ccacctgaag  2820
aacaaggtgg aattcaatga gctgaacctg ctgcagggcc tgctgctgaa gatcctgcac  2880
cggctcgtgg gctacaccag catctgggag cgggacctga gattccggct gaagggcgag  2940
tttcccgaga accactacat cgaggaaatt ttcaatttcg acaactccaa gaatgtgaag  3000
tacaaaagcg gccagatcgt ggaaaagtat atcaacttct acaaagaact gtacaaggac  3060
aatgtggaaa agcggagcat ctactccgac aagaaagtga agaaactgaa gcaggaaaaa  3120
aaggacctgt acatccggaa ctacattgcc cacttcaact acatccccca cgccgagatt  3180
agcctgctgg aagtgctgga aaacctgcgg aagctgctgt cctacgaccg gaagctgaag  3240
aacgccatca tgaagtccat cgtggacatt ctgaaagaat acggcttcgt ggccaccttc  3300
aagatcggcg ctgacaagaa gatcgaaatc cagaccctgg aatcagagaa gatcgtgcac  3360
ctgaagaatc tgaagaaaaa gaaactgatg accgaccgga acagcgagga actgtgcgaa  3420
ctcgtgaaag tcatgttcga gtacaaggcc ctggaa                            3456

SEQ ID NO: 21           moltype = AA  length = 1152
FEATURE                 Location/Qualifiers
REGION                  1..1152
                        note = LwaCas13 amino acid sequence
source                  1..1152
                        mol_type = protein
                        organism = synthetic construct
SEQUENCE: 21
MKVTKVDGIS HKKYIEEGKL VKSTSEENRT SERLSELLSI RLDIYIKNPD NASEEENRIR  60
RENLKKFFSN KVLHLKDSVL YLKNRKEKNA VQDKNYSEED ISEYDLKNKN SFSVLKKILL  120
NEDVNSEELE IFRKDVEAKL NKINSLKYSF EENKANYQKI NENNVEKVGG KSKRNIIYDY  180
YRESAKRNDY INNVQEAFDK LYKKEDIEKL FFLIENSKKH EKYKIREYYH KIIGRKNDKE  240
NFAKIIYEEI QNVNNIKELI EKIPDMSELK KSQVFYKYYL DKEELNDKNI KYAFCHFVEI  300
EMSQLLKNYV YKRLSNISND KIKRIFEYQN LKKLIENKLL NKLDTYVRNC GKYNYYLQVG  360
EIATSDFIAR NRQNEAFLRN IIGVSSVAYF SLRNILETEN ENGITGRMRG KTVKNNKGEE  420
KYVSGEVDKI YNENKQNEVK ENLKMFYSYD FNMDNKNEIE DFFANIDEAI SSIRHGIVHF  480
NLELEGKDIF AFKNIAPSEI SKKMFQNEIN EKKLKLKIFK QLNSANVFNY YEKDVIIKYL  540
KNTKFNFVNK NIPFVPSFTK LYNKIEDLRN TLKFFWSVPK DKEEKDAQIY LLKNIYYGEF  600
LNKFVKNSKV FFKITNEVIK INKQRNQKTG HYKYQKFENI EKTVPVEYLA IIQSREMINN  660
QDKEEKNTYI DFIQQIFLKG FIDYLNKNNL KYIESNNNND NNDIFSKIKI KKDNKEKYDK  720
ILKNYEKHNR NKEIPHEINE FVREIKLGKI LKYTENLNMF YLILKLLNHK ELTNLKGSLE  780
```

```
KYQSANKEET FSDELELINL LNLDNNRVTE DFELEANEIG KFLDFNENKI KDRKELKKFD  840
TNKIYFDGEN IIKHRAFYNI KKYGMLNLLE KIADKAKYKI SLKELKEYSN KKNEIEKNYT  900
MQQNLHRKYA RPKKDEKFND EDYKEYEKAI GNIQKYTHLK NKVEFNELNL LQGLLLKILH  960
RLVGYTSIWE RDLRFRLKGE FPENHYIEEI FNFDNSKNVK YKSGQIVEKY INFYKELYKD  1020
NVEKRSIYSD KKVKKLKQEK KDLYIRNYIA HFNYIPHAEI SLLEVLENLR KLLSYDRKLK  1080
NAIMKSIVDI LKEYGFVATF KIGADKKIEI QTLESEKIVH LKNLKKKKLM TDRNSEELCE  1140
LVKVMFEYKA LE                                                    1152

SEQ ID NO: 22          moltype = DNA  length = 36
FEATURE                Location/Qualifiers
misc_feature           1..36
                       note = LwaCas13a direct repeat
source                 1..36
                       mol_type = other DNA
                       organism = synthetic construct
SEQUENCE: 22
gatttagact accccaaaaa cgaaggggac taaaac                          36

SEQ ID NO: 23          moltype = DNA  length = 3363
FEATURE                Location/Qualifiers
misc_feature           1..3363
                       note = LseCas13a nucleic acid sequence
source                 1..3363
                       mol_type = other DNA
                       organism = synthetic construct
SEQUENCE: 23
atgtggatca gcattaagac cctgatccac catctgggcg tgctgttctt ttgcgattac  60
atgtataacc ggagagagaa gaaaatcatc gaagtcaaaa caatgaggat cactaaggtg  120
gaggtcgatc ggaagaaagt gctgatcagc cgggacaaga atggcgggaa actggtctat  180
gagaacgaaa tgcaggacaa tacagagcag atcatgcacc ataagaaaag ctccttctac  240
aaaagcgtgg tcaacaagac tatttgtcgc cctgagcaga agcagatgaa gaaactggtg  300
cacggcctgc tgcaggagaa cagccaggaa aagatcaagg tgagcgatgt cactaagctg  360
aatatctcaa acttcctgaa tcacagattc aagaagagcc tgtactattt cccagagaac  420
agtcccgata agtcagagga atacagaatc gaaattaatc tgtctcagct gctggaggac  480
agtctgaaga aacagcaggg aaccttcatc tgctgggagt ccttttctaa ggacatggaa  540
ctgtatatta actgggccga gaactacatc tctagtaaga ctaaactgat taagaaaagt  600
atcaggaaca atcgcatcca gtcaaccgag agtaggtcag gccagctgat ggaccgctat  660
atgaaggata ttctgaacaa gaacaagccc ttcgatatcc agagcgtgtc cgagaaatac  720
cagctggaaa agctgacatc cgccctgaag gctactttta aagaagctaa gaaaaacgac  780
aaggagatca attacaagct gaaatctacc ctgcagaacc acgagaggca gatcattgag  840
gaactgaaag agaatagcga actgaaccag ttcaatatcg agattcgcaa gcatctggaa  900
acttacttcc ctattaagaa aaccaacaga aaagtgggag atatcaggaa tctggagatc  960
ggcgaaattc agaagatcgt gaaccaccgc ctgaagaaca agattgtcca gcgaatcctg  1020
caggagggaa agctggcctc ctatgagatc gaatctacag tgaactctaa tagtctgcag  1080
aagatcaaaa ttgaggaagc cttcgctctg aagtttatca acgcttgcct gttcgcatct  1140
aacaatctga ggaatatggt gtaccccgtc tgtaagaaag acattctgat gatcggcgag  1200
ttcaagaaca gcttcaagga gattaagcac aagaagttca tccgccagtg gagccagttc  1260
ttttcccagg aaattactgt ggacgatatc gagctggcct cttggggact gcgaggagca  1320
attgccccta tccggaacga gatcattcac ctgaagaaac atagctggaa gaaattcttt  1380
aacaacccaa ctttcaaagt gaagaaatcc aagatcatta atggcaagac caaagacgtg  1440
accagcgagt tcctgtataa ggaaaccctg ttcaaggatt acttttattc tgagctggac  1500
agtgtgcccg aactgatcat taacaaaatg gagtcaagca agatcctgga ctactattcc  1560
tctgatcagc tgaaccaggt gttcaccatt cctaattttg agctgtcact gctgacaagc  1620
gccgtgccct tcgctccttc ctttaaaaga gtctatctga agggcttcga ctaccagaac  1680
caggatgagg cacagccaga ctataatctg aagctgaaca tctacaatga gaaagccttc  1740
aacagcgaag catttcaggc ccagtactcc ctgtttaaga tggtgtacta tcaggtgttc  1800
ctgccccagt ttaccacaaa caatgatctg ttcaagagtt cagtggactt tatcctgacc  1860
ctgaacaaag agaggaaggg ctatgctaag gcattccagg atatccgcaa aatgaataag  1920
gacgagaaac cttccgaata catgtcttat attcagagtc agctgatgct gtaccagaag  1980
aaacaggagg aaaaggagaa aatcaaccac ttcgaaaagt ttattaacca ggtgtttatc  2040
aaagggttca acagctttat tgagaagaat aggctgacct acatctgcca ccctaccaag  2100
aacacagtgc cagagaacga taatatcgaa attccattcc atacagacat ggacgatagc  2160
aatatcgctt tttggctgat gtgcaaactg ctggatgcaa agcagctgtc cgagctgcgg  2220
aacgaaatga tcaagttcag ctgtagcctg cagagtacag aggaaatttc aacttttacc  2280
aaggcaagag aagtgatcgg cctggccctg ctgaacgggg agaaaggatg taatgactgg  2340
aaggagctgt tcgacgataa agaagcctgg aagaaaaaca tgtcactgta tgtgagcgag  2400
gaactgctgc agtctctgcc ctacacccag gaggatgggc agacacctgt gattaatcgg  2460
agtatcgacc tggtcaagaa atatggaaca gagactatcc tggaaaagct gttcagctcc  2520
tctgacgatt ataaggtgag cgcaaaagat attgccaagc tgcacgagta cgacgtgaca  2580
gaaaagattg ctcagcagga atccctgcat aaacagtgga tcgagaagcc agggctggct  2640
cgggatagcg catggactaa gaaataccag aacgtgatta atgacatctc caactaccag  2700
tgggcaaaga ctaaagtgga gctgacccag gtcagacacc tgcatcagct gaccattgac  2760
ctgctgtccc ggctggccgg atacatgtct atcgctgaca gagatttcca gtttagttca  2820
aactacattc tggagcgcga aaatagcgaa taccgagtga caagctggat tctgctgtcc  2880
gagaacaaga acaagaacaa gtacaacgat tatgaactgt ataacctgaa gaatgcctcc  2940
atcaaagtga gctccaagaa tgatccccag ctgaaagtcg acctgaagca gctgcggctg  3000
accctggagt atctggaact gttcgacaat cgactgaaag agaagcggaa caatatcagt  3060
cactttaact acctgaatgg ccagctgggg aactcaattc tggaactgtt cgacgatgcc  3120
agagatgtgc tgagctatga caggaaactg aagaatgctg tctccaagtc tctgaaagaa  3180
```

-continued

```
atcctgtcta gtcatggcat ggaggtgacc ttcaagccac tgtaccagac taaccaccat  3240
ctgaagattg acaaactgca gcccaagaaa atccaccatc tgggggagaa gtctacagtg  3300
tcaagcaacc aggtcagtaa cgaatactgt cagctggtga gaactctgct gaccatgaag  3360
tga                                                                3363

SEQ ID NO: 24           moltype = AA  length = 1120
FEATURE                 Location/Qualifiers
REGION                  1..1120
                        note = LseCas13a amino acid sequence
source                  1..1120
                        mol_type = protein
                        organism = synthetic construct
SEQUENCE: 24
MWISIKTLIH HLGVLFFCDY MYNRREKKII EVKTMRITKV EVDRKKVLIS RDKNGGKLVY  60
ENEMQDNTEQ IMHHKKSSFY KSVVNKTICR PEQKQMKKLV HGLLQENSQE KIKVSDVTKL  120
NISNFLNHRF KKSLYYFPEN SPDKSEEYRI EINLSQLLED SLKKQQGTFI CWESFSKDME  180
LYINWAENYI SSKTKLIKKS IRNNRIQSTE SRSGQLMDRY MKDILNKNKP FDIQSVSEKY  240
QLEKLTSALK ATFKEAKKND KEINYKLKST LQNHERQIIE ELKENSELNQ FNIEIRKHLE  300
TYFPIKKTNR KVGDIRNLEI GEIQKIVNHR LKNKIVQRIL QEGKLASYEI ESTVNSNSLQ  360
KIKIEEAFAL KFINACLFAS NNLRNMVYPV CKKDILMIGE FKNSFKEIKH KKFIRQWSQF  420
FSQEITVDDI ELASWGLRGA IAPIRNEIIH LKKHSWKKFF NNPTFKVKKS KIINGKTKDV  480
TSEFLYKETL FKDYFYSELD SVPELIINKM ESSKILDYYS SDQLNQVFTI PNFELSLLTS  540
AVPFAPSFKR VYLKGFDYQN QDEAQPDYNL KLNIYNEKAF NSEAFQAQYS LFKMVYYQVF  600
LPQFTTNNDL FKSSVDFILT LNKERKGYAK AFQDIRKMNK DEKPSEYMSY IQSQLMLYQK  660
KQEEKEKINH FEKFINQVFI KGFNSFIEKN RLTYICHPTK NTVPENDNIE IPFHTDMDDS  720
NIAFWLMCKL LDAKQLSELR NEMIKFSCSL QSTEEISTFT KAREVIGLAL LNGEKGCNDW  780
KELFDDKEAW KKNMSLYVSE ELLQSLPYTQ EDGQTPVINR SIDLVKKYGT ETILEKLFSS  840
SDDYKVSAKD IAKLHEYDVT EKIAQQESLH KQWIEKPGLA RDSAWTKKYQ NVINDISNYQ  900
WAKTKVELTQ VRHLHQLTID LLSRLAGYMS IADRDFQFSS NYILERENSE YRVTSWILLS  960
ENKNKNKYND YELYNLKNAS IKVSSKNDPQ LKVDLKQLRL TLEYLELFDN RLKEKRNNIS  1020
HFNYLNGQLG NSILELFDDA RDVLSYDRKL KNAVSKSLKE ILSSHGMEVT FKPLYQTNHH  1080
LKIDKLQPKK IHHLGEKSTV SSNQVSNEYC QLVRTLLTMK                        1120

SEQ ID NO: 25           moltype = DNA  length = 36
FEATURE                 Location/Qualifiers
misc_feature            1..36
                        note = LseCas13a direct repeat
source                  1..36
                        mol_type = other DNA
                        organism = synthetic construct
SEQUENCE: 25
gtaagagact acctctatat gaaagaggac taaaac                            36

SEQ ID NO: 26           moltype = DNA  length = 4023
FEATURE                 Location/Qualifiers
misc_feature            1..4023
                        note = LbmCas13a nucleic acid sequence
source                  1..4023
                        mol_type = other DNA
                        organism = synthetic construct
SEQUENCE: 26
atgcagatct ccaaggtgaa ccacaagcac gtggcagtgg gacagaagga cagggagaga  60
atcaccggct tcatctataa tgacccagtg ggcgatgaga agagcctgga ggacgtggtg  120
gcaaagaggg ccaacgatac caaggtgctg ttcaacgtgt tcaacacaaa ggacctgtac  180
gattctcagg agagcgacaa gtccgagaag gataaggaga tcatctccaa gggcgccaag  240
ttcgtggcca agtcttttaa cagcgccatc acaatcctga agaagcagaa taagatctat  300
tccaccctga catctcagca ggtcatcaag gagctgaagg acaagttcgg cggcgcccgc  360
atctacgacg atgacatcga ggaggccctg accgagacac tgaagaagtc ttttagaaag  420
gagaatgtga ggaacagcat caaggtgctg atcgagaatg cagcaggcat ccggagctcc  480
ctgtccaagg acgaggagga gctgatccag gagtatttcg tgaagcagct ggtggaggag  540
tacaccaaga caaagctgca gaagaacgtg gtgaagagca tcaagaatca gaacatggtc  600
atccagcccg atagcgactc ccaggtgctg tctctgagcg agtcccggag agagaagcag  660
tctagcgccg tgtcctctga caccctggtg aattgcaagg agaaggacgt gctgaaggcc  720
ttcctgacag attacgccgt gctggatgag gacgagcgca acagcctgct gtggaagctg  780
cggaatctgg tgaacctgta cttttatggc tctgagagca tcagggatta ctcttatacc  840
aaggagaaga gcgtgtggaa ggagcacgac gagcagaagg ccaacaagac cctgttcatc  900
gatgagatct gccacatcac aaagatcggc aagaacggca aggagcagaa ggtgctggac  960
tatgaggaga ataggagccg ctgtcggaag cagaatatca actactatcg ctccgccctg  1020
aattacgcca agaacaatac cagcggcatc ttcgagaatg aggattccaa ccacttttgg  1080
attcacctga tcgagaacga ggtggagcgg ctgtataatg gcatcgagaa cggcgaggag  1140
ttcaagtttg agacaggcta catctctgag aaagtgtgga aggccgtgat caaccacctg  1200
agcatcaagt acatcgccct gggcaaggcc gtgtataact atgccatgaa ggagctgagc  1260
tcccccggcg acatcgagcc tggcaagatc gatgactcct atatcaacgg catcacctct  1320
ttcgactacg agatcatcaa ggccgaggag tccctgcaga gagatatctc tatgaatgtg  1380
gtgtttgcca caaactacct ggcctgcgcc accgtggata cagacaagga tttcctgctg  1440
tttagcaagg aggacatcag gtcctgcacc aagaaggatg gcaacctgtg caagaacatc  1500
atgcagttct ggggcggcta ttccacatgg aagaattttt gtgaggagta cctgaaggat  1560
gacaaggacg ccctggagct gctgtactcc ctgaagtcta tgctgtattc tatgagaaac  1620
tctagcttcc acttttctac cgagaatgtg gacaacggca gctgggatac agagctgatc  1680
```

-continued

```
ggcaagctgt tcgaggagga ttgtaaccgc gccgcccgga tcgagaagga gaagttctac  1740
aacaataacc tgcacatgtt ttattcctct agcctgctgg agaaggtgct ggagagactg  1800
tactcctctc accacgagag ggccagccag gtgccttcct tcaacagagt gtttgtgagg  1860
aagaatttcc caagctccct gtccgagcag agaatcaccc ccaagtttac agactccaag  1920
gatgagcaga tctggcagtc tgccgtgtac tatctgtgca aggagatcta ctataacgac  1980
ttcctgcaga gcaaggaggc ctacaagctg tttagggagg gcgtgaagaa tctggacaag  2040
aacgatatca ataaccagaa ggccgccgat agcttcaagc aggccgtggt gtactatggc  2100
aaggccatcg gcaacgccac cctgtcccag gtgtgccagg ccatcatgac agagtataat  2160
aggcagaata acgacggcct gaagaagaag agcgcctacg ccgagaagca gaacagcaac  2220
aagtacaagc actatcctct gttcctgaag caggtgctgc agagcgcctt ttgggagtac  2280
ctggatgaga acaaggagat ctatggcttc atctctgccc agatccacaa gagcaacgtg  2340
gagatcaagg ccgaggactt tatcgccaat tactctagcc agcagtataa gaagctggtg  2400
gataaggtga agaaaacccc tgagctgcag aagtggtata cactgggccg cctgatcaat  2460
ccacggcagg ccaaccagtt cctgggctcc atcagaaatt acgtgcagtt tgtgaaggac  2520
atccagaggc gcgccaagga gaatggcaac ccaatcagga actactatga ggtgctggag  2580
tccgattcta tcatcaagat cctggagatg tgcaccaagc tgaatggcac cacaagcaac  2640
gacatccacg attacttccg cgacgaggat gagtacgccg agtatatctc ccagttcgtg  2700
aactttggcg acgtgcactc tggcgccgcc ctgaatgcct tttgcaacag cgagtccgag  2760
ggcaagaaga acggcatcta ctatgacggc atcaatccca tcgtgaatcg gaactgggtg  2820
ctgtgcaagc tgtatggctc ccctgatctg atctctaaga tcatcagccg cgtgaatgag  2880
aacatgatcc acgacttcca caagcaggag gatctgatcc gggagtacca gatcaagggc  2940
atctgttcta acaagaagga gcagcaggac ctgcgcacct ttcaggtgct gaagaatcgc  3000
gtggagctgc gggatatcgt ggagtacagc gagatcatca acgagctgta tggccagctg  3060
atcaagtggt gctacctgag agagagggac ctgatgtact tccagctggg ctttcactac  3120
ctgtgcctga ataacgcctc ctctaaggag gccgattata tcaagatcaa tgtggatgac  3180
cggaacatca gcggcgccat cctgtaccag atcgccgcca tgtatatcaa tggcctgccc  3240
gtgtactata agaaggatga catgtacgtg gccctgaagt ccggcaagaa ggcctctgac  3300
gagctgaata gcaacgagca gacctccaag aagatcaact acttcctgaa gtatggcaat  3360
aacatcctgg gcgacaagaa ggatcagctg tacctggccg gcctggagct gttcgagaat  3420
gtggccgagc acgagaacat catcatcttt agaaatgaga tcgaccactt ccactacttt  3480
tatgaccgcg atcggtccat gctggatctg tattctgagg tgtttgaccg cttctttacc  3540
tacgatatga agctgcggaa gaatgtggtg aacatgctgt ataacatcct gctggaccac  3600
aatatcgtga gctccttcgt gtttgagaca ggcgagaaga aggtcggcag gggcgatagc  3660
gaagtgatca agccttccgc caagatcaga ctgagggcca ataacggcgt gtctagcgac  3720
gtgttcacct acaaagtggg cagcaaggat gagctgaaga tcgccacact gccagccaag  3780
aacgaggagt ttctgctgaa tgtggccaga ctgatctact atcccgacat ggaggccgtg  3840
tccgagaaca tggtgaggga gggcgtggtg aaggtggaga agtctaatga taagaagggc  3900
aagatcagca gaggctccaa taccaggtcc tctaaccagt ctaagtacaa caacaagagc  3960
aagaacagaa tgaactactc tatgggcagc atcttcgaga agatggacct gaagtttgat  4020
tga                                                                 4023

SEQ ID NO: 27          moltype = AA  length = 1340
FEATURE                Location/Qualifiers
REGION                 1..1340
                       note = LbmCas13a amino acid sequence
source                 1..1340
                       mol_type = protein
                       organism = synthetic construct
SEQUENCE: 27
MQISKVNHKH VAVGQKDRER ITGFIYNDPV GDEKSLEDVV AKRANDTKVL FNVFNTKDLY  60
DSQESDKSEK DKEIISKGAK FVAKSFNSAI TILKKQNKIY STLTSQQVIK ELKDKFGGAR  120
IYDDDIEEAL TETLKKSFRK ENVRNSIKVL IENAAGIRSS LSKDEEELIQ EYFVKQLVEE  180
YTKTKLQKNV VKSIKNQNMV IQPDSDSQVL SLSESRREKQ SSAVSSDTLV NCKEKDVLKA  240
FLTDYAVLDE DERNSLLWKL RNLVNLYFYG SESIRDYSYT KEKSVWKEHD EQKANKTLFI  300
DEICHITKIG KNGKEQKVLD YEENRSRCRK QNINYYRSAL NYAKNNTSGI FENEDSNHFW  360
IHLIENEVER LYNGIENGEE FKFETGYISE KVWKAVINHL SIKYIALGKA VYNYAMKELS  420
SPGDIEPGKI DDSYINGITS FDYEIIKAEE SLQRDISMNV VFATNYLACA TVDTDKDFLL  480
FSKEDIRSCT KKDGNLCKNI MQFWGGYSTW KNFCEEYLKD DKDALELLYS LKSMLYSMRN  540
SSFHFSTENV DNGSWDTELI GKLFEEDCNR AARIEKEKFY NNNLHMFYSS SLLEKVLERL  600
YSSHHERASQ VPSFNRVFVR KNFPSSLSEQ RITPKFTDSK DEQIWQSAVY YLCKEIYYND  660
FLQSKEAYKL FREGVKNLDK NDINNQKAAD SFKQAVVYYG KAIGNATLSQ VCQAIMTEYN  720
RQNNDGLKKK SAYAEKQNSN KYKHYPLFLK QVLQSAFWEY LDENKEIYGF ISAQIHKSNV  780
EIKAEDFIAN YSSQQYKKLV DKVKKTPELQ KWYTLGRLIN PRQANQFLGS IRNYVQFVKD  840
IQRRAKENGN PIRNYYEVLE SDSIIKILEM CTKLNGTTSN DIHDYFRDED EYAEYISQFV  900
NFGDVHSGAA LNAFCNSESE GKKNGIYYDG INPIVNRNWV LCKLYGSPDL ISKIISRVNE  960
NMIHDFHKQE DLIREYQIKG ICSNKKEQQD LRTFQVLKNR VELRDIVEYS EIINELYGQL  1020
IKWCYLRERD LMYFQLGFHY LCLNNASSKE ADYIKINVDD RNISGAILYQ IAAMYINGLP  1080
VYYKKDDMYV ALKSGKKASD ELNSNEQTSK KINYFLKYGN NILGDKKDQL YLAGLELFEN  1140
VAEHENIIIF RNEIDHFHYF YDRDRSMLDL YSEVFDRFFT YDMKLRKNVV NMLYNILLDH  1200
NIVSSFVFET GEKKVGRGDS EVIKPSAKIR LRANNGVSSD VFTYKVGSKD ELKIATLPAK  1260
NEEFLLNVAR LIYYPDMEAV SENMVREGVV KVEKSNDKKG KISRGSNTRS SNQSKYNNKS  1320
KNRMNYSMGS IFEKMDLKFD                                               1340

SEQ ID NO: 28          moltype = DNA  length = 35
FEATURE                Location/Qualifiers
misc_feature           1..35
                       note = LbmCas13a direct repeat
source                 1..35
                       mol_type = other DNA
```

-continued

```
                         organism = synthetic construct
SEQUENCE: 28
gtattgagaa aagccagata tagttggcaa tagac                          35

SEQ ID NO: 29            moltype = DNA  length = 4314
FEATURE                  Location/Qualifiers
misc_feature             1..4314
                         note = LbnCas13a nucleic acid sequence
source                   1..4314
                         mol_type = other DNA
                         organism = synthetic construct
SEQUENCE: 29
atgaagatca gcaaggtgcg ggaggagaac agaggcgcca agctgaccgt gaatgccaag  60
acagccgtgg tgtctgagaa ccggagccag gagggcatcc tgtataatga cccaagcagg  120
tacggcaagt cccgcaagaa cgacgaggat agggaccgct atatcgagag cagactgaag  180
agctccggca agctgtaccg gatctttaac gaggataaga ataagcgcga gacagacgag  240
ctgcagtggt tcctgtccga gatcgtgaag aagatcaacc ggagaaatgg cctggtgctg  300
tccgacatgc tgtctgtgga cgatagagcc ttcgagaagg cctttgagaa gtacgccgag  360
ctgtcttata ccaacaggcg caataaggtg tccggctctc ccgccttcga gacatgcgga  420
gtggatgcag caacagcaga gcggctgaag ggaatcatct ccgagacaaa cttcatcaac  480
agaatcaaga acaacatcga caacaaggtg tctgaggaca tcatcgatcg gatcatcgcc  540
aagtacctga agaagagcct gtgccgggag agagtgaaga gaggcctgaa gaagctgctg  600
atgaatgcct ttgatctgcc atactctgat cccgacatcg atgtgcagag ggacttcatc  660
gattatgtgc tggaggactt ttaccacgtg cgggccaaga gccaggtgag cagatccatc  720
aagaacatga atatgcccgt gcagcctgag ggcgacggca agttcgccat caccgtgagc  780
aagggcggca cagagtctgg caacaagcgc agcgccgaga aggaggcctt caagaagttt  840
ctgagcgatt acgcctccct ggacgagagg gtgcgcgacg atatgctgcg gagaatgagg  900
cgcctggtgg tgctgtactt ttatggctcc gacgattcta agctgagcga tgtgaacgag  960
aagttcgacg tgtgggagga ccacgcagcc cggagagtgg acaataggga gttcatcaag  1020
ctgccactgg agaacaagct ggccaatggc aagaccgaca aggatgccga gcggatcaga  1080
aagaacacag tgaaggagct gtatagaaac cagaatatcg gctgctacag gcaggccgtg  1140
aaggccgtgg aggaggacaa caatggccgg tactttgacg ataagatgct gaacatgttc  1200
tttatccaca gaatcgagta tggcgtggag aagatctacg ccaatctgaa gcaggtgacc  1260
gagttcaagg cccgcacagg ctacctgagc gagaagatct ggaaggatct gatcaactac  1320
atctctatca agtatatcgc catgggcaag gccgtgtata actatgccat ggatgagctg  1380
aatgcctccg acaagaagga gatcgagctg ggcaagatct ccgaggagta tctgtctggc  1440
atctctagct tcgactacga gctgatcaag gccgaggaga tgctgcagag ggagacagcc  1500
gtgtacgtgg cctttgccgc aaggcacctg tcctctcaga cagtggagct ggattccgag  1560
aactctgact tcctgctgct gaagcctaag ggcaccatgg acaagaacga taagaataag  1620
ctggcctcca acaatatcct gaattttctg aaggataagg agacactgcg ggacacaatc  1680
ctgcagtatt tcggcggcca ctctctgtgg acagatttcc catttgacaa gtacctggcc  1740
ggcggcaagg acgatgtgga ttttctgacc gacctgaagg atgtgatcta tagcatgcgg  1800
aacgactcct tccactacgc cacagagaac cacaacaatg gcaagtggaa taaggagctg  1860
atctccgcca tgtttgagca cgagacagag agaatgacag tggtcatgaa ggacaagttc  1920
tattctaaca atctgcccat gttttacaag aacgacgatc tgaagaagct gctgatcgac  1980
ctgtataagg acaatgtgga gagagcctct caggtgccca gcttcaacaa ggtgtttgtg  2040
cgcaagaatt tccctgccct ggtgcgggac aaggataacc tgggcatcga gctggatctg  2100
aaggccgacg ccgataaggg cgagaatgag ctgaagttct acaacgccct gtactacatg  2160
ttcaaggaga tctactacaa cgccttcctg aacgacaaga atgtgaggga gcggttcatc  2220
accaaggcca caaaggtggc cgacaactat gataggaata aggagcgcaa cctgaaggat  2280
aggatcaaga gcgccggctc cgacgagaag aagaagctgc gcgagcagct gcagaattac  2340
atcgccgaga acgatttcgg ccagaggatc aagaatatcg tgcaggtgaa ccctgactat  2400
accctggccc agatctgcca gctgatcatg acagagtaca accagcagaa caatggctgt  2460
atgcagaaga agagcgccgc ccggaaggat atcaataagg actcctacca gcactataag  2520
atgctgctgc tggtgaacct gagaaaggcc ttcctggagt ttatcaagga gaattatgcc  2580
tttgtgctga agccctacaa gcacgacctg tgcgataagg ccgacttcgt gcctgatttt  2640
gccaagtacg tgaagcccta cgccggcctg atcagcaggg tggcaggcag ctccgagctg  2700
cagaagtggt atatcgtgtc ccgctttctg tctcctgccc aggccaacca catgctgggc  2760
ttcctgcact cctacaagca gtacgtgtgg gacatctaca ggcgcgcctc tgagacaggc  2820
accgagatca atcacagcat cgccgaggat aagatcgccg gcgtggacat caccgacgtg  2880
gatgccgtga tcgatctgag cgtgaagctg tgcggcacaa tctctagcga gatctccgac  2940
tacttcaagg acgatgaggt gtacgccgag tatatctcct cttacctgga ttttgagtat  3000
gacggcggca actacaagga tagcctgaat aggttctgta actccgatgc cgtgaatgac  3060
cagaaggtgg ccctgtacta tgacggcgag caccctaagc tgaaccgcaa tatcatcctg  3120
agcaagctgt acggcgagcg gagatttctg gagaagatca ccgatcgggt gagccggagc  3180
gacatcgtgg agtactataa gctgaagaag gagacaagcc agtaccagac aaagggcatc  3240
ttcgatagcg aggacgagca gaagaacatc aagaagtttc aggagatgaa gaatatcgtg  3300
gagttcagag atctgatgga ctatagcgag atcgccgatg agctgcaggg ccagctgatc  3360
aactggatct acctgcggga gcgggacctg atgaatttcc agctgggcta ccactatgcc  3420
tgcctgaaca atgattccaa caagcaggcc acctatgtga cactggacta ccagggcaag  3480
aagaatcgga agatcaacgg cgccatcctg tatcagatct gtgccatgta tatcaatggc  3540
ctgcctctgt actatgtgga caaggatagc tccgagtgga ccgtgtctga cggcaaggag  3600
agcacaggcg ccaagatcgg cgagttctac agatatgcca agtcctttga gaacacctct  3660
gattgctacg ccagcggcct ggagatcttt gagaatatca gcgagcacga caacatcaca  3720
gagctgagga attatatcga gcactttcgc tactacagca gcttcgaccg gagcttcctg  3780
ggcatctact ctgaggtgtt cgatcggttc tttacctacg acctgaagta tagaaagaac  3840
gtgccaacaa tcctgtataa catcctgctg cagcacttcg tgaacgtgag gttcgagttc  3900
gtgagcggca agaagatgat cggcatcgat aagaaggacc gcaagatcgc caaggagaag  3960
gagtgtgccc ggatcaccat cagagagaag aacggcgtgt atagcgagca gtttacctac  4020
```

-continued

```
aagctgaaga atggcacagt gtatgtggat gccagggaca agagatacct gcagtccatc  4080
atcaggctgc tgttctatcc agagaaggtg aacatggatg agatgatcga ggtgaaggag  4140
aagaagaagc cctccgacaa caataccggc aagggctact ctaagaggga tcgccagcag  4200
gaccgcaagg agtacgataa gtataaggag aagaagaaga aggagggcaa tttcctgagc  4260
ggcatgggcg gcaacatcaa ttgggacgag atcaatgccc agctgaagaa ctga        4314

SEQ ID NO: 30          moltype = AA  length = 1437
FEATURE                Location/Qualifiers
REGION                 1..1437
                       note = LbnCas13a amino acid sequence
source                 1..1437
                       mol_type = protein
                       organism = synthetic construct
SEQUENCE: 30
MKISKVREEN RGAKLTVNAK TAVVSENRSQ EGILYNDPSR YGKSRKNDED RDRYIESRLK  60
SSGKLYRIFN EDKNKRETDE LQWFLSEIVK KINRRNGLVL SDMLSVDDRA FEKAFEKYAE  120
LSYTNRRNKV SGSPAFETCG VDAATAERLK GIISETNFIN RIKNNIDNKV SEDIIDRIIA  180
KYLKKSLCRE RVKRGLKKLL MNAFDLPYSD PDIDVQRDFI DYVLEDFYHV RAKSQVSRSI  240
KNMNMPVQPE GDGKFAITVS KGGTESGNKR SAEKEAFKKF LSDYASLDER VRDDMLRRMR  300
RLVVLYFYGS DDSKLSDVNE KFDVWEDHAA RRVDNREFIK LPLENKLANG KTDKDAERIR  360
KNTVKELYRN QNIGCYRQAV KAVEEDNNGR YFDDKMLNMF FIHRIEYGVE KIYANLKQVT  420
EFKARTGYLS EKIWKDLINY ISIKYIAMGK AVYNYAMDEL NASDKKEIEL GKISEEYLSG  480
ISSFDYELIK AEEMLQRETA VYVAFAARHL SSQTVELDSE NSDFLLLKPK GTMDKNDKNK  540
LASNNILNFL KDKETLRDTI LQYFGGHSLW TDFPFDKYLA GGKDDVDFLT DLKDVIYSMR  600
NDSFHYATEN HNNGKWNKEL ISAMFEHETE RMTVVMKDKF YSNNLPMFYK NDDLKKLLID  660
LYKDNVERAS QVPSFNKVFV RKNFPALVRD KDNLGIELDL KADADKGENE LKFYNALYYM  720
FKEIYYNAFL NDKNVRERFI TKATKVADNY DRNKERNLKD RIKSAGSDEK KKLREQLQNY  780
IAENDFGQRI KNIVQVNPDY TLAQICQLIM TEYNQQNNGC MQKKSAARKD INKDSYQHYK  840
MLLLVNLRKA FLEFIKENYA FVLKPYKHDL CDKADFVPDF AKYVKPYAGL ISRVAGSSEL  900
QKWYIVSRFL SPAQANHMLG FLHSYKQYVW DIYRRASETG TEINHSIAED KIAGVDITDV  960
DAVIDLSVKL CGTISSEISD YFKDDEVYAE YISSYLDFEY DGGNYKDSLN RFCNSDAVND  1020
QKVALYYDGE HPKLNRNIIL SKLYGERRFL EKITDRVSRS DIVEYYKLKK ETSQYQTKGI  1080
FDSEDEQKNI KKFQEMKNIV EFRDLMDYSE IADELQGQLI NWIYLRERDL MNFQLGYHYA  1140
CLNNDSNKQA TYVTLDYQGK KNRKINGAIL YQICAMYING LPLYYVDKDS SEWTVSDGKE  1200
STGAKIGEFY RYAKSFENTS DCYASGLEIF ENISEHDNIT ELRNYIEHFR YYSSFDRSFL  1260
GIYSEVFDRF FTYDLKYRKN VPTILYNILL QHFVNVRFEF VSGKKMIGID KKDRKIAKEK  1320
ECARITIREK NGVYSEQFTY KLKNGTVYVD ARDKRYLQSI IRLLFYPEKV NMDEMIEVKE  1380
KKKPSDNNTG KGYSKRDRQQ DRKEYDKYKE KKKKEGNFLS GMGGNINWDE INAQLKN     1437

SEQ ID NO: 31          moltype = DNA  length = 35
FEATURE                Location/Qualifiers
misc_feature           1..35
                       note = LbnCas13a direct repeat
source                 1..35
                       mol_type = other DNA
                       organism = synthetic construct
SEQUENCE: 31
gttgatgaga agagcccaag atagagggca ataac                             35

SEQ ID NO: 32          moltype = DNA  length = 4158
FEATURE                Location/Qualifiers
misc_feature           1..4158
                       note = CamCas13a nucleic acid sequence
source                 1..4158
                       mol_type = other DNA
                       organism = synthetic construct
SEQUENCE: 32
atgaagttct ctaaggtgga ccacacccgg agcgccgtgg gcatccagaa ggccaccgac  60
tctgtgcacg gcatgctgta taccgacccc aagaagcagg aagtgaatga tctggacaag  120
aggtttgatc agctgaacgt gaaggccaag cgcctgtata acgtgttcaa tcagtccaag  180
gccgaggagg acgatgacga gaagcggttt ggcaaggtgg tgaagaagct gaacagagag  240
ctgaaggacc tgctgttcca ccgggaggtg agcagataca actccatcgg caatgccaag  300
tataactact atggcatcaa gtccaaccct gaggagatcg tgtctaatct gggcatggtg  360
gagagcctga agggagagcg ggacccccag aaagtgatca gcaagctgct gctgtactat  420
ctgagaaagg gcctgaagcc tggcaccgac ggcctgagga tgatcctgga ggcctcctgc  480
ggcctgcgca agctgtctgg cgatgagaag gagctgaagg tgttcctgca gaccctggat  540
gaggactttg agaagaaaac cttcaagaag aacctgatcc ggtctatcga gaaccagaat  600
atggccgtgc agccaagcaa cgagggcgac cccatcatcg gcatcaccca gggccggttt  660
aatagccaga agaacgagga gaagtccgcc atcgagagaa tgatgtctat gtacgccgat  720
ctgaacgagg accacaggga ggatgtgctg cgcaagctgc ggagactgaa tgtgctgtat  780
ttcaacgtgg acaccgagaa aaccgaggag cccaccctgc ctggagaggt ggatacaaat  840
ccagtgtttg aagtgtggca cgaccacgag aagggcaagg agaacgatag acagtttgcc  900
accttcgcca agatcctgac cgaggacagg gagacacgca agaaggagaa gctggccgtg  960
aaggaggccc tgaatgacct gaagagcgcc atcagggatc acaacatcat ggcctaccgc  1020
tgttccatca aggtgaccga gcaggataag gacggcctgt tctttgagga ccagcggatc  1080
aatagattct ggattcacca catcgagtct gccgtggaga gaatcctggc cagcatcaac  1140
cccgagaagc tgtataagct gcgcatcggc tatctgggcg agaaagtgtg gaaggatctg  1200
ctgaattacc tgagcatcaa gtatatcgcc gtgggcaagg ccgtgttcca ctttgccatg  1260
gaggacctgg gcaagaccgg ccaggatatc gagctgggca agctgagcaa ctccgtgtct  1320
```

-continued

```
ggcggcctga ccagcttcga ctacgagcag atccgggccg atgagacact gcagagacag  1380
ctgtccgtgg aggtggcctt tgccgccaac aatctgttca gggcagtggt gggacagacc  1440
ggcaagaaga tcgagcagag caagtccgag gagaatgagg aggactttct gctgtggaag  1500
gccgagaaga tcgccgagtc catcaagaag gagggcgagg gcaacacact gaagtctatc  1560
ctgcagttct tggcggcgc cagctcctgg gatctgaatc acttctgcgc agcctacggc  1620
aacgagtcta gcgccctggg ctatgagaca aagtttgccg atgacctgag gaaggccatc  1680
tactccctgc gcaatgagac attccacttt accacactga acaagggctc ttttgactgg  1740
aatgccaagc tgatcggcga tatgttcagc cacgaggcag caaccggcat cgcagtggag  1800
aggacacgct tttacagcaa caatctgcct atgttctatc gggagtccga cctgaagaga  1860
atcatggatc acctgtataa cacctatcac cctcgcgcca gccaggtgcc atctttcaac  1920
agcgtgtttg tgaggaagaa ttttcgcctg ttcctgtcca acaccctgaa caccaataca  1980
tctttcgaca cagaggtgta ccagaagtgg gagtccggcg tgtactatct gtttaaggag  2040
atctactaca actctttcct gccaagcggc gacgcccacc acctgttctt tgagggcctg  2100
aggcgcatca ggaaggaggc cgataatctg cccatcgtgg gcaaggaggc caagaagcgc  2160
aacgccgtgc aggactttgg ccggagatgc gatgagctga agaacctgtc tctgagcgcc  2220
atctgtcaga tgatcatgac cgagtacaat gagcagaaca atggcaacag gaaggtgaag  2280
agcacacggg aggacaagag aaagcccgat atcttccagc actacaagat gctgctgctg  2340
cgcaccctgc aggaggcctt tgccatctat atcaggcgcg aggagttcaa gtttatcttc  2400
gacctgccca agacactgta cgtgatgaag cccgtggagg agtttctgcc taactggaag  2460
tccggcatgt tcgactctct ggtggagcgg gtgaagcagt cccctgatct gcagagatgg  2520
tatgtgctgt gcaagttcct gaatggccgg ctgctgaacc agctgagcgg cgtgatcaga  2580
tcctacatcc agtttgcagg cgacatccag cggagagcaa aggcaaacca caatcggctg  2640
tatatggata atacccagag agtggagtac tattctaacg tgctggaggt ggtggacttc  2700
tgcatcaagg gcacatccag gttctctaac gtgttcagcg attacttccg cgatgaggac  2760
gcctacgccg attatctgga caactatctg cagtttaagg acgagaagat cgccgaggtg  2820
agcagcttcg ccgccctgaa aaccttctgt aacgaggagg aggtgaaggc cggcatctac  2880
atggacggcg agaatcctgt gatgcagagg aacatcgtga tggccaagct gttcggccct  2940
gatgaggtgc tgaagaatgt ggtgccaaag gtgacacggg aggagatcga ggagtactat  3000
cagctggaga agcagatcgc cccatacaga cagaacggct attgtaagtc cgaggaggac  3060
cagaagaagc tgctgaggtt ccagcgcatc aagaatcgcg tggagtttca gaccatcaca  3120
gagttctctg agatcatcaa cgagctgctg ggccagctga tctcctggtc ttttctgcgg  3180
gagagagatc tgctgtactt tcagctgggc ttccactatc tgtgcctgca caatgacacc  3240
gagaagcctg ccgagtacaa ggagatcagc cgggaggatg gcacagtgat cagaaacgcc  3300
atcctgcacc aggtggcagc aatgtacgtg ggaggcctgc cagtgtatac cctggccgac  3360
aagaagctgg ccgccttcga gaagggagag gcagactgta agctgagcat ctccaaggat  3420
acagccggcg ccggcaagaa gatcaaggat ttctttcggt actccaagta tgtgctgatc  3480
aaggacagaa tgctgaccga tcagaaccag aagtacacaa tctatctggc cggcctggag  3540
ctgttcgaga ataccgatga gcacgacaac atcacagacg tgcggaagta cgtggatcac  3600
tttaagtact atgccacctc tgacgagaat gccatgagca tcctggatct gtattccgag  3660
atccacgaca gattctttac atacgatatg aagtaccaga agaacgtggc caatatgctg  3720
gagaacatcc tgctgaggca cttcgtgctg atccgccccg agttctttac cggcagcaag  3780
aaggtcggcg agggcaagaa gatcacatgc aaggccaggg cccagatcga gatcgccgag  3840
aatggcatgc gctccgagga ctttacctac aagctgagcg atggcaagaa gaatatctcc  3900
acatgtatga tcgccgccag ggaccagaag tatctgaaca ccgtggcccg cctgctgtac  3960
tatccacacg aggccaagaa gagcatcgtg gacacacggg agaagaagaa caacaagaaa  4020
accaatagag gcgatggcac attcaacaag cagaagggca ccgccaggaa ggagaaggac  4080
aatggccccc gcgagtttaa cgataccggc ttctccaata caccatttgc cggcttcgat  4140
ccctttagaa actcttga                                                4158

SEQ ID NO: 33          moltype = AA  length = 1385
FEATURE                Location/Qualifiers
REGION                 1..1385
                       note = CamCas13a amino acid sequence
source                 1..1385
                       mol_type = protein
                       organism = synthetic construct
SEQUENCE: 33
MKFSKVDHTR SAVGIQKATD SVHGMLYTDP KKQEVNDLDK RFDQLNVKAK RLYNVFNQSK  60
AEEDDDEKRF GKVVKKLNRE LKDLLFHREV SRYNSIGNAK YNYYGIKSNP EEIVSNLGMV  120
ESLKGERDPQ KVISKLLLYY LRKGLKPGTD GLRMILEASC GLRKLSGDEK ELKVFLQTLD  180
EDFEKKTFKK NLIRSIENQN MAVQPSNEGD PIIGITQGRF NSQKNEEKSA IERMMSMYAD  240
LNEDHREDVL RKLRRLNVLY FNVDTEKTEE PTLPGEVDTN PVFEVWHDHE KGKENDRQFA  300
TFAKILTEDR ETRKKEKLAV KEALNDLKSA IRDHNIMAYR CSIKVTEQDK DGLFFEDQRI  360
NRFWIHHIES AVERILASIN PEKLYKLRIG YLGEKVWKDL LNYLSIKYIA VGKAVFHFAM  420
EDLGKTGQDI ELGKLSNSVS GGLTSFDYEQ IRADETLQRQ LSVEVAFAAN NLFRAVVGQT  480
GKKIEQSKSE ENEEDFLLWK AEKIAESIKK EGEGNTLKSI LQFFGGASSW DLNHFCAAYG  540
NESSALGYET KFADDLRKAI YSLRNETFHF TTLNKGSFDW NAKLIGDMFS HEAATGIAVE  600
RTRFYSNNLP MFYRESDLKR IMDHLYNTYH PRASQVPSFN SVFVRKNFRL FLSNTLNTNT  660
SFDTEVYQKW ESGVYYLFKE IYYNSFLPSG DAHHLFFEGL RRIRKEADNL PIVGKEAKKR  720
NAVQDFGRRC DELKNLSLSA ICQMIMTEYN EQNNGNRKVK STREDKRKPD IFQHYKMLLL  780
RTLQEAFAIY IRREEFKFIF DLPKTLYVMK PVEEFLPNWK SGMFDSLVER VKQSPDLQRW  840
YVLCKFLNGR LLNQLSGVIR SYIQFAGDIQ RRAKANHNRL YMDNTQRVEY YSNVLEVVDF  900
CIKGTSRFSN VFSDYFRDED AYADYLDNYL QFKDEKIAEV SSFAALKTFC NEEEVKAGIY  960
MDGENPVMQR NIVMAKLFGP DEVLKNVVPK VTREEIEEYY QLEKQIAPYR QNGYCKSEED  1020
QKKLLRFQRI KNRVEFQTIT EFSEIINELL GQLISWSFLR ERDLLYFQLG FHYLCLHNDT  1080
EKPAEYKEIS REDGTVIRNA ILHQVAAMYV GGLPVYTLAD KKLAAFEKGE ADCKLSISKD  1140
TAGAGKKIKD FFRYSKYVLI KDRMLTDQNQ KYTIYLAGLE LFENTDEHDN ITDVRKYVDH  1200
FKYYATSDEN AMSILDLYSE IHDRFFTYDM KYQKNVANML ENILLRHFVL IRPEFFTGSK  1260
KVGEGKKITC KARAQIEIAE NGMRSEDFTY KLSDGKKNIS TCMIAARDQK YLNTVARLLY  1320
```

-continued

```
YPHEAKKSIV DTREKKNNKK TNRGDGTFNK QKGTARKEKD NGPREFNDTG FSNTPFAGFD  1380
PFRNS                                                              1385

SEQ ID NO: 34          moltype = DNA  length = 35
FEATURE                Location/Qualifiers
misc_feature           1..35
                       note = CamCas13a direct repeat
source                 1..35
                       mol_type = other DNA
                       organism = synthetic construct
SEQUENCE: 34
gtctattgcc ctctatatcg ggctgttctc caaac                             35

SEQ ID NO: 35          moltype = DNA  length = 3354
FEATURE                Location/Qualifiers
misc_feature           1..3354
                       note = CgaCas13a nucleic acid sequence
source                 1..3354
                       mol_type = other DNA
                       organism = synthetic construct
SEQUENCE: 35
atgcggatca caaaggtgaa gatcaagctg gacaacaagc tgtaccaggt gaccatgcag  60
aaggaggaga agtatggcac actgaagctg aatgaggaga gcaggaagtc caccgccgag  120
atcctgcgcc tgaagaaggc cagcttcaac aagtcttttc acagcaagac catcaattcc  180
cagaaggaga acaagaatgc cacaatcaag aagaacggcg actacatcag ccagatcttc  240
gagaagctgg tgggcgtgga taccaacaag aatatcagga agcccaagat gtccctgaca  300
gacctgaagg atctgcctaa gaaggacctg gccctgttca tcaagcgcaa gtttaagaac  360
gacgatatcg tggagatcaa gaatctggat ctgatctccc tgttttataa tgccctgcag  420
aaggtgccag gcgagcactt caccgacgag tcttgggccg atttttgcca ggagatgatg  480
ccctaccggg agtataagaa caagttcatc gagagaaaga tcatcctgct ggccaactcc  540
atcgagcaga ataagggctt ctctatcaat cccgagacat tcagcaagcg gaagagagtg  600
ctgcaccagt gggcaatcga ggtgcaggag aggggcgact tttccatcct ggatgagaag  660
ctgtctaagc tggccgagat ctacaacttc aagaagatgt gcaagagagt gcaggacgag  720
ctgaacgatc tggagaagag catgaagaag ggcaagaatc ctgagaagga gaaggaggcc  780
tataagaagc agaagaactt taagatcaag accatctgga aggactaccc atataagaca  840
cacatcggcc tgatcgagaa gatcaaggag aatgaggagc tgaaccagtt caatatcgag  900
atcggcaagt acttcgagca ctattttcca atcaagaagg agagatgcac cgaggatgag  960
ccctactatc tgaacagcga gacaatcgcc accacagtga actaccagct gaagaatgcc  1020
ctgatctcct acctgatgca gatcggcaag tataagcagt ttggcctgga gaatcaggtg  1080
ctggactcca agaagctgca ggagatcggc atctatgagg gcttccagac caagtttatg  1140
gatgcctgcg tgttcgccac aagctccctg aagaacatca tcgagcctat gcggagcggc  1200
gacatcctgg gcaagagaga gtttaaggag gccatcgcca catctagctt cgtgaattac  1260
caccacttct ttccctattt ccctttttgag ctgaagggca tgaaggatag ggagtccgag  1320
ctgatcccat ttggcgagca gaccgaggcc aagcagatgc agaacatctg ggccctgagg  1380
ggctctgtgc agcagatccg caatgagatc ttccacagct ttgacaagaa ccagaagttc  1440
aatctgcccc agctggacaa gagcaacttc gagtttgatg cctccgagaa cagcaccggc  1500
aagtctcaga gctacatcga gacagattat aagttcctgt ttgaggccga gaagaaccag  1560
ctggagcagt tctttatcga gcgcatcaag tcctctggcg ccctggagta ctatcccctg  1620
aagtccctgg agaagctgtt cgccaagaag gagatgaagt ttagcctggg ctcccaggtg  1680
gtggccttcg cccctagcta caagaagctg gtgaagaagg gccactccta tcagaccgcc  1740
acagagggca ccgccaacta cctgggcctg tcctactata ataggtatga gctgaaggag  1800
gagtcttttc aggcccagta ctatctgctg aagctgatct accagtacgt gttcctgcct  1860
aacttttccc agggcaattc tccagccttc cgcgagacag tgaaggccat cctgcggatc  1920
aacaaggacg aggccagaaa gaagatgaag aagaataaga agttcctgag gaagtacgcc  1980
tttgagcagg tgcgcgagat ggagttcaag gagacacccg accagtacat gagctatctg  2040
cagtccgaga tgagggagga gaaggtgcgc aaggccgaga agaacgataa gggcttcgag  2100
aagaacatca ccatgaattt tgagaagctg ctgatgcaga tcttcgtgaa gggcttcgac  2160
gtgttcctga ccacatttgc cggcaaggag ctgctgctga gctccgagga gaaagtgatc  2220
aaggagacag agatctccct gtctaagaag atcaacgagc gggagaaaac cctgaaggcc  2280
agcatccagg tggagcacca gctggtggcc accaattctg ccatcagcta ctggctgttc  2340
tgcaagctgc tggactcccg gcacctgaac gagctgagaa atgagatgat caagttcaag  2400
cagagccgga tcaagttcaa ccacacacag cacgccgagc tgatccagaa tctgctgcct  2460
atcgtggagc tgaccatcct gtctaacgac tacgatgaga agaacgactc ccagaatgtg  2520
gacgtgagcg cctattttga ggataagagc ctgtacgaga cagcccctta tgtgcagacc  2580
gacgatagga cacgcgtgtc tttcaggcca atcctgaagc tggagaagta ccacacaaag  2640
agcctgatcg aggccctgct gaaggacaac ccacagtttc gcgtggccgc caccgatatc  2700
caggagtgga tgcacaagag ggaggagatc ggcgagctgg tggagaagcg caagaatctg  2760
cacaccgagt gggcagaggg acagcagaca ctgggagcag agaagcggga ggagtacaga  2820
gactattgta agaagatcga tcggttcaac tggaaggcca ataaggtgac cctgacatac  2880
ctgtctcagc tgcactatct gatcacagac ctgctgggca gaatggtggg cttcagcgcc  2940
ctgtttgaga gggatctggt gtacttcagc cgctcctttt ctgagctggg cggcgagaca  3000
taccacatca gcgattataa gaacctgtcc ggcgtgctgc ggctgaatgc cgaggtgaag  3060
cccatcaaga tcaagaacat caaagtgatc gacaacgagg agaatcctta caagggcaat  3120
gagccagagg tgaagccctt cctggatcgg ctgcacgcct atctggagaa cgtgatcggc  3180
atcaaggccg tgcacggcaa gatcagaaat cagacagccc acctgtccgt gctgcagctg  3240
gagctgtcta tgatcgagag catgaacaat ctgcgggacc tgatggccta cgatagaaag  3300
ctgaagaacg ccgtgaccaa gtctatgatc aagatcctgg acaagcacgg ctga        3354

SEQ ID NO: 36          moltype = AA  length = 1117
```

-continued

```
FEATURE                Location/Qualifiers
REGION                 1..1117
                       note = CgaCas13a amino acid sequence
source                 1..1117
                       mol_type = protein
                       organism = synthetic construct
SEQUENCE: 36
MRITKVKIKL DNKLYQVTMQ KEEKYGTLKL NEESRKSTAE ILRLKKASFN KSFHSKTINS  60
QKENKNATIK KNGDYISQIF EKLVGVDTNK NIRKPKMSLT DLKDLPKKDL ALFIKRKFKN  120
DDIVEIKNLD LISLFYNALQ KVPGEHFTDE SWADFCQEMM PYREYKNKFI ERKIILLANS  180
IEQNKGFSIN PETFSKRKRV LHQWAIEVQE RGDFSILDEK LSKLAEIYNF KKMCKRVQDE  240
LNDLEKSMKK GKNPEKEKEA YKKQKNFKIK TIWKDYPYKT HIGLIEKIKE NEELNQFNIE  300
IGKYFEHYFP IKKERCTEDE PYYLNSETIA TTVNYQLKNA LISYLMQIGK YKQFGLENQV  360
LDSKKLQEIG IYEGFQTKFM DACVFATSSL KNIIEPMRSG DILGKREFKE AIATSSFVNY  420
HHFFPYFPFE LKGMKDRESE LIPFGEQTEA KQMQNIWALR GSVQQIRNEI FHSFDKNQKF  480
NLPQLDKSNF EFDASENSTG KSQSYIETDY KFLFEAEKNQ LEQFFIERIK SSGALEYYPL  540
KSLEKLFAKK EMKFSLGSQV VAFAPSYKKL VKKGHSYQTA TEGTANYLGL SYYNRYELKE  600
ESFQAQYYLL KLIYQYVFLP NFSQGNSPAF RETVKAILRI NKDEARKKMK KNKKFLRKYA  660
FEQVREMEFK ETPDQYMSYL QSEMREEKVR KAEKNDKGFE KNITMNFEKL LMQIFVKGFD  720
VFLTTFAGKE LLLSSEEKVI KETEISLSKK INEREKTLKA SIQVEHQLVA TNSAISYWLF  780
CKLLDSRHLN ELRNEMIKFK QSRIKFNHTQ HAELIQNLLP IVELTILSND YDEKNDSQNV  840
DVSAYFEDKS LYETAPYVQT DDRTRVSFRP ILKLEKYHTK SLIEALLKDN PQFRVAATDI  900
QEWMHKREEI GELVEKRKNL HTEWAEGQQT LGAEKREEYR DYCKKIDRFN WKANKVTLTY  960
LSQLHYLITD LLGRMVGFSA LFERDLVYFS RSFSELGGET YHISDYKNLS GVLRLNAEVK  1020
PIKIKNIKVI DNEENPYKGN EPEVKPFLDR LHAYLENVIG IKAVHGKIRN QTAHLSVLQL  1080
ELSMIESMNN LRDLMAYDRK LKNAVTKSMI KILDKHG                          1117

SEQ ID NO: 37          moltype = DNA  length = 36
FEATURE                Location/Qualifiers
misc_feature           1..36
                       note = CgaCas13a direct repeat
source                 1..36
                       mol_type = other DNA
                       organism = synthetic construct
SEQUENCE: 37
attaaagact acctctaaat gtaagaggac tataac                             36

SEQ ID NO: 38          moltype = DNA  length = 3669
FEATURE                Location/Qualifiers
misc_feature           1..3669
                       note = Cga2Cas13a nucleic acid sequence
source                 1..3669
                       mol_type = other DNA
                       organism = synthetic construct
SEQUENCE: 38
atgatcctga agctgaagat cgacgagaac cacaagaatt tcgagatcga gagcctgatc  60
ccaaaggaga tcatccacct gaaggataag gccatcaaga ccaaccaggt gtccgaggag  120
tactgccagc tggtgctggc cctgctgacc acaaaccccg gcaatcagct gaacatgagg  180
atgacaaagg tgaagatcaa cggcagcccc gtgagcatga atcgcagcaa gctgaacggc  240
cacctggtgt ggaatggcac cacaaatacc gtgaacatcc tgacaaagaa ggagcagagc  300
ttcgccgcct cctttctgaa caagaccctg gtgaaggccg accaggtgaa gggctacaag  360
gtgctggccg agaatatctt catcatcttt gagcagctgg agaagtccaa ctctgagaag  420
cccagcgtgt acctgaacaa tatccggaga ctgaaggagg ccggcctgaa gcggttcttt  480
aagagcaagt accacgagga gatcaagtat acctctgaga agaatcagag cgtgccaaca  540
aagctgaatc tgatccccct gttctttaac gccgtggaca gaatccagga ggacaagttc  600
gatgagaaga actggtccta cttttgcaag gagatgtctc cctacctgga ttataagaag  660
agctatctga ataggaagaa ggagatcctg gccaattcta tccagcagaa caggggcttc  720
agcatgccaa ccgcagagga gcctaacctg ctgtctaagc ggaagcagct gttccagcag  780
tgggccatga agtttcagga gagccctctg atccagcaga acaattttgc cgtggagcag  840
ttcaataagg agtttgccaa taagatcaac gagctggccg ccgtgtataa cgtggacgag  900
ctgtgcaccg ccatcacaga gaagctgatg aacttcgaca aggataagtc caataagacc  960
agaaactttg agatcaagaa gctgtggaag cagcaccctc acaacaagga taaggccctg  1020
atcaagctgt tcaatcagga gggcaacgag gccctgaatc agtttaacat cgagctgggc  1080
aagtacttcg agcactattt tcctaagaca ggcaagaagg agagcgccga gtcctactat  1140
ctgaatccac agaccatcat caagacagtg ggctaccagc tgaggaacgc cttcgtgcag  1200
tatctgctgc aagtgggcaa gctgcaccag tacaacaagg gcgtgctgga cagccagacc  1260
ctgcaggaga tcggcatgta tgagggcttc cagacaaagt ttatggatgc ctgcgtgttc  1320
gccagctcct ctctgcggaa tatcatccag gccaccacaa acgaggacat cctgaccaga  1380
gagaagttta agaaggagct ggagaagaac gtggagctga agcacgacct gttctttaag  1440
accgagatcg tggaggagcg cgatgagaat cctgccaaga agatcgccat gacaccaaac  1500
gagctggacc tgtgggcaat caggggagcc gtgcagaggg tgcgcaatca gatcttccac  1560
cagcagatca ataagagaca cgagcccaac cagctgaagg tcggctcctt tgagaatggc  1620
gatctgggca acgtgtctta ccagaaaacc atctatcaga agctgttcga cgccgagatc  1680
aaggatatcg agatctactt tgccgagaag atcaagagct ccggcgccct ggagcagtat  1740
tccatgaagg acctggagaa gctgttcagc aacaaggagc tgacactgtc cctgggagga  1800
caggtggtgg ccttcgcccc ttcttacaag aagctgtata agcagggcta cttttatcag  1860
aatgagaaaa ccatcgagct ggagcagttt acagactacg atttctctaa tgacgtgttc  1920
aaggccaact actatctgat caagctgatc taccactacg tgttcctgcc acagtttagc  1980
caggccaaca ataagctgtt caaggacacc gtgcactacg tgatccagca gaataaggag  2040
```

-continued

```
ctgaacacca cagagaagga taagaagaac aataagaaga tcagaaagta tgcctttgag  2100
caggtgaagc tgatgaagaa cgagtcccca gagaagtaca tgcagtatct gcagagggag  2160
atgcaggagg agcgcaccat caaggaggcc aagaaaacca acgaggagaa gcccaactac  2220
aatttcgaga agctgctgat ccagatcttt atcaagggct tcgacacctt tctgaggaat  2280
ttcgatctga acctgaatcc tgccgaggag ctggtgggca cagtgaagga gaaggccgag  2340
ggcctgcgga agagaaagga gcgcatcgcc aagatcctga acgtggacga gcagatcaag  2400
accggcgatg aggagatcgc cttctggatc tttgcaaagc tgctggacgc aaggcacctg  2460
agcgagctga gaaacgagat gatcaagttt aagcagtcta gcgtgaagaa gggcctgatc  2520
aagaatggcg atctgatcga gcagatgcag ccaatcctgg agctgtgcat cctgagcaac  2580
gacagcgagt ccatggagaa ggagtccttc gataagatcg aggtgtttct ggagaaggtg  2640
gagctggcca agaatgagcc atacatgcag gaggacaagc tgacccccgt gaagttcagg  2700
tttatgaagc agctggagaa gtatcagaca cgcaatttca tcgagaacct ggtcatcgag  2760
aatccagagt ttaaggtgtc cgagaagatc gtgctgaact ggcacgagga gaaggagaag  2820
atcgccgacc tggtggataa gcggaccaag ctgcacgagg agtgggcctc caaggccaga  2880
gagatcgagg agtacaatga gaagatcaag aagaacaagt ctaagaagct ggacaagccc  2940
gccgagttcg ccaagtttgc cgagtataag atcatctgtg aggccatcga gaacttcaat  3000
aggctggatc acaaggtgcg cctgacatac ctgaagaacc tgcactatct gatgatcgac  3060
ctgatgggca ggatggtggg cttctccgtg ctgtttgagc gggatttcgt gtatatgggc  3120
agatcttata gcgccctgaa gaagcagtct atctacctga atgactatga taccttcgcc  3180
aacatccgcg actgggaggt gaacgagaat aagcacctgt ttggcacatc ctctagcgat  3240
ctgaccttcc aggagacagc cgagtttaag aatctgaaga agcccatgga gaaccagctg  3300
aaggccctgc tgggcgtgac caaccacagc ttcgagatcc ggaacaatat cgcccacctg  3360
cacgtgctga gaaatgatgg caagggcgag ggcgtgtctc tgctgagctg catgaacgac  3420
ctgaggaagc tgatgtccta cgatcgcaag ctgaagaatg ccgtgacaaa ggccatcatc  3480
aagatcctgg acaagcacgg catgatcctg aagctgacca acaatgatca cacaaagccc  3540
ttcgagattg agagcctgaa gcctaagaag atcatccacc tggagaagtc caaccactct  3600
ttccctatgg accaggtgtc ccaggagtac tgtgatctgg tgaagaagat gctggtgttt  3660
accaattga                                                         3669

SEQ ID NO: 39          moltype = AA  length = 1222
FEATURE                Location/Qualifiers
REGION                 1..1222
                       note = Cga2Cas13a amino acid sequence
source                 1..1222
                       mol_type = protein
                       organism = synthetic construct
SEQUENCE: 39
MILKLKIDEN HKNFEIESLI PKEIIHLKDK AIKTNQVSEE YCQLVLALLT TNPGNQLNMR  60
MTKVKINGSP VSMNRSKLNG HLVWNGTTNT VNILTKKEQS FAASFLNKTL VKADQVKGYK  120
VLAENIFIIF EQLEKSNSEK PSVYLNNIRR LKEAGLKRFF KSKYHEEIKY TSEKNQSVPT  180
KLNLIPLFFN AVDRIQEDKF DEKNWSYFCK EMSPYLDYKK SYLNRKKEIL ANSIQQNRGF  240
SMPTAEEPNL LSKRKQLFQQ WAMKFQESPL IQQNNFAVEQ FNKEFANKIN ELAAVYNVDE  300
LCTAITEKLM NFDKDKSNKT RNFEIKKLWK QHPHNKDKAL IKLFNQEGNE ALNQFNIELG  360
KYFEHYFPKT GKKESAESYY LNPQTIIKTV GYQLRNAFVQ YLLQVGKLHQ YNKGVLDSQT  420
LQEIGMYEGF QTKFMDACVF ASSSLRNIIQ ATTNEDILTR EKFKKELEKN VELKHDLFFK  480
TEIVEERDEN PAKKIAMTPN ELDLWAIRGA VQRVRNQIFH QQINKRHEPN QLKVGSFENG  540
DLGNVSYQKT IYQKLFDAEI KDIEIYFAEK IKSSGALEQY SMKDLEKLFS NKELTLSLGG  600
QVVAFAPSYK KLYKQGYFYQ NEKTIELEQF TDYDFSNDVF KANYYLIKLI YHYVFLPQFS  660
QANNKLFKDT VHYVIQQNKE LNTTEKDKKN NKKIRKYAFE QVKLMKNESP EKYMQYLQRE  720
MQEERTIKEA KKTNEEKPNY NFEKLLIQIF IKGFDTFLRN FDLNLNPAEE LVGTVKEKAE  780
GLRKRKERIA KILNVDEQIK TGDEEIAFWI FAKLLDARHL SELRNEMIKF KQSSVKKGLI  840
KNGDLIEQMQ PILELCILSN DSESMEKESF DKIEVFLEKV ELAKNEPYMQ EDKLTPVKFR  900
FMKQLEKYQT RNFIENLVIE NPEFKVSEKI VLNWHEEKEK IADLVDKRTK LHEEWASKAR  960
EIEEYNEKIK KNKSKKLDKP AEFAKFAEYK IICEAIENFN RLDHKVRLTY LKNLHYLMID  1020
LMGRMVGFSV LFERDFVYMG RSYSALKKQS IYLNDYDTFA NIRDWEVNEN KHLFGTSSSD  1080
LTFQETAEFK NLKKPMENQL KALLGVTNHS FEIRNNIAHL HVLRNDGKGE GVSLLSCMND  1140
LRKLMSYDRK LKNAVTKAII KILDKHGMIL KLTNNDHTKP FEIESLKPKK IIHLEKSNHS  1200
FPMDQVSQEY CDLVKKMLVF TN                                          1222

SEQ ID NO: 40          moltype = DNA  length = 36
FEATURE                Location/Qualifiers
misc_feature           1..36
                       note = Cga2Cas13a direct repeat
source                 1..36
                       mol_type = other DNA
                       organism = synthetic construct
SEQUENCE: 40
aatataaact acctctaaat gtaagaggac tataac                           36

SEQ ID NO: 41          moltype = DNA  length = 3465
FEATURE                Location/Qualifiers
misc_feature           1..3465
                       note = PprCas13a nucleic acid sequence
source                 1..3465
                       mol_type = other DNA
                       organism = synthetic construct
SEQUENCE: 41
atgcgggtgt ccaaggtgaa ggtgaaggac ggcggcaagg ataagatggt gctggtgcac  60
agaaagacca caggcgcaca gctggtgtac tctggacagc ccgtgtctaa tgagacaagc  120
```

-continued

```
aacatcctgc ctgagaagaa gaggcagtcc tttgacctgt ctaccctgaa caagacaatc  180
atcaagttcg acacagccaa gaagcagaag ctgaatgtgg atcagtacaa gatcgtggag  240
aagatcttta agtatcctaa gcaggagctg ccaaagcaga tcaaggccga ggagatcctg  300
ccatttctga atcacaagtt ccaggagccc gtgaagtact ggaagaacgg caaggaggag  360
tccttcaatc tgaccctgct gatcgtggag gccgtgcagg cacaggacaa gcgcaagctg  420
cagccctact atgattggaa aacctggtat atccagacaa agagcgacct gctgaagaag  480
tccatcgaga acaataggat cgatctgaca gagaacctgt ctaagcgcaa gaaggccctg  540
ctggcctggg agacagagtt cacagccagc ggctccatcg acctgaccca ctaccacaag  600
gtgtatatga cagacgtgct gtgcaagatg ctgcaggatg tgaagccact gaccgacgat  660
aagggcaaga tcaacacaaa tgcctaccac cggggcctga agaaggccct gcagaatcac  720
cagcctgcca tctttggcac ccgggaggtg ccaaacgagg ccaatagagc cgataaccag  780
ctgtccatct accacctgga ggtggtgaag tacctggagc actatttccc catcaagacc  840
tctaagcgga gaaacacagc cgacgatatc gcccactatc tgaaggccca gaccctgaaa  900
accacaatcg agaagcagct ggtgaacgcc atcagagcca atatcatcca gcagggcaag  960
accaaccacc acgagctgaa ggccgacacc acaagcaatg atctgatccg gatcaagaca  1020
aacgaggcct ttgtgctgaa tctgaccggc acatgtgcct tcgccgccaa caatatcaga  1080
aatatggtgg acaacgagca gaccaatgat atcctgggca agggcgactt catcaagtct  1140
ctgctgaagg acaacacaaa tagccagctg tactccttct tttcggcga gggcctgagc  1200
accaataagg ccgagaagga gacacagctg tggggcatca ggggagccgt gcagcagatc  1260
cgcaacaatg tgaaccacta taagaaggat gccctgaaaa ccgtgttcaa catctccaat  1320
ttcgagaacc ccaccatcac agaccctaag cagcagacca actacgccga tacaatctat  1380
aaggccaggt ttatcaatga gctggagaag atccctgagg ccttcgccca gcagctgaaa  1440
accggcggag ccgtgtctta ctatacaatc gagaatctga agagcctgct gaccacattt  1500
cagttctctc tgtgccgcag caccatccca tttgcccccg gcttcaagaa ggtgtttaac  1560
ggcggcatca attaccagaa cgccaagcag gacgagagct tctacgagct gatgctggag  1620
cagtatctga ggaaggagaa ctttgccgag gagtcctaca atgcccgcta tttcatgctg  1680
aagctgatct ataacaatct gttcctgcca ggctttacca cagatcggaa ggcctttgcc  1740
gacagcgtgg gcttcgtgca gatgcagaac aagaagcagg ccgagaaagt gaatccaagg  1800
aagaaggagg cctacgcctt tgaggccgtg cgccccatga ccgcagcaga ctccatcgcc  1860
gattacatgg cctatgtgca gtctgagctg atgcaggagc agaacaagaa ggaggagaag  1920
gtggccgagg agacaaggat caattttgag aagttcgtgc tgcaggtgtt catcaagggc  1980
tttgactcct tcctgcgcgc caaggagttt gatttcgtgc agatgccaca gcctcagctg  2040
accgcaacag cctctaacca gcagaaggcc gacaagctga atcagctgga ggccagcatc  2100
accgccgatt gcaagctgac accccagtac gccaaggccg acgatgccac ccacatcgcc  2160
ttctacgtgt tctgcaagct gctggacgcc gcccacctga gcaatctgcg gaacgagctg  2220
atcaagttca gagagtccgt gaacgagttt aagttccacc acctgctgga gatcatcgag  2280
atctgcctgc tgagcgccga cgtggtgccc accgactaca gagatctgta tagctccgag  2340
gcagattgtc tggcaaggct gcgccctttt atcgagcagg gcgccgatat cacaaactgg  2400
tccgacctgt tcgtgcagtc cgataagcac tctcctgtga tccacgccaa tatcgagctg  2460
tctgtgaagt acggcaccac aaagctgctg gagcagatca tcaacaagga cacccagttt  2520
aagaccacag aggccaactt caccgcctgg aatacagccc agaagagcat cgagcagctg  2580
atcaagcaga gggaggatca ccacgagcag tgggtgaagg ccaagaacgc cgacgataag  2640
gagaagcagg agcggaagag agagaagtcc aatttcgccc agaagtttat cgagaagcac  2700
ggcgacgatt atctggacat ctgcgattac atcaatacct ataactggct ggacaacaag  2760
atgcacttcg tgcacctgaa tcgcctgcac ggcctgacaa tcgagctgct gggaaggatg  2820
gcaggattcg tggccctgtt tgacagagat ttccagtttt tcgacgagca gcagatcgcc  2880
gatgagttta agctgcacgg cttcgtgaac ctgcactcca tcgacaagaa gctgaatgag  2940
gtgcccacca agaagatcaa ggagatctac gatatccgga acaagatcat ccagatcaac  3000
ggcaataaga tcaacgagtc tgtgcgggcc aatctgatcc agtttatctc tagcaagaga  3060
aactactata acaatgcctt cctgcacgtg agcaatgacg agatcaagga gaagcagatg  3120
tacgatatca gaaaccacat cgcccacttt aattatctga ccaaggacgc cgccgatttc  3180
agcctgatcg acctgatcaa cgagctgagg gagctgctgc actacgatcg caagctgaag  3240
aatgccgtgt ccaaggcctt tatcgacctg ttcgataagc acggcatgat cctgaagctg  3300
aagctgaacg ccgaccacaa gctgaaggtg gagtctctgg agcctaagaa gatctaccac  3360
ctgggctcct ctgccaagga taagccagag taccagtatt gtaccaacca ggtcatgatg  3420
gcctattgca atatgtgccg gagcctgctg gagatgaaga agtga                3465
```

```
SEQ ID NO: 42          moltype = AA  length = 1154
FEATURE                Location/Qualifiers
REGION                 1..1154
                       note = PprCas13a amino acid sequence
source                 1..1154
                       mol_type = protein
                       organism = synthetic construct
SEQUENCE: 42
MRVSKVKVKD GGKDKMVLVH RKTTGAQLVY SGQPVSNETS NILPEKKRQS FDLSTLNKTI  60
IKFDTAKKQK LNVDQYKIVE KIFKYPKQEL PKQIKAEEIL PFLNHKFQEP VKYWKNGKEE  120
SFNLTLLIVE AVQAQDKRKL QPYYDWKTWY IQTKSDLLKK SIENNRIDLT ENLSKRKKAL  180
LAWETEFTAS GSIDLTHYHK VYMTDVLCKM LQDVKPLTDD KGKINTNAYH RGLKKALQNH  240
QPAIFGTREV PNEANRADNQ LSIYHLEVVK YLEHYFPIKT SKRRNTADDI AHYLKAQTLK  300
TTIEKQLVNA IRANIIQQGK TNHHELKADT TSNDLIRIKT NEAFVLNLTG TCAFAANNIR  360
NMVDNEQTND ILGKGDFIKS LLKDNTNSQL YSFFFGEGLS TNKAEKETQL WGIRGAVQQI  420
RNNVNHYKKD ALKTVFNISN FENPTITDPK QQTNYADTIY KARFINELEK IPEAFAQQLK  480
TGGAVSYYTI ENLKSLLTTF QFSLCRSTIP FAPGFKKVFN GGINYQNAKQ DESFYELMLE  540
QYLRKENFAE ESYNARYFML KLIYNNLFLP GFTTDRKAFA DSVGFVQMQN KKQAEKVNPR  600
KKEAYAFEAV RPMTAADSIA DYMAYVQSEL MQEQNKKEEK VAEETRINFE KFVLQVFIKG  660
FDSFLRAKEF DFVQMPQPQL TATASNQQKA DKLNQLEASI TADCKLTPQY AKADDATHIA  720
FYVFCKLLDA AHLSNLRNEL IKFRESVNEF KFHHLLEIIE ICLLSADVVP TDYRDLYSSE  780
ADCLARLRPF IEQGADITNW SDLFVQSDKH SPVIHANIEL SVKYGTTKLL EQIINKDTQF  840
```

-continued

```
KTTEANFTAW NTAQKSIEQL IKQREDHHEQ WVKAKNADDK EKQERKREKS NFAQKFIEKH  900
GDDYLDICDY INTYNWLDNK MHFVHLNRLH GLTIELLGRM AGFVALFDRD FQFFDEQQIA  960
DEFKLHGFVN LHSIDKKLNE VPTKKIKEIY DIRNKIIQIN GNKINESVRA NLIQFISSKR  1020
NYYNNAFLHV SNDEIKEKQM YDIRNHIAHF NYLTKDAADF SLIDLINELR ELLHYDRKLK  1080
NAVSKAFIDL FDKHGMILKL KLNADHKLKV ESLEPKKIYH LGSSAKDKPE YQYCTNQVMM  1140
AYCNMCRSLL EMKK                                                  1154

SEQ ID NO: 43          moltype = DNA  length = 36
FEATURE                Location/Qualifiers
misc_feature           1..36
                       note = PprCas13a direct repeat
source                 1..36
                       mol_type = other DNA
                       organism = synthetic construct
SEQUENCE: 43
cttgtggatt atcccaaaat tgaagggaac tacaac                          36

SEQ ID NO: 44          moltype = DNA  length = 2913
FEATURE                Location/Qualifiers
misc_feature           1..2913
                       note = LweCas13a nucleic acid sequence
source                 1..2913
                       mol_type = other DNA
                       organism = synthetic construct
SEQUENCE: 44
atgctggccc tgctgcacca ggaggtgcct tcccagaagc tgcacaacct gaagagcctg  60
aataccgagt ccctgacaaa gctgtttaag ccaaagttcc agaacatgat cagctatcca  120
ccttccaagg gagcagagca cgtgcagttc tgcctgaccg acatcgccgt gcccgcaatc  180
agggacctgg atgagatcaa gcctgactgg ggcatcttct ttgagaagct gaagccatac  240
acagattggg ccgagtctta catccactat aagcagacca caatccagaa gagcatcgag  300
cagaacaaga tccagagccc agactcccca aggaagctgg tgctgcagaa gtatgtgacc  360
gcctttctga atggagagcc actgggcctg gacctggtgg ccaagaagta caagctggcc  420
gatctggccg agtccttcaa ggtggtggac ctgaacgagg ataagtctgc caattataag  480
atcaaggcct gtctgcagca gcaccagcgg aacatcctgg acgagctgaa ggaggacccc  540
gagctgaatc agtacggcat cgaggtgaag aagtacatcc agcggtattt cccaatcaag  600
agggcaccaa accgcagcaa gcacgccaga gccgactttc tgaagaagga gctgatcgag  660
tccaccgtgg agcagcagtt caagaatgcc gtgtaccact atgtgctgga gcagggcaag  720
atggaggcct acgagctgac cgatcccaag acaaaggacc tgcaggatat cagatctggc  780
gaggccttca gctttaagtt catcaacgcc tgcgcctttg ccagcaacaa tctgaagatg  840
atcctgaatc ctgagtgtga gaaggacatc ctgggcaagg gcgatttcaa gaagaacctg  900
ccaaattcta ccacacagag cgacgtggtg aagaagatga tcccccttctt ttccgacgag  960
atccagaacg tgaatttcga tgaggccatc tgggccatcc ggggctctat ccagcagatc  1020
agaaacgagg tgtatcactg caagaagcac tcttggaaga gcatcctgaa gatcaagggc  1080
tttgagttcg agccaaacaa tatgaagtac accgactccg atatgcagaa gctgatggac  1140
aaggatatcg ccaagatccc cgactttatc gaggagaagc tgaagagctc cggcatcatc  1200
aggttctact cccacgataa gctgcagtct atctgggaga tgaagcaggg ctttagcctg  1260
ctgaccacaa acgccccttt tgtgccatcc ttcaagaggg tgtacgccaa gggccacgac  1320
tatcagacaa gcaagaatcg ctactatgac ctgggcctga ccacattcga tatcctggag  1380
tacggagagg aggacttccg ggcacgctat ttcctgacca agctggtgta ctatcagcag  1440
tttatgcctt ggttcacagc cgacaacaat gcctttcgcg atgccgccaa cttcgtgctg  1500
aggctgaaca agaatcgcca gcaggacgcc aaggccttta tcaatatccg ggaggtggag  1560
gagggcgaga tgcctagaga ttacatgggc tatgtgcagg gccagatcgc catccacgag  1620
gactccaccg aggatacacc aaaccacttt gagaagttca tctctcaggt gtttatcaag  1680
ggcttcgact cccacatgcg gtctgccgat ctgaagttca tcaagaaccc cagaaatcag  1740
ggcctggagc agagcgagat cgaggagatg tcctttgaca tcaaggtgga gcctagcttc  1800
ctgaagaaca aggacgatta tatcgccttt tggaccttct gcaagatgct ggacgcaagg  1860
cacctgtccg agctgagaaa tgagatgatc aagtacgatg gccacctgac aggcgagcag  1920
gagatcatcg gcctggccct gctgggagtg gactctaggg agaacgattg gaagcagttc  1980
ttttctagcg agcgcgagta cgagaagatc atgaagggct atgtgggcga ggagctgtac  2040
cagcgggagc cttatagaca gagcgacggc aagaccccaa tcctgttcag gggagtggag  2100
caggcaagga agtacggcac cgagacagtg atccagcggc tgtttgatgc ctctcctgag  2160
ttcaaggtga gcaagtgtaa catcacagag tgggagagac agaaggagac aatcgaggag  2220
acaatcgagc ggagaaagga gctgcacaac gagtgggaga agaatcccaa gaagcctcag  2280
aacaatgcct tctttaagga gtacaaggag tgctgtgacg ccatcgatgc ctataactgg  2340
cacaagaata agaccacact ggtgtacgtg aatgagctgc accacctgct gatcgagatc  2400
ctgggcaggt acgtgggcta tgtggccatc gccgaccgcg attttcagtg catggccaac  2460
cagtatttca agcactctgg catcaccgag agggtggagt actggggcga caatcgcctg  2520
aagagcatca agaagctgga tacatttctg aagaaggagg gcctgttcgt gtccgagaag  2580
aacgccagga atcacatcgc ccacctgaac tacctgtccc tgaagtctga gtgtaccctg  2640
ctgtatctgt ccgagcggct gagagagatc tttaagtacg acaggaagct gaagaatgcc  2700
gtgtccaagt ctctgatcga catcctggat cgccacggca tgtctgtggt gttcgccaac  2760
ctgaaggaga ataagcaccg gctggtcatc aagagcctgg agccaaagaa gctgagacac  2820
ctgggcgaga agaagatcga taacggctac atcgagacaa atcaggtgag cgaggagtat  2880
tgtggcatcg tgaagagact gctggagatc tga                             2913

SEQ ID NO: 45          moltype = AA  length = 970
FEATURE                Location/Qualifiers
REGION                 1..970
                       note = LweCas13a amino acid sequence
```

```
source                  1..970
                        mol_type = protein
                        organism = synthetic construct
SEQUENCE: 45
MLALLHQEVP SQKLHNLKSL NTESLTKLFK PKFQNMISYP PSKGAEHVQF CLTDIAVPAI  60
RDLDEIKPDW GIFFEKLKPY TDWAESYIHY KQTTIQKSIE QNKIQSPDSP RKLVLQKYVT  120
AFLNGEPLGL DLVAKKYKLA DLAESFKVVD LNEDKSANYK IKACLQQHQR NILDELKEDP  180
ELNQYGIEVK KYIQRYFPIK RAPNRSKHAR ADFLKKELIE STVEQQFKNA VYHYVLEQGK  240
MEAYELTDPK TKDLQDIRSG EAFSFKFINA CAFASNNLKM ILNPECEKDI LGKGDFKKNL  300
PNSTTQSDVV KKMIPFFSDE IQNVNFDEAI WAIRGSIQQI RNEVYHCKKH SWKSILKIKG  360
FEFEPNNMKY TDSDMQKLMD KDIAKIPDFI EEKLKSSGII RFYSHDKLQS IWEMKQGFSL  420
LTTNAPFVPS FKRVYAKGHD YQTSKNRYYD LGLTTFDILE YGEEDFRARY FLTKLVYYQQ  480
FMPWFTADNN AFRDAANFVL RLNKNRQQDA KAFINIREVE EGEMPRDYMG YVQGQIAIHE  540
DSTEDTPNHF EKFISQVFIK GFDSHMRSAD LKFIKNPRNQ GLEQSEIEEM SFDIKVEPSF  600
LKNKDDYIAF WTFCKMLDAR HLSELRNEMI KYDGHLTGEQ EIIGLALLGV DSRENDWKQF  660
FSSEREYEKI MKGYVGEELY QREPYRQSDG KTPILFRGVE QARKYGTETV IQRLFDASPE  720
FKVSKCNITE WERQKETIEE TIERRKELHN EWEKNPKKPQ NNAFFKEYKE CCDAIDAYNW  780
HKNKTTLVYV NELHHLLIEI LGRYVGYVAI ADRDFQCMAN QYFKHSGITE RVEYWGDNRL  840
KSIKKLDTFL KKEGLFVSEK NARNHIAHLN YLSLKSECTL LYLSERLREI FKYDRKLKNA  900
VSKSLIDILD RHGMSVVFAN LKENKHRLVI KSLEPKKLRH LGEKKIDNGY IETNQVSEEY  960
CGIVKRLLEI                                                        970

SEQ ID NO: 46           moltype = DNA  length = 36
FEATURE                 Location/Qualifiers
misc_feature            1..36
                        note = LweCas13a direct repeat
source                  1..36
                        mol_type = other DNA
                        organism = synthetic construct
SEQUENCE: 46
gatttagagt acctcaaaat agaagaggtc taaaac                           36

SEQ ID NO: 47           moltype = DNA  length = 3156
FEATURE                 Location/Qualifiers
misc_feature            1..3156
                        note = LbfCas13a nucleic acid sequence
source                  1..3156
                        mol_type = other DNA
                        organism = synthetic construct
SEQUENCE: 47
atgaagatca ccaagatgcg ggtggacggc agaaccatcg tgatggagcg gacatccaag  60
gagggccagc tgggctatga gggcatcgac ggcaacaaga ccacagagat catctttgat  120
aagaagaagg agagcttcta caagtccatc ctgaacaaga ccgtgagaaa gcctgatgag  180
aaggagaaga atcggagaaa gcaggccatc aacaaggcca tcaataagga gatcacagag  240
ctgatgctgg ccgtgctgca ccaggaggtg cctagccaga agctgcacaa cctgaagagc  300
ctgaataccg agtccctgac aaagctgttt aagccaaagt tccagaatat gatctcttat  360
ccacctagca agggagcaga gcacgtgcag ttctgcctga ccgacatcgc cgtgcccgca  420
atccgggacc tggatgagat caagcctgac tggggcatct tctttgagaa gctgaagcca  480
tacacagatt gggccgagtc ctacatccac tataagcaga ccacaatcca gaagtctatc  540
gagcagaaca agatccagag cccagactcc cccagaaagc tggtgctgca gaagtatgtg  600
accgcctttc tgaatggaga gccactgggc ctggacctgg tggccaagaa gtacaagctg  660
gccgatctgg ccgagtcttt caagctggtg gacctgaacg aggataagag cgccaattat  720
aagatcaagg cctgtctgca gcagcaccag cggaacatcc tggacgagct gaaggaggac  780
cccgagctga atcagtacgg catcgaggtg aagaagtaca tccagaggta tttcccaatc  840
aagagggccc ccaaccgctc taagcacgcc agagccgact ttctgaagaa ggagctgatc  900
gagagcaccg tggagcagca gttcaagaat gccgtgtacc actatgtgct ggagcagggc  960
aagatggagg cctacgagct gaccgatccc aagacaaagg acctgcagga tatcaggtct  1020
ggcgaggcct tcagctttaa gttcatcaac gcctgcgcct ttgcctccaa caatctgaag  1080
atgatcctga accctgagtg tgagaaggac atcctgggca agggcaattt caagaagaac  1140
ctgccaaatt ccaccacacg ctctgatgtg gtgaagaaga tgatcccctt ctttagcgac  1200
gagctgcaga acgtgaattt cgatgaggcc atctgggcca tccggggctc catccagcag  1260
atcagaaatg aggtgtatca ctgcaagaag cactcttgga agagcatcct gaagatcaag  1320
ggctttgagt tcgagccaaa caatatgaag tacgccgaca gcgatatgca gaagctgatg  1380
gacaaggata tcgccaagat ccccgagttt atcgaggaga agctgaagag ctccggcgtg  1440
gtgcggttct acagacacga cgagctgcag agcatctggg agatgaagca gggcttttcc  1500
ctgctgacca caaacgcccc ttttgtgccc agcttcaagc gggtgtacgc caagggccac  1560
gactatcaga cctccaagaa cagatactat aatctggacc tgaccacatt cgatatcctg  1620
gagtacggcg aggaggattt tcgggccaga tatttcctga ccaagctggt gtactatcag  1680
cagtttatgc cctggttcac agccgacaac aatgccttta gggatgccgc caacttcgtg  1740
ctgaggctga acaagaatcg ccagcaggac gccaaggcct ttatcaatat ccgggaggtg  1800
gaggagggcg agatgcctag agattacatg ggctatgtgc agggccagat cgccatccac  1860
gaggacagca tcgaggatac cccaaaccac tttgagaagt tcatctccca ggtgtttatc  1920
aagggcttcg acaggcacat gcgctctgcc aatctgaagt tcatcaagaa cccccgcaat  1980
cagggcctgg agcagtccga gatcgaggag atgtcttttg atatcaaggt ggagccttct  2040
ttcctgaaga acaaggacga ttatatcgcc ttttggatct tctgcaagat gctggacgca  2100
aggcacctga gcgagctgag aaatgagatg atcaagtacg atggccacct gaccggcgag  2160
caggagatca tcggcctgrc cctgctggga gtggactccc gggagaacga ttggaagcag  2220
ttcttttcta gcgagagaga gtacgagaag atcatgaagg gctatgtggt ggaggagctg  2280
taccagcggg agccttatag acagtctgac ggcaagacac caatcctgtt caggggagtg  2340
```

-continued

```
gagcaggcaa ggaagtacgg caccgagaca gtgatccaga ggctgtttga tgccaacccc  2400
gagttcaagg tgagcaagtg taatctggcc gagtgggagc gccagaagga gacaatcgag  2460
gagacaatca agaggcgcaa ggagctgcac aacgagtggg ccaagaatcc caagaagcct  2520
cagaacaatg ccttctttaa ggagtacaag gagtgctgtg acgccatcga tgcctataac  2580
tggcacaaga ataagaccac actggcctac gtgaacgagc tgcaccacct gctgatcgag  2640
atcctgggca ggtacgtggg ctatgtggcc atcgccgacc gcgattttca gtgcatggcc  2700
aaccagtatt tcaagcactc cggcatcacc gagagggtgg agtactgggg cgacaatcgc  2760
ctgaagtcta tcaagaagct ggatacattt ctgaagaagg agggcctgtt cgtgagcgag  2820
aagaacgccc ggaatcacat cgcccacctg aactacctgt ccctgaagtc tgagtgtacc  2880
ctgctgtatc tgtccgagag gctgcgcgag atctttaagt acgaccggaa gctgaagaat  2940
gccgtgtcca agtctctgat cgacatcctg gatagacacg gcatgtccgt ggtgttcgcc  3000
aacctgaagg agaataagca ccggctggtc atcaagagcc tggagcctaa gaagctgcgc  3060
cacctgggcg gcaagaagat cgatggcggc tacatcgaga caaaccaggt gagcgaggag  3120
tattgtggca tcgtgaagag actgctggag atgtga                           3156

SEQ ID NO: 48          moltype = AA  length = 1050
FEATURE                Location/Qualifiers
REGION                 1..1050
                       note = LbfCas13a amino acid sequence
source                 1..1050
                       mol_type = protein
                       organism = synthetic construct
SEQUENCE: 48
MKITKMRVDG RTIVMERTSK EGQLGYEGID GNKTTEIIFD KKKESFYKSI LNKTVRKPDE  60
KEKNRRKQAI NKAINKEITE LMLAVLHQEV PSQKLHNLKS LNTESLTKLF KPKFQNMISY  120
PPSKGAEHVQ FCLTDIAVPA IRDLDEIKPD WGIFFEKLKP YTDWAESYIH YKQTTIQKSI  180
EQNKIQSPDS PRKLVLQKYV TAFLNGEPLG LDLVAKKYKL ADLAESFKLV DLNEDKSANY  240
KIKACLQQHQ RNILDELKED PELNQYGIEV KKYIQRYFPI KRAPNRSKHA RADFLKKELI  300
ESTVEQQFKN AVYHYVLEQG KMEAYELTDP KTKDLQDIRS GEAFSFKFIN ACAFASNNLK  360
MILNPECEKD ILGKGNFKKN LPNSTTRSDV VKKMIPFFSD ELQNVNFDEA IWAIRGSIQQ  420
IRNEVYHCKK HSWKSILKIK GFEFEPNNMK YADSDMQKLM DKDIAKIPEF IEEKLKSSGV  480
VRFYRHDELQ SIWEMKQGFS LLTTNAPFVP SFKRVYAKGH DYQTSKNRYY NLDLTTFDIL  540
EYGEEDFRAR YFLTKLVYYQ QFMPWFTADN NAFRDAANFV LRLNKNRQQD AKAFINIREV  600
EEGEMPRDYM GYVQGQIAIH EDSIEDTPNH FEKFISQVFI KGFDRHMRSA NLKFIKNPRN  660
QGLEQSEIEE MSFDIKVEPS FLKNKDDYIA FWIFCKMLDA RHLSELRNEM IKYDGHLTGE  720
QEIIGLLLGV DSRENDWKQF FSSEREYEKI MKGYVVEELY QREPYRQSDG KTPILFRGVE  780
QARKYGTETV IQRLFDANPE FKVSKCNLAE WERQKETIEE TIKRRKELHN EWAKNPKKPQ  840
NNAFFKEYKE CCDAIDAYNW HKNKTTLAYV NELHHLLIEI LGRYVGYVAI ADRDFQCMAN  900
QYFKHSGITE RVEYWGDNRL KSIKKLDTFL KKEGLFVSEK NARNHIAHLN YLSLKSECTL  960
LYLSERLREI FKYDRKLKNA VSKSLIDILD RHGMSVVFAN LKENKHRLVI KSLEPKKLRH  1020
LGGKKIDGGY IETNQVSEEY CGIVKRLLEM                                  1050

SEQ ID NO: 49          moltype = DNA  length = 36
FEATURE                Location/Qualifiers
misc_feature           1..36
                       note = LbfCas13a direct repeat
source                 1..36
                       mol_type = other DNA
                       organism = synthetic construct
SEQUENCE: 49
gatttagagt acctcaaaac aaaagaggac taaaac                           36

SEQ ID NO: 50          moltype = DNA  length = 3459
FEATURE                Location/Qualifiers
misc_feature           1..3459
                       note = Lwa2Cas13a nucleic acid sequence
source                 1..3459
                       mol_type = other DNA
                       organism = synthetic construct
SEQUENCE: 50
atgaaggtga ccaaggtgga cggcatcagc cacaagaagt acatcgagga gggcaagctg  60
gtgaagtcca cctctgagga gaaccggaca tctgagagac tgagcgagct gctgtccatc  120
aggctggaca tctacatcaa gaaccccgat aatgcctccg aggaggagaa ccgcatccgg  180
agagagaatc tgaagaagtt cttttctaac aaggtgctgc acctgaagga cagcgtgctg  240
tacctgaaga acaggaagga gaagaatgcc gtgcaggata agaattattc cgaggaggac  300
atctctgagt acgatctgaa gaacaagaat agcttctccg tgctgaagaa gatcctgctg  360
aacgaggacg tgaatagcga ggagctggag atcttcagga aggatgtgga ggccaagctg  420
aacaagatca attctctgaa gtatagcttt gaggagaaca aggccaatta ccagaagatc  480
aacgagaaca atgtggagaa agtgggcggc aagagcaagc gcaacatcat ctatgactac  540
tatcgggagt ccgccaagag aaatgattac atcaacaatg tgcaggaggc cttcgacaag  600
ctgtataaga aggaggatat cgagaagctg ttctttctga tcgagaactc caagaagcac  660
gagaagtaca agatccggga gtactatcac aagatcatcg gcagaaagaa cgacaaggag  720
aatttcgcca agatcatcta tgaggagatc cagaacgtga acaatatcaa ggagctgatc  780
gagaagatcc ctgatatgag cgagctgaag aagtcccagg tgttttacaa gtactatctg  840
gacaaggagg agctgaacga taagaatatc aagtatgcct tctgccactt tgtggagatc  900
gagatgagcc agctgctgaa gaactacgtg tataagcggc tgtctaacat cagcaatgac  960
aagatcaaga gaatcttcga gtaccagaat ctgaagaagc tgatcgagaa caagctgctg  1020
aataagctgg acacctatgt gcgcaactgt ggcaagtaca attactatct gcaagtgggc  1080
gagatcgcca catccgattt catcgccagg aaccgccaga atgaggcctt tctgcggaac  1140
```

-continued

```
atcatcggcg tgagctccgt ggcctacttt tctctgagaa atatcctgga gacagagaac  1200
gagaatgaca tcacaggccg gatgagaggc aagaccgtga agaacaataa gggcgaggag  1260
aagtacgtga gcggcgaggt ggataagatc tacaacgaga ataagcagaa cgaggtgaag  1320
gagaatctga agatgttcta cagctatgac tttaacatgg ataacaagaa tgagatcgag  1380
gacttctttg ccaatatcga tgaggccatc tctagcatcc ggcacggcat cgtgcacttc  1440
aacctggagc tggagggcaa ggacatcttc gcctttaaga atatcgcccc atccgagatc  1500
tctaagaaga tgtttcagaa cgagatcaat gagaagaagc tgaagctgaa gatcttcaag  1560
cagctgaact ccgccaacgt gttcaactac tatgagaagg acgtgatcat caagtacctg  1620
aagaacacca agttcaattt tgtgaacaag aatatcccct tcgtgccttc ctttacaaag  1680
ctgtataaca agatcgagga tctgagaaat accctgaagt tcttttggtc tgtgccaaag  1740
gacaaggagg agaaggatgc ccagatctac ctgctgaaga acatctacta tggcgagttc  1800
ctgaacaagt ttgtgaagaa cagcaaggtg ttctttaaga tcacaaatga agtgatcaag  1860
atcaacaagc agcggaatca gaaaaccggc cactacaagt atcagaagtt cgagaacatc  1920
gagaaaaccg tgcccgtgga gtacctggcc atcatccaga gcagagagat gatcaacaat  1980
caggacaagg aggagaagaa cacctatatc gatttcatcc agcagatctt cctgaagggc  2040
tttatcgact atctgaataa gaacaatctg aagtacatcg agtccaacaa caacaacgac  2100
aacaacgata tcttttctaa gatcaagatc aagaaggaca acaaggagaa gtatgataag  2160
atcctgaaga attacgagaa gcacaacagg aataaggaga tcccccacga gatcaacgag  2220
ttcgtgcgcg agatcaagct gggcaagatc ctgaagtata cagagaacct gaatatgttt  2280
tacctgatcc tgaagctgct gaaccacaag gagctgacca atctgaaggg ctctctggag  2340
aagtaccaga gcgccaacaa ggaggagaca ttcagcgatg agctggagct gatcaatctg  2400
ctgaacctgg acaacaatcg ggtgaccgag gattttgagc tggaggccaa cgagatcggc  2460
aagttcctgg actttaacga gaataagatc aaggatagga aggagctgaa gaagttcgac  2520
acaaacaaga tctactttga tggcgagaat atcatcaagc accgcgcctt ctataacatc  2580
aagaagtacg gcatgctgaa tctgctggag aagatcgccg acaaggccaa gtataagatc  2640
agcctgaagg agctgaagga gtactccaat aagaagaacg agatcgagaa gaactatacc  2700
atgcagcaga atctgcacag gaagtacgcc cgccctaaga aggatgagaa gttcaacgac  2760
gaggattaca aggagtatga gaaggccatc ggcaacatcc agaagtacac ccacctgaag  2820
aataaggtgg agtttaatga gctgaacctg ctgcagggcc tgctgctgaa gatcctgcac  2880
aggctggtgg gctatacatc catctgggag cgcgacctga ggttccgcct gaagggcgag  2940
tttccagaga accactacat cgaggagatc ttcaatttcg ataactccaa gaatgtgaag  3000
tacaagtctg gccagatcgt ggagaagtac atcaacttct ataaggagct gtataaggac  3060
aatgtggaga agcggagcat ctactccgat aagaaggtga agaagctgaa gcaggagaag  3120
aaggacctgt atatcagaaa ctacatcgcc cactttaatt atatccctca cgccgagatc  3180
agcctgctgg aggtgctgga gaacctgagg aagctgctgt cttacgaccg caagctgaag  3240
aatgccatca tgaagagcat cgtggatatc ctgaaggagt atggcttcgt ggccaccttc  3300
aagatcggcg ccgacaagaa gatcgagatc cagaccctgg agagcgagaa gatcgtgcac  3360
ctgaagaacc tgaagaagaa gaagctgatg acagatcgga acagcgagga gctgtgcgag  3420
ctggtgaaag tgatgttcga gtacaaggcc ctggagtga                         3459
```

```
SEQ ID NO: 51          moltype = AA  length = 1152
FEATURE                Location/Qualifiers
REGION                 1..1152
                       note = Lwa2Cas13a amino acid sequence
source                 1..1152
                       mol_type = protein
                       organism = synthetic construct
SEQUENCE: 51
MKVTKVDGIS HKKYIEEGKL VKSTSEENRT SERLSELLSI RLDIYIKNPD NASEEENRIR  60
RENLKKFFSN KVLHLKDSVL YLKNRKEKNA VQDKNYSEED ISEYDLKNKN SFSVLKKILL  120
NEDVNSEELE IFRKDVEAKL NKINSLKYSF EENKANYQKI NENNVEKVGG KSKRNIIYDY  180
YRESAKRNDY INNVQEAFDK LYKKEDIEKL FFLIENSKKH EKYKIREYYH KIIGRKNDKE  240
NFAKIIYEEI QNVNNIKELI EKIPDMSELK KSQVFYKYYL DKEELNDKNI KYAFCHFVEI  300
EMSQLLKNYV YKRLSNISND KIKRIFEYQN LKKLIENKLL NKLDTYVRNC GKYNYYLQVG  360
EIATSDFIAR NRQNEAFLRN IIGVSSVAYF SLRNILETEN ENDITGRMRG KTVKNNKGEE  420
KYVSGEVDKI YNENKQNEVK ENLKMFYSYD FNMDNKNEIE DFFANIDEAI SSIRHGIVHF  480
NLELEGKDIF AFKNIAPSEI SKKMFQNEIN EKKLKLKIFK QLNSANVFNY YEKDVIIKYL  540
KNTKFNFVNK NIPFVPSFTK LYNKIEDLRN TLKFFWSVPK DKEEKDAQIY LLKNIYYGEF  600
LNKFVKNSKV FFKITNEVIK INKQRNQKTG HYKYQKFENI EKTVPVEYLA IIQSREMINN  660
QDKEEKNTYI DFIQQIFLKG FIDYLNKNNL KYIESNNNND NNDIFSKIKI KKDNKEKYDK  720
ILKNYEKHNR NKEIPHEINE FVREIKLGKI LKYTENLNMF YLILKLLNHK ELTNLKGSLE  780
KYQSANKEET FSDELELINL LNLDNNRVTE DFELEANEIG KFLDFNENKI KDRKELKKFD  840
TNKIYFDGEN IIKHRAFYNI KKYGMLNLLE KIADKAKYKI SLKELKEYSN KKNEIEKNYT  900
MQQNLHRKYA RPKKDEKFND EDYKEYEKAI GNIQKYTHLK NKVEFNELNL LQGLLLKILH  960
RLVGYTSIWE RDLRFRLKGE FPENHYIEEI FNFDNSKNVK YKSGQIVEKY INFYKELYKD  1020
NVEKRSIYSD KKVKKLKQEK KDLYIRNYIA HFNYIPHAEI SLLEVLENLR KLLSYDRKLK  1080
NAIMKSIVDI LKEYGFVATF KIGADKKIEI QTLESEKIVH LKNLKKKKLM TDRNSEELCE  1140
LVKVMFEYKA LE                                                     1152
```

```
SEQ ID NO: 52          moltype = DNA  length = 36
FEATURE                Location/Qualifiers
misc_feature           1..36
                       note = Lwa2Cas13a direct repeat
source                 1..36
                       mol_type = other DNA
                       organism = synthetic construct
SEQUENCE: 52
gatatagata accccaaaaa cgaagggatc taaaac                           36
```

-continued

```
SEQ ID NO: 53           moltype = DNA  length = 3858
FEATURE                 Location/Qualifiers
misc_feature            1..3858
                        note = RcsCas13a nucleic acid sequence
source                  1..3858
                        mol_type = other DNA
                        organism = synthetic construct
SEQUENCE: 53
atgcagattg gaaaagtgca gggaaggact attagcgagt ttggggaccc cgcaggagga  60
ctgaagagaa agattagcac cgatggaaag aatcgcaagg aactgccagc acacctgtca  120
agtgatccaa aggccctgat tggacagtgg atctcaggga tcgacaaaat ctaccggaag  180
cccgatagta ggaaatccga tggcaaagca atccactccc caacccctag caaaatgcag  240
tttgacgcaa gggatgacct gggagaggca ttctggaaac tggtgtcaga agctggcctg  300
gctcaggata gtgactatga tcagtttaag cggcgactgc atccatacgg agacaaattt  360
cagcctgctg atagcggagc aaaactgaag ttcgaagccg acccacctga gcctcaggcc  420
ttccacggca ggtggtatgg agcaatgtcc aagcgcggga atgacgcaaa ggagctggca  480
gtcgctctgt acgaacatct gcacgtcgat gagaaaagaa tcgatggcca gcctaagcgg  540
aatcctaaga ctgataaatt cgctccaggg ctggtggtgg cccgcgctct ggggattgag  600
tcaagcgtgc tgccaagagg aatggctaga ctggctagga attggggcga agaggaaatc  660
cagacttact ttgtcgtgga tgtggccgca tcagtgaagg aggtggctaa agctgctgtg  720
agcgcagcac aggctttcga tccacctcgc caggtcagcg ggagaagtct gagtcccaaa  780
gtggggttcg cactggcaga gcatctggaa agggtgacag gctccaagag gtgctcattc  840
gatcccgcag ccggcccttc tgtcctggca ctgcacgacg aagtgaagaa aacttataaa  900
agactgtgcg cccggggaaa gaatgcagcc agagcttttc cagccgacaa gaccgaactg  960
ctggctctga tgagacatac ccatgagaac agagtccgga atcagatggt cagaatggga  1020
agggtgtcag aataccgagg ccagcaggcc ggggatctgg ctcagtccca ctattggaca  1080
agtgccggcc agacagaaat caaagaaagc gagatctttg tcaggctgtg ggtgggagct  1140
tttgcactgg ctgggcgcag catgaaagca tggattgacc caatggggaa gatcgtgaac  1200
actgagaaga atgatagaga tctgactgcc gccgtcaaca tcagacaggt aatctccaac  1260
aaggagatgg tcgctgaggc aatggctcgg cgcggaatct atttcggcga gacaccagag  1320
ctggatagac tgggggcaga gggaaatgaa ggcttcgtgt tcgctctgct gcgatacctg  1380
agagggtgta gaaaccagac ttttcatctg gggctcgggg caggatttct gaaggaaatc  1440
cgcaaggagc tggaaaagac acggtggggc aaggcaaaag aagccgagca tgtggtcctg  1500
accgacaaga cagtggcagc cattagagca atcattgaca atgacgccaa agccctgggc  1560
gcccggctgc tggcagacct gagcggagct tttgtggcac actatgcaag caaagaacac  1620
ttcagcacac tgtattccga gatcgtcaaa gcagtgaaag acgctcctga agtgtcatcc  1680
gggctgcctc ggctgaagct gctgctgaaa cgggcagacg gagtcagggg atacgtgcat  1740
ggactgcggg atacccgaaa acatgctttc gccactaagc tgccacctcc tccagctcca  1800
cgggaactgg acgaccctgc aacaaaggcc aggtatatcg ctctgctgcg gctgtatgat  1860
ggcccatttc gggcctacgc aagtggaatc actggaactg ccctggcagg acctgctgcc  1920
agagctaaag aggcagctac tgcactggcc cagtccgtga atgtcactaa agcatattcc  1980
gatgtgatgg agggacgcac ctcacgactg aggccaccta atgatggcga aaccctgagg  2040
gaatacctga gtgcactgac tggcgagact gccacagagt tccgggtgca gattggctat  2100
gagtccgact cagagaatgc tagaaagcag gccgagttta tcgagaacta taggcgagat  2160
atgctggcct tcatgttcga ggattacatt cgagcaaagg ggttcgactg gattctgaag  2220
attgaacctg ggccacagc aatgaccaga gcccctgtgc tgccagagcc aatcgataca  2280
cgaggccagt atgaacactg gcaggccgca ctgtacctgg tcatgcactt cgtcccagct  2340
agtgatgtga gcaacctgct gcaccagctg agaaagtggg aagcactgca gggcaaatac  2400
gagctggtcc aggatgggga cgccacagac caggcagatg cccggaggga ggccctggat  2460
ctggtgaaaa ggttccgcga tgtgctggtc ctgtttctga aaacagggga agccagattt  2520
gaaggccgcg ccgctccatt tgatctgaag cctttccggg cactgtttgc taatccagct  2580
actttcgatc ggctgtttat ggccacacca accactgcta ggcccgctga agatgacccc  2640
gagggcgacg gagcctccga accagagctg cgggtcgcca ggacactgcg cgggctgcgc  2700
cagattgcac gatataacca catggcagtg ctgagcgatc tgttcgctaa acataaagtg  2760
cgggatgagg aagtcgcacg cctggccgag attgaggacg aaactcagga aaaatctcag  2820
attgtcgccg cacaggaact gaggacagat ctgcacgata aagtcatgaa atgccaccct  2880
aaaaccatca gccccgagga gcggcagagt tacgccgccg caatcaaaac cattgaggag  2940
cacaggttcc tggtgggcag agtgtacctg gggggatcacc tgcggctgca tcgcctgatg  3000
atggatgtca tcggccgcct gattgattac gctggcgctt atgagcgcga tactggcact  3060
ttcctgatca acgccagcaa acagctgggg gctggcgctg attgggcagt gaccattgca  3120
ggcgccgcta ataccgacgc acgcacccag acccggaaag acctggcaca tttcaacgtg  3180
ctggatagag ccgacggaac ccccgacctg acagctctgg tgaacagggc aagagaaatg  3240
atggcctacg atcgcaaacg caaaaacgca gtcccacgga gtatcctgga tatgctggct  3300
cggctggggc tgacactgaa gtggcagatg aaggaccacc tgctgcagga cgctacaatc  3360
acccaggctg caatcaaaca cctggataaa gtgcggctga ccgtgggggg ccccgccgcc  3420
gtcaccgaag cacgcttctc acaggactac ctgcagatgg tcgctgcagt gttcaatggg  3480
agcgtgcaga accctaaacc acggcgccgg gatgatgggg acgcctggca caagccaccc  3540
aagcctgcaa ctgctcagtc tcagcctgat cagaaacctc ccaacaaagc accttctgca  3600
gggtccaggc tgccaccccc acaggtcggg gaggtctacg aaggagtcgt ggtcaaagtc  3660
attgataccg gctcactggg ctttctggcc gtggaggggg tggctggcaa tattggcctg  3720
catatctccc gcctgcgacg aatcagagag gacgccatca ttgtcgggcg gagatacaga  3780
ttcagggtcg aaatctatgt cccccccaag agcaacactt ccaaactgaa cgccgctgac  3840
ctggtgcgaa ttgactga                                                3858

SEQ ID NO: 54           moltype = AA  length = 1285
FEATURE                 Location/Qualifiers
REGION                  1..1285
                        note = RcsCas13a amino acid sequence
source                  1..1285
```

```
                         mol_type = protein
                         organism = synthetic construct
SEQUENCE: 54
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA VALYEHLHVD EKRIDGQPKR  180
NPKTDKFAPG LVVARALGIE SSVLPRGMAR LARNWGEEEI QTYFVVDVAA SVKEVAKAAV  240
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRTSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTDARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FRVEIYVPPK SNTSKLNAAD LVRID                                       1285

SEQ ID NO: 55            moltype = DNA  length = 36
FEATURE                  Location/Qualifiers
misc_feature             1..36
                         note = RcsCas13a direct repeat
source                   1..36
                         mol_type = other DNA
                         organism = synthetic construct
SEQUENCE: 55
gcctcacatc accgccaaga cgacggcgga ctgaac                           36

SEQ ID NO: 56            moltype = DNA  length = 3858
FEATURE                  Location/Qualifiers
misc_feature             1..3858
                         note = RcrCas13a nucleic acid sequence
source                   1..3858
                         mol_type = other DNA
                         organism = synthetic construct
SEQUENCE: 56
atgcagattg ggaaagtcca gggcagaacc attagcgagt ttggcgaccc cgcaggaggg  60
ctgaaaagga agattagcac cgacggaaag aaccggaaag aactgcccgc ccatctgtca  120
agcgatccaa aggctctgat cggccagtgg attagcggca ttgataagat ctacaggaag  180
cctgattcaa gaaagagcga tggaaaagcc atccatagcc caactccaag caagatgcag  240
tttgatgcca gggacgacct gggggaagca ttctggaaac tggtgtcaga ggctgggctg  300
gctcaggaca gcgattacga tcagtttaaa aggcggctgc atccctatgg ggataagttt  360
cagcccgccg atagcggcgc taaactgaaa ttcgaagctg atcctccaga gccccaggct  420
tttcacggcc gctggtatgg ggcaatgagc aaaagaggaa acgacgctaa agaactggca  480
gcagcactgt atgaacatct gcatgtcgat gaaaaacgaa ttgatggcca gccaaaaagg  540
aacccaaaga cagataaatt cgcaccaggg ctggtcgtgg ccagggcact ggggatcgag  600
agctctgtgc tgccacgggg gatggcaaga ctggcacgga attgggggga agaggaaatc  660
cagacatact tcgtggtcga cgtggcagca agcgtgaagg aagtggcaaa ggcagccgtg  720
agcgccgcac aggccttcga cccacctcgg caggtgtccg gcaggtcact gagcccaaag  780
gtcgggtttg ccctggctga acatctggag cgggtcacag gctccaaaag gtgcagcttc  840
gatcctgcag ctgggccaag cgtcctggcc ctgcacgacg aagtcaagaa aacctataaa  900
cggctgtgcg cccggggaaa gaacgccgca agagcctttc cagcagacaa aacagaactg  960
ctggccctga tgcggcatac ccacgagaac cgggtgagga atcagatggt cagaatgggg  1020
cgggtgagtg agtatagggg gcagcaggca ggggacctgg cacagagcca ctactggaca  1080
agcgcaggac agaccgaaat caaggagtca gagatttttg tccgcctgtg ggtcggggct  1140
ttcgcactgg ccgggaggtc aatgaaagcc tggattgatc ccatgggaaa gatcgtcaac  1200
actgaaaaga acgatcgcga cctgaccgct gcagtcaaca ttcggcaggt catcagcaac  1260
aaggagatgg tggccgaagc tatggcacga cgggggatct actttggaga aaccccagag  1320
ctggataggc tgggagcaga aggcaatgag ggcttcgtct ttgcactgct gagatacctg  1380
agagggtgca ggaatcagac ctttcacctg gggggccaggg cagggttcct gaaagagatt  1440
agaaaagaac tggaaaaaac ccggtggggg aaggccaagg aggcagagca cgtggtcctg  1500
accgataaaa ctgtcgctgc catcagagcc atcatcgaca acgatgccaa ggcactgggg  1560
gcccggctgc tggcagacct gtcaggggct tttgtcgctc actatgccag taaagaacac  1620
tttagcaccc tgtactcaga aattgtcaag gctgtgaagg acgcaccaga ggtgtcatcc  1680
gggctgcccc ggctgaagct gctgctgaag agggcagacg gagtcagagg ctatgtccat  1740
gggctgaggg atacaaggaa acacgccttt gctactaaac tgccaccacc tccagcacca  1800
agggaactgg atgacccagc caccaaagcc agatacatcg cactgctgag actgtacgat  1860
ggaccattca gggcttatgc atccggcatt actgggacag ctctggccgg gccagctgca  1920
cgagccaagg aggccgcaac cgctctggca cagtccgtga atgtcacaaa agcatacagc  1980
gatgtgatgg agggcaggtc aagcagactg aggccaccca acgatgggga aacactgaga  2040
gaatacctga gcgcactgac aggagaaaca gcaacagaat ttcgggtcca gattggctat  2100
```

-continued

```
gaaagcgact cagagaatgc tcggaagcag gccgagttca ttgagaacta tagacgggat  2160
atgctggctt ttatgtttga ggactacatc cgggctaagg ggttcgactg gattctgaaa  2220
atcgagcccg gagcaactgc aatgacacgg gcacctgtgc tgcccgagcc aattgacacc  2280
cgggggcagt acgaacactg gcaggcagca ctgtatctgg taatgcattt cgtgcccgca  2340
tcagatgtca gcaacctgct gcatcagctg aggaagtggg aggccctgca ggggaaatat  2400
gaactggtgc aggatggcga cgcaacagat caggcagacg cacgacgaga ggccctggat  2460
ctggtcaagc gatttcgcga tgtcctggtg ctgttcctga aaacaggaga ggcccggttc  2520
gagggacggg cagctccatt cgacctgaaa cccttccgag cactgttcgc aaatccagca  2580
actttcgatc ggctgtttat ggctacacct accacagcaa ggccagcaga ggatgatccc  2640
gagggggacg gcgcatcaga accagagctg agggtggccc ggactctgag agggctgcgg  2700
cagattgcca ggtataatca catggcagtc ctgagcgatc tgtttgcaaa gcacaaagtc  2760
cgagatgagg aagtcgcaag gctggcagaa attgaagatg agactcagga gaaatcacag  2820
atcgtcgctg cacaggaact gagaaccgac ctgcatgaca aagtcatgaa gtgtcatccc  2880
aaaaccatct ctcctgaaga aagacagtcc tacgccgcag ctattaagac catcgaagag  2940
cataggtttc tggtggggag ggtctatctg ggagatcatc tgcggctgca cagactgatg  3000
atggatgtga ttggacggct gatcgattac gctggagcct acgagaggga tactgggaca  3060
tttctgatca atgcctcaaa gcagctgggg gccggcgcag actgggcagt gacaattgcc  3120
ggggcagcaa acactggcgc caggactcag actcggaagg acctggccca ctttaacgtg  3180
ctggataggg ccgacgggac acctgacctg accgccctgg tgaatcgagc aagagaaatg  3240
atggcatacg atcggaaaag aaaaaacgca gtcccaagat caattctgga tatgctggcc  3300
aggctgggac tgactctgaa atggcagatg aaggatcacc tgctgcagga tgcaactatt  3360
acccaggctg caattaagca tctggacaaa gtgcggctga cagtgggcgg gcctgcagct  3420
gtgactgagg cacgattctc ccaggactac ctgcagatgg tggccgcagt gtttaacggg  3480
tctgtccaga atccaaagcc aaggaggagg gacgacggcg acgcatggca taaaccacct  3540
aagccagcaa ctgcacagtc ccagcccgac cagaagccac ccaacaaagc acctagcgca  3600
gggtcacggc tgcccccacc acaggtcggg gaagtctatg aaggggtggt ggtgaaagtg  3660
atcgataccg ggtcactggg attcctggca gtcgaagggg tcgcagggaa tatcggcctg  3720
catattagta ggctgaggag aatcagagaa gatgctatta tcgtgggcag gagatacagg  3780
ttttgggtcg agatctacgt gccccccaag tctaatacct ccaaactgaa cgctgctgac  3840
ctggtgcgaa ttgactga                                                3858
```

```
SEQ ID NO: 57           moltype = AA  length = 1285
FEATURE                 Location/Qualifiers
REGION                  1..1285
                        note = RcrCas13a amino acid sequence
source                  1..1285
                        mol_type = protein
                        organism = synthetic construct
SEQUENCE: 57
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA AALYEHLHVD EKRIDGQPKR  180
NPKTDKFAPG LVVARALGIE SSVLPRGMAR LARNWGEEEI QTYFVVDVAA SVKEVAKAAV  240
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRSSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTGARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FWVEIYVPPK SNTSKLNAAD LVRID                                        1285
```

```
SEQ ID NO: 58           moltype = DNA  length = 36
FEATURE                 Location/Qualifiers
misc_feature            1..36
                        note = RcrCas13a direct repeat
source                  1..36
                        mol_type = other DNA
                        organism = synthetic construct
SEQUENCE: 58
gcctcacatc accgccaaga cgacggcgga ctgaac                            36
```

```
SEQ ID NO: 59           moltype = DNA  length = 3858
FEATURE                 Location/Qualifiers
misc_feature            1..3858
                        note = RcdCas13a nucleic acid sequence
source                  1..3858
                        mol_type = other DNA
                        organism = synthetic construct
```

-continued

```
SEQUENCE: 59
atgcagatcg gcaaagtgca gggaaggact attagcgagt tcggggaccc agcaggagga  60
ctgaagagga agatttctac tgacggaaag aaccggaaag aactgccagc tcacctgtca  120
agcgatccaa aggctctgat tggccagtgg attagtggca ttgacaagat ctaccggaaa  180
ccagatagca gaaaatcaga cggcaaggct atccacagtc ctacaccaag caaaatgcag  240
ttcgacgccc gggatgatct gggggaagca ttctggaaac tggtgagtga agcagggctg  300
gcacaggact cagattatga tcagtttaag cgcaggctgc acccttatgg ggacaagttt  360
cagcccgctg acagcggcgc aaaactgaag ttcgaggccg atccccctga gccacaggct  420
ttccacggac gctggtatgg ggccatgtca aagaggggga acgacgcaaa ggaactggca  480
gctgcactgt atgagcatct gcatgtggac gaaaaaagga ttgatggcca gccaaagagg  540
aacccaaaga ctgataaatt tgcccccggg ctggtggtcg caagggcact ggggatcgag  600
agctcagtgc tgccaagggg gatggccagg ctggccagga actggggaga ggaggaaatt  660
cagacttatt tcgtcgtgga cgtggcagcc tcagtgaagg aagtggccaa ggctgccgtg  720
tccgctgctc aggcatttga cccacctcga caggtgtcag gacggagcct gtctccaaag  780
gtcgggtttg ccctggcaga gcacctggaa agggtcaccg gaagcaaaag atgcagcttt  840
gatccagcag ctgggccaag tgtcctggca ctgcacgacg aggtgaaaaa gacctataag  900
cgactgtgcg ccagagggaa aaatgccgca agagcttttc cagcagacaa gacagagctg  960
ctggcactga tgagacacac acacgaaaat agggtgcgca accagatggt caggatgggg  1020
agggtcagcg agtatcgggg acagcaggcc ggggatctgg ctcagagcca ttattggact  1080
agcgcagggc agaccgagat taaggagagc gaaatcttcg tgcggctgtg ggtcggggca  1140
tttgccctgg caggccgatc catgaaggcc tggatcgacc ctatggggaa gatcgtgaac  1200
actgagaaga acgaccggga cctgactgca gcagtgaaca tcaggcaggt catcagcaat  1260
aaggaaatgg tcgccgaggc aatggctaga aggggaatct acttcgggga gactccagag  1320
ctggaccgac tgggggcaga aggaaacgag gggttcgtgt tcgctctgct gcgatacctg  1380
aggggctgta gaaatcagac atttcatctg ggggcaagag ctggctttct gaaagagatt  1440
cggaaagagc tggaaaagac ccggtggggg aaggccaaag aggcagagca tgtggtcctg  1500
acagacaaaa ctgtggcagc tatccgagct atcatcgaca atgatgccaa agcactgggg  1560
gccagactgc tggcagatct gtccggcgcc tttgtcgccc actacgcaag caaggagcac  1620
ttttctacac tgtattctga gatcgtcaag gctgtgaagg atgcacctga agtcagttca  1680
ggactgccca ggctgaagct gctgctgaaa agggccgatg gggtgcgcgg gtatgtccac  1740
gggctgaggg atacaagaaa acatgccttc gcaacaaagc tgccacccc acctgcccca  1800
agagagctgg acgatcccgc aaccaaggcc aggtacatcg ccctgctgcg cctgtatgac  1860
ggcccattca gagcttacgc atccgggatt acagggactg cactggctgg cccagcagct  1920
agggccaaag aggcagcaac agctctggct cagtccgtga atgtcactaa ggcctactct  1980
gacgtgatgg aaggacggtc atcacggctg aggcctccca atgacggaga gactctgaga  2040
gaatacctgt ctgcactgac tggggaaact gcaacagagt ttcgggtcca gatcggatac  2100
gaaagcgaca gcgaaaacgc aagaaaacag gctgagttta ttgagaatta ccggagagat  2160
atgctggctt ttatgttcga ggattatatc agagccaagg ggttcgattg gattctgaaa  2220
attgagcccg ggcaacagc catgactagg gcaccagtgc tgcccgaacc tatcgataca  2280
cgagggcagt acgagcattg gcaggctgca ctgtatctgg tcatgcattt cgtgccagcc  2340
tcagacgtgt ctaacctgct gcaccagctg cggaaatggg aagccctgca ggggaagtac  2400
gagctggtcc aggacgggga cgccacagac caggccgacg cccggcggga agctctggac  2460
ctggtcaagc ggttccgaga tgtcctggtg ctgttcctga aaactggcga ggcacgcttc  2520
gagggaaggg ctgctccttt tgacctgaag ccattccgag ctctgtttgc caaccccgca  2580
acattcgatc gcctgtttat ggcaacacct accacagctc gaccagccga ggatgatcca  2640
gagggggacg gggcatccga gcctgaactg cgggtcgcaa ggacactgcg ggggctgcgg  2700
cagatcgcac ggtacaatca catggcagtc ctgtcagacc tgttcgccaa acataaggtg  2760
cgcgatgaag aggtggcaag gctggccgag attgaggatg aaacccagga gaagtcacag  2820
atcgtcgccg cacaggagct gcggaccgac ctgcacgaca aggtcatgaa gtgccaccct  2880
aagacaatta gccccgagga gcgccagagc tacgcagcag ccatcaaaac tatcgaagag  2940
catagatttc tggtggggag ggtctatctg gggatcatc tgcgactgca ccggctgatg  3000
atggacgtga tcggccgcct gattgactat gctggagcct atgaaagaga tactggcaca  3060
ttcctgatca atgcaagcaa acagctgggg gccggcgcag actgggcagt gacaatcgcc  3120
ggggccgcca atacagatgc tagaactcag acacggaagg atctggctca cttcaacgtg  3180
ctggatcggg ctgatgggac cccgacctg actgcactgg tgaatcgcgc acgggaaatg  3240
atggcctacg atcggaagag aaaaaatgcc gtcccaagga gcattctgga tatgctggca  3300
cggctgggac tgaccctgaa gtggcagatg aaggatcacc tgctgcagga tgcaaccatt  3360
acccaggcag ctatcaagca cctggacaag gtgagactga ccgtgggcgg accagcagca  3420
gtcacagaag ctcggttctc tcaggactac ctgcagatgg tggctgcagt gtttaacgga  3480
tcagtgcaga accccaagcc acggcgcagg gacgacggag atgcttggca taaacctcct  3540
aagccagcca ccgcccagag ccagccagat cagaaacctc ccaacaaagc accttccgca  3600
gggtcccggc tgcccctcc acaggtggga gaggtctacg aaggcgtggt cgtcaaagtc  3660
attgatactg gatctctggg gttcctggct gtcgaaggcg tcgctggaaa tattggcctg  3720
cacatctccc gactgaggcg gattcgggag gatgctatca ttgtcggacg aaggtatagg  3780
ttccgggtgg aaatctacgt gcctccaaag agcaacactt ccaaactgaa cgctgccgac  3840
ctggtgcgga ttgattga                                                3858

SEQ ID NO: 60          moltype = AA  length = 1285
FEATURE                Location/Qualifiers
REGION                 1..1285
                       note = RcdCas13a amino acid sequence
source                 1..1285
                       mol_type = protein
                       organism = synthetic construct
SEQUENCE: 60
MQIGKVQGRT ISEFGDPAGG LKRKISTDGK NRKELPAHLS SDPKALIGQW ISGIDKIYRK  60
PDSRKSDGKA IHSPTPSKMQ FDARDDLGEA FWKLVSEAGL AQDSDYDQFK RRLHPYGDKF  120
QPADSGAKLK FEADPPEPQA FHGRWYGAMS KRGNDAKELA AALYEHLHVD EKRIDGQPKR  180
NPKTDKFAPG LVVARALGIE SSVLPRGMAR LARNWGEEEI QTYFVVDVAA SVKEVAKAAV  240
```

-continued

```
SAAQAFDPPR QVSGRSLSPK VGFALAEHLE RVTGSKRCSF DPAAGPSVLA LHDEVKKTYK  300
RLCARGKNAA RAFPADKTEL LALMRHTHEN RVRNQMVRMG RVSEYRGQQA GDLAQSHYWT  360
SAGQTEIKES EIFVRLWVGA FALAGRSMKA WIDPMGKIVN TEKNDRDLTA AVNIRQVISN  420
KEMVAEAMAR RGIYFGETPE LDRLGAEGNE GFVFALLRYL RGCRNQTFHL GARAGFLKEI  480
RKELEKTRWG KAKEAEHVVL TDKTVAAIRA IIDNDAKALG ARLLADLSGA FVAHYASKEH  540
FSTLYSEIVK AVKDAPEVSS GLPRLKLLLK RADGVRGYVH GLRDTRKHAF ATKLPPPPAP  600
RELDDPATKA RYIALLRLYD GPFRAYASGI TGTALAGPAA RAKEAATALA QSVNVTKAYS  660
DVMEGRSSRL RPPNDGETLR EYLSALTGET ATEFRVQIGY ESDSENARKQ AEFIENYRRD  720
MLAFMFEDYI RAKGFDWILK IEPGATAMTR APVLPEPIDT RGQYEHWQAA LYLVMHFVPA  780
SDVSNLLHQL RKWEALQGKY ELVQDGDATD QADARREALD LVKRFRDVLV LFLKTGEARF  840
EGRAAPFDLK PFRALFANPA TFDRLFMATP TTARPAEDDP EGDGASEPEL RVARTLRGLR  900
QIARYNHMAV LSDLFAKHKV RDEEVARLAE IEDETQEKSQ IVAAQELRTD LHDKVMKCHP  960
KTISPEERQS YAAAIKTIEE HRFLVGRVYL GDHLRLHRLM MDVIGRLIDY AGAYERDTGT  1020
FLINASKQLG AGADWAVTIA GAANTDARTQ TRKDLAHFNV LDRADGTPDL TALVNRAREM  1080
MAYDRKRKNA VPRSILDMLA RLGLTLKWQM KDHLLQDATI TQAAIKHLDK VRLTVGGPAA  1140
VTEARFSQDY LQMVAAVFNG SVQNPKPRRR DDGDAWHKPP KPATAQSQPD QKPPNKAPSA  1200
GSRLPPPQVG EVYEGVVVKV IDTGSLGFLA VEGVAGNIGL HISRLRRIRE DAIIVGRRYR  1260
FRVEIYVPPK SNTSKLNAAD LVRID                                      1285

SEQ ID NO: 61          moltype = DNA  length = 36
FEATURE                Location/Qualifiers
misc_feature           1..36
                       note = RcdCas13a direct repeat
source                 1..36
                       mol_type = other DNA
                       organism = synthetic construct
SEQUENCE: 61
gcctcacatc accgccaaga cgacggcgga ctgaac                           36

SEQ ID NO: 62          moltype = DNA  length = 3537
FEATURE                Location/Qualifiers
misc_feature           1..3537
                       note = PguCas13b nucleic acid sequence
source                 1..3537
                       mol_type = other DNA
                       organism = synthetic construct
SEQUENCE: 62
atgacagagc agagcgagag gccctacaac ggcacctact acaccctgga agataagcac  60
ttctgggccg cctttctgaa cctggccaga cacaacgcct acatcaccct gacacacatc  120
gaccggcagc tggcctacag caaggccgac atcaccaacg accaggacgt gctgagcttc  180
aaggccctgt ggaagaactt cgacaacgac ctggaaagaa agagccggct gcggagcctg  240
atcctgaagc acttcagctt tctggaaggc gccgcttacg gcaagaagct gttcgagtct  300
aagagcagcg gcaacaagag cagcaagaac aaagagctga ccaagaaaga gaaagaggaa  360
ctgcaggcca acgctctgag cctggacaac ctgaagtcta tcctgttcga cttcctgcag  420
aagctgaagg acttccggaa ctactacagc cactaccggc acagcggaag cagcgagctg  480
cctctgttcg acggcaacat gctgcagcgg ctgtacaacg tgttcgacgt gtccgtgcag  540
cgcgtgaaga tcgaccacga gcacaacgat gaggtggacc ctcactacca cttcaaccac  600
ctcgtgcgga agggcaagaa ggacagatac ggccacaacg acaaccccag cttcaagcac  660
cacttcgtgg acggcgaagg catggttaca gaagccggcc tgctgttctt cgtgtccctg  720
ttcctggaaa agcgggacgc catctggatg cagaagaaga tccggggctt caaaggcggc  780
accgagacat accagcagat gaccaacgag gtgttctgcc ggtccagaat cagcctgcct  840
aagctgaagc tggaaagcct gcggatggac gactggatgc tgctggacat gctgaacgaa  900
ctcgtgcggt gccccaagcc tctgtacgac agactgagag aggacgaccg ggcctgcttt  960
agagtgcccg tggatatcct gcctgacgag gacgatacag atggcggcgg agaggacccc  1020
ttcaagaata ccctcgtccg gcaccaggac agattccctt acttcgccct gcggtacttc  1080
gacctgaaga aggtgttcac cagcctgcgg ttccacatcg atctgggcac ctaccacttt  1140
gccatctaca agaagatgat cggcgagcag cccgaggaca gacacctgac cagaaacctg  1200
tacggcttcg gccggatcca ggacttcgcc gaagaacaca gacccgagga atggaagcgg  1260
ctcgtcagag atctggacta cttcgagaca ggcgacaagc cctacatcag ccagacaagc  1320
ccacactacc acatcgagaa gggaaagatc ggcctgagat tcatgcccga gggccagcat  1380
ctttggccct ctccagaagt gggcaccacc agaaccggca gatctaagta cgcccaggac  1440
aagagactga ccgccgaggc ctttctgtct gtgcacgagc tgatgcctat gatgttctac  1500
tacttcctgc tgcgcgagaa gtacagcgag gaagtgtctg ccgagagagt gcagggcaga  1560
atcaagcgcg tgatcgagga tgtgtacgcc gtgtacgatg cctttgccag ggacgagatc  1620
aacacccggg atgagctgga tgcctgcctg gccgataagg gcatcagaag aggccatctg  1680
cctcgccaga tgatcgccat cctgagccaa gagcacaagg acatggaaga gaagattcgg  1740
aagaaactgc aagagatgat ggccgacacc gaccaccggc tggatatgct ggatagacag  1800
accgaccgga agatcagaat cggccggaag aatgccggac tgcctaagag cggagtgatc  1860
gccgattggc tcgtgcggga catgatgaga tttcagcccg tggccaagga cgccagcgga  1920
aagcctctga acaactccaa ggccaacagc accgagtacc ggatgctgca gagagccctg  1980
gctctgtttg gaggcgagaa agagaggctg accccatact tccggcagat gaatctgacc  2040
ggcggaaaca accctcatcc ttttctgcac gaaactcgct gggagagcca caccaacatc  2100
ctgtcctttt accggtccta cctgagagcc cgcaaggcct tcctcgaaag gatcggcaga  2160
tccgacagag tggaaaaccg gccatttctg ctgctgaaag agcccaagac cgacagacag  2220
acactggtgg ctggatggaa gggcgagttc catctgccaa gaggcatctt cacagaggcc  2280
gtgcgggatt gcctgatcga gatgggacac gatgaagtgg ccagctacaa agaagtggga  2340
ttcatggcca aggccgtgcc actgtacttt gagagagcct gcgaggacag ggtgcagccc  2400
ttttacgaca gcccccttcaa cgtgggcaac agcctgaagc ctaagaaggg cagattcctg  2460
agcaaagagg aacgggccga agagtgggag cggggcaaag agagattccg ggatctcgaa  2520
```

-continued

```
gcctggtcct atagcgccgc cagaagaatc gaggacgcct ttgccggcat cgagtatgct  2580
agccccggaa acaagaagaa aatcgagcag ctcctgcggg acctgagcct gtgggaagcc  2640
tttgagagca agctgaaagt gcgggccgac cggatcaatc tggccaagct gaagaaagaa  2700
atcctggaag cccaagaaca cccctaccac gacttcaaga gctggcagaa gttcgagcgc  2760
gagctgcggc tggtcaagaa ccaggatatc atcacctgga tgatgtgccg cgacctgatg  2820
gaagaaaaca aggtggaagg cctggacacc ggcacactgt acctgaagga catcagaccc  2880
aacgtgcaag agcagggcag cctgaacgtg ctgaacagag tgaagcccat gagactgccc  2940
gtggtggtgt acagagccga tagcagaggc cacgtgcaca aagaagaagc ccctctggcc  3000
accgtgtaca tcgaggaaag agacaccaag ctgctgaagc agggcaactt caagtccttc  3060
gtgaaggaca ggcggctgaa cggcctgttc tccttcgttg atactggcgg actggccatg  3120
gaacagtacc ccatctccaa gctgagagtg gaatacgagc tggccaagta ccagaccgcc  3180
agagtgtgtg tgttcgagct gaccctgaga ctggaagagt ccctgctgac ccggtatcct  3240
catctgcccg acgagagctt cagagagatg ctggaatctt ggagcgaccc tctgctggcc  3300
aaatggcctg aactgcacgg aaaagtgcgg ctgctgatcg ccgtgcggaa tgcctttagc  3360
cacaatcagt accctatgta cgacgaggcc gtgttcagct ccatccggaa gtacgatcct  3420
agcagccccg acgccatcga agagagaatg ggcctgaata tcgcccaccg cctgtctgag  3480
gaagtgaagc aggccaaaga aaccgtggaa cggatcattc aggccggatc ccttcaa     3537

SEQ ID NO: 63          moltype = AA  length = 1179
FEATURE                Location/Qualifiers
REGION                 1..1179
                       note = PguCas13b amino acid sequence
source                 1..1179
                       mol_type = protein
                       organism = synthetic construct
SEQUENCE: 63
MTEQSERPYN GTYYTLEDKH FWAAFLNLAR HNAYITLTHI DRQLAYSKAD ITNDQDVLSF  60
KALWKNFDND LERKSRLRSL ILKHFSFLEG AAYGKKLFES KSSGNKSSKN KELTKKEKEE  120
LQANALSLDN LKSILFDFLQ KLKDFRNYYS HYRHSGSSEL PLFDGNMLQR LYNVFDVSVQ  180
RVKIDHEHND EVDPHYHFNH LVRKGKKDRY GHNDNPSFKH HFVDGEGMVT EAGLLFFVSL  240
FLEKRDAIWM QKKIRGFKGG TETYQQMTNE VFCRSRISLP KLKLESLRMD DWMLLDMLNE  300
LVRCPKPLYD RLREDDRACF RVPVDILPDE DDTDGGGEDP FKNTLVRHQD RFPYFALRYF  360
DLKKVFTSLR FHIDLGTYHF AIYKKMIGEQ PEDRHLTRNL YGFGRIQDFA EEHRPEEWKR  420
LVRDLDYFET GDKPYISQTS PHYHIEKGKI GLRFMPEGQH LWPSPEVGTT RTGRSKYAQD  480
KRLTAEAFLS VHELMPMMFY YFLLREKYSE EVSAERVQGR IKRVIEDVYA VYDAFARDEI  540
NTRDELDACL ADKGIRRGHL PRQMIAILSQ EHKDMEEKIR KKLQEMMADT DHRLDMLDRQ  600
TDRKIRIGRK NAGLPKSGVI ADWLVRDMMR FQPVAKDASG KPLNNSKANS TEYRMLQRAL  660
ALFGGEKERL TPYFRQMNLT GGNNPHPFLH ETRWESHTNI LSFYRSYLRA RKAFLERIGR  720
SDRVENRPFL LLKEPKTDRQ TLVAGWKGEF HLPRGIFTEA VRDCLIEMGH DEVASYKEVG  780
FMAKAVPLYF ERACEDRVQP FYDSPFNVGN SLKPKKGRFL SKEERAEEWE RGKERFRDLE  840
AWSYSAARRI EDAFAGIEYA SPGNKKKIEQ LLRDLSLWEA FESKLKVRAD RINLAKLKKE  900
ILEAQEHPYH DFKSWQKFER ELRLVKNQDI ITWMMCRDLM EENKVEGLDT GTLYLKDIRP  960
NVQEQGSLNV LNRVKPMRLP VVVYRADSRG HVHKEEAPLA TVYIEERDTK LLKQGNFKSF  1020
VKDRRLNGLF SFVDTGGLAM EQYPISKLRV EYELAKYQTA RVCVFELTLR LEESLLTRYP  1080
HLPDESFREM LESWSDPLLA KWPELHGKVR LLIAVRNAFS HNQYPMYDEA VFSSIRKYDP  1140
SSPDAIEERM GLNIAHRLSE EVKQAKETVE RIIQAGSLQ                        1179

SEQ ID NO: 64          moltype = DNA  length = 36
FEATURE                Location/Qualifiers
misc_feature           1..36
                       note = PguCas13b direct repeat
source                 1..36
                       mol_type = other DNA
                       organism = synthetic construct
SEQUENCE: 64
gttggatcta ccctctattt gaagggtaca cacaac                           36

SEQ ID NO: 65          moltype = DNA  length = 2943
FEATURE                Location/Qualifiers
misc_feature           1..2943
                       note = RfxCas13d-SV40NLS nucleic acid sequence
source                 1..2943
                       mol_type = other DNA
                       organism = synthetic construct
SEQUENCE: 65
atgagcccca agaagaagag aaaggtggag gccagcatcg aaaaaaaaaa gtccttcgcc  60
aagggcatgg gcgtgaagtc cacactcgtg tccggctcca aagtgtacat gacaaccttc  120
gccgaaggca gcgacgccag gctggaaaag atcgtggagg gcgacagcat caggagcgtg  180
aatgagggcg aggccttcag cgctgaaatg gccgataaaa acgccggcta taagatcggc  240
aacgccaaat tcagccatcc taagggctac gccgtggtgg ctaacaaccc tctgtataca  300
ggacccgtcc agcaggatat gctcggcctg aaggaaactc tggaaaagag gtacttcggc  360
gagagcgctg atggcaatga caatatttgt atccaggtga tccataacat cctggacatt  420
gaaaaaatcc tcgccgaata cattaccaac gccgcctacg ccgtcaacaa tatctccggc  480
ctggataagg acattattgg attcggcaag ttctccacag tgtataccta cgacgaattc  540
aaagaccccg agcaccatag ggccgctttc aacaataacg ataagctcat caacgccatc  600
aaggcccagt atgacgagtt cgacaacttc ctcgataacc ccagactcgg ctatttcggc  660
caggcctttt tcagcaagga gggcagaaat tacatcatca attacggcaa cgaatgctat  720
gacattctgg ccctcctgag cggactggcg cactgggtgg tcgctaacaa cgaagaagag  780
tccaggatct ccaggacctg gctctacaac ctcgataaga acctcgacaa cgaatacatc  840
```

```
tccaccctca actacctcta cgacaggatc accaatgagc tgaccaactc cttctccaag  900
aactccgccg ccaacgtgaa ctatattgcc gaaactctgg gaatcaaccc tgccgaattc  960
gccgaacaat atttcagatt cagcattatg aaagagcaga aaaacctcgg attcaatatc  1020
accaagctca gggaagtgat gctggacagg aaggatatgt ccgagatcag gaaaaatcat  1080
aaggtgttcg actccatcag gaccaaggtc tacaccatga tggactttgt gatttatagg  1140
tattacatcg aagaggatgc caaggtggct gccgccaata agtccctccc cgataatgag  1200
aagtccctga gcgagaagga tatctttgtg attaacctga ggggctcctt caacgacgac  1260
cagaaggatg ccctctacta cgatgaagct aatagaattt ggagaaagct cgaaaatatc  1320
atgcacaaca tcaaggaatt taggggaaac aagacaagag agtataagaa gaaggacgcc  1380
cctagactgc ccagaatcct gcccgctggc cgtgatgttt ccgccttcag caaactcatg  1440
tatgccctga ccatgttcct ggatggcaag gagatcaacg acctcctgac caccctgatt  1500
aataaattcg ataacatcca gagcttcctg aaggtgatgc ctctcatcgg agtcaacgct  1560
aagttcgtgg aggaatacgc ctttttcaaa gactccgcca agatcgccga tgagctgagg  1620
ctgatcaagt ccttcgctag aatgggagaa cctattgccg atgccaggag ggccatgtat  1680
atcgacgcca tccgtatttt aggaaccaac ctgtcctatg atgagctcaa ggccctcgcc  1740
gacacctttt ccctggacga gaacggaaac aagctcaaga aaggcaagca cggcatgaga  1800
aatttcatta ttaataacgt gatcagcaat aaaaggttcc actacctgat cagatacggt  1860
gatcctgccc acctccatga gatcgccaaa aacgaggccg tggtgaagtt cgtgctcggc  1920
aggatcgctg acatccagaa aaaacagggc cagaacggca agaaccagat cgacaggtac  1980
tacgaaactt gtatcggaaa ggataagggc aagagcgtga gcgaaaaggt ggacgctctc  2040
acaaagatca tcaccggaat gaactacgac caattcgaca agaaaaggag cgtcattgag  2100
gacaccggca gggaaaacgc cgagagggag aagtttaaaa agatcatcag cctgtacctc  2160
accgtgatct accacatcct caagaatatt gtcaatatca acgccaggta cgtcatcgga  2220
ttccattgcg tcgagcgtga tgctcaactg tacaaggaga aaggctacga catcaatctc  2280
aagaaactgg aagagaaggg attcagctcc gtcaccaagc tctgcgctgg cattgatgaa  2340
actgccccccg ataagagaaa ggacgtggaa aaggagatgg ctgaaagagc caaggagagc  2400
attgacagcc tcgagagcgc caaccccaag ctgtatgcca attacatcaa atacagcgac  2460
gagaagaaag ccgaggagtt caccaggcag attaacaggg agaaggccaa aaccgccctg  2520
aacgcctacc tgaggaacac caagtggaat gtgatcatca gggaggacct cctgagaatt  2580
gacaacaaga catgtaccct gttcgcaaac aaggccgtcg ccctggaagt ggccaggtat  2640
gtccacgcct atatcaacga cattgccgag gtcaattcct acttccaact gtaccattac  2700
atcatgcaga gaattatcat gaatgagagg tacgagaaaa gcagcggaaa ggtgtccgag  2760
tacttcgacg ctgtgaatga cgagaagaag tacaacgata ggctcctgaa actgctgtgt  2820
gtgcctttcg gctactgtat ccccaggttt aagaacctga gcatcgaggc cctgttcgat  2880
aggaacgagg ccgccaagtt cgacaaggag aaaaagaagg tgtccggcaa ttccggatcc  2940
gga                                                                2943
```

```
SEQ ID NO: 66          moltype = AA  length = 981
FEATURE                Location/Qualifiers
REGION                 1..981
                       note = RfxCas13d-SV40NLS amino acid sequence
source                 1..981
                       mol_type = protein
                       organism = synthetic construct
SEQUENCE: 66
MSPKKKRKVE ASIEKKKSFA KGMGVKSTLV SGSKVYMTTF AEGSDARLEK IVEGDSIRSV  60
NEGEAFSAEM ADKNAGYKIG NAKFSHPKGY AVVANNPLYT GPVQQDMLGL KETLEKRYFG  120
ESADGNDNIC IQVIHNILDI EKILAEYITN AAYAVNNISG LDKDIIGFGK FSTVYTYDEF  180
KDPEHHRAAF NNNDKLINAI KAQYDEFDNF LDNPRLGYFG QAFFSKEGRN YIINYGNECY  240
DILALLSGLA HWVVANNEEE SRISRTWLYN LDKNLDNEYI STLNYLYDRI TNELTNSFSK  300
NSAANVNYIA ETLGINPAEF AEQYFRFSIM KEQKNLGFNI TKLREVMLDR KDMSEIRKNH  360
KVFDSIRTKV YTMMDFVIYR YYIEEDAKVA AANKSLPDNE KSLSEKDIFV INLRGSFNDD  420
QKDALYYDEA NRIWRKLENI MHNIKEFRGN KTREYKKKDA PRLPRILPAG RDVSAFSKLM  480
YALTMFLDGK EINDLLTTLI NKFDNIQSFL KVMPLIGVNA KFVEEYAFFK DSAKIADELR  540
LIKSFARMGE PIADARRAMY IDAIRILGTN LSYDELKALA DTFSLDENGN KLKKGKHGMR  600
NFIINNVISN KRFHYLIRYG DPAHLHEIAK NEAVVKFVLG RIADIQKKQG QNGKNQIDRY  660
YETCIGKDKG KSVSEKVDAL TKIITGMNYD QFDKKRSVIE DTGRENAERE KFKKIISLYL  720
TVIYHILKNI VNINARYVIG FHCVERDAQL YKEKGYDINL KKLEEKGFSS VTKLCAGIDE  780
TAPDKRKDVE KEMAERAKES IDSLESANPK LYANYIKYSD EKKAEEFTRQ INREKAKTAL  840
NAYLRNTKWN VIIREDLLRI DNKTCTLFAN KAVALEVARY VHAYINDIAE VNSYFQLYHY  900
IMQRIIMNER YEKSSGKVSE YFDAVNDEKK YNDRLLKLLC VPFGYCIPRF KNLSIEALFD  960
RNEAAKFDKE KKKVSGNSGS G                                            981
```

```
SEQ ID NO: 67          moltype = DNA  length = 30
FEATURE                Location/Qualifiers
misc_feature           1..30
                       note = RfxCas13d direct repeat
source                 1..30
                       mol_type = other DNA
                       organism = synthetic construct
SEQUENCE: 67
aacccctacc aactggtcgg ggtttgaaac                                   30
```

```
SEQ ID NO: 68          moltype = DNA  length = 24
FEATURE                Location/Qualifiers
misc_feature           1..24
                       note = SV40 Nuclear Localization Signaling nucleic acid
                        sequence
source                 1..24
```

-continued

```
                        mol_type = other DNA
                        organism = synthetic construct
SEQUENCE: 68
ccaaagaaga agcggaaggt cggt                                          24

SEQ ID NO: 69           moltype = AA  length = 7
FEATURE                 Location/Qualifiers
REGION                  1..7
                        note = SV40 Nuclear Localization Signaling amino acid
                         sequence
source                  1..7
                        mol_type = protein
                        organism = synthetic construct
SEQUENCE: 69
PKKKRKV                                                             7

SEQ ID NO: 70           moltype = DNA  length = 1479
FEATURE                 Location/Qualifiers
misc_feature            1..1479
                        note = CMV-BD-2xms2-PPT-exon-bGHpA repair template
source                  1..1479
                        mol_type = other DNA
                        organism = synthetic construct
SEQUENCE: 70
tagttattaa tagtaatcaa ttacggggtc attagttcat agcccatata tggagttccg  60
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta catcaagtgt atcatatgcc  240
aagtacgccc cctattgacg tcaatgacgg taaatggccc gcctggcatt atgcccagta  300
catgacctta tgggactttc ctacttggca gtacatctac gtattagtca tcgctattac  360
catggtgatg cggttttggc agtacatcaa tgggcgtgga tagcggtttg actcacgggg  420
atttccaagt ctccacccca ttgacgtcaa tgggagtttg ttttggcacc aaaatcaacg  480
ggactttcca aaatgtcgta acaactccgc cccattgacg caaatgggcg gtaggcgtgt  540
acggtgggag gtctatataa gcagagctgg tttagtgaac cgtcggatct tccatttcgg  600
gtgtcgtgac gtacgaatac gatctagacc ctgcatcctc tctgggacac tcaacaccct  660
cacggacagc ccgaattcga cccaagctga cgggagcaca tgaggatcac ccatgtgcca  720
cgagcgacat gaggatcacc catgtcgctt tcactagtct gtggtgtgat atccatggcg  780
gcctacttat cctgtccctt ttttttccac aggagcgcac catcttcttc aaggacgacg  840
gcaactacaa gacccgcgcc gaggtgaagt tcgagggcga caccctggtg aaccgcatcg  900
agctgaaggg catcgacttc aaggaggacg gcaacatcct ggggcacaag ctggagtaca  960
actacaacag ccacaacgtc tatatcatgg ccgacaagca gaagaacggc atcaaggtga  1020
acttcaagat ccgccacaac atcgaggacg gcagcgtgca gctcgccgac cactaccagc  1080
agaacacccc catcggcgac ggccccgtgc tgctgcccga caaccactac ctgagcaccc  1140
agtccgccct gagcaaagac cccaacgaga agcgcgatca catggtcctg ctggagttcg  1200
tgaccgccgc cgggatcact ctcggcatgg acgagctgta caagtaacta gagctcgctg  1260
atcagcctcg actgtgcctt ctagttgcca gccatctgtt gtttgcccct cccccgtgcc  1320
ttccttgacc ctggaaggtg ccactcccac tgtcctttcc taataaaatg aggaaattgc  1380
atcgcattgt ctgagtaggt gtcattctat tctggggggt ggggtggggc aggacagcaa  1440
gggggaggat tgggaagaga atagcaggca tgctgggga                         1479

SEQ ID NO: 71           moltype = DNA  length = 3357
FEATURE                 Location/Qualifiers
misc_feature            1..3357
                        note = PinCas13b nucleic acid sequence
source                  1..3357
                        mol_type = other DNA
                        organism = synthetic construct
SEQUENCE: 71
atgaccgagc agaacgagaa gccctacaac ggcacctact acaccctgga agataagcac  60
ttctgggccg cctttctgaa cctggccaga cacaacgcct acatcacact ggcccacatc  120
gacagacagc tggcctacag caaggccgac atcaccaacg acgaggacat cctgttcttc  180
aaaggccagt ggaagaacct ggacaacgac ctggaacgga aggccagact gagaagcctg  240
atcctgaagc acttcagctt tctggaaggc gccgcttacg gcaagaagct gtttgagtct  300
cagagcagcg gcaacaagag cagcaagaag aaagagctgt ccaagaaaga gaaagaggaa  360
ctgcaggcca acgctctgag cctggacaat ctgaagtcta tcctgttcga cttcctgcag  420
aagctgaagg acttccggaa ctactacagc cactacagac accccgagag cagcgagctg  480
cctctgttcg atggcaacat gctgcagcgg ctgtacaacg tgttcgacgt gtccgtgcag  540
cgcgtgaaga gagatcacga gcacaacgac aaggtggacc ctcaccggca cttcaatcac  600
ctcgtgcgga agggcaagaa ggataagtac ggcaacaacg ataacccgtt cttcaagcac  660
cacttcgtgg accgcgaggg cacagtgaca gaagccggac tgctgttctt cgtgtccctg  720
ttcctggaaa agcgggacgc catctggatg cagaagaaga tccggggctt taaaggcggc  780
accgaggcct accagcagat gaccaatgag gtgttctgcc gcagccggat cagcctgcct  840
aagctgaagc tggaaagcct gagaaccgac gactggatgc tgctggacat gctgaacgaa  900
ctcgtgcggt gccacaagag cctgtacgat agactgagag aagaggaccg ggccagattc  960
agagtgcccg tggatatcct gagcgacgag gatgataccg acggcaccga agaggatccc  1020
ttcaagaaca ctctcgtgcg gcaccaggac agattccctt acttcgccct gcggtacttc  1080
gacctgaaga aggtgttcac cagcctgcgg ttccacatcg atctgggcac ctaccacttc  1140
gccatctaca agaagaacat cggcgagcag cccgaggaca gacacctgac cagaaacctg  1200
tacggcttcg gccggatcca ggacttcgcc gaagaacaca gacccgagga atggaagcgg  1260
```

-continued

```
ctcgtcagag atctggacta cttcgagaca ggcgacaagc cttacatcac ccagaccaca  1320
cctcactacc acatcgagaa gggaaagatc ggcctgagat tcgtgcccga gggacagcat  1380
ctttggccct ctccagaagt gggcgccacc agaacaggca gatctaagta cgcccaggac  1440
aagagactga ccgccgaggc ctttctgtct gtgcacgagc tgatgcctat gatgttctac  1500
tacttcctgc tgcgcgagaa gtacagcgag gaagtgtctg ccgagaaggt gcagggcaga  1560
atcaagcgcg tgatcgagga tgtgtacgcc gtgtacgatg ccttcgccag ggacgagatc  1620
aacaccagag atgagctgga tgcctgcctg gccgacaagg gcattagaag aggccatctg  1680
ccaagacaga tgatcgccat cctgagccaa gagcacaagg acatggaaga gaaagtgcgg  1740
aagaaactgc aagagatgat tgccgacacc gaccaccggc tggatatgct ggatagacag  1800
accgaccgga agatcagaat cggccggaaa aatgccggcc tgccaaagtc tggcgtggtg  1860
gctgattggc tcgtgcggga catgatgaga ttccagcctg tggccaagga caccagcggc  1920
aagcctctga acaactccaa ggccaacagc accgagtacc ggatgctgca gagagccctg  1980
gctctgtttg gaggcgagaa agagaggctg accccatact tccggcagat gaatctgacc  2040
ggcggaaaca accctcatcc ttttctgcac gaaactcgct gggagagcca caccaatatc  2100
ctgtccttct accggtccta cctggaagcc cggaaggctt tcctgcagtc catcggcaga  2160
tccgacagag tggaaaacca ccggtttctg ctgctgaaag agcccaagac cgacaggcag  2220
actctggtgg ctggatggaa gggcgagttc catctgccta gaggcatctt tacagaggcc  2280
gtgcgcgact gcctgatcga gatgggctat gatgaagtgg gcagctacaa agaagtggga  2340
ttcatggcca aggccgtgcc tctgtacttt gagagagcca gcaaggaccg ggtgcagccc  2400
ttctacgact accccttcaa cgtgggcaac agcctgaagc ctaagaaggg cagattcctg  2460
tccaaagaga agcgggccga agagtgggag agcggcaaag agagattccg gctggccaag  2520
ctgaagaaag aaatcctcga agccaaagag cacccctacc acgacttcaa gagctggcag  2580
aagttcgagc gcgagctgag actggtcaag aaccaggaca tcatcacctg gatgatgtgc  2640
cgggacctga tggaagaaaa caaagtggaa ggcctggata caggcaccct gtacctgaag  2700
gacatcagga ccgacgtgca agagcagggc agcctgaacg tgctgaacag agtgaagccc  2760
atgagactgc ccgtggtggt gtacagagcc gatagcagag gccacgtgca caaagaacag  2820
gcccctctgg ccaccgtgta catcgaggaa agagacacca agctgctgaa gcagggcaac  2880
ttcaagtcct tcgtgaagga cagacggctg aatggcctgt tcagcttcgt ggatactggc  2940
gccctggcca tggaacagta ccccatctct aaactgcgcg tggaatacga gctggccaaa  3000
taccagaccg ccagagtgtg cgccttcgag cagacactgg aactggaaga gagcctgctg  3060
acccggtatc ctcatctgcc cgacaagaac tttcggaaga tgctcgaatc ttggagcgac  3120
cctctgctgg ataagtggcc tgacctgcac ggaaatgtgc ggctgctgat cgccgtgcgg  3180
aatgccttta gccacaatca gtaccctatg tacgacgaga cactgtttag ctccatccgg  3240
aagtacgacc ctagcagccc tgacgccatt gaggaacgga tgggcctgaa tatcgcccac  3300
agactgtctg aggaagtgaa gcaggccaaa gaaatggtgg aacggatcat tcaggcc     3357
```

```
SEQ ID NO: 72          moltype = AA  length = 1119
FEATURE                Location/Qualifiers
REGION                 1..1119
                       note = PinCas13b amino acid sequence
source                 1..1119
                       mol_type = protein
                       organism = synthetic construct
SEQUENCE: 72
MTEQNEKPYN GTYYTLEDKH FWAAFLNLAR HNAYITLAHI DRQLAYSKAD ITNDEDILFF  60
KGQWKNLDND LERKARLRSL ILKHFSFLEG AAYGKKLFES QSSGNKSSKK KELSKKEKEE  120
LQANALSLDN LKSILFDFLQ KLKDFRNYYS HYRHPESSEL PLFDGNMLQR LYNVFDVSVQ  180
RVKRDHEHND KVDPHRHFNH LVRKGKKDKY GNNDNPFFKH HFVDREGTVT EAGLLFFVSL  240
FLEKRDAIWM QKKIRGFKGG TEAYQQMTNE VFCRSRISLP KLKLESLRTD DWMLLDMLNE  300
LVRCHKSLYD RLREEDRARF RVPVDILSDE DDTDGTEEDP FKNTLVRHQD RFPYFALRYF  360
DLKKVFTSLR FHIDLGTYHF AIYKKNIGEQ PEDRHLTRNL YGFGRIQDFA EEHRPEEWKR  420
LVRDLDYFET GDKPYITQTT PHYHIEKGKI GLRFVPEGQH LWPSPEVGAT RTGRSKYAQD  480
KRLTAEAFLS VHELMPMMFY YFLLREKYSE EVSAEKVQGR IKRVIEDVYA VYDAFARDEI  540
NTRDELDACL ADKGIRRGHL PRQMIAILSQ EHKDMEEKVR KKLQEMIADT DHRLDMLDRQ  600
TDRKIRIGRK NAGLPKSGVV ADWLVRDMMR FQPVAKDTSG KPLNNSKANS TEYRMLQRAL  660
ALFGGEKERL TPYFRQMNLT GGNNPHPFLH ETRWESHTNI LSFYRSYLEA RKAFLQSIGR  720
SDRVENHRFL LLKEPKTDRQ TLVAGWKGEF HLPRGIFTEA VRDCLIEMGY DEVGSYKEVG  780
FMAKAVPLYF ERASKDRVQP FYDYPFNVGN SLKPKKGRFL SKEKRAEEWE SGKERFRLAK  840
LKKEILEAKE HPYHDFKSWQ KFERELRLVK NQDIITWMMC RDLMEENKVE GLDTGTLYLK  900
DIRTDVQEQG SLNVLNRVKP MRLPVVVYRA DSRGHVHKEQ APLATVYIEE RDTKLLKQGN  960
FKSFVKDRRL NGLFSFVDTG ALAMEQYPIS KLRVEYELAK YQTARVCAFE QTLELEESLL  1020
TRYPHLPDKN FRKMLESWSD PLLDKWPDLH GNVRLLIAVR NAFSHNQYPM YDETLFSSIR  1080
KYDPSSPDAI EERMGLNIAH RLSEEVKQAK EMVERIIQA                        1119
```

```
SEQ ID NO: 73          moltype = DNA  length = 36
FEATURE                Location/Qualifiers
misc_feature           1..36
                       note = PinCas13b direct repeat
source                 1..36
                       mol_type = other DNA
                       organism = synthetic construct
SEQUENCE: 73
gttgcatctg cctgctgttt gcaaggtaaa aacaac                           36
```

```
SEQ ID NO: 74          moltype = DNA  length = 3579
FEATURE                Location/Qualifiers
misc_feature           1..3579
                       note = BzoCas13b nucleic acid sequence
source                 1..3579
```

-continued

```
                    mol_type = other DNA
                    organism = synthetic construct
SEQUENCE: 74
atggagaata ccgactccgt gttccgggag ctgggcaaga gactgaaggg caaggagtac  60
acatctgaga acttctttga cgccatcttt aaggagaata tctctctggt ggagtacgag  120
cggtatgtga agctgctgag cgattatttc cccatggccc ggctgctgga caagaaggag  180
gtgcctatca aggagagaaa ggagaacttc aagaagaact tcaagggcat catcaaggcc  240
gtgcgggatc tgagaaactt ttacacccac aaggagcacg gcgaggtgga gatcacagac  300
gagatcttcg gcgtgctgga tgagatgctg aagtccaccg tgctgacagt gaagaagaag  360
aaggtgaaaa ccgacaagac aaaggagatc ctgaagaagt ctatcgagaa gcagctggat  420
atcctgtgcc agaagaagct ggagtacctg agggacaccg cccgcaagat cgaggagaag  480
cggagaaacc agagggagag gggagagaag gagctggtgg cacctttaa gtattctgat  540
aagcgggacg acctgatcgc cgccatctac aatgacgcct tcgacgtgta tatcgacaag  600
aagaaggatt ccctgaagga gagctccaag gccaagtaca acacaaagtc tgaccctcag  660
caggaggagg gcgatctgaa gatcccaatc agcaagaatg gcgtggtgtt cctgctgtcc  720
ctgtttctga ccaagcagga gatccacgcc ttcaagagca agatcgccgg ctttaaggcc  780
acagtgatcg acgaggccac cgtgtccgag gccacagtgt ctcacggcaa gaacagcatc  840
tgtttcatgg ccacccacga gatctttagc cacctggcct acaagaagct gaagaggaag  900
gtgcgcacag ccgagatcaa ctacggcgag gccgagaatg ccgagcagct gtccgtgtat  960
gccaaggaga cactgatgat gcagatgctg gacgagctgt ctaaggtgcc tgatgtggtg  1020
taccagaacc tgagcgagga cgtgcagaaa accttcatcg aggactggaa tgagtatctg  1080
aaggagaaca atggcgacgt gggcacaatg gaggaggagc aggtcatcca cccagtgatc  1140
cggaagagat acgaggataa gttcaactat tttgccatca ggttcctgga cgagttcgcc  1200
cagtttccta ccctgcgctt tcaggtgcac ctgggcaact acctgcacga ttcccggcca  1260
aaggagaatc tgatctctga caggcgcatc aaggagaaga tcacagtgtt tggcagactg  1320
tccgagctgg agcacaagaa ggccctgttc atcaagaaca ccgagacaaa tgaggatagg  1380
gagcactact gggagatctt ccccaaccct aattatgact ttccaaagga gaacatctcc  1440
gtgaatgaca aggattttcc catcgccggc tctatcctgg atcgcgagaa gcagcctgtg  1500
gccggcaaga tcggcatcaa ggtgaagctg ctgaaccagc agtacgtgtc tgaggtggac  1560
aaggccgtga aggcccacca gctgaagcag cggaaggcct ctaagcccag catccagaat  1620
atcatcgagg agatcgtgcc catcaacgag agcaatccta aggaggcaat cgtgttcgga  1680
ggacagccta ccgcctacct gtctatgaac gatatccaca gcatcctgta tgagttcttt  1740
gacaagtggg agaagaagaa ggagaagctg gagaagaagg gcgagaagga gctgagaaag  1800
gagatcggca aggagctgga gaagaagatc gtgggcaaga tccaggccca gatccagcag  1860
atcatcgaca aggataccaa cgccaagatc ctgaagccct accaggacgg caatagcaca  1920
gccatcgata aggagaagct gatcaaggac ctgaagcagg agcagaacat cctgcagaag  1980
ctgaaggatg agcagaccgt gagggagaag gagtacaatg acttcatcgc ctatcaggat  2040
aagaaccgcg agatcaataa ggtgagggat cgcaaccaca agcagtacct gaaggacaat  2100
ctgaagagga agtatcctga ggccccagcc aggaaggagg tgctgtacta tcgcgagaag  2160
ggcaaggtgg ccgtgtggct ggccaacgat atcaagcggt tcatgcctac cgactttaag  2220
aatgagtgga agggcgagca gcactcccta ctgcagaagt ctctggccta ctatgagcag  2280
tgcaaggagg agctgaagaa cctgctgcca gagaaggtgt tccagcacct gccctttaag  2340
ctgggcggct acttccagca gaagtacctg tatcagtttt acacctgcta tctggacaag  2400
aggctggagt atatcagcgg cctggtgcag caggccgaga acttcaagtc cgagaataag  2460
gtgtttaaga aggtggagaa cgagtgtttc aagtttctga agaagcagaa ttacacacac  2520
aaggagctgg atgcccgggt gcagtccatc ctgggctatc caatcttcct ggagagaggc  2580
tttatggacg agaagcccac catcatcaag ggcaagacat tcaagggcaa cgaggccctg  2640
ttcgccgatt ggtttcgcta ctataaggag taccagaact tccagacctt ttacgacaca  2700
gagaattatc cactggtgga gctggagaag aagcaggccg atcggaagag aaagaccaag  2760
atctatcagc agaagaagaa tgacgtgttt acactgctga tggccaagca catcttcaag  2820
agcgtgttca agcaggacag catcgatcag ttctccctgg aggacctgta ccagagccgg  2880
gaggagagac tgggaaacca ggagagggca aggcagaccg gcgagaggaa cacaaattat  2940
atctggaata agaccgtgga cctgaagctg tgcgatggca agatcacagt ggagaacgtg  3000
aagctgaaga atgtgggcga tttcatcaag tacgagtatg accagcgggt gcaggccttt  3060
ctgaagtacg aggagaacat cgagtggcag gccttcctga tcaaggagag caaggaggag  3120
gagaattacc cctatgtggt ggagagagag atcgagcagt acgagaaggt gcggagagag  3180
gagctgctga aggaggtgca cctgatcgag gagtatatcc tggagaaggt gaaggataaa  3240
gaaatcctga agaagggcga caaccagaac ttcaagtact atatcctgaa cggcctgctg  3300
aagcagctga agaatgagga tgtggagtcc tacaaggtgt tcaacctgaa taccgagcca  3360
gaggatgtga acatcaatca gctgaagcag gaggccaccg acctggagca gaaggccttc  3420
gtgctgacat atatccggaa caagtttgcc cacaatcagc tgcccaagaa ggagttctgg  3480
gactactgtc aggagaagta tggcaagatc gagaaggaga aaacctacgc cgagtatttc  3540
gccgaggtgt ttaagaagga gaaggaggcc ctgatcaag                        3579

SEQ ID NO: 75       moltype = AA  length = 1193
FEATURE             Location/Qualifiers
REGION              1..1193
                    note = BzoCas13b amino acid sequence
source              1..1193
                    mol_type = protein
                    organism = synthetic construct
SEQUENCE: 75
MENTDSVFRE LGKRLKGKEY TSENFFDAIF KENISLVEYE RYVKLLSDYF PMARLLDKKE  60
VPIKERKENF KKNFKGIIKA VRDLRNFYTH KEHGEVEITD EIFGVLDEML KSTVLTVKKK  120
KVKTDKTKEI LKKSIEKQLD ILCQKKLEYL RDTARKIEEK RRNQRERGEK ELVAPFKYSD  180
KRDDLIAAIY NDAFDVYIDK KKDSLKESSK AKYNTKSDPQ QEEGDLKIPI SKNGVVFLLS  240
LFLTKQEIHA FKSKIAGFKA TVIDEATVSE ATVSHGKNSI CFMATHEIFS HLAYKKLKRK  300
VRTAEINYGE AENAEQLSVY AKETLMMQML DELSKVPDVV YQNLSEDVQK TFIEDWNEYL  360
KENNGDVGTM EEEQVIHPVI RKRYEDKFNY FAIRFLDEFA QFPTLRFQVH LGNYLHDSRP  420
```

-continued

```
KENLISDRRI KEKITVFGRL SELEHKKALF IKNTETNEDR EHYWEIFPNP NYDFPKENIS  480
VNDKDFPIAG SILDREKQPV AGKIGIKVKL LNQQYVSEVD KAVKAHQLKQ RKASKPSIQN  540
IIEEIVPINE SNPKEAIVFG GQPTAYLSMN DIHSILYEFF DKWEKKKEKL EKKGEKELRK  600
EIGKELEKKI VGKIQAQIQQ IIDKDTNAKI LKPYQDGNST AIDKEKLIKD LKQEQNILQK  660
LKDEQTVREK EYNDFIAYQD KNREINKVRD RNHKQYLKDN LKRKYPEAPA RKEVLYYREK  720
GKVAVWLAND IKRFMPTDFK NEWKGEQHSL LQKSLAYYEQ CKEELKNLLP EKVFQHLPFK  780
LGGYFQQKYL YQFYTCYLDK RLEYISGLVQ QAENFKSENK VFKKVENECF KFLKKQNYTH  840
KELDARVQSI LGYPIFLERG FMDEKPTIIK GKTFKGNEAL FADWFRYYKE YQNFQTFYDT  900
ENYPLVELEK KQADRKRKTK IYQQKKNDVF TLLMAKHIFK SVFKQDSIDQ FSLEDLYQSR  960
EERLGNQERA RQTGERNTNY IWNKTVDLKL CDGKITVENV KLKNVGDFIK YEYDQRVQAF  1020
LKYEENIEWQ AFLIKESKEE ENYPYVVERE IEQYEKVRRE ELLKEVHLIE EYILEKVKDK  1080
EILKKGDNQN FKYYILNGLL KQLKNEDVES YKVFNLNTEP EDVNINQLKQ EATDLEQKAF  1140
VLTYIRNKFA HNQLPKKEFW DYCQEKYGKI EKEKTYAEYF AEVFKKEKEA LIK         1193

SEQ ID NO: 76          moltype = DNA  length = 36
FEATURE                Location/Qualifiers
misc_feature           1..36
                       note = BzoCas13b direct repeat
source                 1..36
                       mol_type = other DNA
                       organism = synthetic construct
SEQUENCE: 76
gttggaactg ctctcatttt ggagggtaat cacaac                            36

SEQ ID NO: 77          moltype = DNA  length = 3381
FEATURE                Location/Qualifiers
misc_feature           1..3381
                       note = PbuCas13b nucleic acid sequence
source                 1..3381
                       mol_type = other DNA
                       organism = synthetic construct
SEQUENCE: 77
atgcagaagc aggacaagct gttcgtggat aggaagaaga acgccatctt cgcctttccc  60
aagtacatca ccatcatgga gaataaggag aagcccgagc ctatctacta tgagctgaca  120
gacaagcact tctgggccgc ctttctgaac ctggcccgcc acaacgtgta taccacaatc  180
aaccacatca atcggagact ggagatcgcc gagctgaagg acgatggcta tatgatgggc  240
atcaagggca gctggaacga gcaggccaag aagctggaca agaaggtgcg gctgagagat  300
ctgatcatga agcacttccc ttttctggag gccgccgcct acgagatgac caatagcaag  360
tccccaaaca ataaggagca gagggagaag gagcagtctg aggccctgag cctgaacaat  420
ctgaagaacg tgctgttcat ctttctggag aagctgcagg tgctgcgcaa ttactatagc  480
cactacaagt attctgagga gagcccaaag cccatcttcg agacatccct gctgaagaac  540
atgtataagg tgtttgacgc caatgtgagg ctggtgaagc gcgattatat gcaccacgag  600
aacatcgaca tgcagagaga tttcacccac ctgaatcgga agaagcaagt gggcagaaca  660
aagaacatca tcgactcccc taatttccac taccactttg ccgataagga gggcaacatg  720
accatcgccg gcctgctgtt cttcgtgagc ctgttcctgg acaagaagga tgccatctgg  780
atgcagaaga agctgaaggg cttcaaggat ggcaggaacc tgcgcgagca gatgaccaat  840
gaggtgtttt gcaggtcccg catctctctg ccaaagctga agctggagaa cgtgcagaca  900
aaggactgga tgcagctgga tatgctgaat gagctggtga ggtgtcccaa gagcctgtac  960
gagcggctga gagagaagga ccgcgagtct ttcaaggtgc ctttcgatat ctttagcgac  1020
gattataacg ccgaggagga gccctttaag aataccctgg tgcggcacca ggacagattc  1080
ccttactttg tgctgaggta tttcgatctg aacgagatct tcgagcagct gcgctttcag  1140
atcgatctgg gcacctacca cttttccatc tataataaga ggatcggcga cgaggatgag  1200
gtgcgccacc tgacacacca cctgtacggc ttcgccagaa tccaggactt tgcccccccag  1260
aaccagtctg aggagtggag aaagctggtg aaggacctgg atcacttcga gacaagccag  1320
gagccctaca tcagcaagac agcccctcac tatcacctgg agaatgagaa gatcggcatc  1380
aagttctgca gcgcccacaa caatctgttt ccctccctgc agaccgacaa gacatgtaac  1440
ggccggtcca agttcaatct gggcacccag ttcacagccg aggcctttct gtctgtgcac  1500
gagctgctgc ctatgatgtt ttactatctg ctgctgacca aggactactc ccggaaggag  1560
tctgccgata aggtggaggg catcatcaga aaggagatct ctaacatcta cgccatctat  1620
gacgccttcg ccaacaatga gatcaatagc atcgccgatc tgaccaggcg cctgcagaac  1680
acaaatatcc tgcagggcca cctgccaaag cagatgatca gcatcctgaa gggcaggcag  1740
aaggatatgg gcaaggaggc cgagcgcaag atcggcgaga tgatcgacga tacccagcgg  1800
agactggacc tgctgtgcaa gcagacaaac cagaagatca ggatcggcaa gcgcaatgcc  1860
ggcctgctga agtccggcaa gatcgccgac tggctggtga acgatatgat gcggttccag  1920
cctgtgcaga aggatcagaa caatatccca atcaacaata gcaaggccaa ctccaccgag  1980
taccggatgc tgcagagagc cctggccctg ttcggctccg agaacttccg gctgaaggcc  2040
tacttcaacc agatgaatct ggtgggcaac gacaatcctc acccatttct ggccgagaca  2100
cagtgggagc accagacaaa catcctgtct ttctacagga attatctgga ggcccgcaag  2160
aagtacctga agggcctgaa gccccagaac tggaagcagt atcagcactt tctgatcctg  2220
aaggtgcaga aaaccaacag gaatacctg gtgacaggct ggaagaacag cttcaatctg  2280
ccacggggca tctttacaca gcccatcaga gagtggttcg agaagcacaa caattccaag  2340
cggatctacg accagatcct gtctttcgat agagtgggct ttgtggccaa ggccatccct  2400
ctgtactttg ccgaggagta taaggacaac gtgcagcctt tctacgatta tcccttcaac  2460
atcggcaatc ggctgaagcc taagaagaga cagttcctgg ataagaagga gcgcgtggag  2520
ctgtggcaga agaacaagga gctgtttaag aattacccat ctgagaagaa gaaaaccgac  2580
ctggcctatc tggatttcct gagctggaag aagtttgagc gggagctgag actgatcaag  2640
aaccaggaca tcgtgacctg gctgatgttc aaggagctgt ttaatatggc cacagtggag  2700
ggcctgaaga tcggcgagat ccacctgcgg gacatcgata ccaacacagc caatgaggag  2760
tccaacaata tcctgaacag aatcatgcca atgaagctgc ccgtgaaaac ctacgagaca  2820
```

-continued

```
gacaacaagg gcaatatcct gaaggagcgg ccactggcca ccttctatat cgaggagaca  2880
gagacaaagg tgctgaagca gggcaacttt aaggccctgg tgaaggacag gcgcctgaat  2940
ggcctgttct cttttgccga gacaacagat ctgaatctgg aggagcaccc catcagcaag  3000
ctgtccgtgg acctggagct gatcaagtac cagaccacaa gaatcagcat cttcgagatg  3060
accctgggcc tggagaagaa gctgatcgac aagtattcca ccctgccaac agattctttt  3120
aggaacatgc tggagcggtg gctgcagtgt aaggccaata ggcccgagct gaagaactac  3180
gtgaatagcc tgatcgccgt gcgcaacgcc ttctcccaca atcagtaccc tatgtatgat  3240
gccacactgt ttgccgaggt gaagaagttc accctgtttc caagcgtgga cacaaagaag  3300
atcgagctga acatcgcccc ccagctgctg gagatcgtgg gcaaggccat caaggagatc  3360
gagaagtccg agaacaagaa t                                            3381

SEQ ID NO: 78          moltype = AA  length = 1127
FEATURE                Location/Qualifiers
REGION                 1..1127
                       note = PbuCas13b amino acid sequence
source                 1..1127
                       mol_type = protein
                       organism = synthetic construct
SEQUENCE: 78
MQKQDKLFVD RKKNAIFAFP KYITIMENKE KPEPIYYELT DKHFWAAFLN LARHNVYTTI  60
NHINRRLEIA ELKDDGYMMG IKGSWNEQAK KLDKKVRLRD LIMKHFPFLE AAAYEMTNSK  120
SPNNKEQREK EQSEALSLNN LKNVLFIFLE KLQVLRNYYS HYKYSEESPK PIFETSLLKN  180
MYKVFDANVR LVKRDYMHHE NIDMQRDFTH LNRKKQVGRT KNIIDSPNFH YHFADKEGNM  240
TIAGLLFFVS LFLDKKDAIW MQKKLKGFKD GRNLREQMTN EVFCRSRISL PKLKLENVQT  300
KDWMQLDMLN ELVRCPKSLY ERLREKDRES FKVPFDIFSD DYNAEEEPFK NTLVRHQDRF  360
PYFVLRYFDL NEIFEQLRFQ IDLGTYHFSI YNKRIGDEDE VRHLTHHLYG FARIQDFAPQ  420
NQSEEWRKLV KDLDHFETSQ EPYISKTAPH YHLENEKIGI KFCSAHNNLF PSLQTDKTCN  480
GRSKFNLGTQ FTAEAFLSVH ELLPMMFYYL LLTKDYSRKE SADKVEGIIR KEISNIYAIY  540
DAFANNEINS IADLTRRLQN TNILQGHLPK QMISILKGRQ KDMGKEAERK IGEMIDDTQR  600
RLDLLCKQTN QKIRIGKRNA GLLKSGKIAD WLVNDMMRFQ PVQKDQNNIP INNSKANSTE  660
YRMLQRALAL FGSENFRLKA YFNQMNLVGN DNPHPFLAET QWEHQTNILS FYRNYLEARK  720
KYLKGLKPQN WKQYQHFLIL KVQKTNRNTL VTGWKNSFNL PRGIFTQPIR EWFEKHNNSK  780
RIYDQILSFD RVGFVAKAIP LYFAEEYKDN VQPFYDYPFN IGNRLKPKKR QFLDKKERVE  840
LWQKNKELFK NYPSEKKKTD LAYLDFLSWK KFERELRLIK NQDIVTWLMF KELFNMATVE  900
GLKIGEIHLR DIDTNTANEE SNNILNRIMP MKLPVKTYET DNKGNILKER PLATFYIEET  960
ETKVLKQGNF KALVKDRRLN GLFSFAETTD LNLEEHPISK LSVDLELIKY QTTRISIFEM  1020
TLGLEKKLID KYSTLPTDSF RNMLERWLQC KANRPELKNY VNSLIAVRNA FSHNQYPMYD  1080
ATLFAEVKKF TLFPSVDTKK IELNIAPQLL EIVGKAIKEI EKSENKN                 1127

SEQ ID NO: 79          moltype = DNA  length = 36
FEATURE                Location/Qualifiers
misc_feature           1..36
                       note = PbuCas13b direct repeat
source                 1..36
                       mol_type = other DNA
                       organism = synthetic construct
SEQUENCE: 79
gttgcatctg ccttcttttt gaaaggtaaa aacaac                            36

SEQ ID NO: 80          moltype = DNA  length = 2859
FEATURE                Location/Qualifiers
misc_feature           1..2859
                       note = AspCas13b nucleic acid sequence
source                 1..2859
                       mol_type = other DNA
                       organism = synthetic construct
SEQUENCE: 80
atgtccaatg agatcggcgc cttcagagag caccagtttg cctacgcccc aggaaacgag  60
aagcaggagg aggccacctt cgccacatac ttcaacctgg ccctgtctaa tgtggagggc  120
atgatgttcg gagaggtgga gtctaaccca gacaagatcg agaagagcct ggataccctg  180
ccccctgcca tcctgagaca gatcgcctcc tttatctggc tgtctaagga ggaccacccc  240
gataaggcct actccaccga ggaggtgaaa gtgatcgtga cagacctggt gcggagactg  300
tgcttctaca ggaattattt cagccactgt ttctatctgg atacacagta cttttattcc  360
gacgagctgg tggataccac agccatcggc gagaagctgc cttacaattt ccaccacttt  420
atcaccaaca gactgttcag gtatagcctg ccagagatca cactgtttcg ctggaacgag  480
ggcgagcgga agtacgagat cctgcgggac ggcctgatct tcttttgctg tctgttcctg  540
aagaggggac aggcagagcg gtttctgaat gagctgagat tctttaagag gaccgacgag  600
gagggccgca tcaagcggac catcttcaca aagtattgca caagagagtc tcacaagcac  660
atcggcatcg aggagcagga tttcctgatc tttcaggaca tcatcggcga tctgaatagg  720
gtgcctaagg tgtgcgacgg cgtggtggat ctgagcaagg agaacgagag atacatcaag  780
aacagggaga caagcaatga gtctgatgag aacaaggccc ggtatagact gctgatcagg  840
gagaaggaca agtttcccta ctatctgatg cgctacatcg tggatttcgg cgtgctgcct  900
tgcatcacct ttaagcagaa cgactacagc acaaaggagg gccggggcca gttccactat  960
caggatgcag cagtggcaca ggaggagagg tgttacaatt ttgtggtgcg caacggcaac  1020
gtgtactatt cctatatgcc tcaggcccag aacgtggtgc ggatcagcga gctgcagggc  1080
accatctccg tggaggagct gagaaatatg gtgtacgcct ctatcaatgg caaggacgtg  1140
aacaagagcg tggagcagta cctgtatcac ctgcacctgc tgtatgagaa gatcctgacc  1200
atctccggcc agacaatcaa ggagggccgg gtggacgtgg aggattacag acctctgctg  1260
gataagctgc tgctgcgccc agcctctaac ggcgaggagc tgaggcgcga gctgaggaag  1320
```

-continued

```
ctgctgccaa agcgcgtgtg cgacctgctg agcaatcggt tcgattgttc tgagggcgtg  1380
agcgccgtgg agaagaggct gaaggccatc ctgctgcgcc acgagcagct gctgctgagc  1440
cagaaccccg ccctgcacat cgacaagatc aagtccgtga tcgattacct gtatctgttc  1500
ttttctgacg atgagaagtt ccggcagcag cctaccgaga aggcccacag aggcctgaag  1560
gacgaggagt ttcagatgta ccactatctg gtgggcgact acgattctca cccactggcc  1620
ctgtggaagg agctggaggc cagcggccgg ctgaagccag agatgagaaa gctgaccagc  1680
gccacatccc tgcacggcct gtatatgctg tgcctgaagg gcaccgtgga gtggtgtcgg  1740
aagcagctga tgtccatcgg caagggcaca gccaaggtgg aggccatcgc cgacagagtg  1800
ggcctgaagc tgtacgataa gctgaaggag tatacccctg agcagctgga gagggaggtg  1860
aagctggtgg tcatgcacgg atacgctgcc gccgccaccc caaagccaaa ggcacaggca  1920
gcaatcccat ctaagctgac agagctgcgg ttctattcct ttctgggcaa gagagagatg  1980
tctttcgccg cctttatccg gcaggacaag aaggcccaga agctgtggct gagaaatttc  2040
tataccgtgg agaacatcaa gacactgcag aagaggcagg ctgccgccga cgcagcctgc  2100
aagaagctgt ataacctggt gggagaggtg gagcgggtgc acaccaacga taaggtgctg  2160
gtgctggtgg cccagaggta tcgcgagcgg ctgctgaatg tgggcagcaa gtgtgccgtg  2220
acactggaca accccgagag gcagcagaag ctggccgacg tgtacgaggt gcagaacgcc  2280
tggctgtcca tccgcttcga cgatctggac tttaccctga cacacgtgaa cctgtctaat  2340
ctgaggaagg cctacaatct gatcccccgc aagcacatcc tggccttcaa ggagtatctg  2400
gacaataggg tgaagcagaa gctgtgcgag gagtgtcgca acgtgcggag aaaggaggat  2460
ctgtgcacct gctgttcccc tcgctactct aatctgacaa gctggctgaa ggagaaccac  2520
tccgagagct ccatcgagag ggaggccgcc accatgatgc tgctggacgt ggagcgcaag  2580
ctgctgagct tcctgctgga tgagaggcgc aaggccatca tcgagtacgg caagttcatc  2640
ccattttccg ccctggtgaa ggagtgccgg ctggccgacg caggcctgtg cggcatcaga  2700
aatgacgtgc tgcacgataa cgtgatcagc tacgccgatg ccatcggcaa gctgagcgcc  2760
tattttccca aggaggcctc cgaggccgtg gagtacatcc ggagaacaaa ggaggtgcgg  2820
gagcagaggc gcgaggagct gatggccaac tctagccag                         2859
```

```
SEQ ID NO: 81          moltype = AA  length = 953
FEATURE                Location/Qualifiers
REGION                 1..953
                       note = AspCas13b amino acid sequence
source                 1..953
                       mol_type = protein
                       organism = synthetic construct
SEQUENCE: 81
MSNEIGAFRE HQFAYAPGNE KQEEATFATY FNLALSNVEG MMFGEVESNP DKIEKSLDTL  60
PPAILRQIAS FIWLSKEDHP DKAYSTEEVK VIVTDLVRRL CFYRNYFSHC FYLDTQYFYS  120
DELVDTTAIG EKLPYNFHHF ITNRLFRYSL PEITLFRWNE GERKYEILRD GLIFFCCLFL  180
KRGQAERFLN ELRFFKRTDE EGRIKRTIFT KYCTRESHKH IGIEEQDFLI FQDIIGDLNR  240
VPKVCDGVVD LSKENERYIK NRETSNESDE NKARYRLLIR EKDKFPYYLM RYIVDFGVLP  300
CITFKQNDYS TKEGRGQFHY QDAAVAQEER CYNFVVRNGN VYYSYMPQAQ NVVRISELQG  360
TISVEELRNM VYASINGKDV NKSVEQYLYH LHLLYEKILT ISGQTIKEGR VDVEDYRPLL  420
DKLLLRPASN GEELRRELRK LLPKRVCDLL SNRFDCSEGV SAVEKRLKAI LLRHEQLLLS  480
QNPALHIDKI KSVIDYLYLF FSDDEKFRQQ PTEKAHRGLK DEEFQMYHYL VGDYDSHPLA  540
LWKELEASGR LKPEMRKLTS ATSLHGLYML CLKGTVEWCR KQLMSIGKGT AKVEAIADRV  600
GLKLYDKLKE YTPEQLEREV KLVVMHGYAA AATPKPKAQA AIPSKLTELR FYSFLGKREM  660
SFAAFIRQDK KAQKLWLRNF YTVENIKTLQ KRQAAADAAC KKLYNLVGEV ERVHTNDKVL  720
VLVAQRYRER LLNVGSKCAV TLDNPERQQK LADVYEVQNA WLSIRFDDLD FTLTHVNLSN  780
LRKAYNLIPR KHILAFKEYL DNRVKQKLCE ECRNVRRKED LCTCCSPRYS NLTSWLKENH  840
SESSIEREAA TMMLLDVERK LLSFLLDERR KAIIEYGKFI PFSALVKECR LADAGLCGIR  900
NDVLHDNVIS YADAIGKLSA YFPKEASEAV EYIRRTKEVR EQRREELMAN SSQ          953
```

```
SEQ ID NO: 82          moltype = DNA  length = 36
FEATURE                Location/Qualifiers
misc_feature           1..36
                       note = AspCas13b direct repeat
source                 1..36
                       mol_type = other DNA
                       organism = synthetic construct
SEQUENCE: 82
gctgttatat ccttaccttt gtaagggaag tacagc                            36
```

```
SEQ ID NO: 83          moltype = DNA  length = 3966
FEATURE                Location/Qualifiers
misc_feature           1..3966
                       note = PsmCas13b nucleic acid sequence
source                 1..3966
                       mol_type = other DNA
                       organism = synthetic construct
SEQUENCE: 83
atgtctaagg agtgcaagaa gcagcgccag gagaagaagc ggagactgca gaaggccaat  60
ttctccatct ctctgaccgg caagcacgtg ttcggcgcct actttaatat ggccagaaca  120
aactttgtga aaaccatcaa ctacatcctg cctatcgccg gcgtgagggg caactatagc  180
gagaatcaga tcaacaagat gctgcacgca ctgttcctga tccaggcagg acgcaatgag  240
gagctgacca cagagcagaa gcagtgggag aagaagctgc ggctgaaccc agagcagcag  300
accaagtttc agaagctgct gttcaagcac tttccagtgc tgggaccaat gatggcagac  360
gtggcagatc acaaggccta tctgaacaag aagaagagca ccgtgcagac agaggacgag  420
acattcgcca tgctgaaggg cgtgtccctg gccgactgcc tggatatcat ctgtctgatg  480
gccgataccc tgacagagtg tagaaacttc tacacacaca aggaccctta taacaagcca  540
```

-continued

```
agccagctgg ccgatcagta cctgcaccag gagatgatcg ccaagaagct ggacaaggtg  600
gtggtggcct ccaggcgcat cctgaaggat agggagggcc tgtctgtgaa tgaggtggag  660
ttcctgaccg gcatcgatca cctgcaccag gaggtgctga aggacgagtt cggcaacgcc  720
aaggtgaagg atggcaaagt gatgaaaacc ttcgtggagt acgacgactt ctacttcaag  780
atctccggca agcggctggt gaatggctac acagtgacca caaaggacga taagcccgtg  840
aatgtgaaca ccatgctgcc tgccctgtct gacttcggcc tgctgtactt ctgcgtgctg  900
tttctgagca agccctatgc caagctgttt atcgatgagg tgcgcctgtt cgagtactct  960
ccttttgacg ataaggagaa catgatcatg tctgagatgc tgagcatcta tcggatcaga  1020
acaccccggc tgcacaagat cgactcccac gattctaagg ccaccctggc catggacatc  1080
ttcggcgagc tgcggagatg tcctatggag ctgtataacc tgctggacaa gaacgccggc  1140
cagccattct ttcacgatga ggtgaagcac cccaaactctc acacccccga cgtgagcaag  1200
cggctgagat acgacgatcg ctttcctaca ctggccctgc ggtatatcga tgagacagag  1260
ctgttcaagc ggatcagatt tcagctgcag ctgggcagct tccgctacaa gttttatgat  1320
aaggagaatt gcatcgacgg ccgggtgaga gtgaggcgca tccagaagga gatcaacggc  1380
tacggcagaa tgcaggaggt ggccgacaag aggatggata agtggggcga cctgatccag  1440
aagagggagg agcgcagcgt gaagctggag cacgaggagc tgtatatcaa tctggaccag  1500
ttcctggagg acaccgccga ttccacacct tacgtgaccg atagacggcc cgcctataat  1560
atccacgcca accggatcgg cctgtactgg gaggactccc agaatcctaa gcagtacaag  1620
gtgtttgatg agaacggcat gtatatcccc gagctggtgg tgaccgagga caagaaggcc  1680
cctatcaaga tgccagcacc taggtgtgca ctgagcgtgt acgacctgcc agccatgctg  1740
ttctacgagt atctgcggga gcagcaggat aacgagtttc ccagcgccga gcaggtcatc  1800
atcgagtacg aggacgatta tcgcaagttc tttaaggccg tggccgaggg caagctgaag  1860
cccttcaagc ggcccaagga gttcagggac tttctgaaga aggagtaccc aaagctgcgg  1920
atggccgata tccccaagaa gctgcagctg tttctgtgca gccacggcct gtgctacaac  1980
aataagcccg agacagtgta tgagcggctg gacagactga ccctgcagca cctggaggag  2040
agagagctgc acatccagaa caggctggag cactaccaga aggacagaga tatgatcggc  2100
aataaggaca accagtatgg caagaagagc ttctccgatg tgcgccacgg cgccctggcc  2160
agatacctgg cacagagcat gatggagtgg cagcccacaa agctgaagga taaggagaag  2220
ggccacgaca agctgaccgg cctgaattat aacgtgctga cagcctacct ggcaacctat  2280
ggccacccac aggtgcctga ggagggcttc accccctagaa cactggagca ggtgctgatc  2340
aatgcccacc tgatcggcgg ctccaatcca caccccttta tcaacaaggt gctggccctg  2400
ggcaatagga acatcgagga gctgtacctg cactatctgg aggaggagct gaagcacatc  2460
aggtcccgca tccagtctct gagctccaac cctagcgaca aggccctgtc cgccctgcca  2520
ttcatccacc acgatcggat gagataccac gagcgcacca gcgaggagat gatggccctg  2580
gccgcacggt ataccacaat ccagctgcca gacggcctgt ttacacccta catcctggag  2640
atcctgcaga agcactatac cgagaacagc gatctgcaga acgccctgtc tcaggacgtg  2700
cctgtgaagc tgaatccaac ctgcaacgcc gcctacctga tcacactgtt ctatcagacc  2760
gtgctgaagg acaatgccca gcccttctac ctgtccgata agacctatac aagaaacaag  2820
gacggcgaga aggccgagtc tttcagcttt aagagggcct acgagctgtt ctctgtgctg  2880
aacaataaca agaaggacac attccccttt gagatgatcc ctctgtttct gaccagcgat  2940
gagatccagg agagactgtc cgccaagctg ctggacggcg atggcaatcc tgtgccagaa  3000
gtgggagaga agggcaagcc agccacagac agccagggca acaccatctg gaagaggcgc  3060
atctactccg aggtggacga ttatgccgag aagctgaccg accgcgatat gaagatctcc  3120
ttcaagggcg agtgggagaa gctgcctcgg tggaagcagg ataagatcat caagcggcgg  3180
gacgagacac ggcggcagat gcgggacgag ctgctgcaga ggatgccacg ctacatccgg  3240
gacatcaagg ataatgagag gacactgcgg agatataaga cccaggatat ggtgctgttc  3300
ctgctggccg agaagatgtt taccaatatc atctccgagc agtctagcga gttcaactgg  3360
aagcagatga ggctgtctaa ggtgtgcaac gaggccttcc tgagacagac cctgaccttc  3420
cgggtgcccg tgacagtggg cgagacaaca atctacgtgg agcaggagaa tatgtctctg  3480
aagaactacg gcgagttcta tcgctttctg acagacgatc ggctgatgag cctgctgaat  3540
aacatcgtgg agacactgaa gcccaatgag aacggcgacc tggtcatcag acacacagac  3600
ctgatgagcg agctggccgc ctacgaccag tataggtcta ccatcttcat gctgatccag  3660
agcatcgaga acctgatcat cacaaataac gccgtgctgg acgatccaga cgccgatggc  3720
ttctgggtga gagaggatct gcccaagagg aataactttg cctccctgct ggagctgatc  3780
aatcagctga ataacgtgga gctgaccgac gatgagcgca agctgctggt ggccatccgg  3840
aacgccttca gccacaattc ctacaacatc gatttttccc tgatcaagga cgtgaagcac  3900
ctgcccgagg tggccaaggg catcctgcag cacctgcagt ctatgctggg cgtggagatc  3960
accaag                                                             3966
```

```
SEQ ID NO: 84          moltype = AA  length = 1322
FEATURE                Location/Qualifiers
REGION                 1..1322
                       note = PsmCas13b amino acid sequence
source                 1..1322
                       mol_type = protein
                       organism = synthetic construct
SEQUENCE: 84
MSKECKKQRQ EKKRRLQKAN FSISLTGKHV FGAYFNMART NFVKTINYIL PIAGVRGNYS  60
ENQINKMLHA LFLIQAGRNE ELTTEQKQWE KKLRLNPEQQ TKFQKLLFKH FPVLGPMMAD  120
VADHKAYLNK KKSTVQTEDE TFAMLKGVSL ADCLDIICLM ADTLTECRNF YTHKDPYNKP  180
SQLADQYLHQ EMIAKKLDKV VVASRRILKD REGLSVNEVE FLTGIDHLHQ EVLKDEFGNA  240
KVKDGKVMKT FVEYDDFYFK ISGKRLVNGY TVTTKDDKPV NVNTMLPALS DFGLLYFCVL  300
FLSKPYAKLF IDEVRLFEYS PFDDKENMIM SEMLSIYRIR TPRLHKIDSH DSKATLAMDI  360
FGELRRCPME LYNLLDKNAG QPFFHDEVKH PNSHTPDVSK RLRYDDRFPT LALRYIDETE  420
LFKRIRFQLQ LGSFRYKFYD KENCIDGRVR VRRIQKEING YGRMQEVADK RMDKWGDLIQ  480
KREERSVKLE HEELYINLDQ FLEDTADSTP YVTDRRPAYN IHANRIGLYW EDSQNPKQYK  540
VFDENGMYIP ELVVTEDKKA PIKMPAPRCA LSVYDLPAML FYEYLREQQD NEFPSAEQVI  600
IEYEDDYRKF FKAVAEGKLK PFKRPKEFRD FLKKEYPKLR MADIPKKLQL FLCSHGLCYN  660
NKPETVYERL DRLTLQHLEE RELHIQNRLE HYQKDRDMIG NKDNQYGKKS FSDVRHGALA  720
```

-continued

```
RYLAQSMMEW QPTKLKDKEK GHDKLTGLNY NVLTAYLATY GHPQVPEEGF TPRTLEQVLI  780
NAHLIGGSNP HPFINKVLAL GNRNIEELYL HYLEEELKHI RSRIQSLSSN PSDKALSALP  840
FIHHDRMRYH ERTSEEMMAL AARYTTIQLP DGLFTPYILE ILQKHYTENS DLQNALSQDV  900
PVKLNPTCNA AYLITLFYQT VLKDNAQPFY LSDKTYTRNK DGEKAESFSF KRAYELFSVL  960
NNNKKDTFPF EMIPLPLTSD EIQERLSAKL LDGDGNPVPE VGEKGKPATD SQGNTIWKRR  1020
IYSEVDDYAE KLTDRDMKIS FKGEWEKLPR WKQDKIIKRR DETRRQMRDE LLQRMPRYIR  1080
DIKDNERTLR RYKTQDMVLF LLAEKMFTNI ISEQSSEFNW KQMRLSKVCN EAFLRQTLTF  1140
RVPVTVGETT IYVEQENMSL KNYGEFYRFL TDDRLMSLLN NIVETLKPNE NGDLVIRHTD  1200
LMSELAAYDQ YRSTIFMLIQ SIENLIITNN AVLDDPDADG FWVREDLPKR NNFASLLELI  1260
NQLNNVELTD DERKLLVAIR NAFSHNSYNI DFSLIKDVKH LPEVAKGILQ HLQSMLGVEI  1320
TK                                                                1322

SEQ ID NO: 85          moltype = DNA  length = 36
FEATURE                Location/Qualifiers
misc_feature           1..36
                       note = PsmCas13b direct repeat
source                 1..36
                       mol_type = other DNA
                       organism = synthetic construct
SEQUENCE: 85
gttgtagaag cttatcgttt ggataggtat gacaac                           36

SEQ ID NO: 86          moltype = DNA  length = 3285
FEATURE                Location/Qualifiers
misc_feature           1..3285
                       note = RanCas13b nucleic acid sequence
source                 1..3285
                       mol_type = other DNA
                       organism = synthetic construct
SEQUENCE: 86
atggagaagc ccctgctgcc taacgtgtat accctgaagc acaagttctt ttggggcgcc  60
ttcctgaata tcgcccggca caacgccttt atcaccatct gccacatcaa tgagcagctg  120
ggcctgaaaa cccccagcaa cgacgataag atcgtggacg tggtgtgcga gacatggaac  180
aatatcctga acaatgacca cgatctgctg aagaagtccc agctgaccga gctgatcctg  240
aagcacttcc cttttctgac agccatgtgc taccaccccc ctaagaagga gggcaagaag  300
aagggccacc agaaggagca gcagaaggag aaggagagcg aggcacagtc ccaggcagag  360
gccctgaacc catccaagct gatcgaggcc ctggagatcc tggtgaatca gctgcactct  420
ctgcggaact actatagcca ctataagcac aagaagcccg acgccgagaa ggatatcttc  480
aagcacctgt ataaggcctt cgacgcctct ctgagaatgg tgaaggagga ttataaggcc  540
cacttcaccg tgaatctgac aagggacttt gcccacctga accgcaaggg caagaacaag  600
caggacaatc ccgacttcaa cagatacaga ttcgagaagg atggcttctt taccgagtct  660
ggcctgctgt tctttacaaa tctgtttctg gacaagaggg atgcctattg gatgctgaag  720
aaggtgtccg gcttcaaggc ctctcacaag cagcgcgaga agatgaccac agaggtgttt  780
tgcaggagcc gcatcctgct gcccaagctg aggctggagt cccgctacga ccacaaccag  840
atgctgctgg atatgctgtc tgagctgagc agatgtccta agctgctgta tgagaagctg  900
agcgaggaga ataagaagca cttccaggtg gaggccgacg gctttctgga tgagatcgag  960
gaggagcaga acccattcaa ggacaccctg atccggcacc aggatagatt cccctacttt  1020
gccctgaggt atctggacct gaatgagtcc ttcaagtcta tccgctttca ggtggatctg  1080
ggcacatacc actattgtat ctacgacaag aagatcggcg atgagcagga gaagaggcac  1140
ctgacccgca cactgctgtc cttcggccgg ctgcaggact ttaccgagat caacagaccc  1200
caggagtgga aggccctgac caaggacctg gattacaagg agacatccaa tcagcctttc  1260
atctctaaga ccacaccaca ctatcacatc accgacaaca agatcggctt tcggctgggc  1320
acaagcaagg agctgtaccc ctccctggag atcaaggatg gcgccaatag aatcgccaag  1380
taccctata actccggctt cgtggcccac gcctttatct ctgtgcacga gctgctgcct  1440
ctgatgttct accagcacct gaccggcaag agcgaggacc tgctgaagga gacagtgcgg  1500
cacatccaga gaatctataa ggacttcgag gaggagcgga tcaataccat cgaggatctg  1560
gagaaggcaa accagggcag actgccactg ggagcctttc ccaagcagat gctgggcctg  1620
ctgcagaata agcagcctga tctgtccgag aaggccaaga tcaagatcga gaagctgatc  1680
gccgagacaa agctgctgtc tcacaggctg aacacaaagc tgaagagctc cccaaagctg  1740
ggcaagcgga gagagaagct gatcaagaca ggcgtgctgg ccgactggct ggtgaaggat  1800
ttcatgcgct ttcagcccgt ggcctacgac gcccagaatc agcctatcaa gtctagcaag  1860
gccaactcca ccgagttctg gtttatcagg cgcgccctgg ccctgtacgg aggagagaag  1920
aataggctgg agggctattt caagcagacc aacctgatcg gcaacacaaa tccacacccc  1980
ttcctgaaca agtttaattg gaaggcctgc aggaatctgg tggatttcta ccagcagtat  2040
ctggagcagc gcgagaagtt tctggaggcc atcaagaacc agccatggga gccctaccag  2100
tattgcctgc tgctgaagat ccctaaggag aacaggaaga atctggtgaa gggatgggag  2160
cagggaggaa tctctctgcc acggggcctg tttaccgagg ccatcagaga gacactgtct  2220
gaggacctga tgctgagcaa gccaatccgc aaggagatca agaagcacgg ccgggtgggc  2280
ttcatcagca gagccatcac cctgtacttt aaggagaagt atcaggataa gcaccagagc  2340
ttctacaatc tgtcctataa gctggaggca aaggcaccac tgctgaagcg ggaggagcac  2400
tacgagtatt ggcagcagaa caagcctcag tctccaaccg agagccagag gctggagctg  2460
cacacaagcg accgctggaa ggattacctg ctgtataaga gatggcagca cctggagaag  2520
aagctgcggc tgtaccggaa tcaggacgtg atgctgtggc tgatgaccct ggagctgaca  2580
aagaaccact tcaaggagct gaacctgaat tatcaccagc tgaagctgga gaatctggcc  2640
gtgaacgtgc aggaggccga tgccaagctg aaccctctga atcagaccct gcccatggtg  2700
ctgcctgtga aggtgtaccc tgccacagcc tttggcgagg tgcagtacca caagacccca  2760
atcaggacag tgtatatccg cgaggagcac accaaggccc tgaagatggg caacttcaag  2820
gccctggtga aggaccggag actgaatggc ctgttctctt ttatcaagga ggagaacgat  2880
acacagaagc acccaatcag ccagctgcgg ctgaggcgcg agctggagat ctaccagtct  2940
```

```
ctgagagtgg acgccttcaa ggagacactg agcctggagg agaagctgct gaataagcac  3000
acatccctgt cctctctgga gaacgagttt agggccctgc tggaggagtg gaagaaggag  3060
tatgccgcca gctccatggt gacagacgag cacatcgcct tcatcgccag cgtgcgcaat  3120
gccttctgcc acaaccagta ccccttctac aaggaggccc tgcacgcccc tatcccactg  3180
ttcaccgtgg cccagcccac cacagaggag aaggatggcc tgggaatcgc agaggccctg  3240
ctgaaggtgc tgagggagta ctgtgagatc gtgaagtccc agatc                  3285

SEQ ID NO: 87          moltype = AA  length = 1095
FEATURE                Location/Qualifiers
REGION                 1..1095
                       note = RanCas13b amino acid sequence
source                 1..1095
                       mol_type = protein
                       organism = synthetic construct
SEQUENCE: 87
MEKPLLPNVY TLKHKFFWGA FLNIARHNAF ITICHINEQL GLKTPSNDDK IVDVVCETWN  60
NILNNDHDLL KKSQLTELIL KHFPFLTAMC YHPPKKEGKK KGHQKEQQKE KESEAQSQAE  120
ALNPSKLIEA LEILVNQLHS LRNYYSHYKH KKPDAEKDIF KHLYKAFDAS LRMVKEDYKA  180
HFTVNLTRDF AHLNRKGKNK QDNPDFNRYR FEKDGFFTES GLLFFTNLFL DKRDAYWMLK  240
KVSGFKASHK QREKMTTEVF CRSRILLPKL RLESRYDHNQ MLLDMLSELS RCPKLLYEKL  300
SEENKKHFQV EADGFLDEIE EEQNPFKDTL IRHQDRFPYF ALRYLDLNES FKSIRFQVDL  360
GTYHYCIYDK KIGDEQEKRH LTRTLLSFGR LQDFTEINRP QEWKALTKDL DYKETSNQPF  420
ISKTTPHYHI TDNKIGFRLG TSKELYPSLE IKDGANRIAK YPYNSGFVAH AFISVHELLP  480
LMFYQHLTGK SEDLLKETVR HIQRIYKDFE EERINTIEDL EKANQGRLPL GAFPKQMLGL  540
LQNKQPDLSE KAKIKIEKLI AETKLLSHRL NTKLKSSPKL GKRREKLIKT GVLADWLVKD  600
FMRFQPVAYD AQNQPIKSSK ANSTEFWFIR RALALYGGEK NRLEGYFKQT NLIGNTNPHP  660
FLNKFNWKAC RNLVDFYQQY LEQREKFLEA IKNQPWEPYQ YCLLLKIPKE NRKNLVKGWE  720
QGGISLPRGL FTEAIRETLS EDLMLSKPIR KEIKKHGRVG FISRAITLYF KEKYQDKHQS  780
FYNLSYKLEA KAPLLKREEH YEYWQQNKPQ SPTESQRLEL HTSDRWKDYL LYKRWQHLEK  840
KLRLYRNQDV MLWLMTLELT KNHFKELNLN YHQLKLENLA VNVQEADAKL NPLNQTLPMV  900
LPVKVYPATA FGEVQYHKTP IRTVYIREEH TKALKMGNFK ALVKDRRLNG LFSFIKEEND  960
TQKHPISQLR LRRELEIYQS LRVDAFKETL SLEEKLLNKH TSLSSLENEF RALLEEWKKE  1020
YAASSMVTDE HIAFIASVRN AFCHNQYPFY KEALHAPIPL FTVAQPTTEE KDGLGIAEAL  1080
LKVLREYCEI VKSQI                                                   1095

SEQ ID NO: 88          moltype = DNA  length = 36
FEATURE                Location/Qualifiers
misc_feature           1..36
                       note = RanCas13b direct repeat
source                 1..36
                       mol_type = other DNA
                       organism = synthetic construct
SEQUENCE: 88
gttgggactg ctctcacttt gaagggtatt cacaac                            36

SEQ ID NO: 89          moltype = DNA  length = 3372
FEATURE                Location/Qualifiers
misc_feature           1..3372
                       note = PauCas13b nucleic acid sequence
source                 1..3372
                       mol_type = other DNA
                       organism = synthetic construct
SEQUENCE: 89
atggaggacg ataagaaaac cacaggcagc atctcctacg agctgaagga caagcacttc  60
tgggccgcct ttctgaacct ggcccgccac aacgtgtata tcaccatcaa ccacatcaat  120
aagctgctgg agatccggga gatcgacaac gatgagaagg tgctggacat caagaccctg  180
tggcagaagg gcaacaagga tctgaatcag aaggccaggc tgcgcgagct gatgacaaag  240
cacttcccct tcctggagac agccatctac acaaagaaca aggaggataa gaaggaggtg  300
aagcaggaga agcaggccga ggcccagtct ctggagagcc tgaaggactg cctgttcctg  360
tttctggata agctgcagga ggcccgcaat tactatagcc actacaagta ttccgagttc  420
tctaaggagc cagagtttga ggagggcctg ctggagaaga tgtataacat ctttggcaac  480
aatatccagc tggtcatcaa cgactatcag cacaacaagg atatcaatcc cgacgaggat  540
ttcaagcacc tggaccggaa gggccagttc aagtactcct ttgccgataa cgagggcaat  600
atcaccgagt ccggcctgct gttcttcgtg agcctgttcc tggagaagaa ggacgccatc  660
tggatgcagc agaagctgaa cggctttaag gataacctgg agaacaagaa gaagatgaca  720
cacgaggtgt tctgccggag cagaatcctg atgcccaagc tgcgcctgga gagcacccag  780
acacaggact ggattctgct ggacatgctg aatgagctga tccggtgtcc taagtccctg  840
tacgagagac tgcagggcga cgatagggag aagttcaagg tgccatttga ccccgccgac  900
gaggattaca acgccgagca ggagcctttt aagaataccc tgatcagaca ccaggacagg  960
ttcccatact ttgtgctgag atacttcgat tacaacgaga tcttcaagaa tctgaggttt  1020
cagatcgacc tgggcaccta ccacttctct atctataaga agctgatcgg cggccagaag  1080
gaggatcgcc acctgacaca caagctgtac ggcttcgagc gcatccagga gtttgccaag  1140
cagaaccggc ctgacgagtg gaaggccatc gtgaaggacc tggataccta cgagacaagc  1200
aacaagcggt atatctccga gacaacacct cactatcacc tggagaatca gaagatcggc  1260
atcaggtttc gcaacggcaa taaggagatc tggcccagcc tgaaaaccaa cgacgagaac  1320
aatgagaagt ctaagtacaa gctggataag cagtatcagg ccgaggcctt tctgtccgtg  1380
cacgagctgc tgcccatgat gttctactat ctgctgctga agaaggagaa gcctaacaat  1440
gacgagatca atgcctctat cgtggagggc ttcatcaagc gggagatcag aaacatcttc  1500
aagctgtacg acgcctttgc caatggcgag atcaacaata tcgacgatct ggagaagtat  1560
```

-continued

```
tgcgccgata agggcatccc caagagacac ctgcctaagc agatggtggc catcctgtac  1620
gacgagcaca aggatatggt gaaggaggcc aagaggaagc agaaggagat ggtgaaggat  1680
accaagaagc tgctggccac cctggagaag cagacacaga aggagaagga ggacgatggc  1740
agaaacgtga agctgctgaa gagcggcgag atcgccagat ggctggtgaa tgacatgatg  1800
aggttccagc ccgtgcagaa ggataacgag ggcaagcctc tgaacaatag caaggccaat  1860
tccaccgagt accagatgct gcagcggagc ctggccctgt ataacaatga ggagaagccc  1920
acaaggtatt ttcgccaggt gaacctgatc gagagcaaca atccccaccc tttcctgaag  1980
tggaccaagt gggaggagtg taacaacatc ctgacctttt actactctta cctgacaaag  2040
aagatcgagt tcctgaacaa gctgaagcca gaggactgga agaagaatca gtattttctg  2100
aagctgatgg agcccaagac caacagagag acactggtgc agggctggaa gaacggcttt  2160
aatctgccta ggggcatctt cacagagcca atccgcgagt ggttcaagcg gcaccagaac  2220
aatagcaagg agtacgagaa ggtggaggcc ctggacagag tgggcctggt gaccaaagtg  2280
atcccccctgt tctttaagga ggagtacttc aaggataagg aggagaactt caaggaggac  2340
acacagaagg agatcaacga ttgcgtgcag ccattctaca attttcccta taacgtgggc  2400
aatatccaca agcctaagga gaaggacttt ctgcaccggg aggagagaat cgagctgtgg  2460
gacaagaaga aggataagtt caagggctac aaggagaaga tcaagagcaa gaagctgacc  2520
gagaaggaca aggaggagtt caggtcttat ctggagtttc agagctggaa caagttcgag  2580
agggagctgc gcctggtgcg gaatcaggat atcgtgacat ggctgctgtg caaggagctg  2640
atcgacaagc tgaagatcga tgagctgaac atcgaggagc tgaagaagct gagactgaac  2700
aatatcgaca ccgatacagc caagaaggag aagaacaata tcctgaatag agtgatgcct  2760
atggagctgc cagtgaccgt gtacgagatc gacgattccc acaagatcgt gaaggacaag  2820
ccactgcaca ccatctatat caaggaggcc gagacaaagc tgctgaagca gggcaacttc  2880
aaggccctgg tgaaggatcg gagactgaat ggcctgttca gcttcgtgaa aaccaacagc  2940
gaggccgaga gcaagcgcaa tcctatctcc aagctgcggg tggagtacga gctgggcgag  3000
tatcaggagg cccggatcga gatcatccag gacatgctgg ccctggagga gaagctgatc  3060
aacaagtaca aggatctgcc aacaaacaag ttttccgaga tgctgaacag ctggctggag  3120
ggcaaggacg aggccgataa ggcccgcttt cagaatgacg tggatttcct gatcgccgtg  3180
cggaacgcct tctcccacaa tcagtaccca atgcacaaca agatcgagtt tgccaatatc  3240
aagcccttca gcctgtatac cgccaacaat tccgaggaga agggcctggg catcgccaac  3300
cagctgaagg acaagaccaa ggagacaaca gataagatca agaagatcga gaagcccatc  3360
gagacaaagg ag                                                      3372
```

```
SEQ ID NO: 90          moltype = AA  length = 1124
FEATURE                Location/Qualifiers
REGION                 1..1124
                       note = PauCas13 amino acid sequence
source                 1..1124
                       mol_type = protein
                       organism = synthetic construct
SEQUENCE: 90
MEDDKKTTGS ISYELKDKHF WAAFLNLARH NVYITINHIN KLLEIREIDN DEKVLDIKTL  60
WQKGNKDLNQ KARLRELMTK HFPFLETAIY TKNKEDKKEV KQEKQAEAQS LESLKDCLFL  120
FLDKLQEARN YYSHYKYSEF SKEPEFEEGL LEKMYNIFGN NIQLVINDYQ HNKDINPDED  180
FKHLDRKGQF KYSFADNEGN ITESGLLFFV SLFLEKKDAI WMQQKLNGFK DNLENKKKMT  240
HEVFCRSRIL MPKLRLESTQ TQDWILLDML NELIRCPKSL YERLQGDDRE KFKVPFDPAD  300
EDYNAEQEPF KNTLIRHQDR FPYFVLRYFD YNEIFKNLRF QIDLGTYHFS IYKKLIGGQK  360
EDRHLTHKLY GFERIQEFAK QNRPDEWKAI VKDLDTYETS NKRYISETTP HYHLENQKIG  420
IRFRNGNKEI WPSLKTNDEN NEKSKYKLDK QYQAEAFLSV HELLPMMFYY LLLKKEKPNN  480
DEINASIVEG FIKREIRNIF KLYDAFANGE INNIDDLEKY CADKGIPKRH LPKQMVAILY  540
DEHKDMVKEA KRKQKEMVKD TKKLLATLEK QTQKEKEDDG RNVKLLKSGE IARWLVNDMM  600
RFQPVQKDNE GKPLNNSKAN STEYQMLQRS LALYNNEEKP TRYFRQVNLI ESNNPHPFLK  660
WTKWEECNNI LTFYYSYLTK KIEFLNKLKP EDWKKNQYFL KLMEPKTNRE TLVQGWKNGF  720
NLPRGIFTEP IREWFKRHQN NSKEYEKVEA LDRVGLVTKV IPLFFKEEYF KDKEENFKED  780
TQKEINDCVQ PFYNFPYNVG NIHKPKEKDF LHREERIELW DKKKDKFKGY KEKIKSKKLT  840
EKDKEEFRSY LEFQSWNKFE RELRLVRNQD IVTWLLCKEL IDKLKIDELN IEELKKLRLN  900
NIDTDTAKKE KNNILNRVMP MELPVTVYEI DDSHKIVKDK PLHTIYIKEA ETKLLKQGNF  960
KALVKDRRLN GLFSFVKTNS EAESKRNPIS KLRVEYELGE YQEARIEIIQ DMLALEEKLI  1020
NKYKDLPTNK FSEMLNSWLE GKDEADKARF QNDVDFLIAV RNAFSHNQYP MHNKIEFANI  1080
KPFSLYTANN SEEKGLGIAN QLKDKTKETT DKIKKIEKPI ETKE                  1124
```

```
SEQ ID NO: 91          moltype = DNA  length = 36
FEATURE                Location/Qualifiers
misc_feature           1..36
                       note = PauCas13b direct repeat
source                 1..36
                       mol_type = other DNA
                       organism = synthetic construct
SEQUENCE: 91
gttgtatctg ccttctgttt gaaaggtaaa aacaac                            36
```

```
SEQ ID NO: 92          moltype = DNA  length = 1422
FEATURE                Location/Qualifiers
misc_feature           1..1422
                       note = CMV-BD-2xms2-PPT-exon-MMP9_intron2-2xms2-BD-bGHpA
source                 1..1422
                       mol_type = other DNA
                       organism = synthetic construct
SEQUENCE: 92
tagttattaa tagtaatcaa ttacggggtc attagttcat agcccatata tggagttccg  60
```

```
cgttacataa cttacggtaa atggcccgcc tggctgaccg cccaacgacc cccgcccatt  120
gacgtcaata atgacgtatg ttcccatagt aacgccaata gggactttcc attgacgtca  180
atgggtggag tatttacggt aaactgccca cttggcagta catcaagtgt atcatatgcc  240
aagtacgccc cctattgacg tcaatgacgg taaatggccc gcctggcatt atgcccagta  300
catgacctta tgggactttc ctacttggca gtacatctac gtattagtca tcgctattac  360
catggtgatg cggttttggc agtacatcaa tgggcgtgga tagcggtttg actcacgggg  420
atttccaagt ctccacccca ttgacgtcaa tgggagtttg ttttggcacc aaaatcaacg  480
ggactttcca aaatgtcgta acaactccgc cccattgacg caaatgggcg gtaggcgtgt  540
acggtgggag gtctatataa gcagagctgg tttagtgaac cgtcggatct tccatttcgg  600
gtgtcgtgac gtacgaatac gatctagacc ctgcatcctc tctgggacac tcaacaccct  660
cacggacagc ccgaattcga cccaagctga cgggagcaca tgaggatcac ccatgtgcca  720
cgagcgacat gaggatcacc catgtcgctt tcactagtct gtggtgtgat atccatggcg  780
gcctacttat cctgtccctt ttttttccac aggagcgcac catcttcttc aaggacgacg  840
gcaactacaa gacccgcgcc gaggtgaagt tcgagggcga caccctggtg aaccgcatcg  900
agctgaaggg catcgacttc aaggaggacg gcaacatcct ggggcacaag ctggagtaca  960
actacaacag ccacaacgtc tatatcatgg ccgacaagca gaagaacggc atcaaggtga  1020
gccggggctg tgaaagctgc gggatggagc gagaaggcct gatctggctc ttgagcctgc  1080
aacggagcac atgaggatca cccatgtgcc acgagcgaca tgaggatcac ccatgtcgaa  1140
ttcgacccaa gctgactgac tgagacgagt taactgtacc gtctccgctt ctagagctcg  1200
ctgatcagcc tcgactgtgc cttctagttg ccagccatct gttgtttgcc cctcccccgt  1260
gccttccttg accctggaag gtgccactcc cactgtcctt tcctaataaa atgaggaaat  1320
tgcatcgcat tgtctgagta ggtgtcattc tattctgggg ggtggggtgg ggcaggacag  1380
caagggggag gattgggaag agaatagcag gcatgctggg ga                    1422
```

```
SEQ ID NO: 93          moltype = DNA  length = 5403
FEATURE                Location/Qualifiers
misc_feature           1..5403
                       note = PspCas13b-ABI1-2a-PYL1-MS2 nucleic acid sequence
source                 1..5403
                       mol_type = other DNA
                       organism = synthetic construct
SEQUENCE: 93
atgaacatcc ccgctctggt ggaaaaccag aagaagtact ttggcaccta cagcgtgatg  60
gccatgctga acgctcagac cgtgctggac cacatccaga aggtggccga tattgagggc  120
gagcagaacg agaacaacga gaatctgtgg tttcaccccg tgatgagcca cctgtacaac  180
gccaagaacg gctacgacaa gcagcccgag aaaaccatgt tcatcatcga gcggctgcag  240
agctacttcc cattcctgaa gatcatggcc gagaaccaga gagagtacag caacggcaag  300
tacaagcaga accgcgtgga agtgaacagc aacgacatct tcgaggtgct gaagcgcgcc  360
ttcggcgtgc tgaagatgta cagggacctg accaacgcat acaagaccta cgaggaaaag  420
ctgaacgacg gctgcgagtt cctgaccagc acagagcaac ctctgagcgg catgatcaac  480
aactactaca cagtggccct gcggaacatg aacgagagat acggctacaa gacagaggac  540
ctggccttca tccaggacaa gcggttcaag ttcgtgaagg acgcctacgg caagaaaaag  600
tcccaagtga ataccggatt cttcctgagc ctgcaggact acaacggcga cacacagaag  660
aagctgcacc tgagcggagt gggaatcgcc ctgctgatct gcctgttcct ggacaagcag  720
tacatcaaca tctttctgag caggctgccc atcttctcca gctacaatgc ccagagcgag  780
gaacggcgga tcatcatcag atccttcggc atcaacagca tcaagctgcc caaggaccgg  840
atccacagcg agaagtccaa caagagcgtg gccatggata tgctcaacga agtgaagcgg  900
tgccccgacg agctgttcac aacactgtct gccgagaagc agtcccggtt cagaatcatc  960
agcgacgacc acaatgaagt gctgatgaag cggagcagcg acagattcgt gcctctgctg  1020
ctgcagtata tcgattacgg caagctgttc gaccacatca ggttccacgt gaacatgggc  1080
aagctgagat acctgctgaa ggccgacaag acctgcatcg acggccagac cagagtcaga  1140
gtgatcgagc agcccctgaa cggcttcggc agactggaag aggccgagac aatgcggaag  1200
caagagaacg gcaccttcgg caacagcggc atccggatca gagacttcga gaacatgaag  1260
cgggacgacg ccaatcctgc caactatccc tacatcgtgg acacctacac acactacatc  1320
ctggaaaaca acaaggtcga gatgtttatc aacgacaaag aggacagcgc cccactgctg  1380
cccgtgatcg aggatgatag atacgtggtc aagacaatcc ccagctgccg gatgagcacc  1440
ctggaaattc cagccatggc cttccacatg tttctgttcg gcagcaagaa aaccgagaag  1500
ctgatcgtgg acgtgcacaa ccggtacaag agactgttcc aggccatgca gaaagaagaa  1560
gtgaccgccg agaatatcgc cagcttcgga atcgccgaga gcgacctgcc tcagaagatc  1620
ctggatctga tcagcggcaa tgcccacggc aaggatgtgg acgccttcat cagactgacc  1680
gtggacgaca tgctgaccga caccgagcgg agaatcaaga gattcaagga cgaccggaag  1740
tccattcgga gcgccgacaa caagatggga aagagaggct tcaagcagat ctccacaggc  1800
aagctggccg acttcctggc caaggacatc gtgctgttc agcccagcgt gaacgatggc  1860
gagaacaaga tcaccggcct gaactaccgg atcatgcaga gcgccattgc cgtgtacgat  1920
agcggcgacg attacgaggc caagcagcag ttcaagctga tgttcgagaa ggcccggctg  1980
atcggcaagg gcacaacaga gcctcatcca tttctgtaca aggtgttcgc ccgcagcatc  2040
cccgccaatg ccgtcgagtt ctacgagcgc tacctgatcg agcggaagtt ctacctgacc  2100
ggcctgtcca acgagatcaa gaaaggcaac agagtggatg tgcccttcat ccggcgggac  2160
cagaacaagt ggaaaacacc cgccatgaag accctgggca gaatctacag cgaggatctg  2220
cccgtggaac tgcccagaca gatgttcgac aatgagatca agtcccacct gaagtccctg  2280
ccacagatgg aaggcatcga cttcaacaat gccaacgtga cctatctgat cgccgagtac  2340
atgaagagag tgctggacga cgacttccag accttctacc agtggaaccg caactaccgg  2400
tacatggaca tgcttaaggg cgagtacgac agaaagggct ccctgcagca ctgcttcacc  2460
agcgtggaag agagagaagg cctctggaaa gagcgggcct ccagaacaga gcggtacaga  2520
aagcaggcca gcaacaagat ccgcagcaac cggcagatga gaaacgccag cagcgaagag  2580
atcgagacaa tcctggataa gcggctgagc aacagccgga acgagtacca gaaaagcgag  2640
aaagtgatcc ggcgctacag agtgcaggat gccctgctgt ttctgctggc caaaaagacc  2700
ctgaccgaac tggccgattt cgacggcgag aggttcaaac tgaaagaaat catgcccgac  2760
gccgagaagg gaatcctgag cgagatcatg cccatgagct tcaccttcga gaaaggcggc  2820
```

-continued

```
aagaagtaca ccatcaccag cgagggcatg aagctgaaga actacggcga cttctttgtg  2880
ctggctagcg acaagaggat cggcaacctg ctggaactcg tgggcagcga catcgtgtcc  2940
aaagaggata tcatggaaga gttcaacaaa tacgaccagt gcaggcccga gatcagctcc  3000
atcgtgttca acctggaaaa gtgggccttc gacacatacc ccgagctgtc tgccagagtg  3060
gaccgggaag agaaggtgga cttcaagagc atcctgaaaa tcctgctgaa caacaagaac  3120
atcaacaaag agcagagcga catcctgcgg aagatccgga acgccttcga tgcaaacaat  3180
taccccgaca aaggcgtggt ggaaatcaag gccctgcctg agatcgccat gagcatcaag  3240
aaggcctttg gggagtacgc catcatgaag ggaagcctgc aggcctatcc ctatgacgtg  3300
cccgattatg ccagcctggg cagcggctcc cccaagaaaa aacgcaaggt ggaagatcct  3360
aagaaaaagc ggaaagtgga cggcattggt agtgggagca acggaggtgg aggctctgga  3420
cctaggacgc gtgtgccttt gtatggtttt acttcgattt gtggaagaag acctgagatg  3480
gaagctgctg tttcgactat accaagattc cttcaatctt cctctggttc gatgttagat  3540
ggtcggtttg atcctcaatc cgccgctcat ttcttcggtg tttacgacgg ccatggcggt  3600
tctcaggtag cgaactattg tagagagagg atgcatttgg ctttggcgga ggagatagct  3660
aaggagaaac cgatgctctg cgatggtgat acgtggctgg agaagtggaa gaaagctctt  3720
ttcaactcgt tcctgagagt tgactcggag attgagtcag ttgcgccgga gacggttggg  3780
tcaacgtcgg tggttgccgt tgttttcccg tctcacatct tcgtcgctaa ctgcggtgac  3840
tctagagccg ttctttgccg cggcaaaact gcacttccat tatccgttga ccataaaccg  3900
gatagagaag atgaagctgc gaggattgaa gccgcaggag ggaaagtgat tcagtggaat  3960
ggagctcgtg ttttcggtgt tctcgccatg tcgagatcca ttggcgatag atacttgaaa  4020
ccatccatca ttcctgatcc ggaagtgacg gctgtgaaga gagtaaaaga agatgattgt  4080
ctgattttgg cgagtgacgg ggtttgggat gtaatgacgg atgaagaagc gtgtgagatg  4140
gcaaggaagc ggattctctt gtggcacaag aaaaacgcgg tggctgggga tgcatcgttg  4200
ctcgcggatg agcggagaaa ggaagggaaa gatcctgcgg cgatgtccgc ggctgagtat  4260
ttgtcaaagc tggcgataca gagaggaagc aaagacaaca taagtgtggt ggtggttgat  4320
ttgaagggat ccggcgcaac aaacttctct ctgctgaaac aagccggaga tgtcgaagag  4380
aatcctggac cgatgggtgg gggcgcgcca actcaagacg aattcaccca actctcccaa  4440
tcaatcgccg agttccacac gtaccaactc ggtaacggcc gttgctcatc tctcctagct  4500
cagcgaatcc acgcgccgcc ggaaacagta tggtccgtgg tgagacgttt cgataggcca  4560
cagatttaca aacacttcat caaaagctgt aacgtgagtg aagatttcga gatgcgagtg  4620
ggatgcacgc gcgacgtgaa cgtgataagt ggattaccgg cgaatacgtc tcgagagaga  4680
ttagatctgt tggacgatga tcggagagtg actgggttta gtataaccgg tggtgaacat  4740
aggctgagga attataaatc ggttacgacg gttcatagat ttgagaaaga agaagaagaa  4800
gaaaggatct ggaccgttgt tttggaatct tatgttgttg atgtaccgga aggtaattcg  4860
gaggaagata cgagattgtt tgctgatacg gttattagat tgaatcttca gaaacttgct  4920
tcgatcactg aagctatgaa cgaattctca agcgctgcag gtactagtcc aaagaagaag  4980
cggaaggtcg gtggatccgg aggaggtgga agcatggctt caaactttac tcagttcgtg  5040
ctcgtggaca atggtgggac aggggatgtg acagtggctc cttctaattt cgctaatggg  5100
gtggcagagt ggatcagctc caactcacgg agccaggcct acaaggtgac atgcagcgtc  5160
aggcagtcta gtgcccagaa gagaaagtat accatcaagg tggaggtccc caaagtggct  5220
acccagacag tgggcggagt cgaactgcct gtcgccgctt ggaggtccta cctgaacatg  5280
gagctcacta tcccaatttt cgctaccaat tctgactgtg aactcatcgt gaaggcaatg  5340
caggggctcc tcaaagacgg taatcctatc ccttccgcca tcgccgctaa ctcaggtatc  5400
tac                                                                5403
```

```
SEQ ID NO: 94          moltype = AA  length = 1801
FEATURE                Location/Qualifiers
REGION                 1..1801
                       note = PspCas13b-ABI1-2a-PYL1-MS2 amino acid seqeunce
source                 1..1801
                       mol_type = protein
                       organism = synthetic construct
SEQUENCE: 94
MNIPALVENQ KKYFGTYSVM AMLNAQTVLD HIQKVADIEG EQNENNENLW FHPVMSHLYN  60
AKNGYDKQPE KTMFIIERLQ SYFPFLKIMA ENQREYSNGK YKQNRVEVNS NDIFEVLKRA  120
FGVLKMYRDL TNAYKTYEEK LNDGCEFLTS TEQPLSGMIN NYYTVALRNM NERYGYKTED  180
LAFIQDKRFK FVKDAYGKKK SQVNTGFFLS LQDYNGDTQK KLHLSGVGIA LLICLFLDKQ  240
YINIFLSRLP IFSSYNAQSE ERRIIIRSFG INSIKLPKDR IHSEKSNKSV AMDMLNEVKR  300
CPDELFTTLS AEKQSRFRII SDDHNEVLMK RSSDRFVPLL LQYIDYGKLF DHIRFHVNMG  360
KLRYLLKADK TCIDGQTRVR VIEQPLNGFG RLEEAETMRK QENGTFGNSG IRIRDFENMK  420
RDDANPANYP YIVDTYTHYI LENNKVEMFI NDKEDSAPLL PVIEDDRYVV KTIPSCRMST  480
LEIPAMAFHM FLFGSKKTEK LIVDVHNRYK RLFQAMQKEE VTAENIASFG IAESDLPQKI  540
LDLISGNAHG KDVDAFIRLT VDDMLTDTER RIKRFKDDRK SIRSADNKMG KRGFKQISTG  600
KLADFLAKDI VLFQPSVNDG ENKITGLNYR IMQSAIAVYD SGDDYEAKQQ FKLMFEKARL  660
IGKGTTEPHP FLYKVFARSI PANAVEFYER YLIERKFYLT GLSNEIKKGN RVDVPFIRRD  720
QNKWKTPAMK TLGRIYSEDL PVELPRQMFD NEIKSHLKSL PQMEGIDFNN ANVTYLIAEY  780
MKRVLDDDFQ TFYQWNRNYR YMDMLKGEYD RKGSLQHCFT SVEEREGLWK ERASRTERYR  840
KQASNKIRSN RQMRNASSEE IETILDKRLS NSRNEYQKSE KVIRRYRVQD ALLFLLAKKT  900
LTELADFDGE RFKLKEIMPD AEKGILSEIM PMSFTFEKGG KKYTITSEGM KLKNYGDFFV  960
LASDKRIGNL LELVGSDIVS KEDIMEEFNK YDQCRPEISS IVFNLEKWAF DTYPELSARV  1020
DREEKVDFKS ILKILLNNKN INKEQSDILR KIRNAFDANN YPDKGVVEIK ALPEIAMSIK  1080
KAFGEYAIMK GSLQAYPYDV PDYASLGSGS PKKKRKVEDP KKKRKVDGIG SGSNGGGGSG  1140
PRTRVPLYGF TSICGRRPEM EAAVSTIPRF LQSSSGSMLD GRFDPQSAAH FFGVYDGHGG  1200
SQVANYCRER MHLALAEEIA KEKPMLCDGD TWLEKWKKAL FNSFLRVDSE IESVAPETVG  1260
STSVVAVVFP SHIFVANCGD SRAVLCRGKT ALPLSVDHKP DREDEAARIE AAGGKVIQWN  1320
GARVFGVLAM SRSIGDRYLK PSIIPDPEVT AVKRVKEDDC LILASDGVWD VMTDEEACEM  1380
ARKRILLWHK KNAVAGDASL LADERRKEGK DPAAMSAAEY LSKLAIQRGS KDNISVVVVD  1440
LKGSGATNFS LLKQAGDVEE NPGPMGGGAP TQDEFTQLSQ SIAEFHTYQL GNGRCSSLLA  1500
QRIHAPPETV WSVVRRFDRP QIYKHFIKSC NVSEDFEMRV GCTRDVNVIS GLPANTSRER  1560
```

-continued

```
LDLLDDDRRV TGFSITGGEH RLRNYKSVTT VHRFEKEEEE ERIWTVVLES YVVDVPEGNS  1620
EEDTRLFADT VIRLNLQKLA SITEAMNEFS SAAGTSPKKK RKVGGSGGGG SMASNFTQFV  1680
LVDNGGTGDV TVAPSNFANG VAEWISSNSR SQAYKVTCSV RQSSAQKRKY TIKVEVPKVA  1740
TQTVGGVELP VAAWRSYLNM ELTIPIFATN SDCELIVKAM QGLLKDGNPI PSAIAANSGI  1800
Y                                                                 1801

SEQ ID NO: 95          moltype = DNA  length = 3414
FEATURE                Location/Qualifiers
misc_feature           1..3414
                       note = dRfxCas13d-MS2 nucleic acid sequence
source                 1..3414
                       mol_type = other DNA
                       organism = synthetic construct
SEQUENCE: 95
atgagcccca agaagaagag aaaggtggag gccagcatcg aaaaaaaaaa gtccttcgcc  60
aagggcatgg gcgtgaagtc cacactcgtg tccggctcca aagtgtacat gacaaccttc  120
gccgaaggca gcgacgccag gctggaaaag atcgtggagg gcgacagcat caggagcgtg  180
aatgagggcg aggccttcag cgctgaaatg gccgataaaa acgccggcta taagatcggc  240
aacgccaaat tcagccatcc taagggctac gccgtggtgg ctaacaaccc tctgtataca  300
ggacccgtcc agcaggatat gctcggcctg aaggaaactc tggaaaagag gtacttcggc  360
gagagcgctg atggcaatga caatatttgt atccaggtga tccataacat cctggacatt  420
gaaaaaatcc tcgccgaata cattaccaac gccgcctacg ccgtcaacaa tatctccggc  480
ctggataagg acattattgg attcggcaag ttctccacag tgtataccta cgacgaattc  540
aaagaccccg agcaccatag ggccgctttc aacaataacg ataagctcat caacgccatc  600
aaggcccagt atgacgagtt cgacaacttc ctcgataacc ccagactcgg ctatttcggc  660
caggcctttt tcagcaagga gggcagaaat tacatcatca attacggcaa cgaatgctat  720
gacattctgg ccctcctgag cggactggcg cactgggtgg tcgctaacaa cgaagaagag  780
tccaggatct ccaggacctg gctctacaac ctcgataaga acctcgacaa cgaatacatc  840
tccaccctca actacctcta cgacaggatc accaatgagc tgaccaactc cttctccaag  900
aactccgccg ccaacgtgaa ctatattgcc gaaactctgg gaatcaaccc tgccgaattc  960
gccgaacaat atttcagatt cagcattatg aaagagcaga aaaacctcgg attcaatatc  1020
accaagctca gggaagtgat gctggacagg aaggatatgt ccgagatcag gaaaaatcat  1080
aaggtgttcg actccatcag gaccaaggtc tacaccatga tggactttgt gatttatagg  1140
tattacatcg aagaggatgc caaggtggct gccgccaata agtccctccc cgataatgag  1200
aagtccctga gcgagaagga tatctttgtg attaacctga ggggctcctt caacgacgac  1260
cagaaggatg ccctctacta cgatgaagct aatagaattt ggagaaagct cgaaaatatc  1320
atgcacaaca tcaaggaatt taggggaaac aagacaagag agtataagaa gaaggacgcc  1380
cctagactgc ccagaatcct gcccgctggc cgtgatgttt ccgccttcag caaactcatg  1440
tatgccctga ccatgttcct ggatggcaag gagatcaacg acctcctgac caccctgatt  1500
aataaattcg ataacatcca gagcttcctg aaggtgatgc ctctcatcgg agtcaacgct  1560
aagttcgtgg aggaatacgc ctttttcaaa gactccgcca agatcgccga tgagctgagg  1620
ctgatcaagt ccttcgctag aatgggagaa cctattgccg atgccaggag ggccatgtat  1680
atcgacgcca tccgtatttt aggaaccaac ctgtcctatg atgagctcaa ggccctcgcc  1740
gacacctttt ccctggacga gaacggaaac aagctcaaga aaggcaagca cggcatgaga  1800
aatttcatta ttaataacgt gatcagcaat aaaaggttcc actacctgat cagatacggt  1860
gatcctgccc acctccatga gatcgccaaa aacgaggccg tggtgaagtt cgtgctcggc  1920
aggatcgctg acatccagaa aaaacagggc cagaacggca agaaccagat cgacaggtac  1980
tacgaaactt gtatcggaaa ggataagggc aagagcgtga gcgaaaaggt ggacgctctc  2040
acaaagatca tcaccggaat gaactacgac caattcgaca agaaaaggag cgtcattgag  2100
gacaccggca gggaaaacgc cgagagggag aagtttaaaa agatcatcag cctgtacctc  2160
accgtgatct accacatcct caagaatatt gtcaatatca acgccaggta cgtcatcgga  2220
ttccattgcg tcgagcgtga tgctcaactg tacaaggaga aaggctacga catcaatctc  2280
aagaaactgg aagagaaggg attcagctcc gtcaccaagc tctgcgctgg cattgatgaa  2340
actgcccccg ataagagaaa ggacgtggaa aaggagatgg ctgaaagagc caaggagagc  2400
attgacagcc tcgagagcgc caaccccaag ctgtatgcca attacatcaa atacagcgac  2460
gagaagaaag ccgaggagtt caccaggcag attaacaggg agaaggccaa aaccgccctg  2520
aacgcctacc tgaggaacac caagtggaat gtgatcatca gggaggacct cctgagaatt  2580
gacaacaaga catgtaccct gttcgcaaac aaggccgtcg ccctggaagt ggccaggtat  2640
gtccacgcct atatcaacga cattgccgag gtcaattcct acttccaact gtaccattac  2700
atcatgcaga gaattatcat gaatgagagg tacgagaaaa gcagcggaaa ggtgtccgag  2760
tacttcgacg ctgtgaatga cgagaagaag tacaacgata ggctcctgaa actgctgtgt  2820
gtgcctttcg gctactgtat ccccaggttt aagaacctga gcatcgaggc cctgttcgat  2880
aggaacgagg ccgccaagtt cgacaaggag aaaaagaagg tgtccggcaa ttccggatcc  2940
ggacctaaga aaaagaggaa ggtggcggcc gcttacccat acgatgttcc agattacgct  3000
gctggatccg gaggaggtgg aagcatggct tcaaacttta ctcagttcgt gctcgtggac  3060
aatggtggga caggggatgt gacagtggct ccttctaatt tcgctaatgg ggtggcagag  3120
tggatcagct ccaactcacg gagccaggcc tacaaggtga catgcagcgt caggcagtct  3180
agtgcccaga agagaaagta taccatcaag gtggaggtcc ccaaagtggc tacccagaca  3240
gtgggcggag tcgaactgcc tgtcgccgct tggaggtcct acctgaacat ggagctcact  3300
atcccaattt tcgctaccaa ttctgactgt gaactcatcg tgaaggcaat gcaggggctc  3360
ctcaaagacg gtaatcctat cccttccgcc atcgccgcta actcaggtat ctac        3414

SEQ ID NO: 96          moltype = AA  length = 1138
FEATURE                Location/Qualifiers
REGION                 1..1138
                       note = dRfxCas13d-MS2 amino acid sequence
source                 1..1138
                       mol_type = protein
                       organism = synthetic construct
```

```
SEQUENCE: 96
MSPKKKRKVE ASIEKKKSFA KGMGVKSTLV SGSKVYMTTF AEGSDARLEK IVEGDSIRSV  60
NEGEAFSAEM ADKNAGYKIG NAKFSHPKGY AVVANNPLYT GPVQQDMLGL KETLEKRYFG  120
ESADGNDNIC IQVIHNILDI EKILAEYITN AAYAVNNISG LDKDIIGFGK FSTVYTYDEF  180
KDPEHHRAAF NNNDKLINAI KAQYDEFDNF LDNPRLGYFG QAFFSKEGRN YIINYGNECY  240
DILALLSGLA HWVVANNEEE SRISRTWLYN LDKNLDNEYI STLNYLYDRI TNELTNSFSK  300
NSAANVNYIA ETLGINPAEF AEQYFRFSIM KEQKNLGFNI TKLREVMLDR KDMSEIRKNH  360
KVFDSIRTKV YTMMDFVIYR YYIEEDAKVA AANKSLPDNE KSLSEKDIFV INLRGSFNDD  420
QKDALYYDEA NRIWRKLENI MHNIKEFRGN KTREYKKKDA PRLPRILPAG RDVSAFSKLM  480
YALTMFLDGK EINDLLTTLI NKFDNIQSFL KVMPLIGVNA KFVEEYAFFK DSAKIADELR  540
LIKSFARMGE PIADARRAMY IDAIRILGTN LSYDELKALA DTFSLDENGN KLKKGKHGMR  600
NFIINNVISN KRFHYLIRYG DPAHLHEIAK NEAVVKFVLG RIADIQKKQG QNGKNQIDRY  660
YETCIGKDKG KSVSEKVDAL TKIITGMNYD QFDKKRSVIE DTGRENAERE KFKKIISLYL  720
TVIYHILKNI VNINARYVIG FHCVERDAQL YKEKGYDINL KKLEEKGFSS VTKLCAGIDE  780
TAPDKRKDVE KEMAERAKES IDSLESANPK LYANYIKYSD EKKAEEFTRQ INREKAKTAL  840
NAYLRNTKWN VIIREDLLRI DNKTCTLFAN KAVALEVARY VHAYINDIAE VNSYFQLYHY  900
IMQRIIMNER YEKSSGKVSE YFDAVNDEKK YNDRLLKLLC VPFGYCIPRF KNLSIEALFD  960
RNEAAKFDKE KKKVSGNSGS GPKKKRKVAA AYPYDVPDYA AGSGGGGSMA SNFTQFVLVD  1020
NGGTGDVTVA PSNFANGVAE WISSNSRSQA YKVTCSVRQS SAQKRKYTIK VEVPKVATQT  1080
VGGVELPVAA WRSYLNMELT IPIFATNSDC ELIVKAMQGL LKDGNPIPSA IAANSGIY    1138

SEQ ID NO: 97          moltype = DNA  length = 3411
FEATURE                Location/Qualifiers
misc_feature           1..3411
                       note = MS2-dRfxCas13d nucleic acid sequence
source                 1..3411
                       mol_type = other DNA
                       organism = synthetic construct
SEQUENCE: 97
atggcttcaa actttactca gttcgtgctc gtggacaatg gtgggacagg ggatgtgaca  60
gtggctcctt ctaatttcgc taatggggtg gcagagtgga tcagctccaa ctcacggagc  120
caggcctaca aggtgacatg cagcgtcagg cagtctagtg cccagaagag aaagtatacc  180
atcaaggtgg aggtccccaa agtggctacc cagacagtgg gcggagtcga actgcctgtc  240
gccgcttgga ggtcctacct gaacatggag ctcactatcc caattttcgc taccaattct  300
gactgtgaac tcatcgtgaa ggcaatgcag gggctcctca aagacggtaa tcctatccct  360
tccgccatcg ccgctaactc aggtatctac ggatccggag gaggtggaag cagccccaag  420
aagaagagaa aggtggaggc cagcatcgaa aaaaaaaagt ccttcgccaa gggcatgggc  480
gtgaagtcca cactcgtgtc cggctccaaa gtgtacatga caaccttcgc cgaaggcagc  540
gacgccaggc tggaaaagat cgtggagggc gacagcatca ggagcgtgaa tgagggcgag  600
gccttcagcg ctgaaatggc cgataaaaac gccggctata agatcggcaa cgccaaattc  660
agccatccta agggctacgc cgtggtggct aacaaccctc tgtatacagg acccgtccag  720
caggatatgc tcggcctgaa ggaaactctg gaaaagaggt acttcggcga gagcgctgat  780
ggcaatgaca atatttgtat ccaggtgatc cataacatcc tggacattga aaaaatcctc  840
gccgaataca ttaccaacgc cgcctacgcc gtcaacaata tctccggcct ggataaggac  900
attattggat tcggcaagtt ctccacagtg tatacctacg acgaattcaa agaccccgag  960
caccataggg ccgctttcaa caataacgat aagctcatca acgccatcaa ggcccagtat  1020
gacgagttcg acaacttcct cgataacccc agactcggct atttcggcca ggcctttttc  1080
agcaaggagg gcagaaatta catcatcaat tacggcaacg aatgctatga cattctggcc  1140
ctcctgagcg gactggcgca ctgggtggtc gctaacaacg aagaagagtc caggatctcc  1200
aggacctggc tctacaacct cgataagaac ctcgacaacg aatacatctc caccctcaac  1260
tacctctacg acaggatcac caatgagctg accaactcct tctccaagaa ctccgccgcc  1320
aacgtgaact atattgccga aactctggga atcaaccctg ccgaattcgc cgaacaatat  1380
ttcagattca gcattatgaa agagcagaaa aacctcggat tcaatatcac caagctcagg  1440
gaagtgatgc tggacaggaa ggatatgtcc gagatcagga aaaatcataa ggtgttcgac  1500
tccatcagga ccaaggtcta caccatgatg gactttgtga tttataggta ttacatcgaa  1560
gaggatgcca aggtggctgc cgccaataag tccctccccg ataatgagaa gtccctgagc  1620
gagaaggata tctttgtgat taacctgagg ggctccttca acgacgacca gaaggatgcc  1680
ctctactacg atgaagctaa tagaatttgg agaaagctcg aaaatatcat gcacaacatc  1740
aaggaattta ggggaaacaa gacaagagag tataagaaga aggacgcccc tagactgccc  1800
agaatcctgc ccgctggccg tgatgtttcc gccttcagca aactcatgta tgccctgacc  1860
atgttcctgg atggcaagga gatcaacgac ctcctgacca ccctgattaa taaattcgat  1920
aacatccaga gcttcctgaa ggtgatgcct ctcatcggag tcaacgctaa gttcgtggag  1980
gaatacgcct ttttcaaaga ctccgccaag atcgccgatg agctgaggct gatcaagtcc  2040
ttcgctagaa tgggagaacc tattgccgat gccaggaggg ccatgtatat cgacgccatc  2100
cgtattttag gaaccaacct gtcctatgat gagctcaagg ccctcgccga cacctttcc   2160
ctggacgaga acggaaacaa gctcaagaaa ggcaagcacg gcatgagaaa tttcattatt  2220
aataacgtga tcagcaataa aaggttccac tacctgatca gatacggtga tcctgcccac  2280
ctccatgaga tcgccaaaaa cgaggccgtg gtgaagttcg tgctcggcag gatcgctgac  2340
atccagaaaa aacagggcca gaacggcaag aaccagatcg acaggtacta cgaaacttgt  2400
atcggaaagg ataagggcaa gagcgtgagc gaaaaggtgg acgctctcac aaagatcatc  2460
accggaatga actacgacca attcgacaag aaaaggagcg tcattgagga caccggcagg  2520
gaaaacgccg agagggagaa gtttaaaaag atcatcagcc tgtacctcac cgtgatctac  2580
cacatcctca agaatattgt caatatcaac gccaggtacg tcatcggatt ccattgcgtc  2640
gagcgtgatg ctcaactgta caaggagaaa ggctacgaca tcaatctcaa gaaactggaa  2700
gagaagggat tcagctccgt caccaagctc tgcgctggca ttgatgaaac tgccccccgat  2760
aagagaaagg acgtggaaaa ggagatggct gaaagagcca aggagagcat tgacagcctc  2820
gagagcgcca accccaagct gtatgccaat tacatcaaat acagcgacga gaagaaagcc  2880
gaggagttca ccaggcagat taacagggag aaggccaaaa ccgccctgaa cgcctacctg  2940
aggaacacca agtggaatgt gatcatcagg gaggacctcc tgagaattga caacaagaca  3000
```

```
tgtaccctgt tcgcaaacaa ggccgtcgcc ctggaagtgg ccaggtatgt ccacgcctat  3060
atcaacgaca ttgccgaggt caattcctac ttccaactgt accattacat catgcagaga  3120
attatcatga atgagaggta cgagaaaagc agcggaaagg tgtccgagta cttcgacgct  3180
gtgaatgacg agaagaagta caacgatagg ctcctgaaac tgctgtgtgt gcctttcggc  3240
tactgtatcc ccaggtttaa gaacctgagc atcgaggccc tgttcgatag gaacgaggcc  3300
gccaagttcg acaaggagaa aaagaaggtg tccggcaatt ccggatccgg acctaagaaa  3360
aagaggaagg tggcggccgc ttacccatac gatgttccag attacgctgc t           3411

SEQ ID NO: 98           moltype = AA  length = 1137
FEATURE                 Location/Qualifiers
REGION                  1..1137
                        note = MS2-dRfxCas13d amino acid sequence
source                  1..1137
                        mol_type = protein
                        organism = synthetic construct
SEQUENCE: 98
MASNFTQFVL VDNGGTGDVT VAPSNFANGV AEWISSNSRS QAYKVTCSVR QSSAQKRKYT  60
IKVEVPKVAT QTVGGVELPV AAWRSYLNME LTIPIFATNS DCELIVKAMQ GLLKDGNPIP  120
SAIAANSGIY GSGGGGSSPK KKRKVEASIE KKKSFAKGMG VKSTLVSGSK VYMTTFAEGS  180
DARLEKIVEG DSIRSVNEGE AFSAEMADKN AGYKIGNAKF SHPKGYAVVA NNPLYTGPVQ  240
QDMLGLKETL EKRYFGESAD GNDNICIQVI HNILDIEKIL AEYITNAAYA VNNISGLDKD  300
IIGFGKFSTV YTYDEFKDPE HHRAAFNNND KLINAIKAQY DEFDNFLDNP RLGYFGQAFF  360
SKEGRNYIIN YGNECYDILA LLSGLAHWVV ANNEEESRIS RTWLYNLDKN LDNEYISTLN  420
YLYDRITNEL TNSFSKNSAA NVNYIAETLG INPAEFAEQY FRFSIMKEQK NLGFNITKLR  480
EVMLDRKDMS EIRKNHKVFD SIRTKVYTMM DFVIYRYYIE EDAKVAAANK SLPDNEKSLS  540
EKDIFVINLR GSFNDDQKDA LYYDEANRIW RKLENIMHNI KEFRGNKTRE YKKKDAPRLP  600
RILPAGRDVS AFSKLMYALT MFLDGKEIND LLTTLINKFD NIQSFLKVMP LIGVNAKFVE  660
EYAFFKDSAK IADELRLIKS FARMGEPIAD ARRAMYIDAI RILGTNLSYD ELKALADTFS  720
LDENGNKLKK GKHGMRNFII NNVISNKRFH YLIRYGDPAH LHEIAKNEAV VKFVLGRIAD  780
IQKKQGQNGK NQIDRYYETC IGKDKGKSVS EKVDALTKII TGMNYDQFDK KRSVIEDTGR  840
ENAEREKFKK IISLYLTVIY HILKNIVNIN ARYVIGFHCV ERDAQLYKEK GYDINLKKLE  900
EKGFSSVTKL CAGIDETAPD KRKDVEKEMA ERAKESIDSL ESANPKLYAN YIKYSDEKKA  960
EEFTRQINRE KAKTALNAYL RNTKWNVIIR EDLLRIDNKT CTLFANKAVA LEVARYVHAY  1020
INDIAEVNSY FQLYHYIMQR IIMNERYEKS SGKVSEYFDA VNDEKKYNDR LLKLLCVPFG  1080
YCIPRFKNLS IEALFDRNEA AKFDKEKKKV SGNSGSGPKK KRKVAAAYPY DVPDYAA     1137

SEQ ID NO: 99           moltype = DNA  length = 57
FEATURE                 Location/Qualifiers
misc_feature            1..57
                        note = dRfxCas13d gRNA
source                  1..57
                        mol_type = other DNA
                        organism = synthetic construct
SEQUENCE: 99
aacccctacc aactggtcgg ggtttgaaac cctgtggatg aagggacaca cacatgc     57

SEQ ID NO: 100          moltype = DNA  length = 5059
FEATURE                 Location/Qualifiers
misc_feature            1..5059
                        note = AAV2_ITR-CMV-dPspCas13b-MS2-bGHpA-AAV2_ITR
source                  1..5059
                        mol_type = other DNA
                        organism = synthetic construct
SEQUENCE: 100
gctgcgcgct cgctcgctca ctgaggccgc ccgggcaaag cccgggcgtc gggcgacctt  60
tggtcgcccg gcctcagtga gcgagcgagc gcgcagagag ggagtggcca actccatcac  120
taggggttcc ttgtagttaa tgattaaccc gccatgctac ttatctacgt agccatgctc  180
tagcgggaca ttgattattg actagttatt aatagtaatc aattacgggg tcattagttc  240
atagcccata tatggagttc cgcgttacat aacttacggt aaatggcccg cctggctgac  300
cgcccaacga cccccgccca ttgacgtcaa taatgacgta tgttcccata gtaacgccaa  360
tagggacttt ccattgacgt caatgggtgg agtatttacg gtaaactgcc cacttggcag  420
tacatcaagt gtatcatatg ccaagtacgc cccctattga cgtcaatgac ggtaaatggc  480
ccgcctggca ttatgcccag tacatgacct tatgggactt tcctacttgg cagtacatct  540
acgtattagt catcgctatt accatggtga tgcggttttg gcagtacatc aatgggcgtg  600
gatagcggtt tgactcacgg ggatttccaa gtctccaccc cattgacgtc aatgggagtt  660
tgttttggca ccaaaatcaa cgggactttc caaaatgtcg taacaactcc gccccattga  720
cgcaaatggg cggtaggcgt gtacggtggg aggtctatat aagcagagct ctctggctaa  780
ctagagaacc cactgcttac tggcttatcg aaattaatac gactcactat agggagaccc  840
aagctggcta gcgtttaaac ttaagcttgc caccatgaac atccccgctc tggtggaaaa  900
ccagaagaag tactttggca cctacagcgt gatggccatg ctgaacgctc agaccgtgct  960
ggaccacatc cagaaggtgg ccgatattga gggcgagcag aacgagaaca acgagaatct  1020
gtggtttcac cccgtgatga gccacctgta caacgccaag aacggctacg acaagcagcc  1080
cgagaaaacc atgttcatca tcgagcggct gcagagctac ttcccattcc tgaagatcat  1140
ggccgagaac cagagagagt acagcaacgg caagtacaag cagaaccgcg tggaagtgaa  1200
cagcaacgac atcttcgagg tgctgaagcg cgccttcggc gtgctgaaga tgtacaggga  1260
cctgaccaac gcatacaaga cctacgagga aaagctgaac gacggctgcg agttcctgac  1320
cagcacagag caacctctga gcggcatgat caacaactac tacacagtgg ccctgcggaa  1380
catgaacgag agatacggct acaagacaga ggacctggcc ttcatccagg acaagcggtt  1440
caagttcgtg aaggacgcct acggcaagaa aaagtcccaa gtgaataccg gattcttcct  1500
```

```
gagcctgcag gactacaacg gcgacacaca gaagaagctg cacctgagcg gagtgggaat  1560
cgccctgctg atctgcctgt tcctggacaa gcagtacatc aacatctttc tgagcaggct  1620
gcccatcttc tccagctaca atgcccagag cgaggaacgg cggatcatca tcagatcctt  1680
cggcatcaac agcatcaagc tgcccaagga ccggatccac agcgagaagt ccaacaagag  1740
cgtggccatg gatatgctca acgaagtgaa gcggtgcccc gacgagctgt tcacaacact  1800
gtctgccgag aagcagtccc ggttcagaat catcagcgac gaccacaatg aagtgctgat  1860
gaagcggagc agcgacagat tcgtgcctct gctgctgcag tatatcgatt acggcaagct  1920
gttcgaccac atcaggttcc acgtgaacat gggcaagctg agatacctgc tgaaggccga  1980
caagacctgc atcgacggcc agaccagagt cagagtgatc gagcagcccc tgaacggctt  2040
cggcagactg gaagaggccg agacaatgcg gaagcaagag aacggcacct tcggcaacag  2100
cggcatccgg atcagagact tcgagaacat gaagcgggac gacgccaatc ctgccaacta  2160
tccctacatc gtggacacct acacacacta catcctggaa aacaacaagg tcgagatgtt  2220
tatcaacgac aaagaggaca gcgcccccact gctgcccgtg atcgaggatg atagatacgt  2280
ggtcaagaca atccccagct gccggatgag caccctggaa attccagcca tggccttcca  2340
catgtttctg ttcggcagca agaaaaccga gaagctgatc gtggacgtgc acaaccggta  2400
caagagactg ttccaggcca tgcagaaaga agaagtgacc gccgagaata tcgccagctt  2460
cggaatcgcc gagagcgacc tgcctcagaa gatcctggat ctgatcagcg gcaatgccca  2520
cggcaaggat gtggacgcct tcatcagact gaccgtggac gacatgctga ccgacaccga  2580
gcggagaatc aagagattca aggacgaccg gaagtccatt cggagcgccg acaacaagat  2640
gggaaagaga ggcttcaagc agatctccac aggcaagctg gccgacttcc tggccaagga  2700
catcgtgctg tttcagccca gcgtgaacga tggcgagaac aagatcaccg gcctgaacta  2760
ccggatcatg cagagcgcca ttgccgtgta cgatagcggc gacgattacg aggccaagca  2820
gcagttcaag ctgatgttcg agaaggcccg gctgatcggc aagggcacaa cagagcctca  2880
tccatttctg tacaaggtgt tcgcccgcag catccccgcc aatgccgtcg agttctacga  2940
gcgctacctg atcgagcgga agttctacct gaccggcctg tccaacgaga tcaagaaagg  3000
caacagagtg gatgtgccct tcatccggcg ggaccagaac aagtggaaaa cacccgccat  3060
gaagaccctg ggcagaatct acagcgagga tctgcccgtg gaactgccca gacagatgtt  3120
cgacaatgag atcaagtccc acctgaagtc cctgccacag atggaaggca tcgacttcaa  3180
caatgccaac gtgacctatc tgatcgccga gtacatgaag agagtgctgg acgacgactt  3240
ccagaccttc taccagtgga accgcaacta ccggtacatg gacatgctta agggcgagta  3300
cgacagaaag ggctccctgc agcactgctt caccagcgtg gaagagagag aaggcctctg  3360
gaaagagcgg gcctccagaa cagagcggta cagaaagcag gccagcaaca agatccgcag  3420
caaccggcag atgagaaacg ccagcagcga agagatcgag acaatcctgg ataagcggct  3480
gagcaacagc cggaacgagt accagaaaag cgagaaagtg atccggcgct acagagtgca  3540
ggatgccctg ctgtttctgc tggccaaaaa gaccctgacc gaactggccg atttcgacgg  3600
cgagaggttc aaactgaaag aaatcatgcc cgacgccgag aagggaatcc tgagcgagat  3660
catgcccatg agcttcacct tcgagaaagg cggcaagaag tacaccatca ccagcgaggg  3720
catgaagctg aagaactacg gcgacttctt tgtgctggct agcgacaaga ggatcggcaa  3780
cctgctggaa ctcgtgggca gcgacatcgt gtccaaagag gatatcatgg aagagttcaa  3840
caaatacgac cagtgcaggc ccgagatcag ctccatcgtg ttcaacctgg aaaagtgggc  3900
cttcgacaca taccccgagc tgtctgccag agtggaccgg gaagagaagg tggacttcaa  3960
gagcatcctg aaaatcctgc tgaacaacaa gaacatcaac aaagagcaga gcgacatcct  4020
gcggaagatc cggaacgcct tcgatgcaaa caattacccc gacaaaggcg tggtggaaat  4080
caaggccctg cctgagatcg ccatgagcat caagaaggcc tttggggagt acgccatcat  4140
gaagggaagc ctgcagccaa agaagaagcg gaaggtcggt ggatccggag gaggtggaag  4200
catggcttca aactttactc agttcgtgct cgtggacaat ggtgggacag gggatgtgac  4260
agtggctcct tctaatttcg ctaatggggt ggcagagtgg atcagctcca actcacggag  4320
ccaggcctac aaggtgacat gcagcgtcag gcagtctagt gcccagaaga gaaagtatac  4380
catcaaggtg gaggtcccca aagtggctac ccagacagtg ggcggagtcg aactgcctgt  4440
cgccgcttgg aggtcctacc tgaacatgga gctcactatc ccaattttcg ctaccaattc  4500
tgactgtgaa ctcatcgtga aggcaatgca ggggctcctc aaagacggta atcctatccc  4560
ttccgccatc gccgctaact caggtatcta ctaagcggcc gctcgagtct agagggcccg  4620
tttaaacccg ctgatcagcc tcgactgtgc cttctagttg ccagccatct gttgtttgcc  4680
cctcccccgt gccttccttg accctggaag gtgccactcc cactgtcctt tcctaataaa  4740
atgaggaaat tgcatcgcat tgtctgagta ggtgtcattc tattctgggg ggtggggtgg  4800
ggcaggacag caagggggag gattgggaag acaatagcag gcatgctggg gatgcggtgg  4860
gctctatggt cgacatctag agcatggcta cgtagataag tagcatggcg ggttaatcat  4920
taactacaag gaacccctag tgatggagtt ggccactccc tctctgcgcg ctcgctcgct  4980
cactgaggcc gggcgaccaa aggtcgcccg acgcccgggc tttgcccggg cggcctcagt  5040
gagcgagcga gcgcgcagc                                               5059
```

```
SEQ ID NO: 101          moltype = DNA  length = 7146
FEATURE                 Location/Qualifiers
misc_feature            1..7146
                        note = 5'LTR-EFS-dPspCas13b-MS2-2a-Blast-WPRE-3'LTR
source                  1..7146
                        mol_type = other DNA
                        organism = synthetic construct
SEQUENCE: 101
gggtctctct ggttagacca gatctgagcc tgggagctct ctggctaact agggaaccca  60
ctgcttaagc ctcaataaag cttgccttga gtgcttcaag tagtgtgtgc ccgtctgttg  120
tgtgactctg gtaactagag atccctcaga cccttttagt cagtgtggaa aatctctagc  180
agtggcgccc gaacagggac ttgaaagcga aagggaaacc agaggagctc tctcgacgca  240
ggactcggct tgctgaagcg cgcacggcaa gaggcgaggg gcggcgactg gtgagtacgc  300
caaaaatttt gactagcgga ggctagaagg agagagatgg gtgcgagagc gtcagtatta  360
agcgggggag aattagatcg cgatgggaaa aaattcggtt aaggccaggg ggaaagaaaa  420
aatataaatt aaaacatata gtatgggcaa gcagggagct agaacgattc gcagttaatc  480
ctggcctgtt agaaacatca gaaggctgta gacaaatact gggacagcta caaccatccc  540
ttcagacagg atcagaagaa cttagatcat tatataatac agtagcaacc ctctattgtg  600
```

-continued tgcatcaaag gatagagata aaagacacca aggaagcttt agacaagata gaggaagagc 660
aaaacaaaag taagaccacc gcacagcaag cggccgctga tcttcagacc tggaggagga 720
gatatgaggg acaattggag aagtgaatta tataaatata aagtagtaaa aattgaacca 780
ttaggagtag cacccaccaa ggcaaagaga agagtggtgc agagagaaaa aagagcagtg 840
ggaataggag ctttgttcct tgggttcttg ggagcagcag gaagcactat gggcgcagcg 900
tcaatgacgc tgacggtaca ggccagacaa ttattgtctg gtatagtgca gcagcagaac 960
aatttgctga gggctattga ggcgcaacag catctgttgc aactcacagt ctggggcatc 1020
aagcagctcc aggcaagaat cctggctgtg gaaagatacc taaaggatca acagctcctg 1080
gggatttggg gttgctctgg aaaactcatt tgcaccactg ctgtgccttg gaatgctagt 1140
tggagtaata aatctctgga acagatttgg aatcacacga cctggatgga gtgggacaga 1200
gaaattaaca attacacaag cttaatacac tccttaattg aagaatcgca aaaccagcaa 1260
gaaaagaatg aacaagaatt attggaatta gataaatggg caagtttgtg gaattggttt 1320
aacataacaa attggctgtg gtatataaaa ttattcataa tgatagtagg aggcttggta 1380
ggtttaagaa tagtttttgc tgtactttct atagtgaata gagttaggca gggatattca 1440
ccattatcgt ttcagaccca cctcccaacc ccgaggggac ccgacaggcc cgaaggaata 1500
gaagaagaag gtggagagag agacagagac agatccattc gattagtgaa cggatcggca 1560
ctgcgtgcgc caattctgca gacaaatggc agtattcatc cacaatttta aaagaaaagg 1620
ggggattggg gggtacagtg caggggaaag aatagtagac ataatagcaa cagacataca 1680
aactaaagaa ttacaaaaac aaattacaaa aattcaaaat tttcgggttt attacaggga 1740
cagcagagat ccagtttggt taattaaggt accgaattcg ctagctaggt cttgaaagga 1800
gtgggaattg gctccggtgc ccgtcagtgg gcagagcgca catcgcccac agtccccgag 1860
aagttggggg gaggggtcgg caattgatcc ggtgcctaga gaaggtggcg cggggtaaac 1920
tgggaaagtg atgtcgtgta ctggctccgc ctttttcccg agggtggggg agaaccgtat 1980
ataagtgcag tagtcgccgt gaacgttctt tttcgcaacg ggtttgccgc cagaacacag 2040
gaccggttct agagcgctgc caccatgaac atccccgctc tggtggaaaa ccagaagaag 2100
tactttggca cctacagcgt gatggccatg ctgaacgctc agaccgtgct ggaccacatc 2160
cagaaggtgg ccgatattga gggcgagcag aacgagaaca acgagaatct gtggtttcac 2220
cccgtgatga gccacctgta caacgccaag aacggctacg acaagcagcc cgagaaaacc 2280
atgttcatca tcgagcggct gcagagctac ttcccattcc tgaagatcat ggccgagaac 2340
cagagagagt acagcaacgg caagtacaag cagaaccgcg tggaagtgaa cagcaacgac 2400
atcttcgagg tgctgaagcg cgccttcggc gtgctgaaga tgtacaggga cctgaccaac 2460
gcatacaaga cctacgagga aaagctgaac gacggctgcg agttcctgac cagcacagag 2520
caacctctga gcggcatgat caacaactac tacacagtgg ccctgcggaa catgaacgag 2580
agatacggct acaagacaga ggacctggcc ttcatccagg acaagcggtt caagttcgtg 2640
aaggacgcct acggcaagaa aaagtcccaa gtgaataccg gattcttcct gagcctgcag 2700
gactacaacg gcgacacaca gaagaagctg cacctgagcg gagtgggaat cgccctgctg 2760
atctgcctgt tcctggacaa gcagtacatc aacatctttc tgagcaggct gcccatcttc 2820
tccagctaca atgcccagag cgaggaacgg cggatcatca tcagatcctt cggcatcaac 2880
agcatcaagc tgcccaagga ccggatccac agcgagaagt ccaacaagag cgtggccatg 2940
gatatgctca acgaagtgaa gcggtgcccc gacgagctgt tcacaacact gtctgccgag 3000
aagcagtccc ggttcagaat catcagcgac gaccacaatg aagtgctgat gaagcggagc 3060
agcgacagat tcgtgcctct gctgctgcag tatatcgatt acggcaagct gttcgaccac 3120
atcaggttcc acgtgaacat gggcaagctg agatacctgc tgaaggccga caagacctgc 3180
atcgacggcc agaccagagt cagagtgatc gagcagcccc tgaacggctt cggcagactg 3240
gaagaggccg agacaatgcg gaagcaagag aacggcacct tcggcaacag cggcatccgg 3300
atcagagact tcgagaacat gaagcgggac gacgccaatc ctgccaacta tccctacatc 3360
gtggacacct acacacacta catcctggaa aacaacaagg tcgagatgtt tatcaacgac 3420
aaagaggaca gcgccccact gctgcccgtg atcgaggatg atagatacgt ggtcaagaca 3480
atccccagct gccggatgag caccctggaa attccagcca tggccttcca catgtttctg 3540
ttcggcagca agaaaaccga gaagctgatc gtggacgtgc acaaccggta caagagactg 3600
ttccaggcca tgcagaaaga agaagtgacc gccgagaata tcgccagctt cggaatcgcc 3660
gagagcgacc tgcctcagaa gatcctggat ctgatcagcg gcaatgccca cggcaaggat 3720
gtggacgcct tcatcagact gaccgtggac gacatgctga ccgacaccga gcggagaatc 3780
aagagattca aggacgaccg gaagtccatt cggagcgccg acaacaagat gggaaagaga 3840
ggcttcaagc agatctccac aggcaagctg gccgacttcc tggccaagga catcgtgctg 3900
tttcagccca gcgtgaacga tggcgagaac aagatcaccg gcctgaacta ccggatcatg 3960
cagagcgcca ttgccgtgta cgatagcggc gacgattacg aggccaagca gcagttcaag 4020
ctgatgttcg agaaggcccg gctgatcggc aagggcacaa cagagcctca tccatttctg 4080
tacaaggtgt tcgcccgcag catccccgcc aatgccgtcg agttctacga gcgctacctg 4140
atcgagcgga agttctacct gaccggcctg tccaacgaga tcaagaaagg caacagagtg 4200
gatgtgccct tcatccggcg ggaccagaac aagtggaaaa cacccgccat gaagaccctg 4260
ggcagaatct acagcgagga tctgcccgtg gaactgccca gacagatgtt cgacaatgag 4320
atcaagtccc acctgaagtc cctgcccacag atggaaggca tcgacttcaa caatgccaac 4380
gtgacctatc tgatcgccga gtacatgaag agagtgctgg acgacgactt ccagaccttc 4440
taccagtgga accgcaacta ccggtacatg gacatgctta agggcgagta cgacagaaag 4500
ggctccctgc agcactgctt caccagcgtg gaagagagag aaggcctctg gaaagagcgg 4560
gcctccagaa cagagcggta cagaaagcag gccagcaaca agatccgcag caaccggcag 4620
atgagaaacg ccagcagcga agagatcgag acaatcctgg ataagcggct gagcaacagc 4680
cggaacgagt accagaaaag cgagaaagtg atccggcgct acagagtgca ggatgccctg 4740
ctgtttctgc tggccaaaaa gaccctgacc gaactggccg atttcgacgg cgagaggttc 4800
aaactgaaag aaatcatgcc cgacgccgag aagggaatcc tgagcgagat catgcccatg 4860
agcttcacct tcgagaaagg cggcaagaag tacaccatca ccagcgaggg catgaagctg 4920
aagaactacg gcgacttctt tgtgctggct agcgacaaga ggatcggcaa cctgctggaa 4980
ctcgtgggca gcgacatcgt gtccaaagag gatatcatgg aagagttcaa caaatacgac 5040
cagtgcaggc ccgagatcag ctccatcgtg ttcaacctgg aaaagtgggc cttcgacaca 5100
taccccgagc tgtctgccag agtggaccgg gaagagaagg tggacttcaa gagcatcctg 5160
aaaatcctgc tgaacaacaa gaacatcaac aaagagcaga gcgacatcct gcggaagatc 5220
cggaacgcct tcgatgcaaa caattacccc gacaaaggcg tggtggaaat caaggccctg 5280
cctgagatcg ccatgagcat caagaaggcc tttggggagt acgccatcat gaagggaagc 5340

-continued

```
ctgcagccaa agaagaagcg gaaggtcggt ggatccggag gaggtggaag catggcttca  5400
aactttactc agttcgtgct cgtggacaat ggtgggacag ggatgtgac agtggctcct  5460
tctaatttcg ctaatggggt ggcagagtgg atcagctcca actcacggag ccaggcctac  5520
aaggtgacat gcagcgtcag gcagtctagt gcccagaaga gaaagtatac catcaaggtg  5580
gaggtcccca aagtggctac ccagacagtg ggcggagtcg aactgcctgt cgccgcttgg  5640
aggtcctacc tgaacatgga gctcactatc ccaattttcg ctaccaattc tgactgtgaa  5700
ctcatcgtga aggcaatgca ggggctcctc aaagacggta atcctatccc ttccgccatc  5760
gccgctaact caggtatcta cgcaacaaac ttctctctgc tgaaacaagc cggagatgtc  5820
gaagagaatc ctggaccgat ggccaagcct ttgtctcaag aagaatccac cctcattgaa  5880
agagcaacgg ctacaatcaa cagcatcccc atctctgaag actacagcgt cgccagcgca  5940
gctctctcta gcgacggccg catcttcact ggtgtcaatg tatatcattt tactgggga  6000
ccttgtgcag aactcgtggt gctgggcact gctgctgctg cggcagctgg caacctgact  6060
tgtatcgtcg cgatcggaaa tgagaacagg ggcatcttga gcccctgcgg acggtgccga  6120
caggtgcttc tcgatctgca tcctgggatc aaagccatag tgaaggacag tgatggacag  6180
ccgacggcag ttgggattcg tgaattgctg ccctctggtt atgtgtggga gggctaaacg  6240
cgttaagtcg acaatcaacc tctggattac aaaatttgtg aaagattgac tggtattctt  6300
aactatgttg ctccttttac gctatgtgga tacgctgctt taatgccttt gtatcatgct  6360
attgcttccc gtatggcttt cattttctcc tccttgtata aatcctggtt gctgtctctt  6420
tatgaggagt tgtggcccgt tgtcaggcaa cgtggcgtgg tgtgcactgt gtttgctgac  6480
gcaaccccca ctggttgggg cattgccacc acctgtcagc tcctttccgg gactttcgct  6540
ttccccctcc ctattgccac ggcggaactc atcgccgcct gccttgcccg ctgctggaca  6600
ggggctcggc tgttgggcac tgacaattcc gtggtgttgt cggggaaatc atcgtccttt  6660
ccttggctgc tcgcctgtgt tgccacctgg attctgcgcg ggacgtcctt ctgctacgtc  6720
ccttcggccc tcaatccagc ggaccttcct tcccgcggcc tgctgccggc tctgcggcct  6780
cttccgcgtc ttcgccttcg ccctcagacg agtcggatct ccctttgggc cgcctccccg  6840
cgtcgacttt aagaccaatg acttacaagg cagctgtaga tcttagccac tttttaaaag  6900
aaaagggggg actggaaggg ctaattcact cccaacgaag acaagatctg ctttttgctt  6960
gtactgggtc tctctggtta gaccagatct gagcctggga gctctctggc taactaggga  7020
acccactgct taagcctcaa taaagcttgc cttgagtgct tcaagtagtg tgtgcccgtc  7080
tgttgtgtga ctctggtaac tagagatccc tcagaccctt ttagtcagtg tggaaaatct  7140
ctagca                                                              7146
```

TARGETED TRANS-SPLICING USING CRISPR/Cas13

RELATED APPLICATION

This application is a continuation of U.S. patent application Ser. No. 16/994,230, filed Aug. 14, 2020, which claims priority to U.S. Provisional Application No. 62/888,210, filed on Aug. 16, 2019, and 62/985,633, filed on Mar. 5, 2020, each of which is incorporated by reference herein in its entirety.

STATEMENT REGARDING FEDERALLY SPONSORED RESEARCH

This invention was made with Government support under Grant No. HL141005 awarded by the National Institutes of Health (NIH). The Government has certain rights in the invention.

REFERENCE TO SEQUENCE LISTING SUBMITTED ELECTRONICALLY

The instant application contains a Sequence Listing which has been submitted electronically in xml format and is hereby incorporated by reference in its entirety. The xml copy, created on Aug. 15, 2023, is named 744480_083474-007USCON_SL.xml and is 284,547 bytes in size.

FIELD

The present disclosure relates to the field of CRISPR/Cas-mediated trans-splicing of nucleic acids for the treatment of disease.

BACKGROUND

Trans-splicing is a form of RNA processing where exons from two different primary pre-mRNA transcripts are joined end to end and ligated. This process is a promising strategy to treat various diseases using the spliceosome ribonucleoprotein complex. However, the efficiency and the specificity of trans-splicing of the current systems need to be improved upon to provide a more effective therapeutic strategy.

CRISPR/Cas systems have been used to edit genomic loci to treat diseases and disorders. This leads to a permanent edit to the DNA. The present invention provides a CRISPR/Cas system to target a trans-splicing element to a desired pre-mRNA sequence, and allows for the option of transient RNA repair while improving both the specificity and the efficiency of trans-splicing events.

SUMMARY

This disclosure provides methods and compositions for mediating a targeted trans-splicing event on a pre-mRNA in a cell. In one aspect, targeted trans-splicing system comprises: a nucleic acid-targeting CRISPR/Cas system; a nucleic acid guide; a specific RNA-binding domain; and a repair template comprising a splice donor and/or acceptor and an RNA sequence that hybridizes under physiological conditions to the specific RNA-binding domain.

In various embodiments, the nucleic acid guide is a RNA guide. In various embodiments, the nucleic acid guide is a DNA guide. In various embodiments the trans-splicing system comprises one nucleic acid guide. In various embodiments, the trans-splicing system comprises more than one nucleic acid guide. In various embodiments, the nucleic acid guides recognize multiple targets. In various embodiments, the nucleic acid guide targets a splice acceptor (SA) site. In various embodiments, the nucleic acid guide targets a splice donor (SD) site. In various embodiments, the nucleic acid guide targets a region near a splice site. In various embodiments, the nucleic acid guide targets a region within 200 nucleotides of a splice site. In various embodiments, the nucleic acid guide targets a region less than or equal to 100 nucleotides from a splice site. In various embodiments, the more than one nucleic acid guides target one nucleic acid of interest. In various embodiments, the more than one nucleic acid guides target multiple nucleic acids of interest.

In various embodiments, the CRISPR/Cas system comprises a Cas13 polypeptide. In various embodiments, the Cas13 is a nuclease-inactive Cas13 polypeptide (dCas13). In various embodiments, the Cas13 is a nuclease-active Cas13 polypeptide. In various embodiments, the specific RNA-binding domain comprises a viral protein. In various embodiments, the viral protein is a MS2 binding protein. In various embodiments, the viral protein is a λN protein. In various embodiments, the viral protein is a PP7 coat protein. In various embodiments, the viral protein is a QBeta coat protein.

In various embodiments, the viral protein is covalently bound to the CRISPR/Cas system. In various embodiments, the viral protein is not covalently bound to the CRISPR/Cas system. In various embodiments, the viral protein and CRISPR/Cas system is a fusion protein.

In one embodiment, the trans-splicing system comprises one repair template. In one embodiment, the trans-splicing system comprises more than one repair template. In various embodiments, the repair template is introduced as DNA. In various embodiments, the repair template is delivered as RNA.

In various embodiments, the repair template is expressed as RNA. In various embodiments, the repair template comprises a splice acceptor. In various embodiments, the repair template comprises a splice donor. In various embodiments, the repair template comprises one or more splice sites. In various embodiments, the repair template comprises an exon. In various embodiments, the repair template comprises more than one exon. In various embodiments, the repair template comprises an intron, the repair template comprises more than one intron. In various embodiments, the repair template comprises one or multiple sequences that hybridize to the target nucleic acid of interest. In various embodiments, at least one portion of the repair template comprises a ms2 hairpin that specifically binds to the MS2 binding protein. In various embodiments, the repair template comprises a boxB hairpin that specifically binds to the λN protein. In various embodiments, the repair template comprises a PP7 hairpin that specifically binds to the PP7 coat protein. In various embodiments, the repair template comprises a QBeta hairpin that specifically binds to the QBeta coat protein.

In various embodiments, the targeted trans-splicing system further comprises a cell. In various embodiments, at least one portion of the trans-splicing system is introduced into the cell.

In various embodiments, expression and/or activity of at least one portion of the trans-splicing system is transient. In various embodiments, the activity of at least one portion of the trans-splicing system is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and Auxin. In various embodiments, the at least one portion is a Cas13 protein. In various embodiments, the Cas13 protein further comprises a small molecule binding domain. In various embodiments, the Cas13 protein and the small molecule binding domain are linked by a glycine-serine linker. In various embodiments, the small molecule binding domain is an ABA-binding domain. In various embodiments, the ABA-binding domain comprises an ABI1 polypeptide.

In various embodiments, the targeted trans-splicing system further comprises a viral protein. In various embodiments, the viral protein further comprises a small molecule binding domain. In various embodiments, the viral protein and the small molecule binding domain are linked by a glycine-serine linker. In various embodiments, the small molecule binding domain is an ABA-binding domain. In various embodiments, the ABA-binding domain comprises a PYL1 polypeptide. In various embodiments, the addition of ABA induces targeted trans-splicing of a target pre-mRNA.

In various embodiments, delivery of at least one portion of the trans-splicing system to the cell is viral. In various embodiments, the virus is a retrovirus, adenovirus, adeno-associated virus, herpes simplex virus, anellovirus, or baculovirus. In various embodiments, delivery of at least one portion of the trans-splicing system to a cell is non-viral. In various embodiments, the non-viral delivery system is selected from a cationic lipid vehicle, electroporation, calcium phosphate transfection, mechanical transfection, and nanoparticle delivery.

In various embodiments, the CRISPR/Cas system is targeted to a nucleic acid. In various embodiments, the nucleic acid is RNA. In various embodiments, the nucleic acid is DNA. In various embodiments, the CRISPR/Cas system is associated with RNA in the cell. In various embodiments, the RNA is a pre-mRNA. In various embodiments, the CRISPR/Cas system is associated with DNA in the cell. In various embodiments, the CRISPR/Cas system is not associated with DNA in the cell. In various embodiments, the CRISPR/Cas system mediates trans-splicing of pre-mRNA in the nucleus of the cell. In various embodiments, the CRISPR/Cas system mediates trans-splicing of pre-mRNA in the cytoplasm of the cell.

In various embodiments, the trans-splicing occurs in dividing cells. In various embodiments, the trans-splicing occurs in post-mitotic cells. In various embodiments, post-mitotic cells are neurons, myocytes, or adipocytes.

In various embodiments, expression of at least one portion of the trans-splicing system is inducible. In various embodiments, activity of at least one portion of the trans-splicing system is inducible.

In another aspect, provided herein is a method of mediating a targeted trans-splicing event on a pre-mRNA in a cell, the method comprises introducing at least one portion of a targeted trans-splicing CRISPR/Cas system into the cell. In one aspect, the CRISPR/Cas system comprises: a nucleic acid-targeting CRISPR/Cas system; a nucleic acid guide that specifically hybridizes to a nucleic acid locus of interest; a specific RNA-binding domain; and a repair template comprising a splice donor and/or a splice acceptor and an RNA sequence that hybridizes under physiological conditions to the specific RNA-binding domain.

In one embodiment, the nucleic acid guide comprises RNA. In another embodiment, the nucleic acid guide comprises DNA.

In one embodiment, a single nucleic acid guide is introduced into the cell. In another embodiment, multiple nucleic acid guides are introduced into the cell.

In one embodiment, the multiple nucleic acid guides target one nucleic acid of interest. In another embodiment, the multiple nucleic acid guides target more than one nucleic acid of interest.

In various embodiments, the nucleic acid guide targets a splice acceptor (SA) site. In other embodiments, the nucleic acid guide targets a splice donor (SD) site.

In various embodiments, the nucleic acid guide targets a region near the splice site.

In various embodiments, the nucleic acid guide targets a region within 200 nucleotides of the splice site. In other embodiments, the nucleic acid guide targets a region less than or equal to 100 nucleotides of the splice site.

In various embodiments, a plurality of nucleic acid guides is delivered to a plurality of cells.

In various embodiments, the CRISPR/Cas system comprises a Cas13 polypeptide.

In various embodiments, the Cas13 polypeptide is a Cas13b polypeptide. In various embodiments, the Cas13b polypeptide is a nuclease-inactive Cas13b (dCas13b). In various embodiments, the Cas13b polypeptide is a nuclease-active Cas13b.

In various embodiments, the specific RNA-binding domain comprises a viral protein. In various embodiments, the viral protein is a MS2 binding protein. In various embodiments, the viral protein is a λN protein.

In various embodiments, the viral protein is a PP7 coat protein. In various embodiments, the viral protein is a QBeta coat protein.

In various embodiments, the viral protein is covalently bound to the CRISPR/Cas system. In various embodiments, the viral protein is not covalently bound to the CRISPR/Cas system. In various embodiments, the viral protein and CRISPR/Cas system is a fusion protein.

In various embodiments, the trans-splicing system comprises one splice acceptor repair template. In various embodiments, the trans-splicing system comprises more than one splice acceptor repair template. In various embodiments, the trans-splicing system comprises one splice donor repair template.

In various embodiments, the trans-splicing system comprising more than one splice donor repair template.

In various embodiments, the repair template comprises a ms2 hairpin that specifically binds to the MS2 binding protein. In various embodiments, the repair template comprises a boxB hairpin that specifically binds to the λN protein.

In various embodiments, the repair template comprises a PP7 hairpin that specifically binds to the PP7 coat protein. In various embodiments, the repair template comprises a QBeta hairpin that specifically binds to the QBeta coat protein.

In various embodiments, expression of at least one portion of the trans-splicing system is transient. In various embodiments, the activity of at least one portion of the trans-splicing system is transient. In various embodiments, the activity of at least one portion of the trans-splicing system is regulated by a small molecule. In various embodiments, the small molecule is selected from abscisic acid (ABA), rapamycin (or rapalog), FK506, Cyclosporine A, FK1012, Gibberellin3-AM, FKCsA, AP1903/AP20187, and Auxin.

In various embodiments, at least one portion of the trans-splicing system comprises a Cas13 polypeptide. In various embodiments, the Cas13 polypeptide further comprises a small molecule binding domain.

In various embodiments, the Cas13 polypeptide and the small molecule binding domain are linked by a glycine-serine linker. In various embodiments, the small molecule binding domain is an ABA-binding domain.

In various embodiments, the ABA-binding domain comprises an ABI1 polypeptide. In various embodiments, the method further comprises a viral protein. In various embodiments, the viral protein further comprises a small molecule binding domain. In various embodiments, the viral protein and the small molecule binding domain are linked by a glycine-serine linker.

In various embodiments, the small molecule binding domain is an ABA-binding domain.

In various embodiments, the ABA-binding domain comprises a PYL1 polypeptide.

In various embodiments, the addition of ABA induces targeted trans-splicing of a target pre-mRNA.

In various embodiments, delivery of at least one portion of the trans-splicing system to a cell is viral.

In various embodiments, the virus is a retrovirus, adenovirus, adeno-associated virus, herpes simplex virus, anellovirus or baculovirus.

In various embodiments, delivery of at least one portion of the trans-splicing system to a cell is non-viral.

In various embodiments, the non-viral delivery system is selected from a cationic lipid vehicle, electroporation, calcium phosphate transfection, mechanical transfection, and nanoparticle delivery.

In various embodiments, the CRISPR/Cas system associates with RNA in the cell.

In various embodiments, the RNA is a pre-mRNA.

In various embodiments, the CRISPR/Cas system associates with DNA in the cell.

In various embodiments, the CRISPR/Cas system does not associate with DNA in the cell.

In various embodiments, the CRISPR/Cas system mediates trans-splicing of pre-mRNA in the nucleus of the cell.

In various embodiments, the CRISPR/Cas system mediates trans-splicing of pre-mRNA in the cytoplasm of the cell.

In various embodiments, the CRISPR/Cas system mediates trans-splicing of a pre-mRNA at intron-exon junctions.

In various embodiments, wherein the CRISPR/Cas system mediates trans-splicing of a pre-mRNA at exon-intron junctions.

In various embodiments, the splice repair template does not comprise a splice acceptor.

In various embodiments, the splice repair template does not comprise a splice donor.

In various embodiments, the splice repair template comprises both a splice acceptor and a splice donor.

In various embodiments, the CRISPR/Cas system mediates trans-splicing of a pre-mRNA at the 5' end of the pre-mRNA. In various embodiments, the CRISPR/Cas system mediates trans-splicing of a pre-mRNA at the 3' end of the pre-mRNA. In various embodiments, the CRISPR/Cas system mediates trans-splicing of a pre-mRNA at an internal site within a pre-mRNA. In various embodiments, the CRISPR/Cas system mediates trans-splicing of a pre-mRNA within the 3' untranslated region (UTR). In various embodiments, the CRISPR/Cas system mediates trans-splicing of a pre-mRNA within the 5' untranslated region (UTR).

In various embodiments, the cell is a dividing cell. In various embodiments, the cell is a post-mitotic cell.

In various embodiments, the post-mitotic cell is selected from the group consisting of a neuron, myocyte, and adipocyte.

In various embodiments, expression of at least one portion of the trans-splicing system is inducible.

In various embodiments, activity of at least one portion of the trans-splicing system is inducible.

In various embodiments, the cell is in a subject suffering from a disease or disorder.

In various embodiments, the disease or disorder is a neurodegenerative, neurological, or neuromuscular disease or disorder.

In various embodiments, the neurodegenerative, neurological, or neuromuscular disease or disorder is selected from the group consisting of spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

In yet another aspect, disclosed herein is a targeted trans-splicing system comprising: a nucleic acid binding protein domain; a specific RNA-binding domain; and a repair template comprising a splice donor and/or a splice acceptor and an RNA sequence that hybridizes under stringent conditions to the specific RNA-binding domain.

In various embodiments, the nucleic acid binding protein domain targets a splice acceptor (SA) site. In various embodiments, the nucleic acid binding protein domain targets a splice donor (SD) site. In various embodiments, the specific RNA-binding domain comprises a viral protein. In various embodiments, the viral protein is a MS2 binding protein. In various embodiments, the viral protein is a λN protein. In various embodiments, the viral protein is a PP7 coat protein. In various embodiments, the viral protein is a QBeta coat protein. In various embodiments, the viral protein is covalently bound to the nucleic acid binding protein domain. In various embodiments, the viral protein is not covalently bound to the nucleic acid binding protein domain. In various embodiments, the viral protein and nucleic acid binding protein domain is a fusion protein.

In various embodiments, the trans-splicing system comprises one splice acceptor repair template. In various embodiments, the trans-splicing system comprises more than one splice acceptor repair template. In various embodiments, the trans-splicing system comprises one splice donor repair template. In various embodiments, the trans-splicing system comprises more than one splice donor repair template. In various embodiments, the trans-splicing system comprises a repair template comprising a splice donor and/or a splice acceptor. In various embodiments, at least one portion of the repair template comprises a ms2 hairpin that specifically binds to the MS2 binding protein. In various embodiments, the splice repair template comprises a boxB hairpin that specifically binds to the λN protein. In various embodiments, the splice repair template comprises a PP7 hairpin that specifically binds to the PP7 coat protein. In various embodiments, the splice repair template comprises a QBeta hairpin that specifically binds to the QBeta coat protein.

In various embodiments, the targeted trans-splicing system further comprises a cell. In various embodiments, at least one portion of the trans-splicing system is introduced into the cell.

In various embodiments, expression and/or activity of at least one portion of the trans-splicing system is transient. In various embodiments, the activity of at least one portion of the trans-splicing system is regulated by a small molecule.

In various embodiments, the small molecule is selected from abscisic acid (ABA), rapamycin (or rapalog), FK506, Cyclosporine A, FK1012, Gibberellin3-AM, FKCsA, AP1903/AP20187, and Auxin. In various embodiments, at least one portion is the nucleic acid binding protein domain. In various embodiments, the nucleic acid binding protein domain further comprises a small molecule binding domain. In various embodiments, the nucleic acid binding protein domain and the small molecule binding domain are linked by a glycine-serine linker. In various embodiments, the small molecule binding domain is an ABA-binding domain. In various embodiments, the ABA-binding domain comprises an ABI1 polypeptide. In various embodiments, the trans-splicing system further comprises a viral protein. In various embodiments, the viral protein further comprises a small molecule binding domain. In various embodiments, the viral protein and the small molecule binding domain are linked by a glycine-serine linker. In various embodiments, the small molecule binding domain is an ABA-binding domain. In various embodiments, the ABA-binding domain comprises a PYL1 polypeptide. In various embodiments, the addition of ABA induces targeted trans-splicing of a target pre-mRNA.

In various embodiments, delivery of at least one portion of the trans-splicing system to the cell is viral. In various embodiments, the virus is a retrovirus, adenovirus, adeno-associated virus, herpes simplex virus, anellovirus, or baculovirus. In various embodiments, delivery of at least one portion of the trans-splicing system to a cell is non-viral. In various embodiments, the non-viral delivery system is selected from a cationic lipid vehicle, electroporation, calcium phosphate transfection, mechanical transfection, and nanoparticle delivery.

In various embodiments, the nucleic acid binding protein domain is targeted to DNA. In various embodiments, the nucleic acid binding protein domain is targeted to RNA. In various embodiments, the nucleic acid binding protein domain is associated with RNA in the cell. In various embodiments, the RNA is a pre-mRNA. In various embodiments, the nucleic acid binding protein domain is associated with DNA in the cell. In various embodiments, the nucleic acid binding protein domain is not associated with DNA in the cell.

In various embodiments, the system mediates trans-splicing of pre-mRNA in the nucleus of the cell. In various embodiments, the system mediates trans-splicing of pre-mRNA in the cytoplasm of the cell. In various embodiments, the system mediates trans-splicing of a pre-mRNA at intron-exon junctions. In various embodiments, the nucleic acid binding protein domain mediates trans-splicing of a pre-mRNA at exon-intron junctions. In various embodiments, the splice repair template does not comprise a splice donor. In various embodiments, the splice repair template does not comprise a splice acceptor. In various embodiments, the splice repair template comprises both a splice acceptor and a splice donor.

In various embodiments, the system comprises multiple splice templates. In various embodiments, the multiple splice templates comprise splice repair templates that comprise a splice acceptor and splice repair templates that comprise a splice donor. In various embodiments, at least some of the multiple splice repair templates comprise a splice acceptor and a splice donor.

In various embodiments, the system mediates trans-splicing of a pre-mRNA at the 5' end of the pre-mRNA. In various embodiments, the system mediates trans-splicing of a pre-mRNA at the 3' end of the pre-mRNA. In various embodiments, the system mediates trans-splicing of a pre-mRNA at an internal site within a pre-mRNA. In various embodiments, the system replaces the 5' or the 3' end of the target mRNA.

In various embodiments, the target mRNA is a pre-mRNA. In various embodiments, the system comprises replacing one or more exons of the target mRNA, excluding the first and last exon of the target mRNA. In various embodiments, the nucleic acid binding protein domain mediates trans-splicing of a pre-mRNA within the 3' untranslated region (UTR). In various embodiments, the nucleic acid binding protein domain mediates trans-splicing of a pre-mRNA within the 5' untranslated region (UTR).

In various embodiments, the trans-splicing occurs in dividing cells. In various embodiments, the trans-splicing occurs in post-mitotic cells. In various embodiments, the post-mitotic cells are neurons, myocytes, or adipocytes.

In various embodiments, expression of at least one portion of the trans-splicing system is inducible. In various embodiments, activity of at least one portion of the trans-splicing system is inducible. In various embodiments, the nucleic acid binding protein domain is a domain from a zinc finger nuclease (ZFNs) or a Pumby module, or is an RNA recognition motif.

BRIEF DESCRIPTION OF THE FIGURES

FIG. 8A illustrates a dCas13b polypeptide fused to abscisic acid (ABA)-binding protein ABI1, and MS2 fused to PYL1.

FIG. 9A illustrates RNAseq reads spanning possible junctions.

FIG. 10A illustrates a strategy for 5' targeting of trans-splicing.

FIG. 11A illustrates dPspCas13b-MS2, gRNA, target and internal repair template constructs to test if CRISPR-mediated internal exon repair is possible.

DETAILED DESCRIPTION

Figures 1A, 1B, 1C, 1D, 1E:
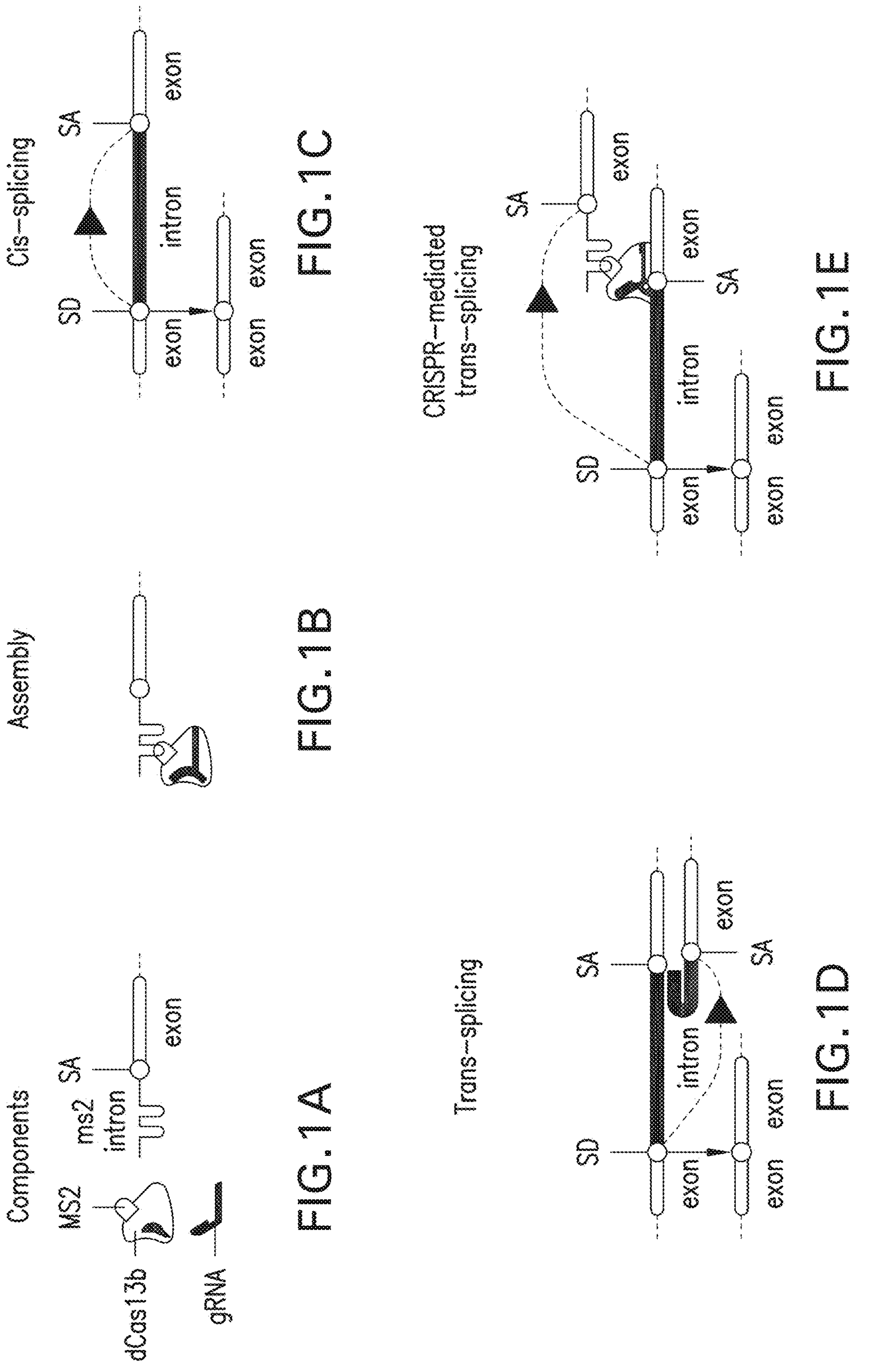
FIG. 1A-1E illustrates the components of the CRISPR/Cas system, cis- and trans-splicing that can occur within a pre-mRNA, and the CRISPR-mediated trans-splicing.

This disclosure provides compositions and methods of using these compositions to mediate a targeted trans-splicing event on a pre-mRNA in a cell. In various embodiments, the targeted trans-splicing event is mediated by a CRISPR/Cas system. In various embodiments, the CRISPR/Cas system that mediates a targeted trans-splicing event is used to treat a neurodegenerative disease or disorder. These compositions and methods include a trans-splicing event mediated by a CRISPR/Cas system comprising a nuclease-inactive Cas13.

As used within the Claims, the Summary, and the Detailed Description herein, the term "a" or "an" entity refers to one or more of that entity; for example, "a cell" is understood to represent one or more cells.

Furthermore, "and/or" where used herein is to be taken as specific disclosure of each of the two specified features of components with or without the other. Thus, the term "and/or" as used in a phrase such as "A and/or B" herein is intended to include "A and B," "A or B," "A" (alone), and "B" (alone).

It is understood that wherever aspects are described herein with the language "comprising," otherwise analogous aspects described in terms of "consisting of" are also provided.

The term "near a splice site" means within 500 bp of a splice site.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition, and may include, for example, minimal changes or improvements in one or more measurable markers of the disease or condition being treated.

The terms "patient," "subject," "individual," and the like are used interchangeably herein, and refer to any animal, or cells thereof whether in vitro or in situ, amenable to the methods described herein. In certain non-limiting embodiments, the patient, subject, or individual is a human.

In aspects of the invention the terms "guide nucleic acid, "RNA guide," "DNA guide," and "single guide nucleic acid," are used interchangeably and refer to the polynucleotide sequence comprising the guide sequence, and the tracr sequence. In certain embodiments, the guide nucleic acid comprises only a crispr RNA (crRNA). The term "guide sequence" refers to a 10-80 bp sequence within the RNA or DNA guide that specifies the target site. In aspects of the invention, the terms "guide sequence" and "spacer" are used interchangeably. In aspects of the invention, the terms "direct repeat" and "scaffold" are used interchangeably.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. In some embodiments, stringent conditions include hybridization in 6× sodium chloride/sodium citrate (SSC) at about 45° C., followed by one or more washes in 0.2×SSC, 0.1% SDS at 50-65° C. Other examples of stringent conditions are known to those skilled in the art and can be found in Current Protocols in Molecular Biology, Ausubel et al., eds., John Wiley & Sons, Inc. (1995), sections 2, 4, and 6, the teachings of which are hereby incorporated by reference herein. Additional stringent conditions can be found in Molecular Cloning: A Laboratory Manual, Sambrook et al., Cold Spring Harbor Press, Cold Spring Harbor, N.Y. (1989), chapters 7, 9, and 11, the teachings of which are hereby incorporated by reference herein.

As used herein, the term "physiological condition" typically refers to biologic parameters that are valid for an animal, specifically a mammal, more specifically a human. The term may relate to biochemical and biophysical paramters commonly found in mammals, especially in the human body (especially body fluids). The "physiological condition" may relate to parameters found in a sick mammal or human patient, as well as that corresponding parameters found in a healthy body. For example, a sick mammal or human patient may have a high but "physiological" temperature condition when the mammal or the human is suffering from a fever. Regarding "physiological conditions" the most important parameters are temperature (37° C. for human body), pH (7.35-7.45 for human blood), osmotic pressure (280-300 mmol/Kg H 2 O) and, if necessary, protein content (66-85 g/1 serum). However, those skilled in the art will appreciate that these parameters may vary. For example, such temperature, pH, osmotic pressure, and protein content may be different in a given body or tissue, such as blood or cerebrospinal fluid (Klinke (2005) Physiologie, 5th ed., Georg Thieme Verlag, Stuttgart). "Physiological condition" can also refer to conditions in a buffer system, solvent, and/or excipient that mimic conditions in an animal.

"Hybridization" or "hybridizes" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these.

As used herein, "expression" refers to the process by which a polynucleotide is transcribed from a DNA template (such as into a mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide," "peptide," "protein," and "enzyme" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component, as used herein the term "amino acid" includes natural and/or unnatural or synthetic amino acids, including glycine and both the D or L optical isomers, and amino acid analogs and peptidomimetics.

The term "nucleic acid" or nucleic acid sequence" refers to a deoxyribonucleic or ribonucleic oligonucleotide in either single- or double-stranded form. The term encompasses nucleic acids, i.e., oligonucleotides, containing known analogues of natural nucleotides. The term also encompasses nucleic-acid-like structures with synthetic backbones, see, e.g., Eckstein, Biomed Biochim Acta. 1991; 50(10-11):S114-7; Baserga et al. Genes Dev. 1992 June; 6(6):1120-30; Milligan et al., Nucleic Acids Res. 1993 Jan. 25; 21(2):327-33; WO 97/03211; WO 96/39154; Mata, Toxicol Appl Pharmacol. 1997 May; 144(1):189-97; Strauss-Soukup, Biochemistry. 1997 Aug. 19; 36(33): 10026-32; and Samstag, Antisense Nucleic Acid Drug Dev. 1996 Fall; 6(3):153-6.

"Inducible" as used herein refers to inducing expression or activity of a protein or a system, e.g., the trans-splicing system of the instant application. Known inducible gene expression systems have been designed to allow for chemically induced activation of an inserted nucleic acid sequence, resulting in gene overexpression or repression. Inducing activity of a protein or system can include release of a molecule to allow for activity or the addition of an effector molecule to induce activity of a protein or system.

The term "nuclease-inactive" is used to describe a Cas enzyme which no longer has nuclease activity. In some embodiments, a Cas enzyme that no longer has nuclease activity can have a small amount of residual activity. In some embodiments, this small amount of residual activity is less than 5, 1, 0.1, 0.05, 0.01 or 0.005% of wild type nuclease activity of the Cas enzyme. A nuclease-inactive Cas protein may interchangeably be referred to as a "dCas" protein, e.g., dCas13b. In some embodiments, the dCas protein can be a dCas13b protein. In some embodiments, a polynucleotide sequence set forth in SEQ ID NOs: 1, 62, 71, 74, 77, 80, 83, 86, or 89 encodes a dCas13b protein. In some embodiments, dCas13b corresponds to, or comprises in part or in whole, the amino acid sequence set forth as SEQ ID NOs: 2, 63, 72, 75, 78, 81, 84, 87, or 90. In some embodiments, the dCas protein can be a dCas13a protein. In some embodiments, a dCas13a protein is encoded by a polynucleotide sequence set forth in any one of SEQ ID NOs: 17, 20, 23, 26, 29, 32, 35, 38, 41, 44, 47, 50, 53, 56, or 59. In some embodiments, dCas13a corresponds to, or comprises in part or in whole, any one of the amino acid sequence set forth as SEQ ID NOs: 18, 21, 24, 27, 30, 33, 36, 39, 42, 45, 48, 51, 54, 57, or 60. In some embodiments, the dCas protein can be a dCas13d protein. In some embodiments, the dCas13d protein is encoded by the polynucleotide sequence set forth in SEQ ID NO: 65. In some embodiments, the dCas13d protein corresponds to, or comprises in part or in whole, the amino acid sequence set forth in SEQ ID NO: 66. Nuclease-inactive Cas proteins may be variants having mutations which result in nuclease activity inactivated.

"Targeted" is used to describe a molecule, protein, or complex that comprise a targeting moiety which specifically binds to one or more targets associated with a specific pre-mRNA of interest.

As used herein, the term "RNA-binding" is used to describe a molecule, protein, nucleic acid, or complex that specifically binds to RNA.

"Pre-mRNA" refers to a precursor mRNA and is an RNA which contains both exons and intron(s). Pre-mRNA is a type of primary transcript that becomes a messenger RNA after processing. It is synthesized from a DNA template in the cell nucleus by transcription. In some embodiments, RNA is from a mammalian cell. In other embodiments, the RNA is from the mitochondria of a mammalian cell.

The phrase "associates with DNA" refers to nucleic acids, systems, proteins, and molecules that may bind or be in the same vicinity as DNA.

The term "post-mitotic" refers to a non-replicating cell, such as a cell of the nervous system, bone marrow cells, muscle cells, liver cells, and the like. Cells of the nervous system include neurons, glial cells, etc. that is no longer capable of undergoing mitosis.

The term "non-dividing cells" refers to a cell that does not frequently undergo mitosis. Many non-dividing cells may be blocked at any point in the cell cycle (e.g., G0/G1, G1/S, G2/M), as long as most of the cells are not actively dividing. In some embodiments, non-dividing cells are from tissue types that do not frequently divide. Examples of non-dividing cells in the body include, but are not limited to, neuronal, muscle (myocytes), liver, skin, heart, lung, adipose, and bone marrow cells, and their derivatives. "Dividing cells" would be a cell that frequently actively undergoes mitosis. In some embodiments, dividing cells are from tissue types that do not frequently divide. Examples of dividing cells in the body include, but are not limited to, epithelial cells and hematopoietic cells.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health. Diseases and disorders include spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, herpes simplex virus, anellovirus, baculovirus, retroviral vectors, and the like.

The term "specifically binds," or the like, means that a given molecule forms a complex with another molecule that is relatively stable under physiologic conditions. Methods for determining whether a given molecule specifically binds to another molecule are well known in the art and include, for example, equilibrium dialysis, surface plasmon resonance, and the like. For example, an RNA hairpin that "specifically binds" a viral protein, as used herein, includes RNA hairpins that bind viral proteins or a portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay.

"Variant" as used herein means a polypeptide or nucleotide sequence that differs from a given polypeptide or nucleotide sequence in amino acid or nucleic acid sequence by the addition (e.g., insertion), deletion, or conservative substitution of amino acids or nucleotides, but that retains the biological activity of the given polypeptide (e.g., a variant nucleic acid could still encode the same or a similar amino acid sequence). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of 2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity. Use of "variant" herein is intended to encompass fragments of a variant unless otherwise contradicted by context.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively, or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 70% sequence identity to its parent polynucleotide. The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl-?page=/NPSA/npsa_clustalw.html. Preferred parameters used are the default parameters as they are set on http://www.ebi.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:I54-I62) or Markov random fields. When percentages of sequence identity are referred to in the present application, these percentages are calculated in relation to the full length of the longer sequence, if not specifically indicated otherwise.

Trans-Splicing

Figure 7:
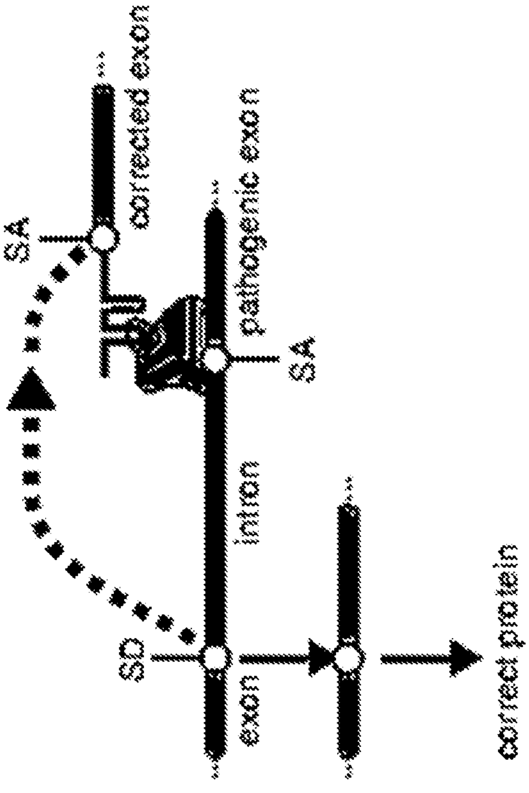
FIG. 7 is a schematic that illustrates the components of the CRISPR/Cas system in trans-splicing in the context of correcting a pathogenic exon.

A number of gene therapy techniques have been devised to address specific pathologies. These different approaches range from gene supplementation using viral vectors to genome editing using CRISPR/Cas9 technology. However, there are times when these approaches are not applicable or effective to achieve significant therapeutic effect. Currently, there are efforts to address this problem by repairing mutant transcripts to make clean transcripts without altering gene expression levels by exploiting the spliceosome to catalyze therapeutic trans-splicing events. (See, e.g., FIG. 7).

Splicing is a reaction found in the nucleus of eukaryotic cells catalyzed by the spliceosome, a large ribonucleoproteic complex. Splicing results in the elimination of introns in the pre-mRNA. This reaction is considered cis-splicing as it involves a donor site, a branch point, and an acceptor site located on the same RNA molecule.

The spliceosome can also catalyze trans-splicing events. Unlike cis-splicing, trans-splicing occurs between two different RNA molecules. The molecular process is the same, except that the final mRNA is composed of the first exon(s) of the first pre-mRNA and the exon(s) of another, thus creating a chimeric molecule. With the discovery of naturally occurring trans-splicing, it was demonstrated to be useful for bioengineering purposes. In 1999, Puttaraju et al. (Nature Biotech., 17:246-52) demonstrated the ability of diverting trans-splicing to induce repair of an endogenous mRNA using exon exchange mediated by an artificial RNA capable of inducing trans-splicing in cell culture. Subsequent studies showed the feasibility of using this in vivo, leading to the functional restoration of mutant cystic fibrosis transmembrane conductance regulator (CFTR) in a human bronchial xenograft model system. This led to the study of and use of the spliceosome-mediated RNA trans-splicing, or SMaRT system, as a gene therapy strategy. While this technology has been used to mediate repair of various mRNA sequences associated with disease, there are drawbacks and limitations to the SMaRT technology.

There are some important drawbacks to the current SMaRT technology that one must take into account. One drawback of the SMaRT technology is the specificity of the molecule. Theoretically, off-target trans-splicing with random mRNAs should be processed by nonsense mediated decay or nonstop decay, it is essential to validate the specificity of the pre-mRNA trans-splicing molecule for the target sequence and limit nonspecific events. It has been found that increasing the length of the binding domain sequence up to 153 bases dramatically decreases the probability of finding the entire and exact corresponding sequence in a human genome and increases efficiency. Another drawback is the efficiency of the system. With certain diseases, even a low level of expression of the mutated protein will lead to a diseased phenotype.

CRISPR/Cas

The present disclosure includes compositions and methods that comprise a targeted trans-splicing system comprising a nuclease-inactive CRISPR/Cas system, a nucleic acid guide, a specific RNA-binding domain, and a repair template comprising an RNA sequences that hybridizes under stringent conditions to the specific RNA-binding domain. Clustered regularly interspaced short palindromic repeats, known more widely as CRISPR, and a family of enzymes known as Cas (CRISPR-associated) proteins is a prokaryotic immune system that confers resistance to foreign genetic elements such as those present within plasmids and phages that provides a form of acquired immunity. Recently, CRISPR/Cas systems have been developed as tools used in basic molecular biology research, the development of biotechnology products, and treatment of disease. These systems have been widely adopted for mediating targeted DNA cleavage which in turn drives targeted gene disruption through non-homologous end joining (NHEJ) or precise gene editing through template-dependent homology-directed repair (HDR).

In certain embodiments, the CRISPR/Cas system described herein comprises a Cas13 enzyme encoded by a polynucleotide sequence of any one of SEQ ID NOs: 1, 17, 20, 23, 26, 29, 32, 35, 38, 41, 44, 47, 50, 53, 56, 59, 62, 65, 71, 74, 77, 80, 83, 86, or 89 or variants thereof. In certain embodiments, the CRISPR/Cas system comprises a Cas13 enzyme comprising an amino acid sequence of any one of SEQ ID NOs: 2, 18, 21, 24, 27, 30, 33, 36, 39, 42, 45, 48, 51, 54, 57, 60, 63, 66, 72, 75, 78, 81, 84, 87, or 90 or variants thereof. Cas13 enzymes are classified as Type VI CRISPR-Cas systems and have two Higher Eukaryotes and Prokaryotes Nucleotide-binding (HEPN) endoRNase domains that mediate precise RNA cleavage with a preference for targets with protospacer flanking site motif observed biochemically and in bacteria. Three Cas13 protein families have been identified to date. Cas13a, previously known as C2c2, can be adapted as tools for nucleic acid detection. Cas13b has been used for both RNA editing and nucleic acid detection, and is unique among the type VI CRISPR effectors in its linear domain architecture and CRISPR RNA (crRNA) structures. Cas13 enzymes are programmable in nature, and makes them an attractive starting point to develop tools for RNA binding and perturbation applications (Cox et al. (2017) Science. 358:1019-1027, incorporated by reference herein in its entirety).

The term "nucleic acid binding protein domain" refers to a domain of a protein that is capable of targeting a specific nucleic acid sequence. In some embodiments, the nucleic acid sequence is DNA. In other embodiments, the nucleic acid sequence is RNA. In some embodiments, the nucleic acid binding protein domain specifically binds to a splice acceptor or a splice donor site. Some examples of nucleic acid binding protein domains include, but are not limited to, zinc finger nucleases (ZFNs), and Pumby modules (Adamala et al. (2016) Proc Natl Acad Sci. 113(19):E2579-E2588, incorporated by reference herein in its entirety), or humanized CRISPR, e.g., CRISPR-Cas-Inspired RNA Targeting System (CIRTS) (Rauch et al. (2019) Cell. 178(1): P122-134, incorporated by reference herein in its entirety), or RNA recognition motif (Maris et al. (2005) The FEBS journal 272: 2118-2131).

The RNA-targeting systems, the vector systems, the vectors and the compositions described herein may be used in various RNA-targeting applications, altering or modifying synthesis of a gene product, such as a protein, RNA cleavage, RNA editing, RNA splicing; trafficking of target RNA, tracing of target RNA, isolation of target RNA, visualization of target RNA, etc.

The term “splice donor” refers to the 5' end of the intron.

The term “splice acceptor” refers to the 3' end of the intron.

The term “repair template” refers to a nucleic acid molecule with comprising a desired sequence to be spliced to a nucleic acid locus of interest. In some embodiments, the desired sequence to be spliced is an exon. In some embodiments, the repair template further comprises one or more introns.

In certain embodiments, the nucleic acid guide is a RNA guide. In certain embodiments, the nucleic acid guide is a DNA guide. In some embodiments, the guide nucleic acid, such as a guide RNA or gRNA, is a specific sequence that recognizes the target pre-mRNA of interest and directs the Cas protein to said pre-mRNA. In some embodiments, the guide nucleic acid targets the DNA locus where transcription is occurring. Generally, the guide nucleic acid is made of two components—a crispr RNA (crRNA), which is a 17-20 nucleotide sequence complementary to the target sequences, and a tracr RNA, which serves as a binding scaffold for the Cas nuclease. More recently, the crRNA and tracr RNA components have been fused into one molecule to create a single guide RNA (sgRNA). In certain embodiments, the trans-splicing system comprises one nucleic acid guides. For currently characterized CRISPR/Cas13 systems, a crispr RNA (crRNA) is comprised of a spacer and a direct repeat. For Cas13b, the spacer is 5' and the direct repeat is the 3' of the crRNA. For Cas13b, crRNA and guide RNA can be used interchangeably. For Cas13a and Cas13d, the spacer is 3' and the direct repeat is the 5' of the crRNA (Zhang F (2019). Development of CRISPR-Cas systems for genome editing and beyond. Quarterly Reviews of Biophysics 52, e6, 1-31. https://doi.org/10.1017/S0033583519000052, incorporated by reference herein in its entirety). In certain embodiments, the trans-splicing system comprises more than one nucleic acid guide. In certain embodiments, more than one nucleic acid guides are in an array operably linked to one promoter, which are then cleaved and processed by Cas13. In some embodiments, an array has direct repeats between multiple spacers wherein each spacer targets a different nucleic acid. In certain embodiments, more than one nucleic acid guides are expressed by separate promoters, such as U6 promotors. In certain embodiments, the guide RNAs have a direct repeat (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91) at the 5' end, and a spacer at the 3' end. In other embodiments, the guide RNAs have a direct repeat (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91) at the 3' end, and a spacer at the 5' end. In other embodiments, spacers are flanked by direct repeats (e.g., SEQ ID NOs: 10, 19, 22, 25, 28, 31, 34, 37, 40, 43, 46, 49, 52, 55, 58, 61, 64, 67, 73, 76, 79, 82, 85, 88, and 91). In certain embodiments, the direct repeats have at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with the direct repeat nucleic acid sequences of SEQ ID NOs: 10, 19, 22, 25, 28, 31, 34, 37, 40, 43, 46, 49, 52, 55, 58, 61, 64, 67, 73, 76, 79, 82, 85, 88, or 91. In certain embodiments, the nucleic acid guides recognize multiple targets. In certain embodiments, the instant disclosure provides nucleic acid guide sequences having at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with the nucleic acid sequence of SEQ ID NO: 11 or 12.

The invention uses nucleic acids to bind target RNA sequences. This is advantageous as nucleic acids are much easier and cheaper to produce than proteins, and the specificity can be varied according to the length of the stretch where homology is sought. Complex 3-D positioning of multiple fingers, for example is not required. The terms “polynucleotide”, “nucleotide”, “nucleotide sequence”, “nucleic acid” and “oligonucleotide” are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

In certain embodiments, the specific RNA binding domain of the CRISPR/Cas system comprises a viral protein fused to the Cas protein. The term “viral protein” can be used to describe a protein of viral origin that is bound to the Cas protein that binds to a hairpin of the splice acceptor template. Coat proteins of single-stranded RNA bacteriophages are translational repressors of viral replicase. They accomplish this by specifically binding an RNA hairpin that encompasses the replicase start codon. Some examples would be the coat proteins of RNA phages MS2, λN, QBeta, and PP7 (e.g. SEQ ID NOs: 5-9). In certain embodiments, the specific RNA binding domain comprises an amino acid sequence of any one of SEQ ID NOs: 6, 7, 8, or 9, or variants thereof. The term “binding”, or the like, means that a viral protein forms a complex with a corresponding hairpin that is relatively stable under physiologic conditions. In certain embodiments, the instant disclosure provides hairpin sequences having at least 70% (e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%) sequence identity with any one of the nucleic acid sequences of SEQ ID NOs: 13-16.

In certain embodiments, the viral protein is covalently bound to the CRISPR/Cas system. In certain embodiments, the viral protein is not covalently bound to the CRISPR/Cas system. In certain embodiments, the viral protein and CRISPR/Cas system is a fusion protein. As used herein, the term "covalently bound" refers to a chemical bond that involves the sharing of electrons between atoms. The term "fusion protein" refers to proteins created through the joining of two or more genes that originally coded for separate proteins.

In some embodiments, the specific RNA binding domain of the CRISPR/Cas system comprises an RNA binding protein that is not of viral origin.

In certain embodiments, the trans-splicing system comprises one repair template. In certain embodiments, the trans-splicing system comprises more than one repair template.

In certain embodiments, the trans-splicing system comprises a nucleic acid guide-binding protein domain comprising a nuclease-inactive CRISPR/Cas system.

In certain embodiments, expression and/or the activity of the trans-splicing system is transient. "Transient expression" refers to the temporary expression of genes that are expressed for a time after a nucleic acid has been introduced into eukaryotic cells. In some embodiments, transient expression of the trans-splicing system may be controlled with a small molecule. As used herein, the term "small molecule" refers to a a non-nucleic acid/non-amino acid molecule. As used herein, the term "small molecule binding domain" refers to a portion of a molecule, often a protein, that specifically binds to a given small molecule. These can include a tet-ON or tet-OFF system or chemogetic control using synthetic transcription factors and protease inhibitors. For example, dCas13-NLS-NS3-MS2 remains active and uncleaved in the presence of BILN-2061. (Tague et al., Nature Methods, Volume 15, pages 519-522 (2018) and Wagner et al. Nature Chemical Biology, Volume 14, pages 1043-1050 (2018), incorporated by reference herein in their entireties). In some embodiments, transient expression of the trans-splicing system can be controlled by degradation of the delivery particle. In some embodiments, expression of the trans-splicing system may be controlled with a light-activated transcription factor (Konermann et al., Nature, Volume 500, pages 472-476 (22 Aug. 2013), incorporated by reference herein in its entirety). In some embodiments, assembly of the trans-splicing system may be controlled with a small molecule, e.g., chemically induced dimerization. Examples include, dCas13-NLS-FKBP and FKBP-NLS-MS2, assembled by FK1012; dCas13-NLS-FKBP and CNA-NLS-MS2, assembled by FK506; and dCas13-NLS-FRB and MS2-FKBP transiently assembled by rapamycin, and rapidly disassembled by FK506. (Braun et al., Nature Communications, DOI: 10.1038/s41467-017-00644-y, incorporated by reference herein in its entirety). Additional examples include dCas13-NLS-ABI1 and PYL1-MS2, assembled by abscisic acid (Gao et al., Nature Methods, DOI: https://doi.org/10.1038/nmeth.4042, incorporated by reference herein in its entirety). Other examples of small molecules and their chemically induced systems are included in Stanton et al. (Science, DOI: http://dx.doi.org/10.1126/science.aao5902, incorporated by reference herein in its entirety). In some embodiments, activity of the trans-splicing system can be controlled using a small molecule to degrade the system. In some embodiments, the small molecule binding domain may be linked to the CRISPR system via a self-cleaving peptide. In some embodiments, the self-cleaving peptide is a 2A self-cleaving peptide. Some examples include, but are not limited to, T2A, P2A, E2A, and F2A sequences.

In some embodiments, assembly of the trans-splicing system is mediated by a SunTag (Tanenbaum et al., Cell, 2014, DOI: https://doi.org/10.1016/j.cell.2014.09.039). In some embodiments, assembly of the trans-splicing system is mediated by hairpins on the guide RNA, either native or modified, such as the SAM system (Konermann et al., Nature, 2015, DOI: 10.1038/nature14136).

In some embodiments, transient expression is performed by delivering the trans-splicing system as RNA as shown in Hewitt et al., Science Translational Medicine 30 Jan. 2019: Vol. 11, Issue 477, eaat9143, incorporated by reference herein in its entirety. In some embodiments, the trans-splicing system assembly can be controlled via light. For example, dCas13-NLS-CRY2 and CIB1-NSL-MS2 are assembled by 466 nm light. (Konermann et al. (2013)). In some embodiments, transient expression is performed by delivering the trans-splicing system with an episomal or non-integrating virus. These viruses include Ad5, AAV, HSV-1, or baculovirus. In some embodiments, activity of the trans-splicing system is mediated by conditionally active inteins, such as inteins that undergo protein splicing in the presence of 4-hydroxytamoxifen (4-HT) or other small molecules. In some embodiments, activity of the trans-splicing system is controlled by 4-HT by including a 4-HT sensitive intein into Cas13 at a location that disrupts Cas13 activity until 4-HT mediated protein splicing has taken place, similar to Davis et al. (Nature Chemical Biology, 2015, DOI: https://doi.org/10.1038/nchembio.1793).

Delivery

In some embodiments, the nucleic acid introduced into the eukaryotic cell is a plasmid DNA or viral vector.

Preferably, delivery is in the form of a vector which may be a viral vectors, such as a lenti- or baculo- or adeno-viral/adeno-associated viral vectors, but other means of delivery are known (such as yeast systems, microvesicles, gene guns/means of attaching vectors to gold nanoparticles) and are provided. The viral vector may be selected from a variety of families/genera of viruses, including, but not limited to Myoviridae, Siphoviridae, Podoviridae, Corticoviridae, Lipothrixviridae, Poxviridae, Irdoviridae, Adenoviridae, Polyomaviridae. Papillomaviridae, Mimiviridae, Pandoravirusa, Salterprovirusa, Inoviridae, Microviridae. Parvoviridae, Circoviridae, Hepadnaviridae, Caulimoviridae, Retroviridae, Cystoviridae, Reoviridae, Birnaviridae, Totiviridae, Partitiviridae, Filoviridae, Orthomyxoviridae, Deltavirusa, Leviviridae, Picornaviridae, Mamaviridae, Secoviridae, Potyviridae, Caliciviridae, Hepeviridae, Astroviridae, Nodaviridae, Tetraviridae, Luteoviridae, Tombusviridae, Coronaviridae, Arteriviridae, Flaviviridae, Togaviridae, Virgaviridae, Bromoviridae, Tymoviridae, Alphaflexiviridac, Sobemovirusa, or Idacovirusa.

A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. While in herein methods the vector may be a viral vector and this is advantageously AAV, other viral vectors as herein discussed can be employed, such as lentivirus. For example, baculoviruses may be used for expression in insect cells. These insect cells may, in turn be useful for producing large quantities of further vectors, such as AAV or lentivirus adapted for delivery of the present invention. Also envisaged is a method of delivering the present CRISPR enzyme comprising delivering to a cell mRNA encoding the CRISPR enzyme. It will be appreciated that in certain embodiments the CRISPR enzyme is truncated, and/or comprised of less than one thousand amino acids or less than four thousand amino acids, and/or is a nuclease or nickase, and/or is codon-optimized, and/or comprises one or more mutations, and/or comprises a chimeric CRISPR enzyme, and/or the other options as herein discussed.

In some embodiments, expression of a nucleic acid sequence encoding a CRISPR enzyme may be driven by a promoter. In some embodiments, a single promoter drives expression of a nucleic acid sequence encoding a CRISPR enzyme and one or more of the guide sequences. In some embodiments, the CRISPR enzyme and guide sequence(s) are operable linked to and expressed from the same promoter. In some embodiments, the CRISPR enzyme and guide sequence(s) are expressed from different promoters. For example, the promoter(s) can be, but are not limited to, a UBC promtoer, a PGK promoter, an EF1A promoter, a CMV promoter, an EFS promoter, a SV40 promtoer, and a TRE promoter. The promoter may be a weak or a strong promoter. The promoter may be a constitutive promoter or an inducible promoter. In some embodiments, the promoter can also be an AAV ITR, and can be advantageous for eliminating the need for an additional promoter element, which can take up space in the vector. The additional space freed up by use of an AAV ITR can be used to drive the expression of additional elements, such as guide sequences. In some embodiments, the promoter may be a tissue specific promoter.

In some embodiments, an enzyme coding sequence encoding a CRISPR enzyme is codon-optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus. Pa.), are also available. In some embodiments, one or more codons (e.g., 1, 2, 3, 4, 5, 10, 15, 20, 25, 50, or more, or all codons) in a sequence encoding a Cas protein correspond to the most frequently used codon for a particular amino acid.

In some embodiments, a vector encodes a Cas protein comprising one or more nuclear localization sequences (NLSs), such as about or more than about 1, 2, 3, 4, 5, 6, 7, 8, 9, 10, or more NLSs. In some embodiments, the Cas protein comprises about or more than 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, bur other types of NLS are known. In some embodiments, the NLS is between two domains, for example between the Cas13 protein and the viral protein. The NLS may also be between two functional domains separated or flanked by a glycine-serine linker.

In general, the one or more NLSs are of sufficient strength to drive accumulation of the Cas protein in a detectable amount in the nucleus of a eukaryotic cell. In general, strength of nuclear localization activity may derive from the number of NLSs in the Cas protein, the particular NLS used, or a combination of these factors. Detection of accumulation in the nucleus may be performed by any suitable technique. For example, a detectable marker may be fused to the Cas protein, such that location within a cell may be visualized, such as in combination with a means for detecting the location of the nucleus (e.g., a stain specific for the nucleus such as DAPI). Examples of detectable markers include fluorescent proteins (such as green fluorescent proteins, or GFP. RFP; CFP), and epitope tags (HA tag. FLAG tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR complex activity), as compared to a control not exposed to the CRISPR complex, or exposed to a Cas protein lacking the one or more NLSs.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, ClustalX, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay.

In some aspects, the invention provides methods comprising delivering one or more polynucleotides, such as one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a Cas protein in combination with (and optionally complexed) with a guide sequence is delivered to a cell. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g., a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-8313 (1992); Navel and Felgner. TIBTECH 11:211-217 (1993): Mitani and Caskey, TIBTECH 11:162-166 (1993); Dillon, TIBTECH 11:167-175 (1993); Miller, Nature 357: 455-460 (1992); Van Brunt. Biotechnology 6(10):1149-1154 (1988); Vigne, Restorative Neurology and Neuroscience 8:35-36 (1995); Kremer and Perricaudet. British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

The CRISPR/Cas system as described herein, can be delivered using adeno-associated virus (AAV), lentivirus, adenovirus, or other viral vector types, or combinations thereof. Cas protein(s) and one or more guide RNAs can be packaged into one or more viral vectors. In some embodiments, the targeted trans-splicing system is delivered via AAV as a split intein system, similar to Levy et al. (Nature Biomedical Engineering, 2020, DOI: https://doi.org/10.1038/s41551-019-0501-5). In other embodiments, the targeted trans-splicing system can be delivered via AAV as a trans-splicing system, similar to Lai et al. (Nature Biotechnology, 2005, DOI: 10.1038/nbt1153). In some embodiments, the viral vector is delivered to the tissue of interest by, for example, an intramuscular injection, while other times the viral delivery is via intravenous, transdermal, intranasal, oral, mucosal, intrathecal, intracranial or other delivery methods. Such delivery may be either via a single dose, or multiple doses. One skilled in the art understands that the actual dosage to be delivered herein may vary greatly depending upon a variety of factors, such as the vector chosen, the target cell, organism, or tissue, the general condition of the subject to be treated, the degree of transformation/modification sought, the administration route, the administration mode, the type of transformation/modification sought, etc.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. Viral-mediated in vivo delivery of Cas13 and guide RNA provides a rapid and powerful technology for achieving precise mRNA perturbations within cells, especially in post-mitotic cells and tissues.

In certain embodiments, delivery of the trans-splicing system to a cell is viral. In certain embodiments, the virus is a retrovirus, adenovirus, adeno-associated virus, herpes simplex virus, anellovirus, or baculovirus.

In certain embodiments, delivery of the trans-splicing system to a cell is non-viral. In certain embodiments, the non-viral delivery system is selected from a cationic lipid vehicle, electroporation, calcium phosphate transfection, transfection through membrane disruption using mechanical shear forces, mechanical transfection, and nanoparticle delivery.

Preferably, the vector is a viral vector, such as a lenti-, baculo-, or adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun.

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

In another embodiment, minimal non-primate lentiviral vectors based on the equine infectious anemia virus (EIAV) are also contemplated, especially for ocular gene therapy (see. e.g., Balagaan, J gene Med 2006: 8:275-285, Published online 21 Nov. 2005 in Wiley InterScience (www.interscience.wiley.com). DOI: 10.1002/jgm.845). In another embodiment. RetinoStat, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) may be modified for the CRISPR-Cas system of the present invention.

Lentiviral vectors have been disclosed as in the treatment for Parkinson's Disease, see. e.g., US Patent Publication No. 20120295960 and U.S. Pat. Nos. 7,303,910 and 7,351,585. Lentiviral vectors have also been disclosed for delivery to the brain, see, e.g., US Patent Publication Nos. US20110293571, US20040013648; US20070025970, US20090111106, and U.S. Pat. No. 7,259,015.

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386; 4,946,787; and 4,897,355; and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g., in vitro or ex vivo administration) or target tissues (e.g., in vivo administration).

The preparation of lipid:nucleic acid complexes, including targeted liposomes such as immunolipid complexes, is well known to one of skill in the art (see. e.g., Crystal, Science 270:404-410 (1995); Blaese et al., Cancer Gene Ther. 2:291-297 (1995); Behr et al., Bioconjugate Chem. 5:382-289 (1994): Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183; 4,217,344; 4,235,871; 4,261,975; 4,485,054; 4,501,728; 4,774,085; 4,837,028; and 4,946,787).

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. Cell lines are available from a variety of sources known to those with skill in the art (see. e.g., the American Type Culture Collection (ATCC) (Manassas, VA)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rate, or rabbit. In certain embodiments, the organism or subject is a plant. In certain embodiments, the organism or subject or plant is algae. Methods for producing transgenic plants and animals are known in the art, and generally begin with a method of cell transfection, such as described herein.

In one aspect, the invention provides for methods of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence.

With recent advances in crop genomics, the ability to use CRISPR/Cas systems to perform efficient and cost effective gene editing and manipulation will allow the rapid selection and comparison of single and multiplexed genetic manipulations to transform such genomes for improved production and enhanced traits. In this regard, reference is made to US patents and publications: U.S. Pat. No. 6,603,061—Agrobacterium-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morell et al "Crop genomics: advances and application" Nat Rev Genet. 2011 Dec. 29: 13(2):85-96 are also herein incorporated by reference in their entirety.

Any components of the instant CRISPR/Cas system can be delivered in the form of RNA. Cas and/or viral protein mRNA can be generated using in vitro transcription. For example, Cas mRNA can be synthesized using a PCR cassette containing the following elements: T7 promoter-Kozak sequence (GCCACC)-Cas13-3' UTR from beta globin-polyA tail (a string of 120 or more adenines). The cassette can be used for transcription by T7 polymerase. Guide RNAs can also be transcribe using in vitro transcription from a cassette containing T7 promoter-GG-guide RNA sequence.

The components of the instant CRISPR/Cas system may be delivered simultaneously using nanoparticles or lipid envelopes. For example, Su X. Fricke J. Kavanaugh D G, Irvine D J ("In vitro and in vivo mRNA delivery using lipid-enveloped pH-responsive polymer nanoparticles" Mole Phar. 2011 Jun. 6: 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self-assembling bioadhesive polymers are contemplated, which may be applied to oral delivery of peptides, intravenous delivery of peptides and nasal delivery of peptides, all to the brain. Other embodiments, such as oral absorption and ocular deliver of hydrophobic drugs are also contemplated. The molecular envelope technology involves an engineered polymer envelope which is protected and delivered to the site of the disease (see, e.g., Mazza, M. et al. ACSNano. 2013. 7(2):1016-1026: Siew, A., et al. Mol Pharm, 2012. 9(1):14-28; Lalatsa, A., et al. J Contr Rel, 2012. 161(2):523-36: Lalatsa, A., et al., Mol Pharm, 2012. 9(6):1665-80; Lalatsa, A., et al. Mol Phar, 2012. 9(6):1764-74; Garrett. N. L., et al. J. Biophotonics, 2012. 5(56):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

US Patent Application 20110293703 relates to lipidoid compounds are also particularly useful in the administration of polynucleotides, which may be applied to deliver the CRISPR/Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Application 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofueling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolte complex capsules for cell encapsulation. The invention may also have many other biological applications such as antimicrobial coatings, DNA or siRNA delivery, and stem cell tissue engineering. The teachings of US Patent Application No. 20130302401 may be applied to the CRISPR/Cas system of the present invention.

In another embodiment, lipid nanoparticles (LNPs) are contemplated. In particular, an antitransthyretin small interfering RNA encapsulated in lipid nanoparticles (see, e.g., Coelho et al., N Engl J Med 2013; 369:819-29) may be applied to the CRISPR/Cas system of the present invention.

The charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see. e.g., Rosin et al. Molecular therapy, vol. 19, no. 12, pages 1286-2200. December 2011). Negatively charged polymers such as siRNA oligonucleotides may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminoproane (DLinKDMA), and 1,2-dilinoleyl-4-(2-dimethylaminoethyl)-[1,3]-dioxolane (DLinKC2-DMA).

Self-assembling nanoparticles with siRNA may be constructed with polyethyleneimine (PEI) that is PEGylated with an Arg-Gly-Asp (RGD) peptide ligand attached at the distal end of the polyethylene glycol (PEG), for example, as a means to target tumor neovasculature expressing integrins and used to deliver siRNA inhibiting vascular endothelial growth factor receptor-2 (VEGFR2) expression and thereby tumor angiogenesis (see, e.g., Schiffelers et al., Nucleic Acids Research, 2004. Vol. 32. No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to her as nanoplexes.

Exosomes are endogenous nano-vesicles that transport RNAs and proteins which can deliver short interfering (si)RNA to the brain in mice. To reduce immunogenicity. Alvarez-Erviti et al. (2011, Nat Biotechnol 29: 341) used self-derived dendritic cells for exosome production.

In certain embodiments, the invention provides a method of treating or inhibiting a condition caused by a defect in a target sequence in a mRNA of interest in a subject (e.g., mammal or human) or a non-human subject (e.g., mammal) in need thereof comprising modifying the subject or a non-human subject by manipulation of the target sequence and wherein the condition is susceptible to treatment or inhibition by manipulation of the target sequence comprising providing treatment comprising: delivering a non-naturally occurring or engineered composition comprising an AAV or lentivirus vector system comprising one or more AAV or lentivirus vectors operably encoding a composition for expression thereof, wherein the target sequence is manipulated by the composition when expressed, wherein the composition comprises: (A) a non-naturally occurring or engineered composition comprising a vector system comprising one or more vectors comprising a targeted trans-splicing system comprising a non-natural nucleic acid guide-binding protein domina, a nucleic acid guide, a specific RNA-binding domain, and a repair template comprising a splice donor and/or splice acceptor and an RNA sequence that hybridizes under stringent conditions to the specific RNA-binding domain.

Targeting of Cells

The work herein supports the use of CRISPR/Cas systems to target pre-mRNA in post-mitotic cells through delivery of the CRISPR/Cas system to the appropriate location (i.e., to cells within the organs or tissues of interest) to mediate trans-splicing events to pre-mRNA.

In certain embodiments, the CRISPR/Cas system further comprises a cell. In certain embodiments, the CRISPR/Cas system is targeted to RNA. In certain embodiments, the CRISPR/Cas system is associated with RNA in the cell. In certain embodiments, the RNA is a pre-mRNA. In certain embodiments, the CRISPR/Cas system mediates trans-splicing of pre-mRNA at intron-exon junctions. In certain embodiments, the CRISPR/Cas system mediates trans-splicing of pre-mRNA at exon-intron junctions. In certain embodiments, the CRISPR/Cas system mediates trans-splicing of a pre-mRNA at the 3' end of the pre-mRNA. Examples of a sequence targeting the 3' end of a pre-mRNA may include, but is not limited to SEQ ID NO: 70, as disclosed herein. In certain embodiments, the CRISPR/Cas system mediates trans-splicing of pre-mRNA within the 3' untranslated region (UTR). Trans-splicing within the 3' UTR can lead to stronger translation of the resulting mRNA. In certain embodiments, the CRISPR/Cas system mediates trans-splicing of a pre-mRNA at na internal site within a pre-mRNA. Examples of a sequence targeting an internal site within a pre-mRNA may include, but is not limited to SEQ ID NO: 92, as disclosed herein. In various embodiments, the CRISPR/Cas system mediates trans-splicing of pre-mRNA within the 5' untranslated region (UTR). The 3' and 5' UTRs of mRNA are known to contain multiple regulatory elements and are critical for the stability and translation of mRNA into protein. Warren et al. (Cell Stem Cell, Volume 7, pages 618-630 (2010), incorporated by reference herein in its entirety) used an artificial 5' UTR containing a strong Kozak translation signal and the alpha globin 3' UTR to improve protein production during reprogramming of fibroblasts to induced pluripotent stem cells. In certain embodiments, the CRISPR/Cas system can mediate trans-splicing to provide a 3'UTR sequence to change the strength of translation, in some cases leading to stronger translation and significant increases in protein production. For example, 3' UTRs from genes including, but are not limited to, AGXT, ALB, APOA2, ASL, C3, CYP2E1, FBA, HPX, and/or ORM, can be used to change the strength of translation. Also, for example, 5' UTRs from genes including, but are not limited to, AGXT, ALB, APOA2, ASL, C3, CYP2E1, FBA, HPX, and/or ORM, can be used to change the strength of translation.

In certain embodiments, the CRISPR/Cas system is associated with DNA in the cell. In certain embodiments, the CRISPR/Cas system is not associated with DNA in the cell.

In certain embodiments, the trans-splicing system is introduced into the cell. In certain embodiments, the CRISPR/Cas system mediates trans-splicing of pre-mRNA in the nucleus of a cell. In certain embodiments, the CRISPR/Cas system mediates trans-splicing of pre-mRNA in the cytoplasm of a cell. In another aspect of the invention, provided herein is a method of mediating a targeted trans-splicing event on a pre-mRNA in a cell, the method comprising introducing a targeted trans-splicing CRISPR/Cas system into the cell, wherein the system comprises a nuclease-inactive nucleic acid-targeting CRISPR/Cas system, a nucleic acid guide that specifically hybridizes to a nucleic acid locus of interest, a specific RNA-binding domain, and a repair template comprising an RNA sequence that hybridizes under stringent conditions to the specific-RNA-binding domain.

Gene editing using Type II, and more recently Type V, CRISPR systems can be accomplished through either of two pathways: non-homologous end joining (NHEJ) or homology-directed repair (HDR). NHEJ does not require the cells to be actively dividing, however HDR is only active in dividing cells. In certain embodiments, the CRISPR/Cas system mediates trans-splicing of pre-mRNA in the nucleus of the cell. In certain embodiments, the CRISPR/Cas system mediates trans-splicing of pre-mRNA in the cytoplasm of the cell. The cell can be a dividing cell, or a post-mitotic cell. In certain embodiments, the post-mitotic cell can be simply one or post-mitotic cells, or an organ per se or a tissue within it. In certain embodiments, the post-mitotic cell can be selected from the group consisting of a neuron, myocyte, and adipocyte. The post-mitotic cells may be comprised within a vertebrate animal, either a patient (in the sense of an animal in need of trans-splicing mediated treatment) or a model organism, or may be in cell culture, an organoid, or other ex vivo tissue, such a "liver on a chip" for instance where hepatocytes are seeded and grown on a scaffold. With the development of 3-D printing techniques being applied to biology, printed tissues are within grasp and it is entirely feasible that liver cells or tissues printed I this way to create an organoid or onto a chip could also be targeted. Non-liver alternatives are also envisaged, particularly for other post-mitotic cells/tissues.

Thus, provided is a model organism comprising post-mitotic cells, such as neurons or kidney cells, to which the present CRISPR-Cas system has been delivered. Such collections may include post-mitotic organs, organoids, or cells populating a scaffold ('kidney on a chip').

In particular, such post-mitotic cells may express, or comprise polynucleotides capable of expressing, a Cas enzyme. As discussed herein, this has the advantage of providing a ready model for interrogating gene product function through targeted-trans-splicing of pre-mRNA. This is particularly useful in studying conditions of the post-mitotic cells, such as the kindey or brain, such as those listed herein, as well as broader conditions such as obesity.

Also provided is a method of inducing transcript perturbation in one or more post-mitotic cells, comprising transducing population of cells with a CRISPR/Cas system according to the present invention to thereby alter transcripts of a population of cells. The method may be ex vivo or in vitro, for instance in a cell culture or in an ex vivo or in vitro model (such as an organoid). Alternatively, the method may be in vivo, in which case it may also include isolating a population of cells from the subject, and transplanting the population of cells (back) into the subject. Transcript perturbation may be for one or more, or two or more, or three or more, or four or more genes. However, if the cells already comprise Cas, whether expressed as a protein or encoded by polynucleotides already comprised within the cells, then only the CRISPR polynucleotide needs to be delivered. The method may include extraction from and, optionally, re-insertion back into the post-mitotic cell. By delivering, it is meant actually physical delivery of the polynucleotides to the nucleus of the cell, but also transtection. Therefore, delivery should also be read as including transfection unless otherwise apparent.

Gene Therapy

Because the described invention can be used to mediate trans-splicing in a non-dividing cell, in certain embodiments the cell is in a subject suffering from a disease or disorder. In certain embodiments the disease or disorder is a neurodegenerative, neurological, or neuromuscular disease or disorder. In certain embodiments, the disease or disorder is selected from the group consisting of spinal muscular atrophy, Rett Syndrome, Angelman syndrome, Parkinson's disease, Alzheimer's disease, Huntington's disease, frontotemporal dementia, lysosomal storage diseases, multiple sclerosis, and amyotrophic lateral sclerosis (ALS).

The approaches taken herein demonstrate that the instant invention can be applied to gene therapy. For instance, correction of one or more deficient genotypes (for example single point mutations) is achievable through the use of the present CRISPR-Cas system in the post-mitotic cells discussed herein. Monogenic conditions associated with the post-mitotic are particularly preferred and are exemplified herein.

Although one guide may be used, so-called multiplexing with two, three, four or more guides, is particularly useful in gene therapy where multiple defective genotypes are to be corrected (either multiple errors in a single gene or multiple errors spread across several genes.

Accordingly, in certain embodiments the invention provides a method of modifying post-mitotic cells of an organism, e.g., mammal including a human or a non-human mammal or organism by manipulation of a target sequence in a genomic locus of interest comprising delivering a non-naturally occurring or engineered composition comprising a viral or plasmid vector system comprising one or more viral or plasmid vectors operably encoding a composition for expression thereof, wherein the composition comprises: (A) a non-naturally occurring or engineered composition comprising a vector system comprising one or more vectors comprising a targeted trans-splicing system comprising a non-natural nucleic acid guide-binding protein domain, a nucleic acid guide, a specific RNA-binding domain, and a repair template comprising a splice donor and/or splice acceptor and an RNA sequence that hybridizes under stringen conditions to the specific RNA-binding domain.

The trans-splicing system as described herein can be used to interrogate the function of one or more genes in post-mitotic cells. This may be achieved through delivery and expression of the CRISPR/Cas system to the post-mitotic cell, wherein the guide(s) of the CRISPR/Cas system are designed to recruit the CRISPR/Cas system to the pre-mRNA target or targets of interest. Equally, where the CRISPR/Cas is already comprised within the post-mitotic cell, protein (transcribed) form, then delivery of the guides to the post-mitotic cell will suffice. Having a CRISPR/Cas system induced by a small molecule may be advantageous here. Where the CRISPR/Cas is already within the post-mitotic cell, in polynucleotide (untranscribed), then delivery of the guides to the post-mitotic cell as well as induction of transcription of the Cas9 polynucleotide will be necessary. Having the CRISPR/Cas system under the control of an inducible or repressible promoter, such as the tet (tetracycline) on-off system may be advantageous here.

One aspect that is particularly promising is the integration of CRISPR techniques with phenotypic assays to determine the phenotypic changes, if any, resulting from gene perturbations, especially knock downs. Use of the CRISPR/Cas system can be combined with biochemical, sequencing, electrophysiological, and behavioral analysis to study the function of the targeted genomic element.

This, in one aspect, there is provided a method of interrogating the function of one or more genes in a post-mitotic cell, comprising inducing an expression of a modulated mRNA and determining changes in phenotype due to one or more genes in the condition thereby interrogating the function of the one or more proteins translated from the modulated pre-mRNA.

The following applies broadly to appropriate aspects of the invention. The cell may be in a subject, such as a human, animal, or model organism, so that protein function is interrogated in vivo, however, it is also envisaged that the cell may be ex vivo, for instance in a cell culture or in a model organ or organoid. In some embodiments, the method may include isolation of a first population of cells from the subject, optionally culturing them and transducing them with one or more CRISPR/Cas systems. Further optional culturing may follow. Transplantation of the transduced cells back into the subject may then occur.

The cell may be from any of the tissues or organism described herein. The brain is one preferred example, providing for said method of interrogating the function of one or more gene products, such as pre-mRNA, wherein the post-mitotic cell is a brain cell, for instance a neuron. Particularly in vivo, this allows for the interrogation of mutated or modified protein function on animal behavior. The animal is preferably a mammal, for instance a rodent. Given the complexity of the nervous system, which consists of intricate networks of heterogeneous cell types, being able to efficiently edit pre-mRNAs of neurons in vivo enables direct testing of gene function in relevant cell types embedded in native contexts.

Kits

The present disclosure provides kits for carrying out a method. In one aspect, the invention provides kits containing any one or more of the elements disclosed in the above methods and compositions. In some embodiments, the kit comprises a vector system and instructions for using the kit. In some embodiments, the kit comprises a vector system comprising regulatory elements and polynucleotides encoding the CRISPR/Cas trans-splicing system. In some embodiments, the kit comprises a viral delivery system of the CRISPR/Cas trans-splicing system. In some embodiments, the kit comprises a non-viral delivery system of the CRISPR/Cas trans-splicing system. Elements may be provided individually or in combinations, and may be provided in any suitable container, such as a vial, a bottle, or a tube. In some embodiments, the kit includes instruction in one or more languages, for examples, in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element.

The invention is further described in detail by reference to the following experimental examples. These examples are included merely for purposes of illustration of certain aspects and embodiments of the present invention, and are not intended to limit the invention. Thus, the invention should in no way be construed as being limited to the following examples, but rather, should be construed to encompass any and all variation which become evident as a result of the teaching provided herein.

EXAMPLES

Example 1—Engineering of the CRISPR-Based Trans-Splicing System

A CRISPR-based trans-splicing system was engineered to comprise a guide RNA, such as a guide RNA (gRNA), an exon or a group of exons of interest conjugated to an engineered intron with ms2 hairpins, and a catalytically inactive Cas13b (dCas13b) linked to a MS2 binding protein (FIG. 1A). Assembly of the trans-splicing system relies on the dCas13b recognizing the gRNA scaffold, and the MS2 binding protein recognizing the ms2 hairpins of the engineered intron (FIG. 1B). Instead of inducing a cis-splicing reaction (FIG. 1C), the CRISPR-dCas13b system induces a trans-splicing event similar to the endogenous spliceosome-based reaction that is illustrated in FIG. 1D. In the CRISPR/Cas-based system, the trans-splicing event occurs when the above described CRISPR-dCas13b assembly binds to a pre-mRNA. When the dCas13b that is linked to a MS2 binding protein binds to the pre-mRNA, the cis-splice acceptor is blocked. The MS2 binding protein tethers a trans-splicing RNA molecule of interest, and with the binding of the dCas13b to the target pre-mRNA, directs the trans-splicing RNA to the pre-mRNA. This enables highly efficient trans-splicing (FIG. 1E).

Figure 2A:
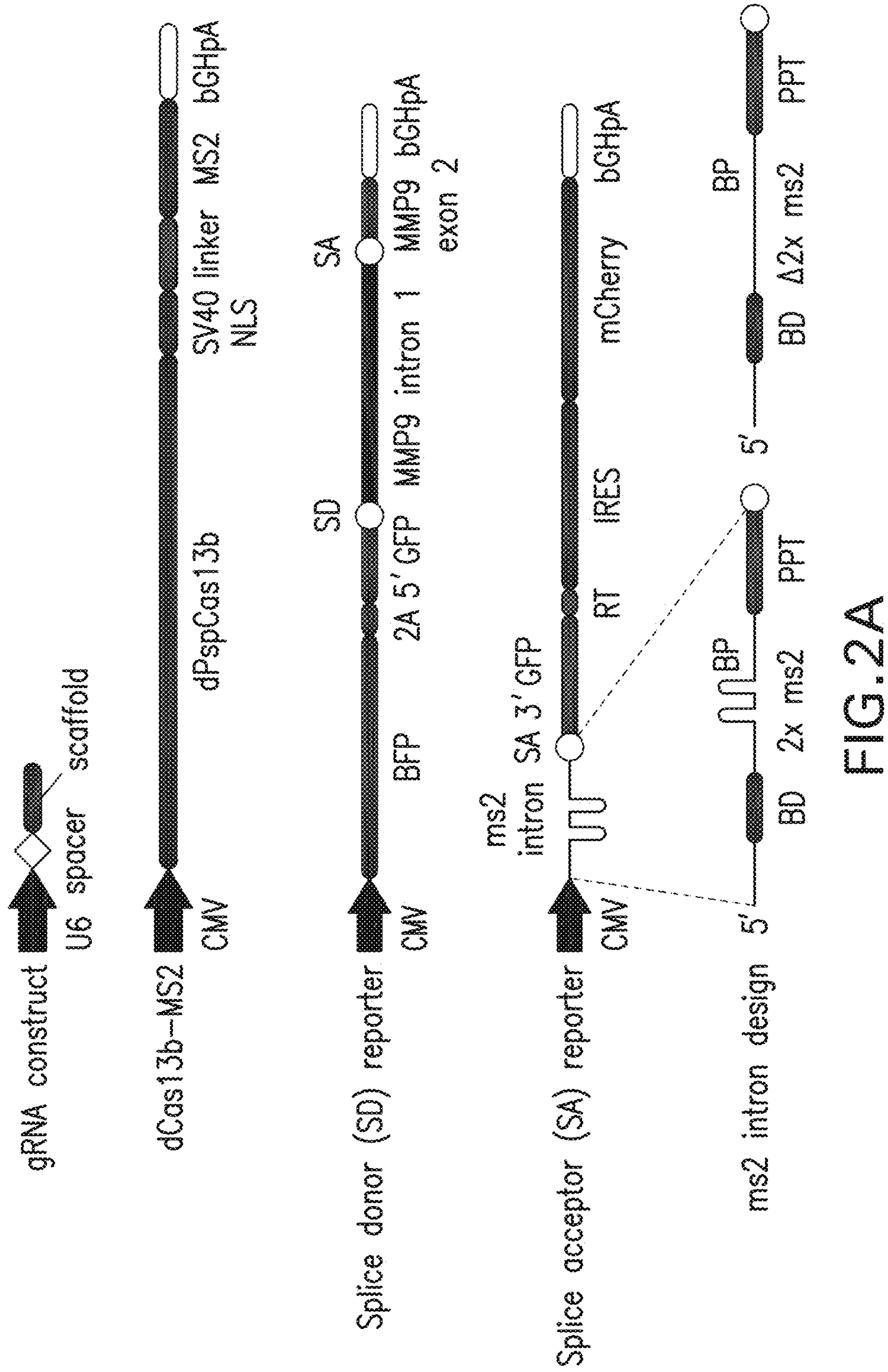
FIG. 2A illustrates the DNA constructs encoding the endoribonuclease-inactive Cas13 (dCas13b)-MS2 fusion protein, the gRNA construct, the splice donor (SD) and splice acceptor (SA) reporters, and the ms2 intron design.

Several DNA constructs were utilized to reduce CRISPR-mediated trans-splicing to practice (FIG. 2A). First, a U6 promoter-driven gRNA construct with a *Prevotella* sp. Cas13b (PspCas13b) RNA scaffold was used to drive expression of the gRNA in the cells. The dCas13b was linked to a MS2 binding protein via a SV40 nuclear localization signal (SV40 NLS) and glycine-serine linker. Bovine growth hormone polyadenylation signal (bGHpA) was used to allow for stable expression of the construct. A splice donor was used to generate expression of a pre-mRNA that could be assayed for trans-splicing. Blue fluorescent protein (BFP) was used as a marker to validate expression of the splice donor, and a self-cleaving p2A linker was used on truncated GFP (5' GFP). To ensure the splice acceptor would undergo trans-splicing, Matrix Metallopeptidase 9 (MMP9) intron 1 and exon 2 were placed downstream, followed by bGHpA to ensure stable expression. A splice acceptor reporter was designed, such that trans-splicing would generate a complete GFP, which could be observed by flow cytometry. The designed ms2 intron consists of i) a binding domain (BD) which hybridizes to MMP9 intron 1 in the splice donor reporter, ii) two ms2 loops, iii) a branch point (BP), and iv) a polypyrimidine tract (PPT), followed by v) a splice acceptor sequence. The second half of the truncated GFP was placed behind the ms2 intron, which was then followed by a reverse transcription primer binding site (RT), allowing for generation of next generation sequencing libraries (NGS) to validate trans-splicing via RNAseq. To confirm expression of the splice acceptor reporter, an internal ribosome entry site (IRES) was used to drive translation of mCherry, thus allowing mCherry measurement via flow cytometry independent of trans-splicing. Lastly, a ms2 null (Δ2× ms2) splice acceptor reporter was used to measure the effect of ms2 loops on CRISPR-mediated trans-splicing efficiency.

Figure 2B:
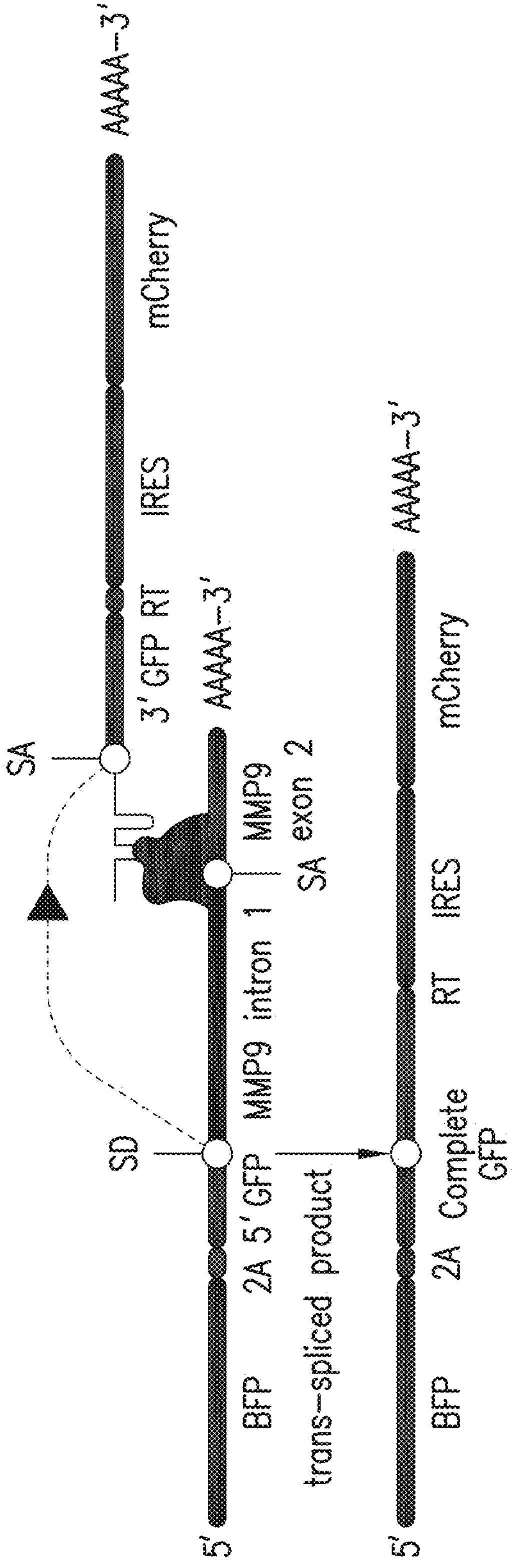
FIG. 2B illustrates the trans-splicing reporter assay.

Upon successful trans-splicing, the truncated GFP exons (5' GFP, 3' GFP) introduced by the splice donor and acceptor reporters are spliced together, generating a transcript that contains a complete GFP mRNA sequence capable of creating a functional GFP protein product (FIG. 2B). Cells were gated for BFP+ and mCherry+ using flow cytometry, to validate expression of both the splice donor (SD) and splice acceptor (SA) reporters respectively. From the gated double positive BFP+mCherry+ population, trans-splicing activity was measured by the fraction of cells that were GFP+.

Example 2—Measuring CRISPR-Mediated Trans-Splicing

Figure 3A:
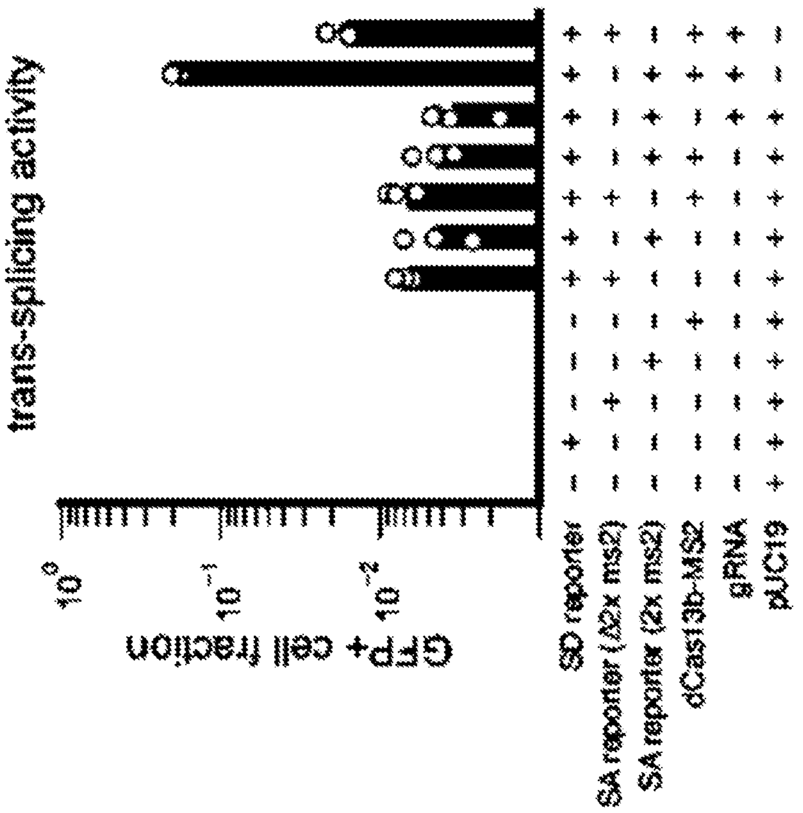
FIG. 3A illustrates the trans-splicing activity of the CRISPR/Cas system compared to negative controls in HEK193FT cells. Columns 1-5 represent activity in the negative controls. Column 11 is the activity of the CRISPR/Cas system.

HEK293FT cells were transfected in a 12-well plate format, with a total of 1250 ng of DNA and 4 uL of Lipofectamine 2000 per condition. Each construct was one fourth of the total DNA transfection, with the exception of pUC19, which was used as non-coding control DNA in conditions where less than four components were delivered. A total of 1250 ng of DNA was delivered. Media was changed 6 hours post-transfection, and the cells were analyzed via flow cytometry 48 hours after transfection. Negative controls (columns 1-5 of FIG. 3A) showed no detection of trans-splicing via the GFP reporter assay. Column 6, which represents the state-of-the-art for trans-splicing, led to detection of trans-splicing in 0.69%±0.08% (mean±SD, n=4) of BFP+mCherry+ cells. CRISPR-mediated trans-splicing (column 11) led to detection of trans-splicing in 19.58%±1.01% (mean±SD, n=4) of BFP+mCherry+ cells, which was a 28.03±1.45-fold increase. As expected, CRISPR-mediated trans-splicing had a significant decrease in efficiency when utilizing the ms2 null (Δ2× ms2) SA reporter (column 12). Interestingly, there was a significant increase in trans-splicing compared to the case where dCas13b-MS2 and a gRNA were not expressed (column 6) by 2.45±0.45-fold (p=0.00074), suggesting that binding dCas13b to the SA prevents cis-splicing, thereby promoting trans-splicing in contexts where there are no further exons for cis-splicing.

Figure 3B:
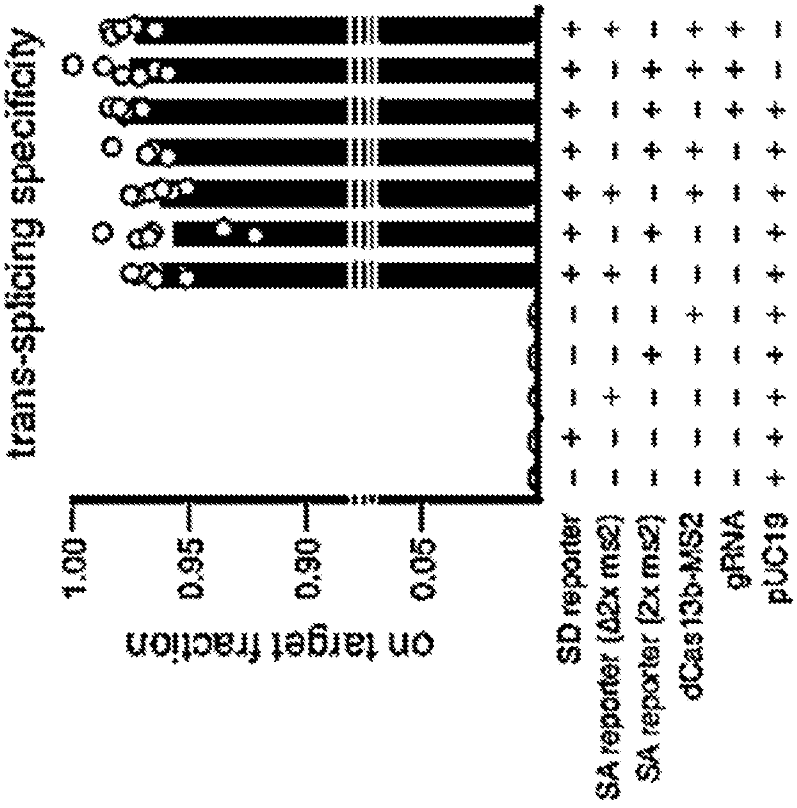
FIG. 3B illustrates the trans-splicing specificity of the CRISPR/Cas system. RNAseq libraries were created using primers that bind to the SA reporter mRNA, and on-target reactions of reads were calculated and plotted.

RNAseq libraries were created by carrying out reverse transcription on the SA reporter using a reverse transcription primer that binds to the RT site on the SA reporter mRNA. The RT site was designed to also carry a TruSeq adapter sequence, such that read 1 of the final library would be the 3' end of GFP. The read 2 sequencing adapter was randomly inserted via tagmentation. Reads were filtered by having read 1 match the 3' end of GFP. Read 2 was then aligned using BWA to a whole transcriptome reference concatenated with the SD and SA reporters. The on-target fraction (plotted) was calculated by dividing the number of reads that map to the SD reporter by the number of total reads that align to the transcriptome (including the SD reporter) but do not align to the SA reporter (FIG. 3B).

Example 3—Generation of RNAseq Library to Measure On-Target Trans-Splicing

Figure 4A:
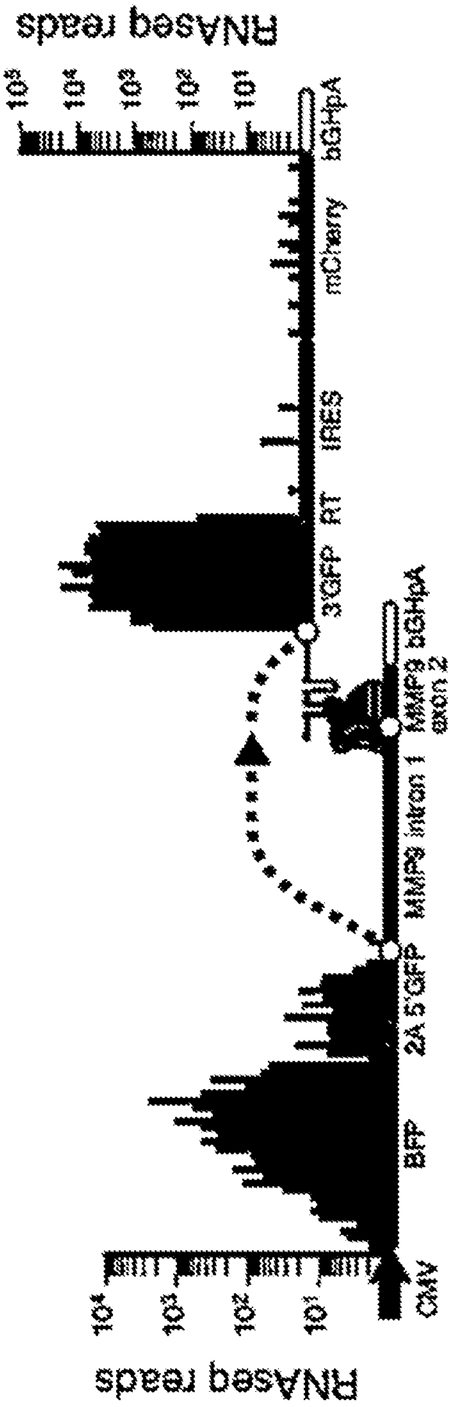
FIG. 4A is RNAseq mapping of RNAseq libraries to demonstrate trans-splicing.

RNAseq libraries generated by RT of the SA reporter were analyzed for mapping position of read 2. As expected, read 2 showed high mapping to the exonic region of the SD reporter, demonstrating trans-splicing. In contrast, only 1 read mapped to the MMP9 intron and MMP9 exon 2, which was likely from index-hopping or chimeric events (FIG. 4A).

Figure 4B:
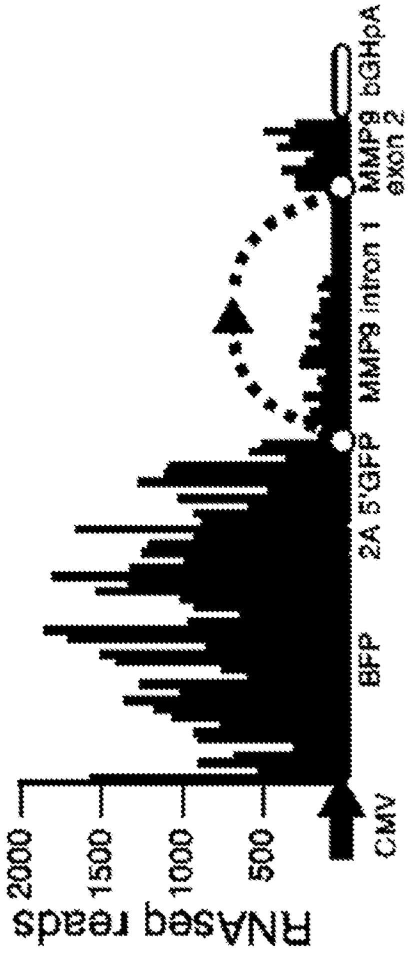
FIG. 4B illustrates validation that there was cis-splicing of the SD reporter.

To validate cis-splicing of the SD reporter, RNAseq libraries were generated by reverse transcription of the poly(A) tail. As expected, cis-splicing was observed as the number of reads was lower for the intronic region (MMP intron 1) and higher for the exonic regions (BFP-2A-5'GFP and MMP9 exon 2) (FIG. 4B).

Figure 5:
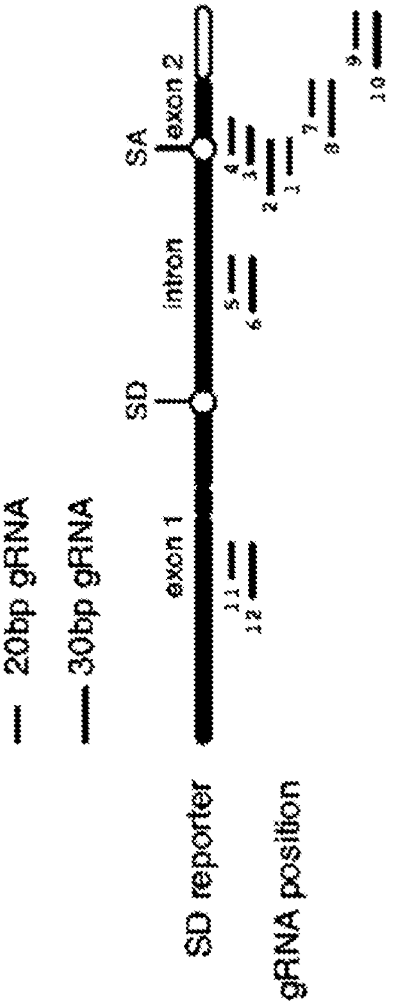
FIG. 5 is a schematic of gRNA target sites. Several gRNAs were designed to target different regions of the SD reporter.

To better understand the gRNA design constraints for CRISPR-mediated trans-splicing, several gRNAS were designed to target different regions of the SD reporter, gRNAS-1-4 targeted the SA site, while gRNAs 5 and 6 targeted the intron. gRNAs 7 and 8 targeted MMP9 exon 2, while gRNAs 9 and 10 targeted bGHpA. gRNAs 11 and 12 targeted BFP in the first exon (FIG. 5).

Figure 6A:
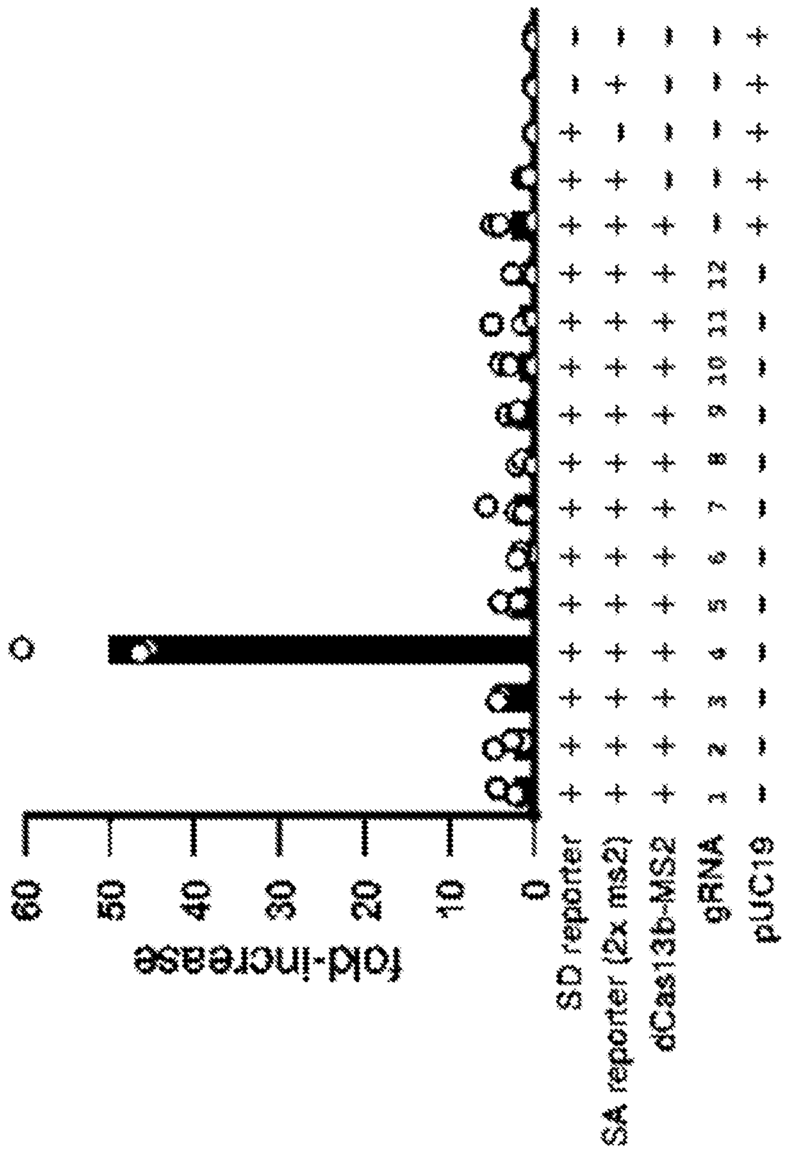
FIG. 6A illustrates fold-increase in targeted trans-splicing with dCas13b-MS2 as measured by using a truncated GFP trans-splicing reporter assay.

Targeted trans-splicing was measured by using the truncated GFP trans-splicing reporter assay. Flow cytometry was conducted on transfected cells with 3 biological replicates per condition. When using a gRNA that targets the splice acceptor site, CRISPR-mediated trans-splicing improved trans-splicing efficiency by ~50-fold with a gRNA designed to target the splice acceptor site. In this case, the most effective gRNA (gRNA 4) has 3' guide mapping to the splice acceptor site. As expected, targeting the CRISPR system to alternative regions of the SD reporter result in marginal gains in trans-splicing efficiency (FIG. 6A).

Figure 6B:
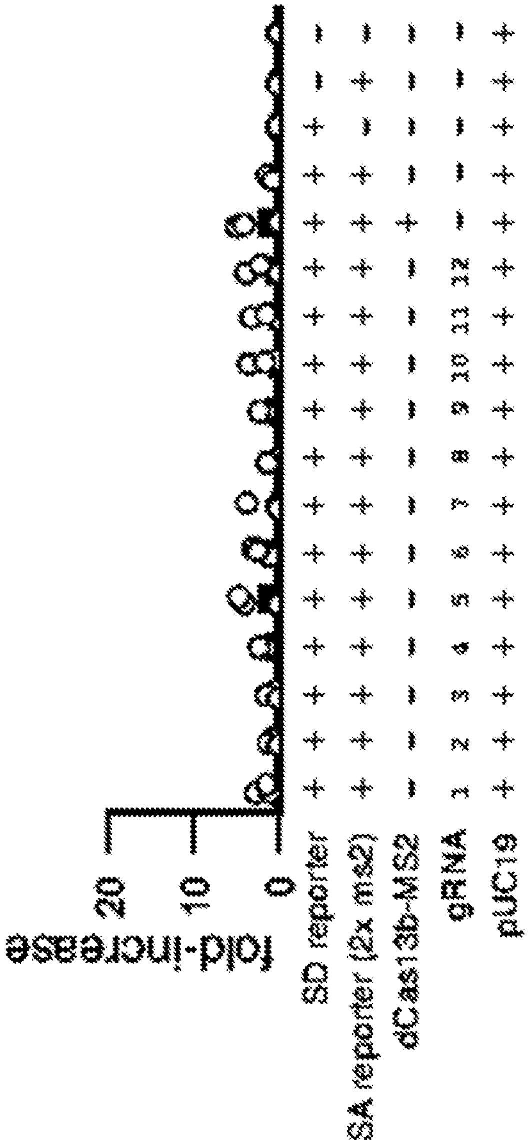
FIG. 6B illustrates the targeted trans-splicing without dCas13b-MS2.

Fold-increases in targeted trans-splicing are marginal when excluding dCas13b-MS2, as measured by the truncated GFP trans-splicing reporter assay (FIG. 6B). Flow cytometry was conducted on transfected cells with three biological replicates per condition.

Example 4—Trans-Splicing Induced by a Small Molecule

Figure 8A:
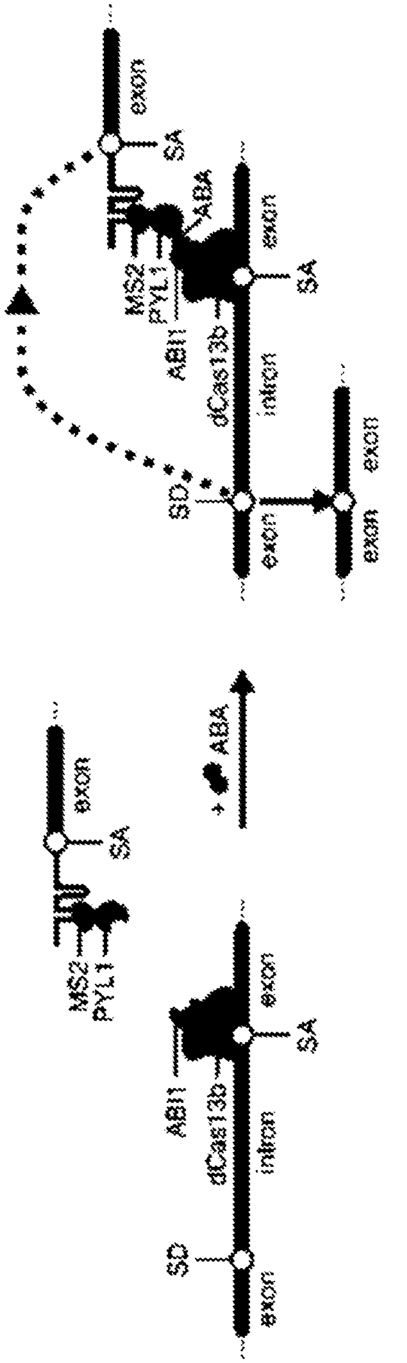
FIG. 8A illustrates induction of the trans-splicing complex with a small molecule.

In order to test if the trans-splicing dCas13b complex could be modified to induce trans-splicing with a small molecule, dCas13b was fused to ABI1, and the MS2 was fused to PYL1, both via glycine-serine linkers (FIG. 8A). It was hypothesized that with this architecture, trans-splicing can be transiently induced via introduction of abscisic acid (ABA), as the machinery assembles in the presence of ABA. The construct delivered by a single expression cassette was a CMV-dPspCas13b-ABI1-2A-PYL1-MS2. A split GFP reporter was utilized to assay trans-splicing activity via GFP measurement through flow cytometry.

Figure 8B:
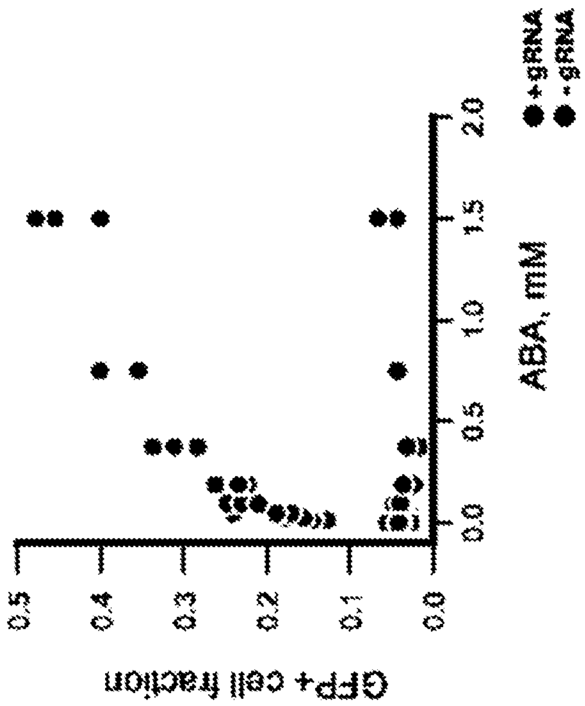
FIG. 8B is a graph demonstrating expression of GFP after induction of trans-splicing in the presence of a range of ABA concentrations, shown with a no guide control as a negative control.
Figure 8C:
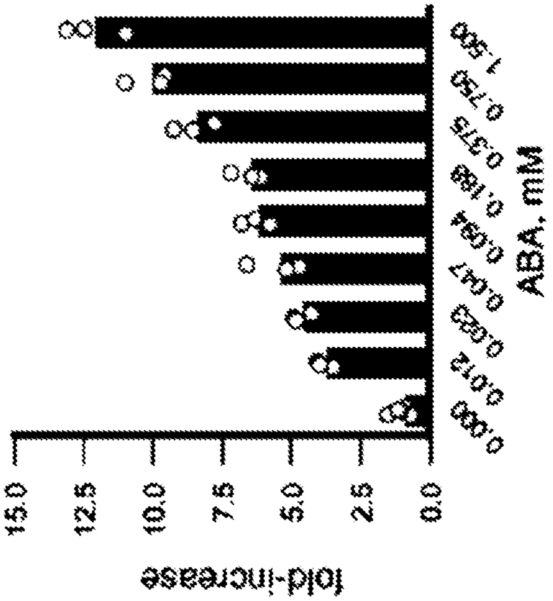
FIG. 8C demonstrates that ABA could control induced targeted trans-splicing by measuring fold-increase in expression of GFP with increasing concentrations of ABA (mM).

Using the construct as described above, the split GFP reporter was trans-spliced in the presence of 1.5 mM ABA, resulting in >40% of cells being GFP+(FIG. 8B). HEK293FT cells were transfected using Lipofectamine 2000 per the manufacturer's instructions, and flow cytometry was conducted 72 hours after transfection. ABA was titrated across multiple samples, and 3 biological replicates per ABA concentration were measured via flow cytometry. To demonstrate that ABA could control the induced targeted trans-splicing, a split GFP reporter was trans-spliced in the presence of ABA, and the fold-change in GFP translation was tightly controlled by ABA concentration (FIG. 8C).

Example 5—Measuring Trans-Splicing at Splice Junctions

Figure 9A:
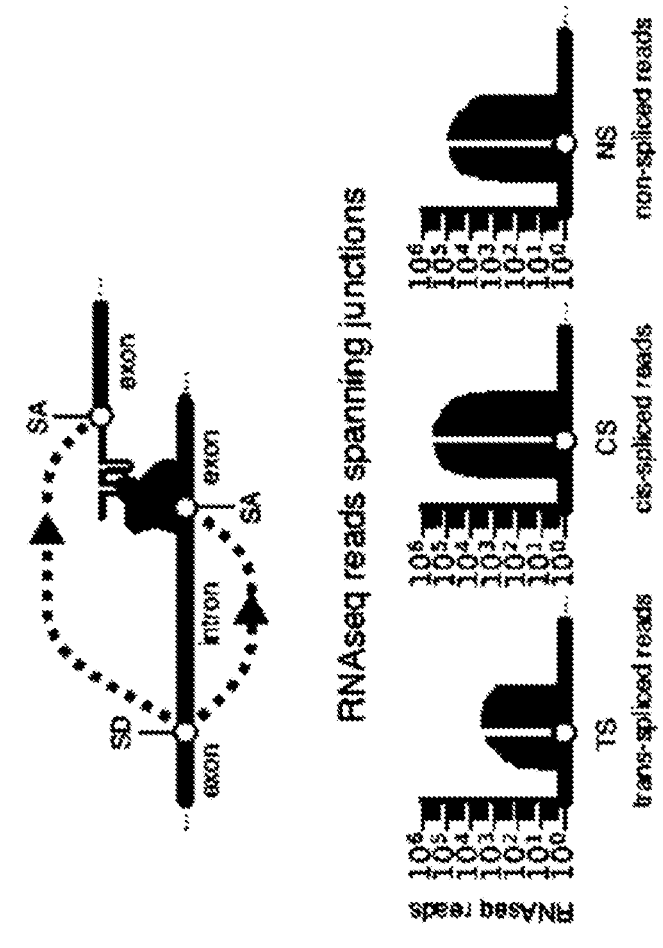
FIG. 9A is a measurement of trans-splicing at splice junctions.

To measure exon junctions, full-length RNAseq was conducted on 293FT cells transfected with dCas13b-MS2, gRNA, and the split GFP reporter system (SD reporter, SA reporter with 2× ms2). Cells were gated for BFP+ and mCherry+ via flow cytometry, to validate expression of both the splice donor (SD) and splice acceptor (SA) reporters respectively, and were then sorted into TCL buffer to lyse the cells prior to RNAseq library construction. RNAseq reads spanning all possible junctions were filtered using regular expressions, and were subsequently mapped onto all possible junction sequences, namely, trans-spliced junctions (TS), cis-spliced junctions (CS), and non-spliced junctions (NS). The mapping positions were the plotted to illustrate reads spanning possible junctions (FIG. 9A).

Figure 9B:
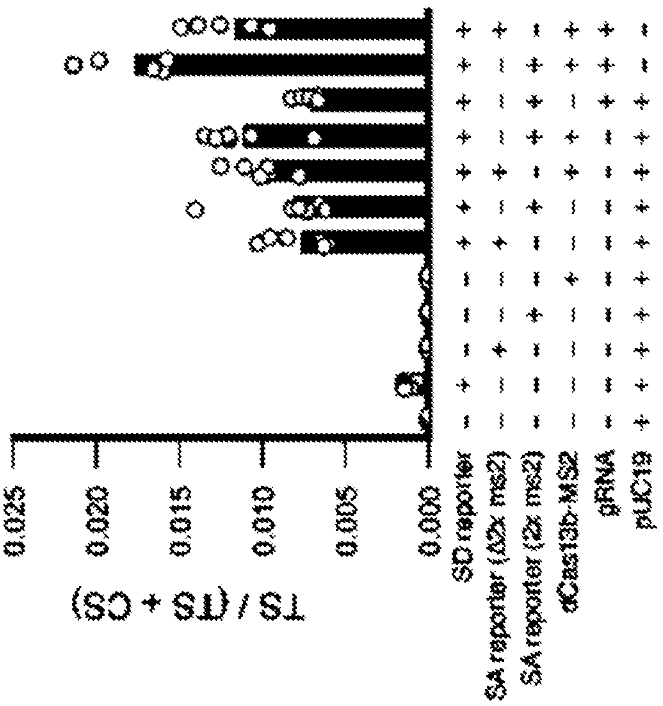
FIG. 9B is a plot of spliced reads that were trans-spliced for all transfection conditions.
Figure 9C:
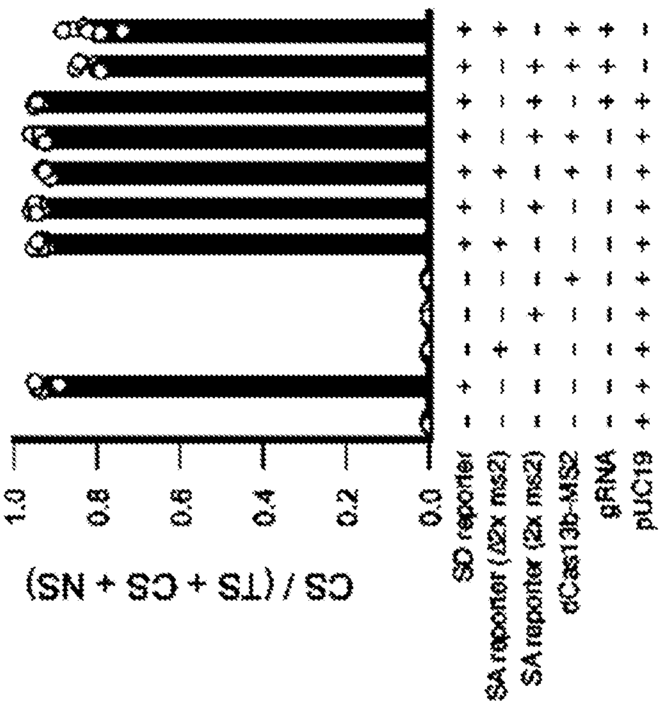
FIG. 9C is a plot of spliced reads that were cis-spliced for all transfection conditions.

Full length RNAseq reads spanning all possible junctions were filtered using regular expressions, and were subsequently mapped onto all possible junction sequences, namely, the trans-spliced junction (TS), cis-spliced junction (CS), and non-spliced junction (NS). A fraction of spliced reads that were trans-spliced were calculated and plotted for all transfection conditions (FIG. 9B). Full length RNAseq reads spanning all possible junctions were filtered using regular expressions, and were subsequently mapped onto all possible junction sequences, namely the TS, CS, and NS as above. Fractions of the spliced reads that were cis-spliced was calculated and plotted for all transfection conditions (FIG. 9C). Results how that the reporter undergoes efficient splicing, and that dCas13 inhibits cis-splicing in the presence of a targeting gRNA.

Example 6—Strategies for Targeted Trans-Splicing

Figure 10A:
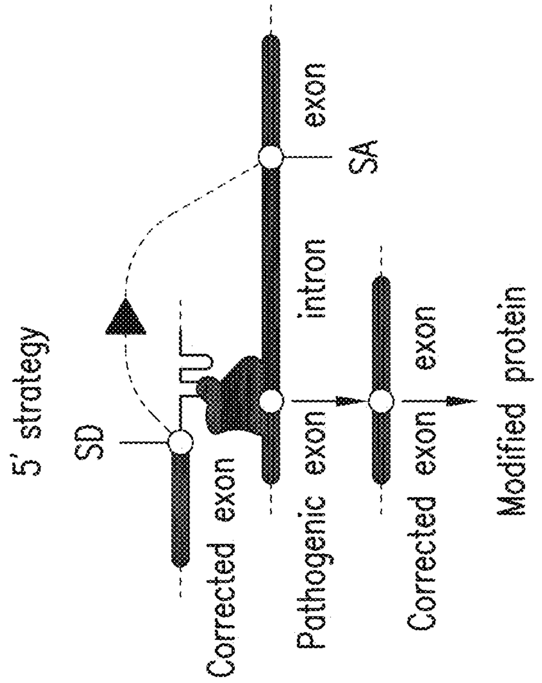
FIG. 10A is an illustration of strategies for targeted trans-splicing.
Figure 10B:
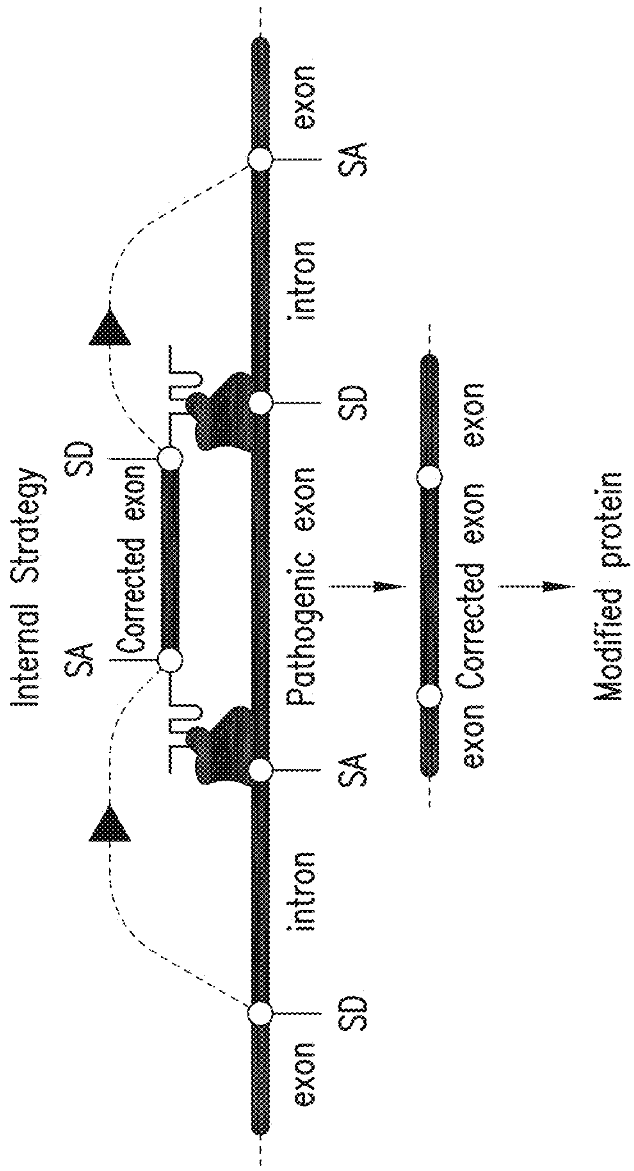
FIG. 10B illustrates an internal targeted trans-splicing strategy.
Figure 10C:
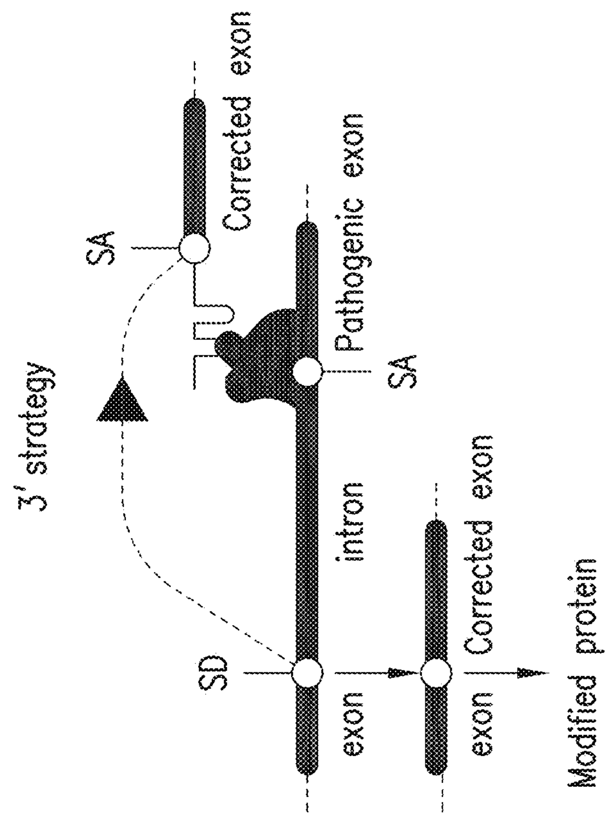
FIG. 10C illustrates a strategy for 3' trageting of trans-splicing.

FIG. 10A illustrates a strategy for 5' targeting of trans-splicing. For this strategy, a dCas13b-MS2 or analogue, can be targeted to a splice donor (SD), while simultaneously providing a 5' repair template for 5' correction or modification of RNA. Such a strategy may be advantageous when the correction or modification is near the 5' end of the mRNA. FIG. 10B illustrates an internal targeted trans-splicing strategy. A dCas13b-MS2 or analogue, can be targeted both to a splice acceptor, and a splice donor, while simultaneously providing a repair template with an exon, or group of exons, possessing both a splice acceptor and splice donor. FIG. 10C illustrates a strategy for 3' targeting of trans-splicing. For this strategy, a 3' repair template may be provided for 3' correction or modification of RNA, along with a dCas13b-MS2, or analogue, targeting a splice acceptor (SA). Such a strategy may be advantageous when the correction or modification is near the 3' end of the mRNA.

Example 7—Internal Exon Repair

Figure 11A:
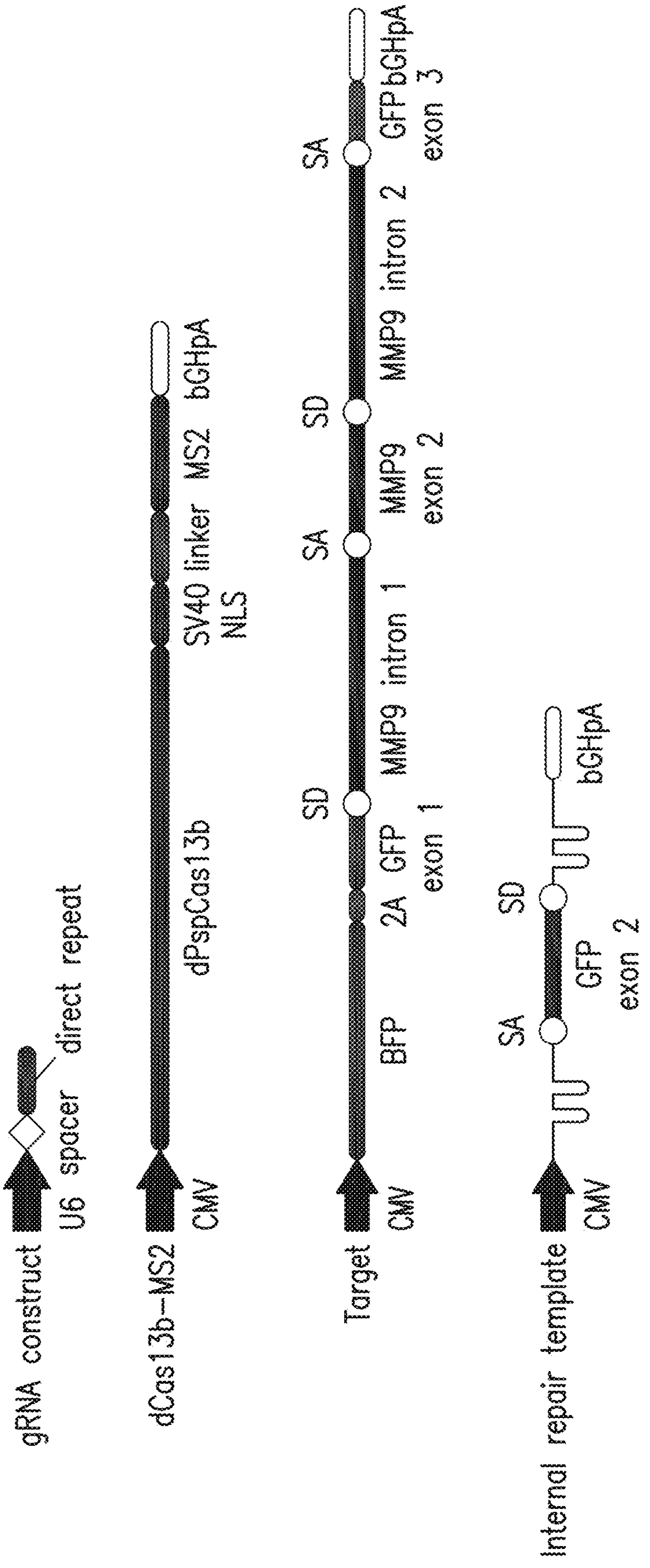
FIG. 11A illustrates a strategy for internal exon repair.

FIG. 11A illustrates a construct to be used for internal exon repair. Standard gRNA constructs were used, along with CMV-dPspCas13b-MS2 to test whether internal exon repair is possible with CRISPR-mediated trans-splicing. GFP was split into three exons, and GFP exons 1 and 3 were utilized in the target RNA molecule design. To simulate a pathogenic exon, MMP9 exon 2 was placed between GFP exons 1 and 3 on the target molecule, along with corresponding flanking introns: MMP9 intron 1 and MMP9 intron 2. The internal repair template was designed to have GFP exon 2 flanked by two synthetic introns, each with an ms2 hairpin.

Figure 11B:
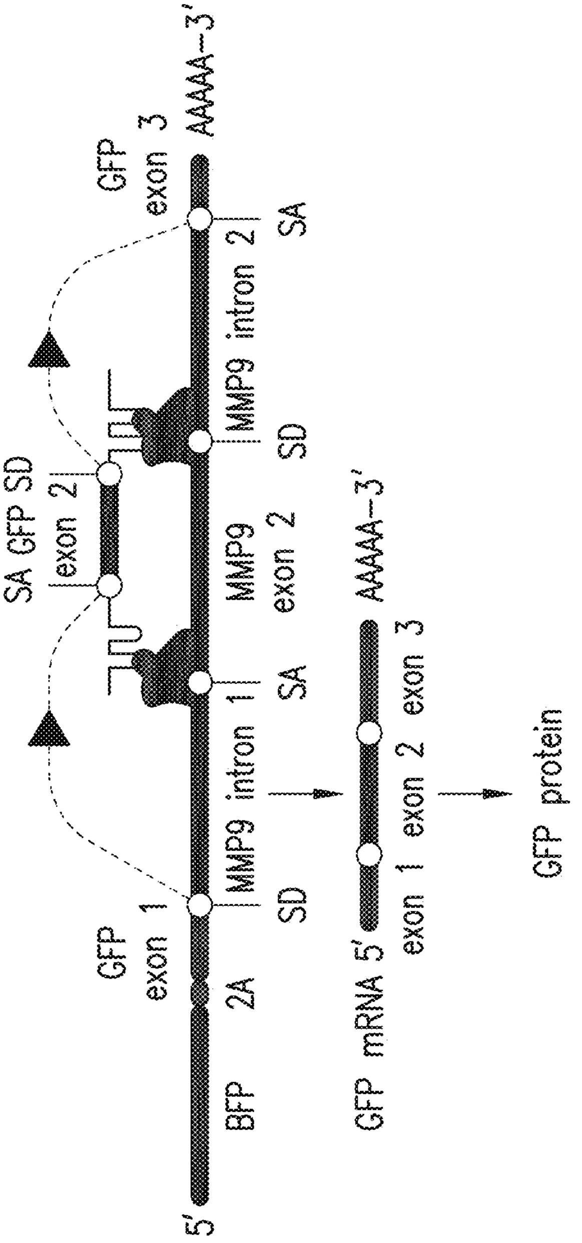
FIG. 11B illustrates monitoring of expression of the target transcript via expression of blue fluorescent protein (BFP), and monitoring internal exon repair via expression of green fluorescent protein (GFP).

FIG. 11B illustrates an assay for monitoring internal exon repair. The target transcript is monitored via expression of blue fluorescent protein (BFP). Cells expressing the target transcript are GFP negative, as the middle exon of GFP (GFP exon 2) is missing from the transcript. Upon internal exon repair, GFP exon 2 from the repair template is trans-spliced in order to create a complete GFP mRNA, and the BFP moiety is lost via the T2A self cleaving peptide. The presence of GFP mRNA leads to translation and expression of GFP protein, which can be measured through flow cytometry.

Figure 11C:
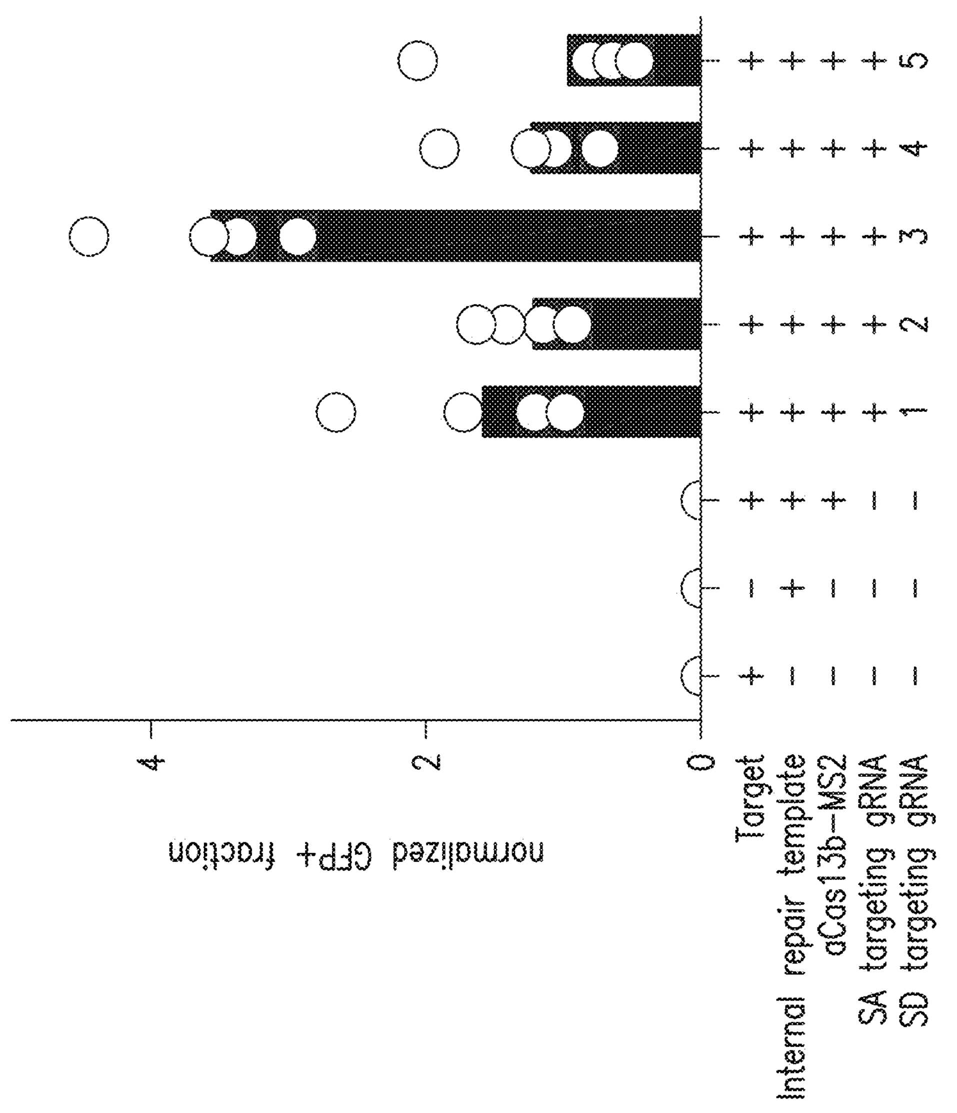
FIG. 11C measures GFP expression following internal exon repair, demonstrating that GFP expression is only possible in the presence of the CRISPR system along with gRNAs targeting splice sites.

FIG. 11C is a readout of GFP expression following internal exon repair. 293FT cells were transfected using lipofectamine 2000 per manufacturer's instructions and cells were transfected in a 96 well format (100 ng per well) with four biological replicates for each condition. Flow cytometry was conducted 48 hours after transfection. Several gRNAs targeting the splice donor (SD) were designed (SD targeting gRNAs 1-5), and delivered in conjunction with a splice acceptor (SA) targeting gRNA. In the absence of gRNAs, no GFP+ cells were detected. However, upon introduction of gRNAs, GFP+ cells were detected and the fraction of GFP+ cells varied depending on the placement of the gRNA relative to the splice donor.

Example 8—Use of Cas13 Orthologs

Figure 12:
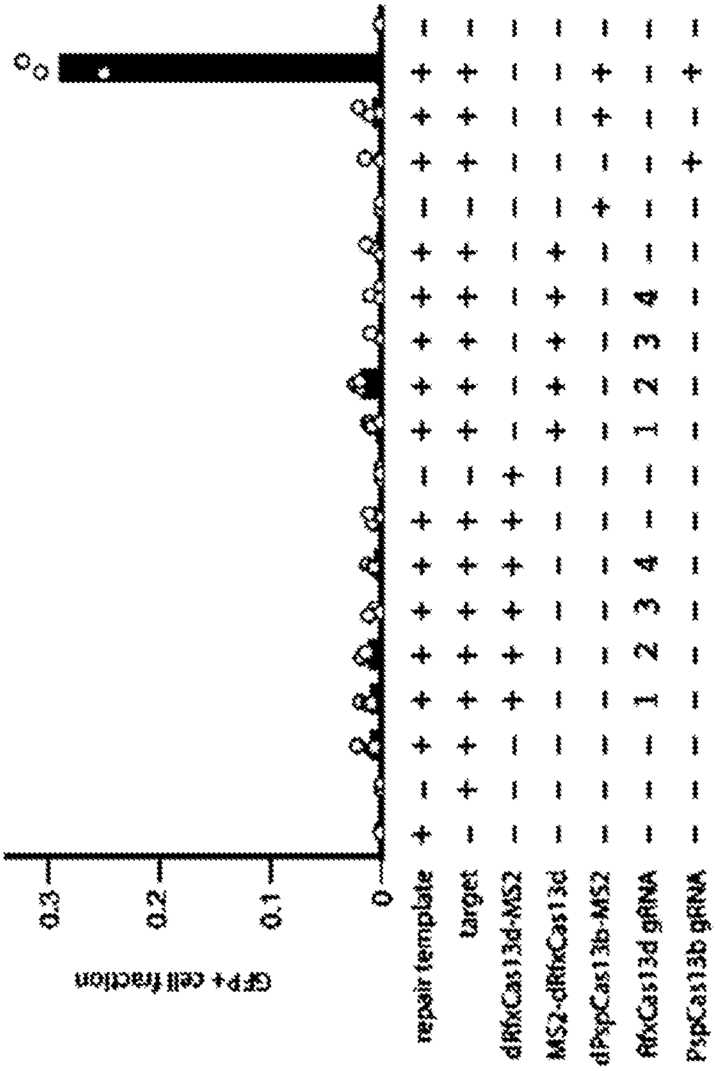
FIG. 12 is fluorescence measurements to illustrate that trans-splicing can be mediated using other Cas13 orthologs, such as Cas13d.

To test whether Cas13d could also lead to CRISPR-mediated trans-splicing, dRfxCas13d was benchmarked against dPspCas13b. Four guides were designed for RfxCas13d, which all targeted the splice acceptor site in the target reporter. MS2 was fused to the N and C-terminus in two different Cas13d architectures. 293FT cells were transfected using lipofectamine 2000 per manufacturer's instructions and cells were transfected in a 96 well format (100 ng per well) with three biological replicates per condition. Flow cytometry was conducted 48 hours after transfection, and cells were gated on BFP and mCherry in order to only consider cells with both target and repair template reporters. BFP+mCherry+ cells were gated on GFP to determine trans-splicing frequency. Mild trans-splicing was observed in the RfxCas13d systems, which were far outperformed by the PspCas13b system (FIG. 12).

Example 9—AAV-Based Delivery of CRISPR Trans-Splicing System

Figure 13:
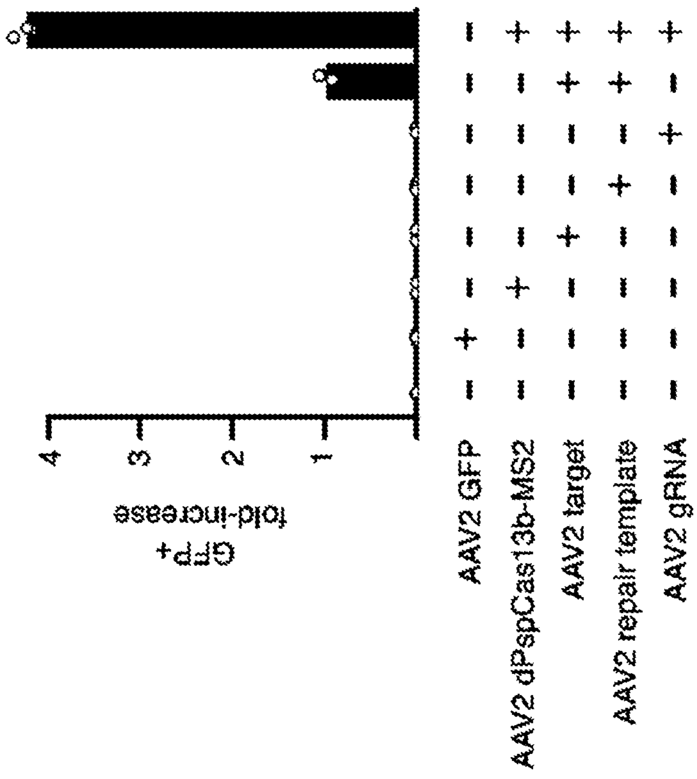
FIG. 13 demonstrates CRISPR-mediated trans-splicing accomplished with a construct delivered with a multi-vector AAV-based approach.

To test whether the CRISPR system could be delivered with a multi-vector AAV-based approach, individual components were cloned into constructs with AAV2 ITRs to enable AAV packaging. AAV2/8 was produced in 293FT cells by PEI co-transfecting each transfer vector with Rep2/Cap8 (pAAV2/8) and AAV helper plasmid (pAdDeltaF6) in a 3:5:6 ratio at 30 ug of DNA per 150 mm dish. Media was changed 24 hours after transfection, and supernatants were harvested 72 hours after transfection. Supernatant was then filtered with a 0.45 um cellulose acetate filter and AAV was concentrated by using a 100 kDa MWCO amicon filter at 4000 ref for 30 minutes at 4 C. 293FT cells were then transduced in suspension using 3 uL of AAV per well in a 96 well plate with four biological replicates per condition. Flow cytometry was conducted 72 hours after AAV transduction in order to measure CRISPR-mediated trans-splicing. Cells were gated on BFP and mCherry in order to only consider cells with both target and repair template reporters. BFP+ mCherry+ cells were gated on GFP to determine trans-splicing frequency. Delivery of the CRISPR system via a multi-vector AAV approach showed significant increase in trans-sicing as measured by GFP+ fluorescence in flow cytometry (FIG. 13).

The invention claimed is:

1. A system for targeting a pre-mRNA nucleic acid for trans-splicing, the system comprising:

(i) a CRISPR/Cas 13 polypeptide comprising two Higher Eukaryotes and Prokaryotes Nucleotide-binding (HEPN) endoRNAse domains or a variant thereof;

(ii) a nucleic acid guide that recognizes the target pre-mRNA and directs the CRISPR/Cas 13 polypeptide to the pre-mRNA; and (ii) a trans-splicing RNA template comprising a splice donor and/or acceptor.

2. The system of claim 1, wherein the nucleic acid guide is an RNA guide.

3. The system of claim 1, wherein the nucleic acid guide is a DNA guide.

4. The system of claim 1, wherein the system comprises one nucleic acid guide.

5. The system of claim 1, wherein the system comprises more than one nucleic acid guide.

6. The system of claim 5, wherein the more than one nucleic acid guides target one nucleic acid of interest.

7. The system of claim 5, wherein the more than one nucleic acid guides target multiple nucleic acids of interest.

8. The system of claim 1, wherein the nucleic acid guide targets a splice acceptor (SA) site.

9. The system of claim 1, wherein the nucleic acid guide targets a splice donor (SD) site.

10. The system of claim 1, wherein the nucleic acid guide targets a region near a splice site.

11. The system of claim 9, wherein the nucleic acid guide targets a region within 200 nucleotides of a splice site.

12. The system of claim 1, wherein the Cas polypeptide is a nuclease-inactive Cas polypeptide.

13. The system of claim 1, comprising more than one trans-splicing RNA template.

14. The system of claim 1, wherein the trans-splicing RNA template comprises the splice acceptor.

15. The system of claim 1, wherein the trans-splicing RNA template comprises the splice donor.

16. The system of claim 1, wherein the trans-splicing RNA template comprises a sequence that binds to the nucleic acid.

17. The system of claim 1, comprising one or more polynucleotides encoding the CRISPR/Cas polypeptide, the nucleic acid-guide, and/or the trans-splicing RNA template.

18. The system of claim 17, comprising a polynucleotide encoding the CRISPR/Cas polypeptide and a polynucleotide encoding the nucleic acid-guide and the trans-splicing RNA template.

19. The system of claim 17, comprising one or more vectors comprising the one or more polynucleotides.

* * * * *